US007507752B2

(12) United States Patent
He et al.

(10) Patent No.: US 7,507,752 B2

(45) Date of Patent: Mar. 24, 2009

(54) BIOSYNTHETIC GENE CLUSTER FOR THE PRODUCTION OF A COMPLEX POLYKETIDE

(75) Inventors: Min He, Congers, NY (US); Melissa M. Wagenaar, Nyack, NY (US); Edmund Graziani, Ridgewood, NJ (US)

(73) Assignee: Wyeth, Madison, NJ (US)

( * ) Notice: Subject to any disclaimer, the term of this patent is extended or adjusted under 35 U.S.C. 154(b) by 401 days.

(21) Appl. No.: 11/143,980

(22) Filed: Jun. 3, 2005

(65) Prior Publication Data

US 2005/0272133 A1 Dec. 8, 2005

Related U.S. Application Data

(60) Provisional application No. 60/664,483, filed on Mar. 23, 2005, provisional application No. 60/576,895, filed on Jun. 3, 2004.

(51) Int. Cl.
*A01N 43/40* (2006.01)
*A01N 43/16* (2006.01)

(52) U.S. Cl. ........................ 514/317; 514/318; 435/456

(58) Field of Classification Search ................. 514/317, 514/318, 456; 435/456
See application file for complete search history.

(56) References Cited

U.S. PATENT DOCUMENTS

| | | | |
|---|---|---|---|
| 6,312,957 | B1 | 11/2001 | Einerhand et al. |
| 6,500,843 | B2 | 12/2002 | Steiner et al. |
| 7,247,650 | B2 | 7/2007 | Summers |
| 2002/0010328 | A1 | 1/2002 | Reeves et al. |
| 2005/0197356 | A1 | 9/2005 | Graziani |
| 2006/0135549 | A1 | 6/2006 | Graziani |
| 2006/0135550 | A1 | 6/2006 | Graziani |

FOREIGN PATENT DOCUMENTS

| | | | |
|---|---|---|---|
| WO | WO 94/18207 | A1 | 8/1994 |
| WO | WO 2004/007709 | A2 | 1/2004 |

OTHER PUBLICATIONS

Cane, Introduction: Polyketide and Nonribosomal Polypeptide Biosynthesis. From Collie to Coli, Chemical Reviews, vol. 97, No. 7, (Nov. 1997).

Challis et al, Predictive, Structure-Based Model of Amino Acid Recognition by Nonribosomal Peptide Synthetase Adenylation Domains, Chemistry & Biology, 7:211-224, (Feb. 2000).

He et al, Biosynthesis of Neuroprotective Polyketides Meridamycin and 3-Normeridamycin, Abstract, Presentation, 14th International Symposium of The Biology of Actinomycetes, (Aug. 27, 2007) Newcastle, UK.

Katz et al, Novel Macrolides Through Genetic Engineering, Med. Res. Rev., 19(6):543-58, (Nov. 1999).

Marahiel et al, Modular Peptide Synthetases Involved in Nonribosomal Peptide Synthesis, Chemical Reviews, vol. 97, No. 7, pp. 2651-2673, (Nov. 1997).

Nicholson et al, Design and Utility of Oligonucleotide Gene Probes for Fungal Polyketide Synthases, Chemistry & Biology 8, pp. 157-178, (Feb. 2001).

Sun et al, Organization of the Biosynthetic Gene Cluster in *Streptomyces* sp. DSM 4137 for the Novel Neuroprotectant Polyketide Meridamycin, Microbiology, 152, pp. 3507-3515, (Dec. 2006).

He et al, Isolation and Characterization of Meridamycin Biosynthetic Gene cluster From *Streptomyces* sp. NRRL 30748, Gene, 377, pp. 109-118, (May 2006).

Reeck, GR et al, "Homology" in Proteins and Nucleic Acids: a Terminologuy Muddle and a Way Out of It. Cell, vol. 50, (5):667, (Aug. 28, 1987).

Saiki et al, Primer-Directed Enzymatic Amplification of DNA with a Thermostable DNA Polymerase, Science, 239(4839):487-91, (Jan. 29, 1988).

Salituro et al, Meridamycin: A Novel Nonimmunosuppressive FLBP12 Ligand From *Streptomyces hygroscopicus*, Tetrahedron Letters, vol. 36, No. 7, pp. 997-1000, (Feb. 13, 1995).

Motamedi et al, The biosynthetic Gene Cluster for the Macrolactone Ring of the Immunosuppressant FK506, Eur. J. Biochem, 256, pp. 528-534, (Sep. 15, 1998).

Motamedi et al, Structural Organization of a Multifunctional Polyketide Synthase Involved in the Biosynthesis of the Macrolide Immunosuppressant FK506, Euro. J. Biochem, vol. 244, No. 1, pp. 74-80, (Feb. 15, 1997).

Wu et al, The FK520 Gene Cluster of *Streptomyces hygroscopicus varascomyceticus* (ATCC 14891) Contains Genes for Biosynthises of Unusual Polyketide Extender Units, Gene vol. 251, No. 1, pp. 81-90, (Jun. 2000).

Schwecke et al, The Biosynthetic Gene Cluster for the Polyketide Immunosuppressant Rapamycin, Proc. Natl. Acad. Sci., vol. 92, pp. 7839-7843, (Aug. 1995).

Aparicio et al, Organization of the Biosynthetic Gene Cluster for Rapamycin in *Streptomyces hygroscopicus*: Analysis of the Enzymatic Domains in the Modular Polyketide Synthase, Gene, vol. 169, No. 1, (Feb. 22, 1996).

Ayuso et al, *Streptomyces hygtoscopicus* Isolate ASH21 Ketosynthase/Methyl-Malonyl-CoA Transferase (pksI) Gene, XP002376039, Abstract, (Dec. 31, 2003).

Omura et al, *S. avermitilis*-MA4680 Genomic Sequence, Complete Genome, XP002376040, Database EMBL, Online, (Oct. 31, 2004).

Omura et al, Genome Sequence of an Industrial Microorganism *Streptomyces avermitilis*: Deducing the Ability of Producing Secondary Metabolites, PNAS, vol. 98, No. 21, pp. 12215-12220, (Oct. 9, 2001).

Ikeda et al, *Complete Genome Sequence and Comparative Analysis of the Industrial Microorganism Streptomyces Avermitilis*, Nature Biotechnology, vol. 21, (May 2003).

(Continued)

*Primary Examiner*—Maryam Monshipouri

(57) ABSTRACT

A polyketide synthase complex composed of polyketide synthase with 15 total modules, a non-ribosomal peptide synthetase with 1 module, and a cytochrome P450 hydroxylase is described. Also provided are novel *Streptomyces* species and methods of modified *Streptomyces* species. Further described are novel compounds, 36-ketomeridamycin, C9-deoxomeridamycin, and C9-deoxoprolylmeridamcyin and uses thereof.

2 Claims, 5 Drawing Sheets

OTHER PUBLICATIONS

Bentley et al, S. Coelicolor A3(2), Database EMBL, online, XP002376041, Abstract, (Oct. 25, 2002).

Bentley et al, Complete Genome Sequence of the Model Actinomucete *Streptomyces* coelicolor A3(2), Nature, vol. 417, No. 6885, pp. 141-147, XP002233530, (May 9, 2002).

BIOSYNTHETIC GENE CLUSTER FOR THE PRODUCTION OF A COMPLEX POLYKETIDE

CROSS-REFERENCE TO RELATED APPLICATIONS

This is an application claiming the benefit under 35 USC 119(e) of U.S. Provisional Patent Application No. 60/664,483, filed Mar. 23, 2005 and U.S. Provisional Patent Application No. 60/576,895, filed Jun. 3, 2004.

BACKGROUND OF THE INVENTION

The present invention relates to the cloning and sequencing of the biosynthetic gene cluster that encodes a Type I polyketide synthase (PKS) and a non-ribosomal peptide synthase responsible for the production of meridamycin. The present invention also relates to methods for genetically manipulating the meridamycin biosynthetic pathway to produce derivatives of meridamycin.

Polyketides represent a large group of natural products that are derived from successive condensations of simple carboxylates, such as acetate, propionate or butyrate. Naturally occurring polyketides possess a broad range of biological activities, including antibiotics such as tetracyclines and erythromycin, anticancer agents such as daunomycin and bryostatin, immunosuppressants such as FK506 and rapamycin, and veterinary products such as monensin and avermectin. Polyketides are produced in most groups of organisms and are especially abundant in a class of mycelial bacteria, the *actinomycetes*, which produce various types of polyketides.

The enzymes responsible for the biosynthesis of polyketides are called polyketide synthases (PKSs). Two general classes of PKSs exist. One class, known as Type I PKSs, is represented by the PKSs for the synthesis of macrolide polyketides such as erythromycin and rapamycin. This type of PKSs has a modular enzymatic structure, in which a module is defined as a set of enzymatic domains that are necessary to catalyze the recognition and incorporation of a specific 2-carbon extending unit (usually a malonyl-CoA, a methyl malonyl-CoA or a propionyl-CoA) into the growing polyketide chain. A minimal type I PKS module contains three enzymatic domains: (1) a ketosynthase domain (KS) which is responsible for catalyzing the Claisen condensation reaction between a starter unit or a growing polyketide chain and an extender unit; (2) an acyltransferase domain (AT) which selectively binds a specific extender unit from the intracellular pools of the various CoA carboxylates and then transfers it to the acyl carrier center; (3) an acyl carrier protein domain (ACP) which contains a serine residue that has been post-translationally modified with a 4-phosphopantethein group and serves as the acceptor for the extender unit or a growing polyketide chain. In addition to the KS, AT, and ACP domains, a type I PKS module can also have one, two or three of the following domains: a ketoreductase domain (KR) which reduces the β-ketone to the hydroxyl function, a dehydratase domain (DH) which eliminates water from the α, β carbon centers to generate a double bond between them, and a enoylreductase domain (ER) which further reduces the double bond generated by DH domain to yield the β-methylene group.

A co-linear relationship exists between the primary organization of the Type I PKS and the structure of the polyketide backbone. For examples, the number of modules in the PKS determines the number of the two-carbon units in the carbon backbone of the final polyketide product, the presence of a specific AT domain determines which extender (malonate, methylmalonate or ethylmalonate, etc.) is incorporated into the growing polyketide chain, and the presence of the reduction domains (KR, DH and ER) in a module determines the extent of reduction of the β-carbon formed at the give condensation.

The second class of PKSs, called Type II PKSs, is responsible for the synthesis of aromatic polyketides such as daunorubicin and tetracenomycin. Type II PKSs have a single set of enzymatic activities (KS, AT, ACP, KR etc.) that reside in individual proteins and are used iteratively to generate polyketides with poly-cyclic ring structure. There is no clear correlation between the type II PKS enzymatic organization and the final polyketide structure.

The genes encoding PKSs and the necessary tailoring enzymes to make a polyketide compound have been shown in all cases to be clustered together on the chromosome of the producing microorganism, and thus are collectively called "PKS biosynthetic gene cluster". Tremendous research work has been done in academic and industrial fields aimed at generating novel polyketide compounds with potential therapeutic applications through genetic manipulation of PKS biosynthetic gene clusters. There is a continuing need in the art to determine the genes encoding novel PKS complexes.

SUMMARY OF THE INVENTION

The present invention provides a biosynthetic gene cluster encoding a polyketide synthase complex for producing a polyketide compound. The invention further provides a meridamycin synthase complex comprising four polyketide synthases, each comprises at least one module, a non-ribosomal peptide synthase, which in one embodiment comprises 4 catalytic domains, and, in one embodiment, a cytochrome P450 hydroxylase. In one embodiment, the polyketide synthases comprise 15 modules in total.

In one embodiment, the modules of the polyketide synthase comprise a ketosynthase domain, an acyltransferase domain, and an acyl carrier protein.

In another embodiment, the modules further comprise a ketoreductase domain, a dehydratase domain and an enoylreductase domain.

The present invention also provides isolated nucleic acids which comprise open reading frames comprised within the polyketide synthase and encode polypeptides required for synthesis of a polyketide compound. The corresponding amino acid sequences are also provided.

The present invention also provides nucleic acid sequences which are complementary to, and/or hybridize under stringent conditions to the nucleic acids comprising the polyketide synthase.

Further provided by the present invention is a method of producing a polyketide compound produced by the polyketide synthase. In one embodiment, the polyketide compound is meridamycin.

The present invention also provides a method of modifying the polyketide synthase of the invention to produce modified polyketide compounds, and the modified polyketide compounds thereof.

In one embodiment, the modification comprises addition, removal, or substitution of at least one amino acid, wherein such modification results in alterations of i) the ring size, ii) the reduction extent of a β-keto group on the ring, iii) a side chain at an α-carbon, or iv) the starting unit of the polyketide compound.

In another embodiment, the modified polyketide compound is a keto-derivative of meridamycin.

The present invention further provides a method for preventing neurodegeneration by contacting neuronal cells with an effective amount of a polyketide compound produced by the polyketide synthase of SEQ ID NO: 1, which sequence may contain appropriate modifications.

A method for promoting neuroregeneration by contacting neuronal cells with an effective amount of a polyketide compound produced by the polyketide synthase having a nucleic acid sequence comprising SEQ ID NO: 1, which sequence may contain appropriate modifications.

In one aspect, the present invention relates macrolides and other chemical compounds produced by a novel *actinomycete* strain, as well as pharmaceutical compositions containing such compounds.

In particular, the invention relates to meridamycin compounds, including meridamycin and derivatives thereof of formula:

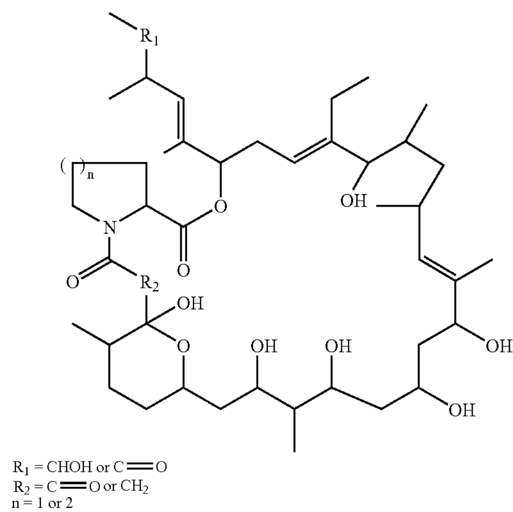

a salt thereof, or mixtures thereof. Such compounds can be used to prepare compositions further comprising one or more pharmaceutically acceptable carriers, excipients, or diluents. Also provided are methods for treating a mammal comprising administering to the mammal a compound or composition of the invention, particularly for treatment of a neurological disorder.

The invention further relates to methods of producing the compounds in an *actinomycete* strain, such as by growth in cell culture of the *actinomycete* strain LL-BB0005. Cell culture of the *actinomycete* strain LL-BB0005, for example, has been found to produce compounds having formulas (I), which can be isolated from the fermentation broth.

Other aspects and advantages of the invention will be readily apparent from the following detailed description of the invention.

DETAILED DESCRIPTION OF THE INVENTION

Figure 1:
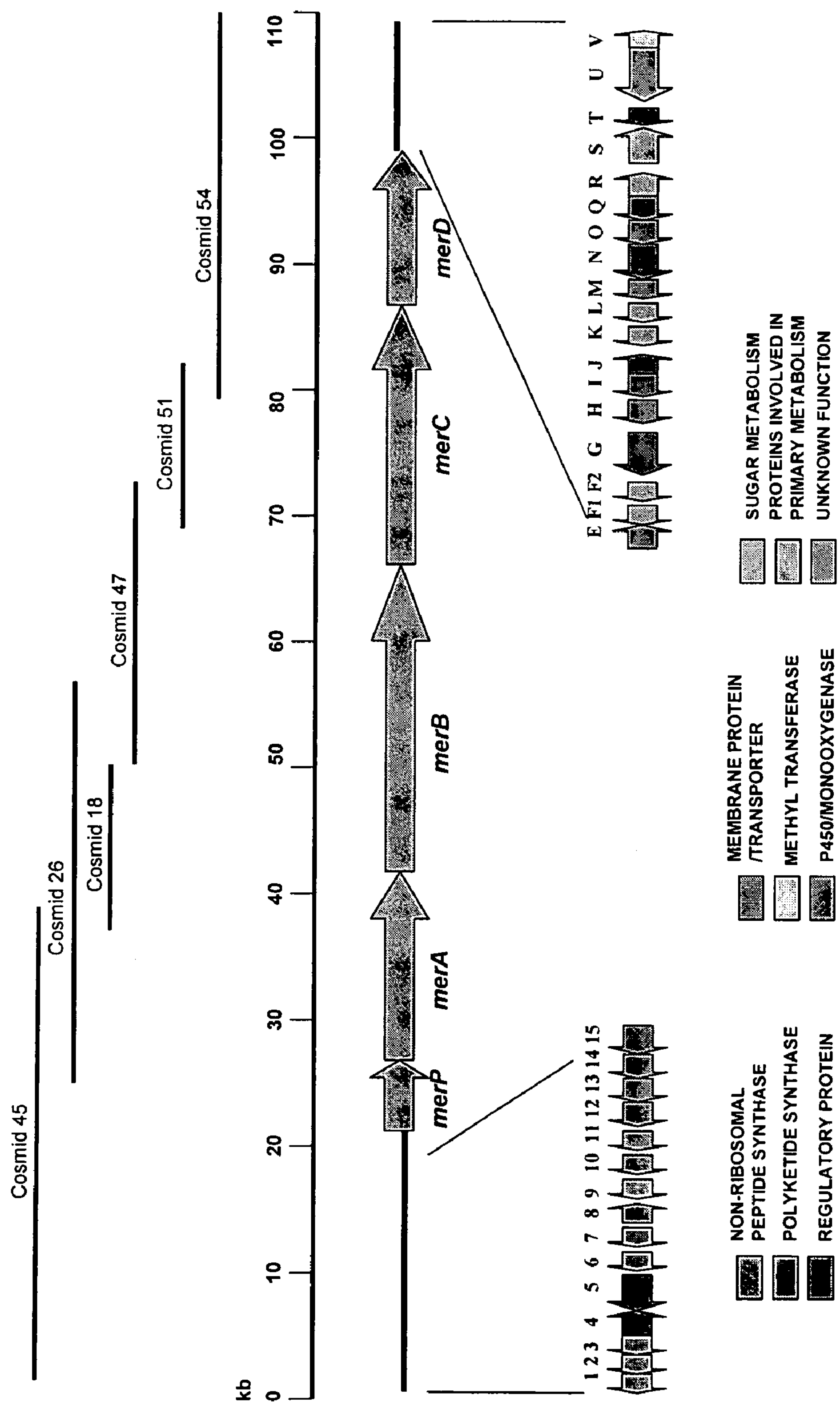
FIG. 1 is a schematic representation of the genetic organization of the meridamycin biosynthetic gene cluster.
Figure 2A:
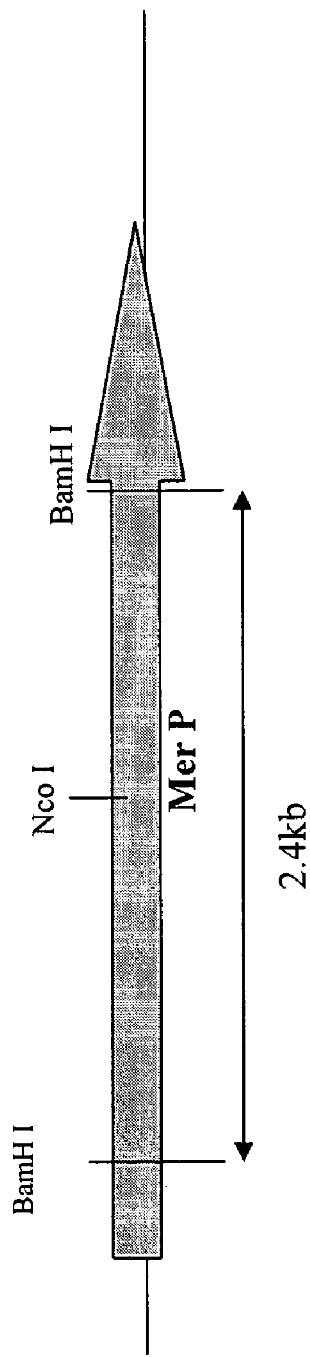
FIG. 2A is a schematic representation of the wild-type genomic DNA of a MerP gene.
Figure 2B:
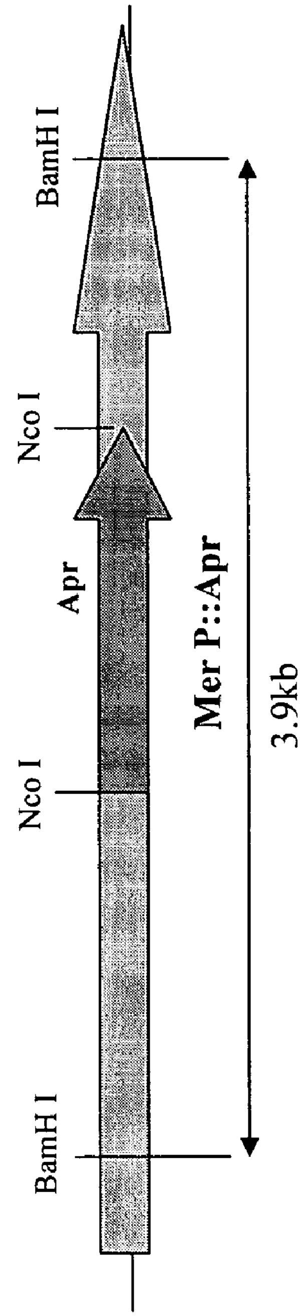
FIG. 2B is a schematic representation of the MerP::Apr mutant construct.

The present invention provides an isolated biosynthetic gene cluster for a polyketide compound. Suitably, the biosynthetic gene cluster is a meridamycin biosynthetic nucleic acid sequence isolated from cellular materials, i.e., an *Actinomycete* species, with which it is naturally found.

In one embodiment, the biosynthetic gene cluster nucleic acid sequence encodes four polyketide synthases which comprise 15 modules in total, and a non-ribosomal peptide synthase, which comprises 4 catalytic domains. In one embodiment, the modules of the polyketide synthase comprise a ketosynthase domain, an acyltransferase domain, and an acyl carrier protein. In another embodiment, the modules further comprise a ketoreductase domain, a dehydratase domain and an enoylreductase domain.

The present invention further provides nucleic acids of genes and/or open reading frames encoding these polypeptides and enzymes, such as polyketide synthases (PKS), non-ribososomal peptide synthases (NRPS), of an isolated meridamycin biosynthetic cluster.

The present invention also provides nucleic acids which comprise open reading frames comprised within the biosynthetic gene cluster and encode polypeptides and enzymes required for synthesis of a polyketide compound. The corresponding amino acid sequences are also provided.

In one embodiment, the present invention provides for the use of recombinant technology to produce one or more of the polypeptides and/or enzymes of the meridamycin biosynthetic pathway using the sequences provided herein.

In one embodiment, the invention provides a method of generating mutant *Streptomyces* strains, generated by modification of one or more of the genes of the biosynthetic gene cluster.

The present invention advantageously permits specific changes to be made to individual modules of the meridamycin biosynthetic gene cluster, either by site directed mutagenesis or replacement, to genetically modify the polyketide core. Additionally, the modules can be used to modify other biosynthetic gene clusters that direct the synthesis of other useful peptides through module swapping.

In another embodiment, the present invention provides methods of modifying one or more of the genes and/or open reading frames of the meridamycin biosynthetic gene cluster. Such modifications can be used to generate macrolide compounds, e.g., meridamycin, 36-ketomeridamycin, 9-deoxomeridamycin.

The present invention further provides nucleic acids of genes and/or open reading frames I. Definitions The following definitions are provided for the full understanding of terms and abbreviations used in this specification.

Meridamycin is a macrolide polyketide that has been shown to have strong FKBP12 binding activity and significant neuroprotective activity in vitro, having the structure (I):

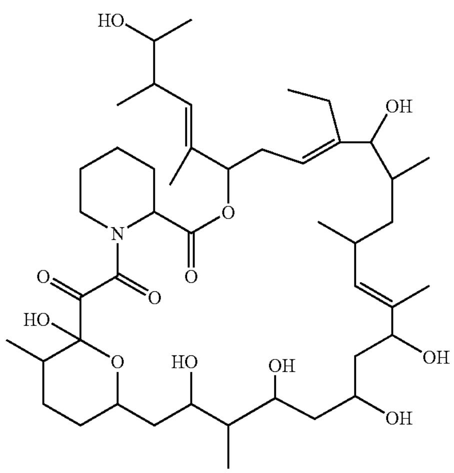

It is produced by terrestrial *actinomycetes* Wyeth culture LL-BB0005, deposited under the terms of the Budapest Treaty with the Agricultural Research Service Culture Collection (NRRL) on May 18, 2004 (Accession No. NRLL 30748). Meridamycin functions as an immunophilin which binds to FK-binding proteins.

*Streptomyces* sp. refers to terrestrial *actinomycete* which produces macrolide antibiotic complexes.

Wyeth strain LL-BB0005 refers to a strain of *Streptomyces* sp. that has been deposited under the terms of the Budapest Treaty with the Agricultural Research Service Culture Collection (NRRL) on May 18, 2004 (Accession No. NRRL 30748).

The abbreviations in the specification correspond to units of measure, techniques, properties or compounds as follows: "hr" means hour(s), "μL" means microliter(s), "nM" means nanomolar, "μM" means micromolar, "M" means molar, "mmole" means millimole(s), "kb" means kilobase, "bp" means base pair(s), and "polymerase chain reaction" is abbreviated PCR; "non-ribosomal peptide synthetase" is abbreviated NRPS; dopamine is abbreviated "DA"; polyketide synthase is abbreviated "PKS".

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.).

Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence that is not part of the DNA sequence. In this context, the heterologous DNA sequence refers to a DNA sequence that is not naturally located within the biosynthetic gene cluster sequence. Alternatively, the heterologous DNA sequence can be naturally located within the biosynthetic gene cluster at a location where it does not natively occur. For example, a sequence encoding a functional enzyme or domain may be natively located within the NRPS sequence, but deleted from this site and inserted elsewhere in the biosynthetic gene cluster sequence. A heterologous expression regulatory element is an element operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

The term "expression control sequence" refers to a promoter, any enhancer element, or suppression elements (e.g., an origin of replication) that combine to regulate the transcription of a coding sequence. The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As used herein, the term "amino acid equivalent" refers to compounds which depart from the structure of the naturally occurring amino acids, but which have substantially the structure of an amino acid, such that they can be substituted within a peptide that retains biological activity. Thus, for example, amino acid equivalents can include amino acids having side chain modifications and/or substitutions, and also include related organic acids, amides or the like. The term "amino acid" is intended to include amino acid equivalents. The term "residues" refers both to amino acids and amino acid equivalents.

As used herein, the terms "homologous" and "homology" refer to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90% or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar. Preferably, the amino acids are functionally identical. Preferably, the similar or homologous sequences are identified by alignment using, for example, the GCG (Genetics Computer Group, Program Manual for the GCG Package, Version 10, Madison, Wis.) pileup program, or any of the programs described above (BLAST, FASTA, etc.).

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., *Molecular Cloning: A Laboratory Manual*, Second Edition (1989) Cold Spring Harbor Laboratory Press, Cold Spring Harbor, N.Y. (herein "Sambrook et al., 1989"). The conditions of temperature and ionic strength determine the "stringency" of the hybridization. For preliminary screening for homologous nucleic acids, low stringency hybridization conditions, corresponding to a Tm (melting temperature) of 55° C., can be used, e.g., 5×SSC, 0.1% SDS, 0.25% milk, and no formnamide; or 30% formamide, 5×SSC, 0.5% SDS). Moderate stringency hybridization conditions correspond to a higher Tm, e.g., 40% formamide, with 5× or 6×SCC. High stringency hybridization conditions correspond to the highest Tm, e.g., 50% formamide, 5× or 6×SCC. SCC is a 0.15M NaCl, 0.015M Na citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a Tm of 55° C., and utilizes conditions as set forth above. In a preferred embodiment, the Tm is 60° C.; in a more preferred embodiment, the Tm is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligoncucleotide molecules used. Exemplary temperatures may be 37° C. (for 14-base oligonucleotides), 48° C. (for 17-base oligoncucleotides), 55° C. (for 20-base oligonucleotides) and 60° C. (for 23-base oligonucleotides). Exemplary suitable hybridization conditions for oligonucleotides include washing in 6×SSC/0.05% sodium pyrophosphate, or other conditions that afford equivalent levels of hybridization.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence.

The term "variant" may also be used to indicate a modified or altered gene, DNA sequence, enzyme, cell, etc., i.e., any kind of mutant. Two specific types of variants are "sequence conservative variants", a polynucleotide sequence where a change of one or more nucleotides in a given codon position results in no alteration in the amino acid encoded at that position, and "function conservative variants", where a given amino acid residue in a protein or enzyme has been changed without altering the overall conformation and function of the polypeptide. Amino acids with similar properties are well known in the art. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Clustal Method, wherein similarity is based on the algorithms available in MEGALIGN. A "function conservative variant" also includes a polypeptide or enzyme which has at least 60% amino acid identity as determined by BLAST or FASTA alignments, preferably at least 75%, more preferably at least 85%, and most preferably at least 90%, and which has the same or substantially similar properties or functions as the native or parent protein or enzyme to which it is compared.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning. A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1 986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

II. Biosynthetic Gene Cluster

In one aspect, the invention provides an isolated meridamycin biosynthetic gene cluster. See, examples, describing isolation of a group of cosmids identified as pMH45, pMH18, pMH26, pMH47, pMH51 and pMH54, which contain the genetic information for the biosynthesis of meridamycin. SEQ ID NO:1 provides the nucleic acid sequence of the isolated meridamycin biosynthetic gene cluster. Also included in the present invention are the strands complementary to the nucleic acid sequences of Table 1, as wells as natural variants and engineered modifications of the sequences of the biosynthetic gene cluster and their complementary strands. Such modifications include, for example, labels which are known in the art, methylation, and substitution of one or more of the naturally occurring nucleotides with a degenerate nucleotide. These modifications may be to increase expression, yield, and/or to improve purification in the selected expression systems, or for another desired purpose.

Further, the invention encompasses functional fragments of the nucleic acid sequences of SEQ ID NO:1 and its reverse complement. Examples of suitable fragments are provided in Table 1 with reference to the nucleic acid sequences of SEQ ID NO: 1. Table 1 further identifies the length of the polypeptides encoded by the coding sequences and references the relevant sequence identification number and function for each.

Notably, some of the coding sequences are located on the sense strain of SEQ ID NO:1, including, e.g., ORF4, ORF8, ORF 21, MerA, MerB, MerC, MerD, MerE, ORF F-2, MerJ, ORFr, MerS, and ORFV. In addition, some of the coding sequences are located on the strand which is the reverse complement of SEQ ID NO:1, including e.g., ORF1-3, ORF5-7, ORF9-15, MerM-MerQ, MerT, and MerU. For convenience, separate SEQ ID NO:s are provided for those coding sequences located on the reverse strand of SEQ ID NO:1. Other suitable nucleic acid fragments include nucleic acid sequences encoding the amino acids of Table 1 [SEQ ID NO:31-68] and nucleic acid sequences encoding the amino acid sequences of the modules and catalytic domains provided in Table 2, i.e., the specified fragments of SEQ ID NO:47, 48, 49 and 50. Still other suitable fragments will be readily apparent to one of skill in the art.

Thus, the present invention provides an isolated nucleic acid sequence of a coding region from the meridamycin biosynthetic gene cluster. These include, e.g., any of ORF1-15, ORF F1-1, ORF F-2, ORFK, ORFR, ORFV, MerP, MerA, MerB, MerC, MerD, MerE, any of MerG-J, Mer M-O, MerQ, or Mer S-U. In one embodiment, the isolated nucleic acid sequence contains a single open reading frame or gene. In another embodiment, the isolated nucleic acid sequence contains one or more open reading frames or genes. For example, a selected host cell may contain the sequences spanning of MerP and MerA-MerD, optionally also in combination with MerE, nucleotides 26284-99586 of SEQ ID NO:1. Alternatively, a selected host cell may contain the isolated sequences of one or more of these coding regions, e.g., MerP [nt 21592-26311 of SEQ ID NO:1], MerA [nt 26284-43422 of SEQ ID NO:1], MerB [nt 43480-64788 of SEQ ID NO:1], MerC [nt 64785-88691 of SEQ ID NO:1], MerD [nt 889131-98352 of SEQ ID NO:1], and/or MerD [nt 98393-99586 of SEQ NO:1]. Alternatively, a vector host cell may contain any combination of sequences encoding MerP [SEQ ID NO:46], MerA [SEQ ID NO:47], MerB [SEQ ID NO:48], MerC [SEQ ID NO:49], MerD [SEQ ID NO:50], and/or MerE [SEQ ID NO:51].

Also included are modifications of the fragments of the biosynthetic gene cluster and their complementary strands. Such modifications include, for example, labels which are known in the art, methylation, and substitution of one or more of the naturally occurring nucleotides with a degenerate nucleotide. These modifications may be to increase expression, yield, and/or to improve purification in the selected expression systems, or for another desired purpose.

TABLE 1

Summary of ORFs in Meridamycin Biosynthetic Gene Cluster

| Orf | SEQ ID NO. | Position (bp) With reference to SEQ ID NO: 1 | No. of Amino Acids/ SEQ ID NO: | Function |
|---|---|---|---|---|
| Orf1 | SEQ ID NO: 6 | 1108 . . . 221 | 295 SEQ ID NO: 31 | Purine synthase |
| Orf2 | SEQ ID NO: 7 | 2830 . . . 1265 | 521 SEQ ID NO: 32 | Purine synthase |
| Orf3 | SEQ ID NO: 8 | 3483 . . . 2827 with RBS | 218 SEQ ID NO: 33 | Purine synthase |
| Orf4 | | 3885 . . . 4727 | 280 SEQ ID NO: 34 | Ion transport protein |
| Orf5 | SEQ ID NO: 9 | 6643 . . . 4790 | 617 SEQ ID NO: 35 | Membrane protein |
| Orf6 | SEQ ID NO: 10 | 7762 . . . 6878 | 294 SEQ ID NO: 36 | Succinyl-CoA synthetase (α chain) |
| Orf7 | SEQ ID NO: 11 | 8902 . . . 7784 | 372 SEQ ID NO: 37 | Succinyl-CoA synthetase (β chain) |
| Orf8 | | 9320 . . . 10960 | 546 SEQ ID NO: 38 | β-1,4-endo glucanase |
| Orf9 | SEQ ID NO: 12 | 12377 . . . 11037 | 446 SEQ ID NO: 39 | Argininosuccinate synthase |
| Orf 10 | SEQ ID NO: 13 | 14809 . . . 12677 | 710 SEQ ID NO: 40 | Mycodextranase |
| Orf 11 | SEQ ID NO: 14 | 16517 . . . 14919 | 532 SEQ ID NO: 41 | α-1,4-glucosidase |
| Orf 12 | SEQ ID NO: 15 | 17423 . . . 16548 | 291 SEQ ID NO: 42 | Sugar transporter (ABC type permease, inner portion)) |
| Orf 13 | SEQ ID NO: 16 | 18442 . . . 17420 | 340 SEQ ID NO: 43 | Sugar transporter (ABC type permease, inner portion) |
| Orf 14 | SEQ ID NO: 17 | 19811 . . . 18381 | 476] SEQ ID NO: 44 | Sugar transporter (extracellular sugar binding portion) |
| Orf 15 | SEQ ID NO: 18 | 20919 . . . 19942 | 325 SEQ ID NO: 45 | LacI family transcription regulator |
| MerP | | 21592 . . . 26311 | 1572 SEQ ID NO: 46 | NRPS for incorporating pipecolic acid (single module with 4 domains: C A T C) |

TABLE 1-continued

| Summary of ORFs in Meridamycin Biosynthetic Gene Cluster | | | | |
|---|---|---|---|---|
| MerA | | 26284-43422 | 5712 SEQ ID NO: 47 | Type I PKS (4 modules) |
| MerB | | 43480 . . . 64788 | 7102 SEQ ID NO: 48 | Type I PKS (4 modules) |
| MerC | | 64785 . . . 88691 | 7968 SEQ ID NO: 49 | Type I PKS (5.5 modules) |
| MerD | | 89131 . . . 98352 | 3073 SEQ ID NO: 50 | Type I PKS (1.5 modules) |
| MerE | | 98393 . . . 99586 | 397 SEQ ID NO: 51 | Cytochrome P450 hydroxylase |
| ORF F-1 | SEQ ID NO: 19 | 100254 . . . 99736 | 172 SEQ ID NO: 52 | |
| ORF F-2 | | 100528 . . . 101037 | 169 SEQ ID NO: 53 | |
| MerG | SEQ ID NO: 20 | 102698 . . . 101214 | 494 SEQ ID NO: 54 | Drug efflux transporter |
| Mer H | SEQ ID NO: 21 | 103296 . . . 102817 | 159 SEQ ID NO: 55 | Drug resistance regulatory protein |
| Mer I | SEQ ID NO: 22 | 104322 . . . 103378 | 314 SEQ ID NO: 56 | Regulatory protein |
| Mer J | | 104277 . . . 105272 | 331 SEQ ID NO: 57 | Membrane protein |
| ORF K | SEQ ID NO: 23 | 106206 . . . 105382 | 274 SEQ ID NO: 58 | |
| Mer L | SEQ ID NO: 24 | 107368 . . . 106319 | 349 SEQ ID NO: 59 | |
| Orf | SEQ ID NO. | Position (bp) | No. of Amino Acids/SEQ ID NO: | Function |
| Mer M | SEQ ID NO: 25 | 107845 . . . 107438 | 135 SEQ ID NO: 60 | Resistance related regulator |
| Mer N | SEQ ID NO: 26 | 109423 . . . 107930 | 497 SEQ ID NO: 61 | Putative drug efflux transporter |
| Mer O | SEQ ID NO: 27 | 110061 . . . 109420) | 213 SEQ ID NO: 62 | Drug resistant related regulator |
| Mer Q | SEQ ID NO: 28 | 111197 . . . 110151 | 348 SEQ ID NO: 63 | LysR family regulator |
| ORF R | | 111062 . . . 111718 | 218 SEQ ID NO: 64 | |
| Mer S | | 111847 . . . 113226 | 459 SEQ ID NO: 66 | FAD-dependent monooxygenase |
| Mer T | SEQ ID NO: 29 | 113683 . . . 113276 | 135 SEQ ID NO: 79 | Putative short membrane protein with unknown function |
| Mer U | SEQ ID NO: 30 | 116366 . . . 113916 | 816 SEQ ID NO: 67 | |
| ORF V | | 116454 . . . 116855, (incomplete) | 134 SEQ ID NO: 68 | (quinone) methyl transferase |

As indicated in Table 1, the MerP, MerA, MerB, MerC, MerD, and MerE genes are those responsible for producing the core of the meridamycin molecule. MerP encodes a non-ribosomal peptide synthetase. Each of MerA, MerB, MerC and MerD encodes a type I polyketide synthetase (PKS), each composed of multiple modules. Each module provides a catalytic domain, e.g., a ketosynthase reduction (KR), acyltransferase reduction (AT), dehydratase reduction domain (DH) or enoylreductase (ER) reduction domain. For example, MerA contains 4 modules, MerB contains 4 modules, MerC contains 5.5 modules, and MerD provides 1.5 modules. See Table 2.

TABLE 2

Module and catalytic domain organization in meridamycin PKSs:

| Protein | Module | Start position (aa #) | End position (aa #) | Catalytic domain (start aa#-end aa#), with reference to SEQ ID NO: of referenced Mer Gene |
|---|---|---|---|---|
| MerA SEQ | Loading module | 1 | 1050 | KS(21-442), AT(580-879), ACP (970-1040) |
| ID NO: 47 | 1 | 1051 | 2510 | KS(1060-1484), AT(1589-1877), KR(2147-2322), ACP(2411-2496) |

TABLE 2-continued

Module and catalytic domain organization in meridamycin PKSs:

| Protein | Module | Start position (aa #) | End position (aa #) | Catalytic domain (start aa#-end aa#), with reference to SEQ ID NO: of referenced Mer Gene |
|---|---|---|---|---|
| | 2 | 2511 | 4183 | KS(2523-2943), AT(3041-3330), DH(3385-3548), KR3823-4002), ACP(4091-4176) |
| | 3 | 4184 | 5172 | KS(4195-4621), AT(4719-4989), KR(5299-5472), ACP(5553-5629) |
| MerB SEQ ID NO: 48 | 4 | 1 | 1717 | KS(33-455), AT(556-857), DH(914-1078), KR(1355-1537), ACP(1623-1708) |
| | 5 | 1718 | 3263 | KS(1728-2155), AT(2266-2555), KR(2896-3072), ACP(3168-3253) |
| | 6 | 3264 | 5293 | KS(3276-3704), AT(3806-4096), DH(4154-4320), ER(4633-4939), KR(4940-5126), ACP(5211-5296) |
| | 7 | 5294 | 7102 | KS (5317-5744), AT(5841-6129), DH(6188-6354), KR(6664-6848), ACP(6935-7020) |
| MerC SEQ ID NO: 49 | 8 | 1 | 1496 | KS(49-476), AT(540-714), KR(1141-1317), ACP(1409-1487) |
| | 9 | 1497 | 2942 | KS(1507-1929), AT(2024-2294), KR(2598-2774), ACP(2848-2933) |
| | 10 | 2943 | 4470 | KS(2953-3371), AT(3475-3765), KR(4104-4280), ACP(4376-4461) |
| | 11 | 4471 | 5930 | KS((4481-4909), AT(5004-5274), KR(5578-5751), ACP(5837-5918) |
| | 12 | 5931 | 7386 | KS(5941-6368), AT(6458-6728), KR(7038-7211), ACP(7292-7376) |
| | 13 | 7387 | 7968 | KS(7396-7823) |
| MerD SEQ ID NO: 50 | 13 | 1 | 1385 | AT(156-427), DH(540-714), ER(1059-1361), KR(1360-1549), ACP(1641-1726) |
| | 14 | 1386 | 3425 | KS(1747-2172), AT(2288-2577), ACP(3286-3371) |

After production of the core modules (e.g., by MerP, MerA, MerB, MerC and MerD), a polyketide core can then modified by additional enzymes that are herein termed "tailoring enzymes". These enzymes alter the side chains of the polyketide core without altering the number of the carbon atoms present within the polyketide core. Such tailoring enzymes may include, but are not limited to, hydroxylation and methylation. An example of one such tailoring enzyme, a cytochrome P450-like hydroxylase, is encoded by MerE.

Other functional polypeptides and enzymes including, e.g., a purine synthase, succinyl-CoA synthetase, a glucanase, argininosuccinate synthase, mycodextranase, glucosidase, sugar transporter, regulatory proteins, drug efflux transporters, and membrane proteins, have been identified.

In one embodiment, a host cell is provided which contains the genes encoding at least the polyketide core. The host cell may be a modified *streptomyces* and/or *actinomycete* strain. Alternatively, the host cell may be of type that does not natively carry these biosynthetic genes. In one embodiment, the host cell contains one or more of the other genes of the biosynthetic gene cluster, e.g., merE, (any one from merG-U), ORF1-15, ORFF-1, ORFF-2, or ORFK, ORFR or ORFV.

In one embodiment, the invention provides a mutant gene in which the function of one or more of the catalytic domains (e.g., modules) within the gene region is eliminated. This mutation can be accomplished by deletion, a frame shift mutation, or other methods known in the art. Desirably, the function of each of these modules is retained, where the function of the selected gene is retained.

In another embodiment, the invention provides novel amino acid sequences, including, inter alia, polypeptides, and enzymes of the meridamycin biosynthetic synthase complex provided in Table 1 and 2 [SEQ ID NO:31-68 and fragments thereof, e.g., those in Table 2]. The amino acid sequences of the invention may be expressed from the nucleic acid sequences of the invention, e.g., from SEQ ID NO:1 or fragments thereof such as are identified herein, or from other nucleic acid sequences encoding these amino acids.

In still another embodiment, these amino acid sequences, or fragments thereof, may be produced synthetically using techniques known to those of skill in the art, including, e.g., by chemical synthesis. For example, peptides can also be synthesized by the well-known solid phase peptide synthesis methods (Merrifield, *J. Am. Chem. Soc.,* 85:2149 (1962); Stewart and Young, Solid Phase Peptide Synthesis (Freeman, San Francisco, 1969) pp. 27-62).

Suitable production techniques are well known to those of skill in the art. See, e.g., Sambrook et al, Molecular Cloning: A Laboratory Manual, Cold Spring Harbor Press (Cold Spring Harbor, N.Y.). The sequences of any of the amino acid sequences provided herein can be readily generated using a variety of techniques. These and other suitable production methods are within the knowledge of those of skill in the art and are not a limitation of the present invention.

In one particularly embodiment, the amino acid sequences of the invention are produced by expression of one or more of the ORFs or genes in a selected host cell. Typically, a vector is designed to carry the nucleic acid sequences encoding one or more ORFs or genes into a desired host cell.

The terms "vector", "cloning vector" and "expression vector" refer to the vehicle by which DNA can be introduced into a host cell, resulting in expression of the introduced sequence. In one embodiment, vectors comprise a promoter and one or more control elements (e.g., enhancer elements) that are heterologous to the introduced DNA but are recognized and used by the host cell. In another embodiment, the sequence that is introduced into the vector retains its natural promoter that may be recognized and expressed by the host cell (Bormann et al., J. Bacteriol 1996;178:1216-1218). In one embodiment, the vector compatible with the present invention is an intergeneric shuttle vector that permits conjugation between e.g., *Streptomyces* and *E. coli*. In another embodiment, the vector is a cosmid.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

An "intergeneric vector" is a vector that permits intergeneric conjugation, i.e., utilizes a system of passing DNA from *E. coli* to *actinomycetes* directly (Keiser, T. et al., Practical *Streptomyces* Genetics (2000) John Innes Foundation, John Innes Centre (England)). Intergeneric conjugation has fewer manipulations than transformation.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA (which may be circular), usually of bacterial origin, that can readily accept additional (foreign) DNA and which can readily be introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes.

Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal).

The host cell itself may be selected from any biological organism, including prokaryotic (e.g., bacterial) cells, plant cells, and eukaryotic cells, including, insect cells, yeast cells and mammalian cells. Representative examples of appropriate host cells include bacterial cells, such as, *E. coli, Streptomyces* and *Bacillus subtilis* cells; fungal cells, such as yeast cells and *Aspergillus* cells; and insect cells such as *Drosophila* S2 and *Spodoptera* Sf9 cells.

The term "expression system" means a host cell and compatible vector under suitable conditions, e.g. for the expression of a protein coded for by foreign DNA carried by the vector and introduced to the host cell. A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids, BAC vector and phagemids. The expression systems may contain control regions that regulate as well as engender expression. Generally, any system or vector that is able to maintain, propagate or express a polynucleotide to produce an enzyme in a host may be used. The appropriate nucleotide sequence may be inserted into an expression system by any of a variety of well-known and routine techniques, such as, for example, those set forth in Sambrook et al., Molecular Cloning: A Laboratory Manual, 2nd Ed., Cold Spring Harbor Laboratory Press, Cold Spring Harbor, N.Y. (1989). Appropriate secretion signals may be incorporated into the desired enzyme to allow secretion of the translated protein into the lumen of the endoplasmic reticulum, the periplasmic space or the extracellular environment. These signals may be endogenous to the enzyme or they may be heterologous signals.

Thus, the determination of the biosynthetic pathway of meridamycin by the inventors permits, in one embodiment, one of ordinary skill in the art to clone and express the pathway, and thus, a polyketide, in a heterologous organism. The invention also permits portions of isolated nucleic acid sequences of the biosynthetic gene cluster (e.g., one or more ORFs or genes) to be expressed in a heterologous host cell, i.e., another *streptomycete* strain, a non-*Streptomycete* and/or a non-*Actinomycete*. Although the examples illustrate use of a bacterial strain, any organism or expression system can be used, as described herein. The choice of organism is dependent upon the needs of the skilled artisan. For example, a strain that is amenable to genetic manipulation may be used in order to facilitate modification and production of meridamycin.

III. Method of Modifying Units within Biosynthetic Gene Cluster

In one aspect, the present invention provides methods of modifying one or more of the genes, open reading frames, modules or catalytic domains of the meridamycin biosynthetic gene cluster. Alterations can be for the purpose of improving expression in a selected expression system. Other alterations can be to extinguish, modify, or enhance function of a selected domain.

In one embodiment, the nucleic acid sequences of such altered units can be provided to a heterologous host cell (i.e., another *streptomycete* strain, a non-*Streptomycete* and/or a non-*Actinomycete*) via a suitable vector in a selected host cell and used to express a product. Examples of suitable vectors, expression systems and host cells are described herein. In another embodiment, the invention provides a method of generating mutant *Streptomyces* strains, generated by modification of one or more of the genes of the biosynthetic gene cluster. Such a mutant *actinomycete* strain which contains the biosynthetic gene cluster in which the function of one or more of the genes is partially or entirely altered or destroyed according to the present invention, can be used to generate macrolide compounds, e.g., meridamycin, 36-ketomeridamycin, or 9-deoxomeridamycin.

Where production of a macrolide compound is desired, a host cell expresses the functions necessary to produce the polyketide core, i.e., MerP, MerA, MerB, MerC and MerD. However, ancillary functions may be altered or extinguished. For example, after production of the core modules, a polyketide core can then modified by additional enzymes which are herein termed "tailoring enzymes". These enzymes alter the side chains of the polyketide core without altering the number of the carbon atoms present within the polyketide core. Such tailoring enzymes may include, but are not limited to, hydroxylation and methylation. In one embodiment, the function of the tailoring enzyme Cytochrome P450 hydroxylase (SEQ ID NO: 52) can be destroyed.

In another example, one or more of the 4 modules, or the catalytic domains thereof, of the non-ribosomal peptide synthase which composes part of the biosynthetic gene cluster is modified. In another embodiment, one or more of the four polyketide synthases, which comprise 15 modules in total is modified. In another embodiment, one of the modules of the polyketide synthase, e.g., a ketosynthase domain, an acyltransferase domain, and an acyl carrier protein is modified. In still another embodiment, another of the modules, e.g., a ketoreductase domain, a dehydratase domain or an enoylreductase domain is altered. Other suitable mutations, including mutations to genes other than tailoring enzymes, can be readily made by one of skill in the art.

The present invention contemplates any method of altering any of the nucleic acid sequences encoding the proteins of the present invention. More specifically, the invention contemplates any method that inserts amino acids, deletes amino acids or replaces amino acids in the proteins of the invention. Additionally, a whole domain in a module may be replaced, such as the KR, DH or ER domains, which alters the reduction extent of the β-keto group on the polyketide ring. The modifications may be performed at the nucleic acid level. These modifications are performed by standard techniques and are well known within the art. For example, in one embodiment of the invention, the gene encoding the NRPS of the biosynthetic cluster, which is responsible for incorporation of a pipcoleic acid in to the meridamycin macrolide core, is inactivated.

Given the information in the present specification regarding the co-linear relationship between the primary organization of the meridamycin polyketide synthases and the structure of the meridamycin polyketide core structure, one of skill in the art can readily to introduce specific changes in one or more of the individual PKS modules by manipulating the genes encoding these modules, therefore modify certain portions of the polyketide backbone of meridamycin that cannot be easily accessed by chemical modification.

In one embodiment, the invention provides changes of the reduction extent of the β-keto group on the polyketide ring by inactivation, deletion or insertion of a selected reduction domains, e.g., KR, DH, or ER, in selected modules. For example, the hydroxyl function at C36 of meridamycin is derived from a keto group by the action of the KR domain of Module 1 in meridamycin polyketide synthetase A (MerA). By eliminating this KR domain from MerA, the keto group would be restored at C36 position. This has been successfully done, as described in detail in Example 4 (see below).

In another embodiment, the invention provides a meridamycin having a polyketide ring size modified by deletion or addition of one or more PKS modules. The number of the two-carbon units in the polyketide ring (the size of the ring) is determined by the number of modules present in the PKS. Therefore, the size of the polyketide ring can be increased or decreased by two carbon unit through addition or deletion of a module into the corresponding PKS. This can be achieved through inserting a DNA fragment which encodes such a module into selected PKS gene (merA, merB or merC) in a way that maintains the integrity of the whole open reading frame.

In yet another embodiment, the invention provides a meridamycin polyketide ring having one or more side chains modified by site-directed mutagenesis or replacement of AT domains. As mentioned before, the composition of the side chain at the α-carbon of a macrolide polyketide is determined by the specificity of the AT domain present in the corresponding module. For example, an ethyl group is present at C28 of meridamycin because the AT domain in module 4 has the specificity of recognizing ethylmalonyl CoA and incorporate it into the polyketide ring during the 4th cycle of condensation. If this AT domain is replaced by another AT domain which specifically recognizes methylmalonyl CoA, a methyl group, instead of ethyl group, will be present at C28. Alternatively, if this AT domain is replaced by another AT domain which specifically recognizes malonyl CoA, a hydrogen will be present at C28. All these changes can be achieved either by introducing point mutations into the DNA fragment encoding a specific AT domain through site-directed mutagenesis, or by replacing the DNA fragment encoding the AT domain with another DNA fragment which encodes another AT domain with different substrate specificity.

In yet a further embodiment, the invention provides for meridamycin having a starting unit altered by replacement of the loading module. C36 and C37 in meridamycin are incorporated by the loading module of mer PKS from malonyl-CoA. Sequencing analysis of the mer PKS gene cluster revealed a loading module comprising a KSQ-AT-ACP tridomain, suggesting a type of chain initiation as found in the biosynthetic gene clusters of tylosin, pikromycin/methymycin, spinosyn and monensin. Previous studies have demonstrated that this type of loading module has a strict substrate specificity, in contrast to the relaxed specificity of the AT-ACP didomain loading modules found in erythromycin and avermectin PKSs. Therefore, a mutated meridamycin producing strain can be generated, in which the mer PKS loading module is replaced with one of broad substrate specificity. Such a mutated meridamycin may provide more than one meridamycin analog, dependent on the various substrates added to the culture.

The present invention also contemplates a method for using an intergeneric conjugation vector, described infra in the examples, to manipulate, modify, or isolate a protein involved in the synthesis of a specific product. For example, the vector may be used to alter an enzyme which is involved in incorporation of the pipecolic acid residue into the polyketide core, so that a proline residue is incorporated instead. The effect of this modification on peptide function may then be evaluated for biological efficacy. In the above example, modifications to the enzyme may include, but are not limited to, removal of amino acids and/or sequences that specifically recognize pipecolic acid and/or incorporation of amino acids and/or sequences that specifically recognize proline.

Therefore, in general terms, an intergeneric vector may be used to alter a gene sequence by insertion of nucleic acid sequences, deletion of nucleic acid sequences, or alteration of specific bases within a nucleic acid sequence to alter the sequence of a protein of interest; thereby producing a modified protein of interest. Preferably, the protein of interest is involved in the synthesis of a compound of interest. The method of modifying a protein comprises (i) transfecting a first bacterial cell with the vector, (ii) culturing the first bacterial cell under conditions that allow for replication of the vector, (iii) conjugating the first bacterial cell with a second bacterial cell under conditions that allow for the direct transfer of the vector from the first bacterial cell to the second bacterial cell, and (iv) isolating the second bacterial cell transformed with the vector. In a preferred embodiment, the first cell is a Gram-negative bacterial cell and the second cell is a Gram-positive cell.

In one embodiment, based on the fact that the genes encoding the PKSs for the production of the meridamycin core structure are linked together on the chromosome of LL-BB0005, those skilled in the art will be able to transfer these genes into the chromosome of another bacterium that has been optimized for the high yield production of macrolide compound, e.g., rapamycin. This can be done in two steps: first, by deleting the native rapamycin PKS genes from the rapamycin high producer; followed by integration of the meridamycin PKS genes into the chromosome of the mutated rapamycin high producer.

The role of the proteins encoded by a mutant gene generated according to the present invention and/or MerA-V, or ORF1-ORF15 is evaluated using any methods known in the art. For example, specific modifications to a protein sequence may be produced to alter the final product. Other non-limiting examples of studies that may be conducted with these proteins include (i) evaluation of the biological activity of a protein and (ii) manipulation of a synthetic pathway to alter the final product from bacteria. More detailed discussion of these proposed uses follows.

Genetic manipulations and expression of the proteins discussed herein may be conducted by any method known in the art. For example, the effect of point mutations may be evaluated. The mutations may be produced by any method known in the art. In one specific method the manipulations and protein expression may be conducted using a vector that comprises at least one Gram-negative and at least one Gram-positive origin of replication. The origins of replication allow for replication of the nucleic acid encoded by the vector, in either a Gram-negative or a Gram-positive cell line. In one embodiment, the vector comprises one Gram-negative and one Gram-positive origin of replication. Additionally, the vector comprises a multiple cloning site that allows for the insertion of a heterologous nucleic acid that may be replicated and transcribed by a host cell.

The most evolved mechanism of transfer of nucleic acids is conjugation. As used herein, the term "conjugation" refers to the direct transfer of nucleic acid from one prokaryotic cell to another via direct contact of cells. The origin of transfer is determined by a vector, so that the donor cells retain and the recipient cells obtain copies of the vector. Transmissibility by conjugation is controlled by a set of genes in the tra region, which also has the ability to mobilize the transfer of chromosomes when the origin of transfer is integrated into them (Pansegrau et al., *J. Mol. Biol.,* 239:623-663, 1994; Fong and Stanisich, *J. Bact.,* 175:448-456, 1993).

Upon production of the nucleic acid encoding the modified protein, the protein can be expressed in a host cell. Then the host cell can be cultured under conditions that permit production of a product of the altered pathway.

Once the product is isolated, the activity of the product may be assessed using any method known in the art. The activity can be compared to the product of the non-modified biosynthetic pathway and to products produced by other modifications. Correlations may be drawn between specific alterations and activity. For example, it may be determined that an active residue at a specific position may increase activity. These types of correlations will allow one of ordinary skill to determine the most preferred product structure for specified activity.

Evaluation of the mechanism of a protein and role the protein plays in the synthesis of a compound has traditionally been determined using sequence homology techniques. Intergeneric shuttle vectors described previously, e.g., pNWA200 (see U.S. Published patent application Ser. No. 2003-0219872 A1 (Ser. No. 10/402,842 filed Mar. 28, 2003)) may be used to assess the biological activity of an unknown protein. The vector may be used to disrupt a protein, either by partial or complete removal of the gene encoding the protein, or by disruption of that gene. Evaluation of the products produced when the altered protein is present is useful in determining the function of the protein.

IV. Mutant *Actinomycete* Strains

In one embodiment, the present invention provides a mutant *Streptomcyes* strain produced by modification of one or more of the biosynthetic genes of the invention.

The invention further provides a mutant strain MH1104-1, produced according to the present invention, which has been deposited under the terms of the Budapest Treaty with the Agricultural Research Service Culture Collection (NRRL) on Mar. 14, 2005 (Accession No. NRRL B-30829).

Fermentation conditions to culture the *Streptomyces* species described herein can be performed in flasks. Alternatively, production of higher volumes can be performed in fermentors under similar conditions.

Media useful for the cultivation of *Streptomyces* species and the production of the macrolide compounds include assimilable carbon sources such as, for example, dextrose, sucrose, glycerol, molasses, starch galactose, fructose, corn starch, malt extract and combinations thereof; an assimilable source of nitrogen such as, for example, ammonium chloride, ammonium sulfate, ammonium nitrate, sodium nitrate, amino acids, protein hydrolysates, corn steep liquor, casamino acid, yeast extract, peptone, tryptone and combinations thereof; and inorganic anions and cations such as, for example, potassium, sodium, sulfate, calcium, magnesium, chloride. Trace elements such as, for example, zinc, cobalt, iron, boron, molybdenum, and copper are supplied as impurities of other constituents of the media. Aeration in tanks and bottles is supplied by forcing sterile air through or onto the surface of the fermenting medium. A mechanical impeller provides further agitation in tanks. An antifoam agent such as polypropylene glycol can be added as needed.

In one embodiment, a fermentation production medium is prepared by combining dextrose in a weight percentage of about 1% to about 2%; about 1% to about 3% of a soy source, about 0.25% to about 1% of yeast, about 0.1% of a calcium source, about 5% to about 10%, and preferably 6% to 8% maltodextrin, and, optionally, proline, from 0 to 0.5%. Optionally, other components may be included. Suitably, the media is adjusted to a pH in the range of about 6.5 to 7.5, and preferably about 6.8 to 7. Typically, the culture is allowed to ferment with suitable agitation and aeration. Alternatively, other suitable fermentation media may be prepared by one of skill in the art substituting other appropriate carbon source or other components and/or purchased commercially. See, generally, e.g., Sigma Aldrich (St. Louis, Mo.); G. J. Tortora et al, Microbiology: An Introduction Media Update (Benjamin Cummings Publishing Co; Oct. 1, 2001); Maintaining Cultures for Biotechnology and Industry, eds. J. C. Hunter-Cevera and A. Bet (Academic Press, Jan. 25, 1996).

After about 5 to 10 days, and preferably about 7 days of fermentation, the cells from the culture are pelleted by centrifugation. In one embodiment, the cells are extracted with a suitable solvent, e.g., ethyl acetate. The extract is concentrated in vacuo and resuspended in a minimum volume of a suitable solvent, e.g., methanol. The solution is loaded onto a reverse phase silica column and eluted with 20%-100% methanol in water. The fractions eluting from 60% methanol to 100% methanol are concentrated in vacuo. The meridamycin and/or meridamcyin analog(s) containing fractions are separated by suitable means, e.g., chromatographic methods.

In another embodiment, the supernatant is mixed with a suitable resin and allowed to rest from about 8 to 16 hours. Thereafter, the resin is washed with a suitable solvent, e.g., methanol, and the filtrate collected. To the cell pellet, an ethyl acetate-methanol mixture is added. This is repeatedly shaken and centrifuged, and the supernatant collected. The cell supernatant and the broth methanol filtrate are combined and concentrated in vacuo. Crude extract is adsorbed onto silica, and fractionated by vacuum liquid chromatography (VLC). The compound is eluted with a suitable solvent, e.g., methanol in dichloromethane. This extract is concentrated, adsorbed onto silica and loaded onto a flash silica column. The compound is eluted with a suitable solvent, concentrated and further purified by column chromatography.

Enzymes of the present invention can be recovered and purified from cell cultures by well-known methods including ammonium sulfate or ethanol precipitation, acid extraction, anion or cation exchange chromatography, phosphocellulose chromatography, hydrophobic interaction chromatography, high performance liquid chromatography, hydroxylapatite chromatography and lectin chromatography. Most preferably, affinity chromatography is employed for purification. Well-known techniques for refolding proteins may be employed to regenerate active conformation when the enzyme is denatured during isolation and or purification.

The presence of a compound produced by the organism in the crude or semi-purified material can be confirmed by conventional methods, e.g., liquid chromatography mass spectrometric (LCMS) analysis of fractions. These fractions may be pooled and further purified by chromatographic methods, and optionally concentrated, e.g., in vacuo.

The resulting purified compounds are free of cells and cellular materials, by-products, reagents, and other foreign material as necessary to permit handling and formulating of the compound for laboratory and/or clinical purposes. It is preferable that purity of the compounds used in the present invention have a purity of greater than 80% by weight; more preferably at least 90% by weight, even more preferably greater than 95% by weight; yet even more preferably at least 99% by weight. In one embodiment, the invention provides compositions containing the compounds of the invention, regardless of how such compounds are produced.

In yet another embodiment, the invention provides a novel compound produced by modification of a gene in the biosynthetic gene cluster. The compound may be generated by a mutant *Streptomyces* species generated as described herein, or by recombinant production of a modified gene in the biosynthetic gene cluster as described herein.

V. Polyketide Compounds

In another aspect, the invention provides novel meridamycin compounds. These compounds include, 36-ketomeridamycin, C9-deoxomeridamycin, and C9-deoxoprolylmeridamycin.

In one embodiment, the invention provides a C36-ketomeridamycin compound of formula (II), or a pharmaceutically acceptable salt thereof.

(II)

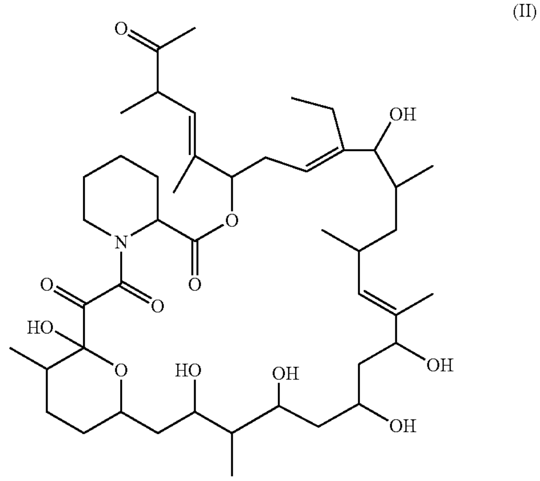

In another embodiment, the invention provides a 9-deoxo-meridamycin compound characterized by the structure (III):

(III)

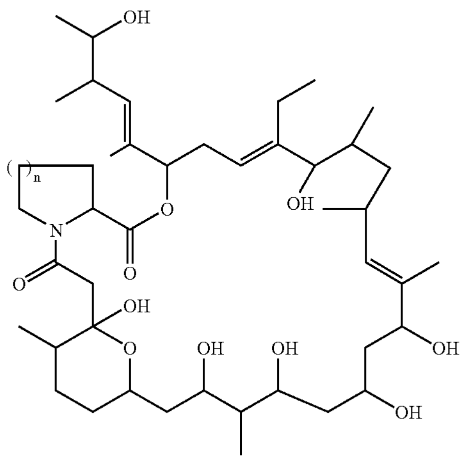

The terms "pharmaceutically acceptable salts" and "pharmaceutically acceptable salt" refer to salts derived from organic and inorganic acids such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

While shown without respect to stereochemistry in formula (II) or (III), the compounds of formula (II) and (III) can contain one or more chiral centers. Reference to "compound of formula (II) or (III)" is understood to include any compound of the implicated structural formula including all stereoisomers thereof.

The physicochemical characteristics of the compound of formula (III), wherein n=2, are as follows:

Apparent molecular formula: $C_{45}H_{77}NO_{11}$

Figure 4:
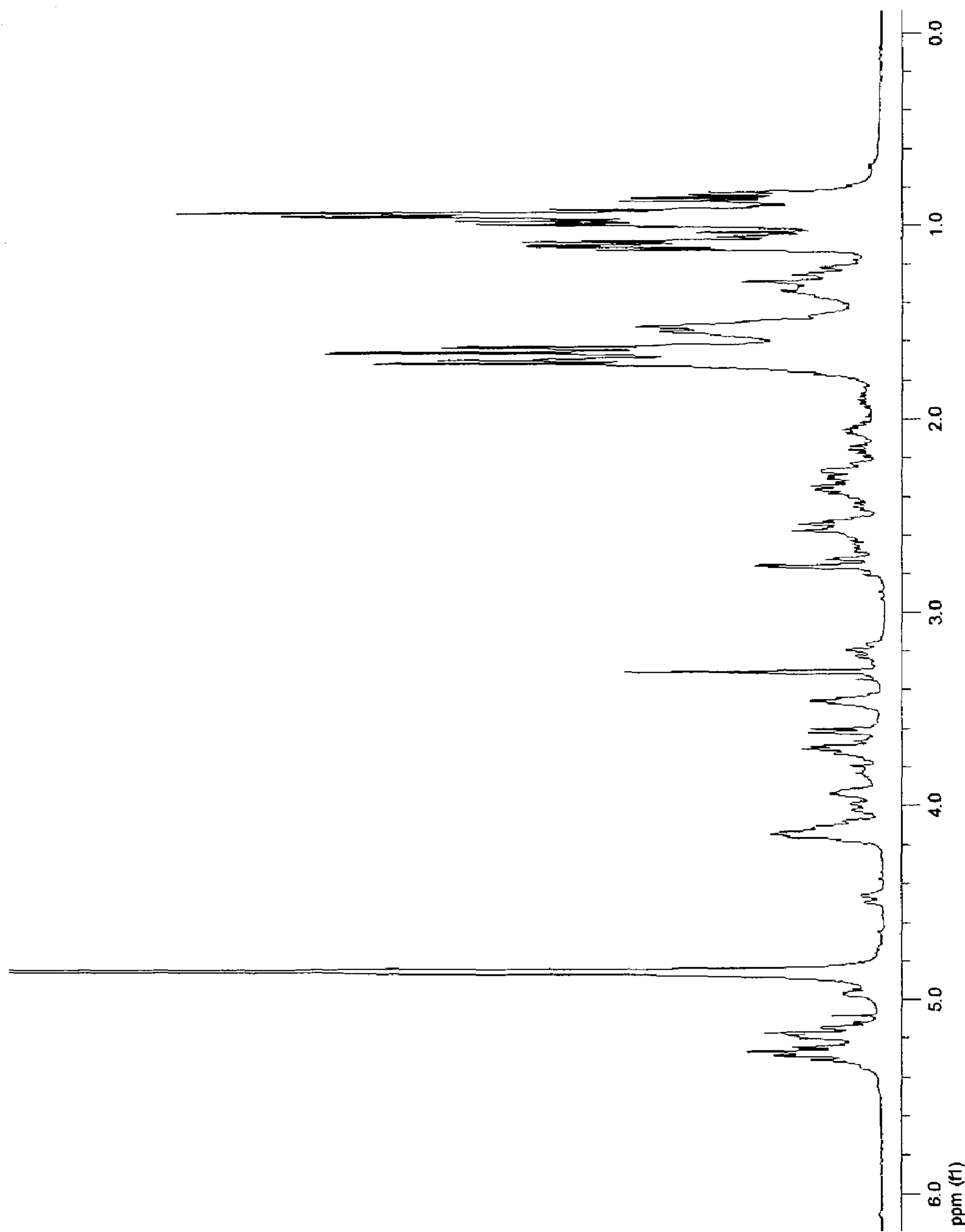
FIG. 4 is a proton NMR spectrum of the compound of formula (III), wherein n=2, in $CD_3OD$ at 400 MHz.

Molecular weight: Positive Ion Electrospray MS m/z=808.1 $(M+H)^+$; Negative Ion Electrospray MS m/z=806.5 $(M-H)^-$; High Resolution Fourier Transform MS m/z=830.53683 $(M+Na)^+$ Ultraviolet Absorption Spectrum: $\lambda_{max}$ nm (acetonitrile/water)=210 nm, end absorption Proton Magnetic Resonance Spectrum: (400 MHz, $CD_3OD$): See FIG. 4

Carbon Magnetic Resonance Spectrum: (100 MHz, $CD_3OD$): See FIG. 5

The production of the neuroprotective compounds (II) or (III) of the invention are not limited to a particular organism, for example, *actinomycete* species designated LL-BB0005. In fact, it is desired and intended to include the use of naturally-occurring mutants of this organism, as well as induced mutants produced according to the present invention, or alternatively, from BB0005 by various mutagenic means known to those skilled in the art, for example, exposure to nitrogen mustard, X-ray radiation, ultraviolet radiation, N'-methyl-N'-nitro-N-nitrosoguanidine, or actinophages. It is also desired and intended to include inter- and intraspecific genetic recombinants produced by genetic techniques known to those skilled in the art such as, for example, conjugation, transduction and genetic engineering techniques. In one particularly desirable embodiment, the organism used for production of compound (III) is the mutant designated M507 of *actinomycete* LL-BB0005.

The culture designated *actinomycete* LL-BB0005, was deposited under the terms of the Budapest Treaty with the Agricultural Research Service Culture Collection (NRRL), 1815 North University Avenue, Peoria, Ill. 61604, on May 18, 2004 and assigned Accession No. NRRL 30748.

The invention also provides a mutant strain of *actinomycete* LL-BB0005, designated M507. This organism was deposited under the terms of the Budapest Treaty with Agricultural Research Service Culture Collection (NRRL), 1815 North University Avenue, Peoria, Ill. 61604, on Jan. 24, 2005 and assigned Accession No. NRRL 30815. This mutant strain has been found, when cultured under appropriate conditions, to generate higher yields of the compounds of formula (III) of the invention than its parent strain. For example, M507 can generate about 3-fold greater yields of the compound of formula (III wherein n=2) than the parent strain when metyrapone is added during the fermentation process. The mutant strain M507 can generate 3-fold greater yields of meridamycin than the parent strain as well as generate significantly lower amounts of undesired products. The mutant strain M507 sporulates which makes it amenable to genetic manipulation.

The invention further provides mutants, recombinants, and modified forms of the *actinomycete* strain of the invention, which are characterized by the ability to produce a compound of formula (III).

Fermentation of culture *actinomycete* strains for production of compound (III) can be performed in flasks. Alternatively, production of higher volumes can be performed in fermentors under similar conditions.

Media useful for the cultivation of *actinomycete* strain LL-BB0005 and mutants thereof including the M507 mutant, and the production of the compound include assimilable carbon sources such as, for example, dextrose, sucrose, glycerol, molasses, starch; an assimilable source of nitrogen such as, for example, ammonium chloride, amino acids, protein hydrolysates, corn steep liquor; and inorganic anions and cations such as, for example, potassium, sodium, sulfate, calcium, magnesium, chloride. Trace elements such as, for example, zinc, cobalt, iron, boron, molybdenum, and copper are supplied as impurities of other constituents of the media. Aeration in tanks and bottles is supplied by forcing sterile air through or onto the surface of the fermenting medium. A mechanical impeller provides further agitation in tanks. An antifoam agent such as polypropylene glycol can be added as needed.

The compound III (wherein n=2) is produced under standard fermentation conditions by the parent strain LL-BB0005 in very small amounts detectable by LCMS after partial purification. Without adding metyrapone to the fermentation, LL-BB0005 and M507 produce compound III (n=2) at the level of 1-2 mg/L. To increase the titer of compound II wherein n=2, one can add metyrapone to either the parent strain or the mutant M507. When metyrapone is added, M507 produces compound III (n=2) at the level of 15-20 mg/L. Metyrapone is a known P450 inhibitor which prevents the final oxidative step in the production of meridamycin resulting in the production of compound III wherein n=2.

Typically, for production of a compound of the invention (e.g., compound III), the *actinomycete* strain LL-BB0005 is cultured in a suitable media for several days, e.g., 2-4, preferably at a temperature in the range of about 25° C. to about 30° C., and preferably, about 28° C. Typically, after a total of about 2 to 5 days incubation, 2-methyl-1,2-di-3-pyridyle-1-propanone (metyrapone) is added and fermentation continued for about 3 to 6 days.

Following culture of the *actinomycete* under suitable conditions to produce a compound of the invention, the compound is isolated and purified using methods known to those of skill in the art. For example, the culture can be centrifuged to separate the broth and cell pellet which contain the compounds of the invention. Typically, the cell pellet is extracted and the extract concentrated. The broth is then treated to obtain any compound which was excreted by the cells, or released during centrifugation. The semi-crude material is then further purified, e.g., by chromatographic methods.

The resulting purified compounds are free of cells and cellular materials, by-products, reagents, and other foreign material as necessary to permit handling and formulating of the compound for laboratory and/or clinical purposes. It is preferable that purity of the compounds used in the present invention have a purity of greater than 80% by weight; more preferably at least 90% by weight, even more preferably greater than 95% by weight; yet even more preferably at least 99% by weight. In one embodiment, the invention provides compositions containing the compounds of the invention, regardless of how such compounds are produced.

VI. Use of Polyketide Compounds

In one aspect, the invention provides the use of compounds produced by the novel strains described herein and the novel compounds of the invention in pharmaceutical compositions and methods for a variety of neurological disorders. Thus, a meridamycin compound produced by a mutant or other novel host cell described herein, 36-ketomeridamycin, or 9-deoxomeridamycin, or 9-deoxoprolylmeridamycin can be so used.

The term "preventing neurodegeneration" refers to preventing neuronal cell death by apoptosis, or any other mechanism, resulting from a pathological condition including but not limited to a neurodegenerative disease, ischemia, trauma, and any condition resulting from an excess of an excitatory amino acid such as glutamate.

The term "promoting neuroregeneration" refers to inducing in a neuronal cell events which include but are not limited to neurite outgrowth or long term potentiation. Neuroprotective agents are useful for the treatment of e.g., neurodegenerative diseases such as Alzheimer's and Parkinson's diseases, neuronal damage following ischemia or trauma, and any other pathological condition in which neuronal damage is implicated. Other compounds derived from meridamycin (described in commonly owned International Patent Application No. PCT/US2005/06246, formerly provisional patent application 60/549,430, filed Mar. 2, 2004) have been shown to demonstrate neuroprotective effects (see also, commonly owned international application PCT/US2005/005895 and U.S. patent application Ser. No. 11/065,934 (formerly U.S. Provisional Application No. 60/549,480, filed Mar. 2, 2004), as does the meridamycin of the present invention.

Although not intending to be limited in its therapeutic applications, it is desirable to use a 36-ketomeridamycin or other macrolide compounds described herein for treatment of conditions of the central nervous system, neurological disorders, and disorders of the peripheral nervous system. Conditions affecting the central nervous system include, but are not limited to, epilepsy, stroke, cerebral ischemia, cerebral palsy, multiple sclerosis, Alper's disease, Parkinson's disease, Alzheimer's disease, Huntington's disease, amyotrophic lateral sclerosis (ALS), dementia with Lewy bodies, Rhett syndrome, neuropathic pain, spinal cord trauma, or traumatic brain injury.

Neurological disorders according to the invention include, but are not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone, ticks, porphyria, Gullain-Barre syndrome, dimentia, Alzheimer's disease, Parkinson's disease, and Huntington's chorea.

Specific situations in which neurotrophic therapy is indicated to be warranted include, but are not limited to, central nervous system disorders, Alzheimer's disease, aging, Parkinson's disease, Huntington's disease, multiple sclerosis, amyotrophic lateral sclerosis, traumatic brain injury, spinal cord injury, epilepsy, inflammatory disorders, rheumatoid arthritis, autoimmune diseases, respiratory distress, emphysema, psoriasis, adult respiratory distress syndrome, central nervous system trauma, and stroke.

The compounds of this invention are also useful in preventing, treating or inhibiting senile dementias, dementia with Lewy bodies, mild cognitive impairment, Alzheimer's disease, cognitive decline, associated neurodegenerative disorders, as well as providing neuroprotection or cognition enhancement.

The term "subject" or "patient," as used herein, refers to a mammal, which may be a human or a non-human animal.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "effective amount" and "therapeutically effective amount," as used herein, refer to the amount of a compound that, when administered to a patient, is effective to at least partially ameliorate a condition from which the patient is suspected to suffer.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual subject being treated. Effective administration of the macrolide compounds of this invention may be given at monthly, weekly, or daily, or other suitable intervals. For example, a parenteral dose may be delivered on a weekly basis at a dose of about 10 mg to about 1000 mg, about 50 mg to about 500 mg, or about 100 mg to about 250 mg per week. A suitable oral dose may be greater than about 0.1 mg/day. Preferably, administration will be greater than about 10 mg/day, more specifically greater than about 50 mg/day in a single dose or in two or more divided doses. The oral dose generally will not exceed about 1,000 mg/day and more specifically will not exceed about 600 mg/day. The projected daily dosages are expected to vary with route of administration.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The macrolide compounds can also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The invention further provides products, including packaging, containing the compounds formulated for delivery. In another aspect, the invention provides kits including, e.g., needles, syringes, and other packaging, for delivery of the compound of the invention. Optionally, such a kit may include directions for administration of the drug, diluent, and or a carrier for mixing of a solid form of a compound of the invention.

The reagents used in the preparation of the compounds of this invention can be either commercially obtained or can be prepared by standard procedures described in the literature.

The preparation of representative examples of this invention are described in the following examples.

EXAMPLES

The invention is also described by means of particular examples. However, the use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

Cloning and Isolation of the Meridamycin Biosynthetic Gene Cluster

Methods

A. Generation of DNA Probes.

Two pairs of degenerate PCR primers were used to amplify DNA fragments from the genomic DNA of *Streptomyces* sp. LL-BB0005 by PCR. The first pair of primers were designed based on the conserved amino acid motifs in type I PKS ACP and KS domains. The forward primer (ACP sense) had the sequence 5'-GA(GC) CT(GC) GG(GC) (TC)T(GC) GAC TC(CG) CT(AC)-3' (SEQ ID NO: 2), and the reverse primer (KS antisense) had the sequence 5'-(GC)GA (GC)GA (AG) CA (GC)GC (GC)GT GTC (GC)AC-3' (SEQ ID NO: 3). The second pair of primers were designed based on the highly conserved core motifs of the adenylation domain of nonribosomal peptide synthetases. The forward primer (A3 motif) had the sequence 5'-AC(GC) TC(GC) GGC (TA)C (GC) ACC GGC CIG CC(GC) AAG-3' (SEQ ID NO: 4), and the reverse primer (A8 motif) had the sequence 5'-AGC TC(GC) A(TC)GC CG(GC) (TA)(GA)G CC(GC) CG(GC) A(TC)C TT(GC) ACC TG-3' (SEQ ID NO: 5). Each 50 μL PCR mixture contained: approximately 0.1 μg *Streptomyces* sp. LL-BB0005 genomic DNA, 1.6 μM of each primer, 8% DMSO, 1×Pfu reaction buffer (Stratagene, La Jolla, Calif.), 200 μM of each dNTP, and 2.5 unit of Pfu Turbo DNA polymerase.

The PCR reaction was performed on the Whatman Biometra TGRADIENT thermocycler system with the following condition: 1 cycle of initial denaturation (96° C., 4 min), 34 cycles of denaturation (96° C., 1 min)/annealing (gradient from 45° C. to 650C, 1 min)/extension (72° C., 1 min), and 1 cycle of a final extension (72° C., 5 min). The about 0.7 kb DNA fragment obtained with the ACP/KS primers and the 0.7~0.8 kb mixed DNA fragments obtained with the A3/A8 primers were cloned into pCR4Blunt-TOPO vector following the manufacture's instruction. Several clones of each cloning were subjected to DNA sequencing analysis using the M13 Reverse and Forward primers.

B. Isolation of the Meridamycin Biosynthetic Gene Cluster.

A cosmid library of size-fractionated genomic DNA of *Streptomyces* sp. LL-BB0005 was constructed using vector pWEB (Epicentre, Madison Wis.), following the manufacture's instruction. About 800 cosmid clones were screened with the above-mentioned type I PKS gene probe by colony hybridization. Cosmids from 56 positive clones were extracted, digested with BamH I, and then hybridized with the above-mentioned pipecolate acid-incorporating enzyme gene probe after electrophoresis. Cosmid 45 was identified to contain an approximately 2.5 kb DNA fragment which encodes a pipecolate-specific peptide synthetase. The insert of Cosmid 45 was completely sequenced by custom sequencing (MWG Biotech, High Point, N.C.) and was used to identify several other cosmids through restriction mapping, chromosomal walking and end-sequencing of the cosmid inserts.

C. Results.

One DNA fragment from the PCR using ACP/KS primers was identified to encode a type I PKS, and another DNA fragment from the PCR using A3/A8 primers was identified to encode a non-ribosomal peptide synthetase homologous to the pipecolate-incorporating enzymes for rapamycin biosynthesis (RapP) and FK506 biosynthesis (FKBP). These two fragments were purified and later used to screen the *Streptomcyes* sp. LL-BB0005 cosmids library.

Cosmid 45 was sequenced and used to identify other cosmids, resulting in the set of overlapping inserts. Inserts of these cosmids were completely sequenced and assembled, giving a contiguous DNA stretch of 116,856 nt which includes the meridamycin biosynthesis cluster. The complete nucleotide sequence of this DNA assembly is depicted in SEQ ID NO: 1.

Example 2

Computational Sequence Analysis of the Meridamycin Biosynthetic Gene Cluster

A. Methods.

DNA sequence analysis was done using Lasergene (DNASTAR, Madison, Wis.) and Vector NTI (InforMax, Frederick, Md.). A correlation between the open reading frames that have been identified in this gene cluster and their proposed function are summarized in Table 1.

B. Results.

A biosynthetic pathway for the production of meridamycin has been proposed based on the sequence analysis of the cloned gene cluster.

Example 3

Genetic Disruption of the merP Gene

To confirm the cloned gene cluster is responsible for the production of meridamycin, a disruption experiment was conducted to inactivate the gene encoding the NRPS which is responsible for the incorporation of a pipecolic acid into the meridamycin macrolide core.

A. Methods and Results.

A 2450 bp BamH I fragment from Cosmid 45, which spans the internal part of merP gene, was cloned into pUC19 to give pMH100. About a 1.5 kb Nco I fragment containing apramycin resistant gene from pUC120 was cloned into a Nco I site located in the middle of the 2450bp BamH I fragment. The resulting about 3.9 kb BamH I insert was then excised and cloned into the BamH I site of a *Streptomyces/E. coli* conjugation shuttle vector pNWA200 to give pBWA27. Conjugation between *E. coli* ET12567(Z8002pUB307) harboring pBWA27 and *Streptomcyes* sp. LL-BB0005 was performed according to the following: Briefly, equal volume of donor cells and the spore suspension of LL-BB0005 were mixed and plated on pre-dried R6 agar medium. The plates were incubated at 37° C. for 20 hours before being overlaid with 1 mL of $ddH_2O$ containing 0.5 gmb/mL apramycin and 0.5 gmb/mL nalidixic acid on each of them. The plates were then incubated at 30° C. for 5 to 7 days. Apramycin resistant exconjugants were isolated and then grown under non-selective condition. Apramycin resistant/kanamycin sensitive colonies were identified and the double crossover mutation was confirmed by Southern hybridization analysis of their genomic DNA.

B. LC/MS Analysis of Metabolites

Wild type LL-BB0005 and three individual Pmerp::apr mutants were grown in a seed medium (dextrose 10 g/L, soluble starch 20 g/L, yeast extract 5 g/L, NZ-amine A 5 g/L, calcium carbonate 1 g/L, pH 7.3) for 3 days at 28° C. before inoculated into the fermentation medium (dextrose 30 g/L, soy flour 15 g/L, sodium chloride 2 g/L, calcium carbonate 1 g/L, pH 6.8-7) and grew at 28° C. for 5 days. 1 mL broth samples were taken at day 4 and day 5 and extracted with equal volume of ethyl acetate. The extracts were then dried down to dryness and then re-suspended in 100 μL methanol for liquid chromatography/mass spectrometry (LC/MS) analysis.

Example 4

Generation of a Keto-Derivative of Meridamycin by Inactivating the KR1 Domain in Module 1 Keto-Reductase of Meridamycin Polyketide Synthetase A This example describes the generation of a mutated LL-BB0005 strain in which the DNA encoding KR domain in Module 1 of meridamycin polyketide synthase has been deleted, thereby resulting in the production of a novel meridamcyin analogue, C-36 keto-meridamycin.

A. Generation of C3.6-Keto-Meridamycin.

A DNA fragment of about 4158 basepair (bp) encoding the majority of Module 1 of Mer A was cut from Cosmid 45 through digestion with restriction enzyme EcoR I and Not I and cloned into a vector pUC19 at Hinc II site. The resulting construct was then digested by restriction enzyme Nco I to delete a 1291 bp DNA fragment that encodes the KR domain. The remainder of the construct was then religated into a circular plasmid. The insert of this plasmid was excised by digestion with Hind III and Xba I, and then cloned into a *Streptomyces-E. coli* conjugation shuttle vector pKC1139. The resulting construct was named pMH1102. pMH1102 was then introduced into LL-BB0005 strain through conjugation between LL-BB0005 and *E. coli* ET12567/pMH1102. Double cross-over between pMH1102 and the chromosomal DNA of LL-BB0005 resulted in a complete deletion of a 1291 bp DNA fragment that encodes the KR domain of the module 1 of Mer A. This mutated strain was named MH1102, deposited under the terms of the Budapest Treaty with the Agricultural Research Service Culture Collection (NRRL) on May 3, 2004 (Accession No. NRRL 30743).

B. Chemical Detection of C36-Keto-Meridamycin by LC/MS.

For LC/MS analysis, fermentation broth supernatants were extracted with equal volume of ethyl acetate and concentrated 10×. Extracts were then fractionated on the LC/MS using a linear gradient of 5% to 95% acetonitrile in water on a YMC-ODS 4.6×150 mm 5u column. Fractions were collected every minute into a 96 well plate. The plate was concentrated by speed vacuum for the high-resolution and accurate mass measurement (HRMS). HRMS was conducted using a Bruker (Billerica, MA) APEXII FTICR mass spectrometer equipped with an actively shielded 7.1 Tesla superconducting magnet (Magnex Scientific Ltd., UK), an external Bruker APOLLO ESI source, and a Synrad 50W CO2 CW laser. Typically, 5 μl sample was loaded into NanoESI tip (New Objective, Woburn, Mass.) and a high voltage about 800 V was applied between the NanoESI tip and the capillary. Data reported here are based on internal calibration using HP tuning mix.

C. Production

Figures 3A, 3B:
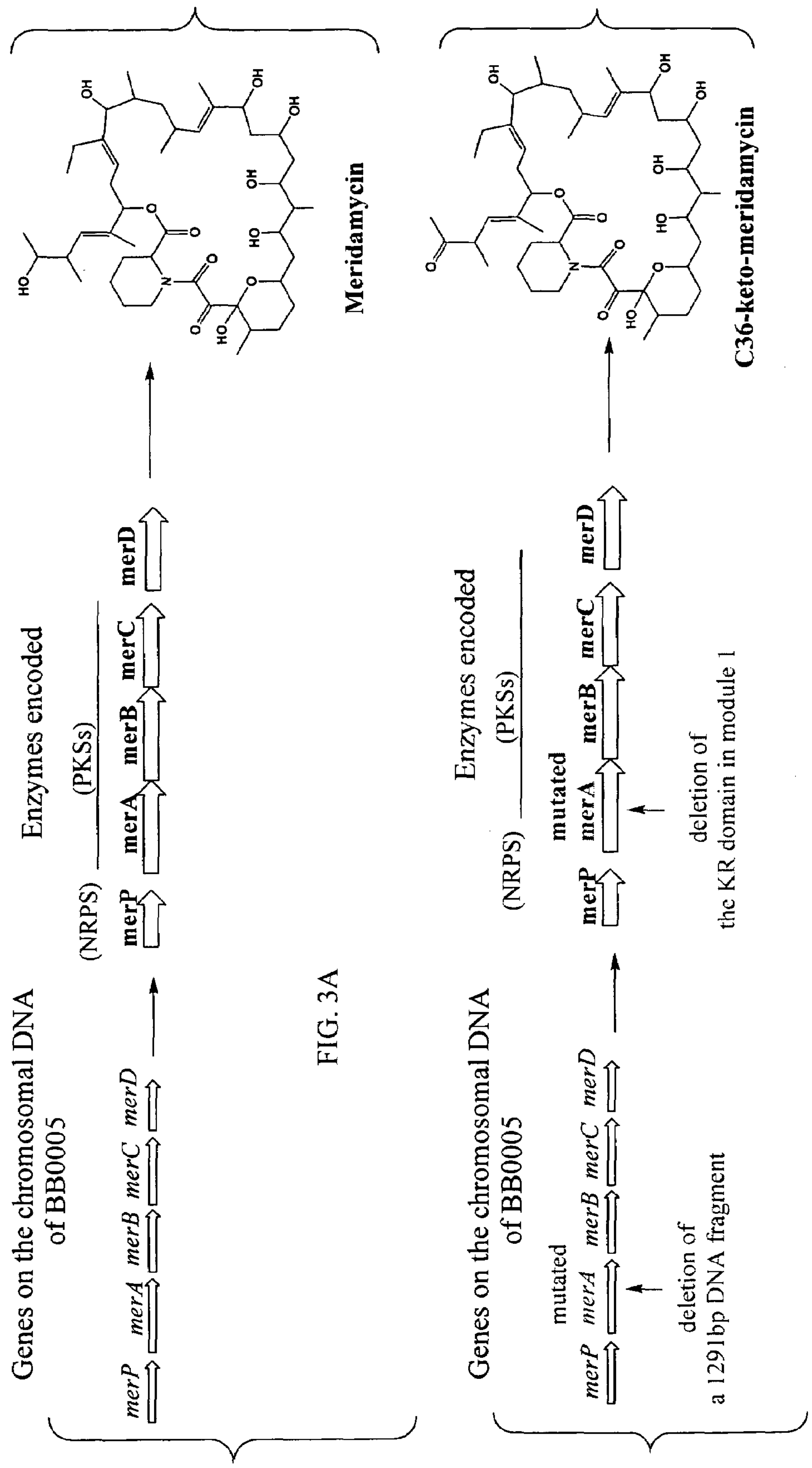
FIG. 3A shows a schematic representation of the production of meridamycin.
FIG. 3B shows a schematic representation of the production of C36-keto-meridamycin.

Fermentation of this MH1102 strain gave the production of C36-keto-meridamycin. The schematic representation of the experiment is shown in FIG. 3B.

D. Detection

Sodium adduct molecular ion was detected in the positive ESI detection mode with average m/z=842.50245 (842.50435, 842.50409, 842.50187, 842.50156, 842.50190, 842.50192, 842.50149), and this agrees with the calculated value ($[M+Na]^{1+}$, calculated: 842.50250, Δ=−0.05 mmu, see Table 3). The measured isotopic distribution of the sodium adduct molecular ions also agrees very well with the simulated one. There is no indication of the presence of meridamycin ions from the positive mode ESI FTMS mass spectra. Deprotonated molecular ion was also detected in the negative ESI detection mode with m/z=818.50531, and this agrees very well with the calculated value ($[M-H]^{1-}$, calculated: 818.50600, Δ=−0.69 mmu, see Table 3). The measured isotopic distribution of the deprotonated molecular ions also agrees very well with the simulated one. There is no indication of the presence of meridamycin ions in the negative mode ESI FTMS mass spectra either.

TABLE 3

Accurate mass measurement by FTMS

| Sample ID | ESI mode | Experimental Mass | Elemental Formula | Theoretical Mass | Δ (mDa) | Ion Assignment |
|---|---|---|---|---|---|---|
| LL-BB0005 (ΔKR1) | Positive | 842.50245 | $C45H73NO12Na^{1+}$ | 842.50250 | −0.05 | $[M + Na]^{1+}$ |
| LL-BB0005 (ΔKR1) | Negative | 818.50531 | $C45H72NO12^{1-}$ | 818.50600 | −0.69 | $[M - H]^{1-}$ |

Example 5

Generation and Yield Improvement of Meridamycin Analogues Through Manipulation of the NRPS Gene and/or the P450 Hydroxylase Gene The pipecolyl moiety in the meridamycin macrolactam ring is incorporated by the NRPS MerP (SEQ ID: 46) encoded by MerP gene (nt 21592-26311 of SEQ ID NO:1). The amino acid sequence of the adenylation domain of merP shows significant homology with the adenylation domains from other NRPSs that recognize pipecolic acid, and with those that recognize proline. Accordingly, a meridamycin analogue, prolylmeridamycin (see co-owned international Patent Application PCT/US2005/005895 and U.S. patent application Ser. No. 11/065,934, formerly provisional patent application 60/549,480, filed Mar. 2, 2004, herein incorporated by reference), was also produced by the wild type LL-BB0005 at a very low level. The yield of this compound will be significantly improved by those of ordinary skill in the art, using well-known techniques, by replacing the NRPS gene with another gene which encodes a NRPS that exhibits much higher preference to proline than pipecolic acid. Similarly, the merP gene could also be replaced with any other NRPS gene that recognizes a specific amino acid other than pipecolic acid, thus giving more novel meridamycin analogues with different amino acid residues within the macrolactam ring.

The wild type LL-BB0005 strain also produces another analogue, C9-deoxomeridamycin, at a very low level. This compound resulted from omitting the last step in the biosynthesis of meridamycin: the hydroxylation of C9 by the P450 hydroxylase MerE (SEQ ID: 51) encoded by the merE gene (nt 98393-99586 of SEQ ID NO: 1). The yield of this compound thus will be significantly improved through genetic knock-out of merE gene, either through insertion of an antibiotic resistant gene into merE or through deletion of merE gene, by those of ordinary skill in the art, using well-known techniques.

Further, more meridamycin analogues will also be generated by combining the two types of genetic modifications described above, thereby resulting in another set of meridamycin analogues that have pipecolyl moiety replaced with another amino acid residue in the C9-deoxyl macrolactam ring.

Example 6

Increasing the Yield of Meridamycin and/or its Analogues through Genetic Manipulation of the Regulatory Genes At least six genes in the cloned DNA assembly (SEQ ID NO:1) are predicted to be pathway specific regulatory genes. The protein (SEQ ID NO:45) encoded by Orf15 (SEQ ID NO:18) belongs to the Lac I family of bacterial regulatory proteins. Both Mer I (SEQ ID NO:56) and MerQ (SEQ ID NO:63) belong to the LysR family of prokaryotic transcriptional regulatory proteins. MerH (SEQ ID NO:55) shares high sequence similarity with the MarR group of repressors that appeared to be involved in the multiple antibiotic resistance, a non-specific resistance system. MerM (SEQ ID NO:60) appears to be a member of the MerR family regulatory proteins that have been found to be involved in the resistance to certain small molecules. MerO (SEQ ID NO:62) belongs to the tetR family of bacterial regulatory proteins.

It is possible for those skilled in the art to generate a mutated strain with improved production of meridamycin, and/or its analogues, through manipulation of these regulatory genes. This can be achieved in several ways. For example, targeted disruption or deletion (i.e., knock-out) of each individual regulatory gene would identify its protein product as an activator or repressor of meridamycin production. This can be done either through insertion of an antibiotic resistant gene into each regulatory gene, or by deletion of the regulatory gene. If the investigated gene encodes a pathway repressor, knock-out of this gene would directly increase the yield of meridamycin and/or its analogue(s). If the gene encodes an activator, the yield of meridamycin and/or its analogue(s) might be improved through introducing extra copies of this activator gene into the wild-type producing strain. This can be achieved either through insertion of the activator gene into the chromosomal DNA, or through transfecting the activator gene in a plasmid which can replicate inside a meridamycin producing strain. In either case, the activator gene should be placed under the control of an appropriate promoter to ensure its expression.

Example 7

Neuroprotective Effects of Meridamycin and Assay

Neuroprotective effects of compounds produced by *actinomycetes* (LL-C31037 having NRRL Accession number 30721) are described in commonly-owned International Patent Application No. PCT/US2005/005895 and U.S. patent application Ser. No. 11/065,934 (formerly U.S. provisional patent application 60/549,480, filed Mar. 4, 2004), which is herein incorporated by reference in its entirety.

A. Isolation of Mesecephalic Neurons.

Ventral mesencephalic cultures were prepared from E15 rat embryos and maintained for 7 divisions before experimentation according to the method of Pong et al., *J. Neurochem.* 69: 986-994, 1997.

B. Drug Treatment and Assay.

Cultures were pre-treated with designated drugs: immunophilin ligands meridamycin, rapamycin and FK-506 (1, 10, 100 and 1000 nM), cyclophilin ligand cyclosporine (CsA) at the same concentrations, and glial-derived neurotrophic factor (GDNF-control-1 and 10 ng/ml) for 1 hr or 24 hr. Cultures were then exposed to 10 μM 1-methyl-4-phenylpyridinium (MPP+) for 1 hr, in the presence of drug. After the 1 hr exposure, media was changed 3×, and fresh drug was added for an additional 24 hr or 48 hr. At the end of the 24 hr or 48 hr recovery period, high-affinity $^{3}$H-DA uptake was determined as percent of untreated controls (Prochiantz et al., *Nature* 293: 570-572, 1981).

C. Results

GDNF and FK506 enhanced DA uptake in normal mesencephalic dopanergic neuron cultures. Uptake was reduced by the addition of 10 mM MPP+ in addition to treatment. Pretreatment with GDNF, FK506, CsA and meridamycin provided partial, but significant protection against MPP toxicity.

Increased neuroprotection was seen following increases in post-treatment and recovery time.

Example 8

Generation of a Mutated Strain of BB0005 by Inactivating the merE Gene which Encodes a P450 Monooxygenase This example describes the generation of a BB0005 strain in which the DNA encoding a P450 Monooxygenase has been deleted. The resulted mutant, designated MH1104-1, produces a compound of formula (III). This organism was deposited under the terms of the Budapest Treaty with Agricultural Research Service Culture Collection (NRRL), 1815 North University Avenue, Peoria, Ill. 61604, on Mar. 14, 2005, and assigned accession number NRRL B-30829.

A. Generation of MH1104-1.

Two DNA fragments were amplified from cosmid 54, which contains the 3' end of the biosynthetic gene cluster, including a 3' portion of merC, full-length merD, merE, F1, F2, G, and H-V, which was isolated from BB0005.

The first fragment (~1450 bp) was amplified using forward primer 5'-TGCAAGCTTCTCGCGTCTGGTGCTGGTG-3' [SEQ ID NO:69] and reverse primer 5'-ATCTTCGCCCTTGTCCCGCAGTC-3' [SEQ ID NO:70], with a Hind III restriction site introduced at the 5'. The second fragment (~1440 bp) was amplified using forward primer 5'-ATCGCTCTGCGGCTGGCGGTG-3' [SEQ ID NO:71] and reverse primer 5'-TGCTCTAGAGCCACGAAGACGCCGGAAC-3' [SEQ ID NO:72], with a Xba I restriction site introduced at the 3'. These two fragments were then ligated into pUC18 through Hind III and Xba I site. A EcoR V restriction site was generated at the join site of the two DNA fragments, which was used to insert a ~800 bp DNA fragment encoding the apromycin resistance gene. The insert of the final construct was excised by digestion with Hind III and Xba I, and then cloned into a *Streptomyces-E. coli* conjugation shuttle vector pNWA200. The resulting construct was named pMH1104. pMH1104 was then introduced into BB0005 strain through conjugation between BB0005 and *E. coli* ET12567/pMH1104. Double cross-over between pMH1104 and the chromosomal DNA of BB0005 resulted in merE gene, which encodes a P450 Monooxygenase.

This mutated BB0005 strain was named MH1104-1, deposited under the terms of the Budapest Treaty with the Agricultural Research Service Culture Collection (NRRL) on Mar. 14, 2005 (Accession No. NRRL B-30829).

B. Production.

Fermentation of this MH1104-1 strain produced C9-deoxomeridamycin at the titer of 30 mg/L, which was an increase as compared with the titer of ~1 mg/L C9-deoxomeridamycin produced by BB0005.

Example 9

The Compound C9-deoxomeridamycin

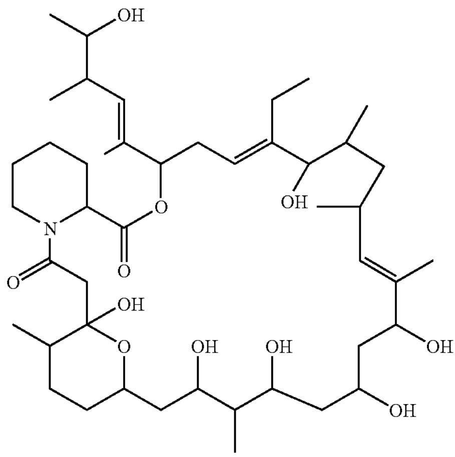

A. Production of Compound

A 50 μL aliquot of spore suspension of strain M507 was inoculated into 5 mL seed medium (dextrose 10 g/L, soluble starch 20 g/L, yeast extract 5 g/L, NZ-amine A 5 g/L, calcium carbonate 1 g/L, pH 7.3) and incubated for 3 days at 28° C. on a rotary shaker with an agitation rate of 200 rpm. This seed culture was then transferred into five 250-mL Erlenmeyer flasks, each containing 25 mL fresh seed medium (1 mL aliquot of seed culture per flask). The second stage seed cultures were incubated for 2 days under the same conditions and then were used to inoculate eighty 250-mL Erlenmeyer flasks each containing 25 mL fermentation medium (dextrose 30 g/L, soy flour 15 g/L, sodium chloride 2 g/L, calcium carbonate 1 g/L, pH 6.8-7) (1 mL aliquot of second stage seed culture to each flask). After shaking at 200 rpm for one day at 28° C., metyrapone (2-methyl-1,2-di-3-pyridyl-1-propanone) was added to the fermentation to a final concentration of 2 mM. The fermentation was subsequently continued for another four days under the same conditions.

Upon harvesting, the whole broth was centrifuged to separate the broth and cell pellet. The cell pellet was extracted with ethyl acetate (3×600 ml) and the ethyl acetate extract was concentrated in vacuo. The broth was stirred with 300 ml Diaion HP20 resin and poured into a column. The column was washed with 1 L water and then eluted using a step gradient (1:3, 1:1, 3:1, 1:0 MeOH:$H_2O$; 500 ml each). The 75% and 100% MeOH in $H_2O$ fractions were combined, concentrated in vacuo, and combined with the EtOAc extract of the cells. This material was dissolved in methylene chloride/methanol, loaded onto 50 ml silica gel (ICN silica gel, 32-63 μm, 60A), and concentrated in vacuo. This material was then processed using Si VLC (400 ml ICN silica gel) eluting with a step gradient (1 L each of 100:0, 95:5, 90:10, 80:20 $CH_2Cl_2$:MeOH) collecting 500 ml per fraction. Fractions 4-6 were combined, concentrated in vacuo, redissolved in 45:45:10 hexanes:EtOAc:isopropanol, and loaded onto a flash Si column (ICN silica gel; 5.0 cm×8.5 in; 45:45:10 hex:EtOAc:iPrOH). The column was eluted with 2 L 45:45:10 hex:EtOAc:iPrOH and 40 ml fractions were collected. Fractions 17-40 were combined and concentrated. This semi-crude material was chromatographed by reversed phase (RP) high performance liquid chromatography (HPLC) (YMC ODS-A 30×250 mm S-5 column; 65% to 85% MeOH in $H_2O$ over 50 minutes, then 85% to 100% MeOH in $H_2O$ over 20 minutes, flow rate of 12 ml/min). The title compound eluted from 44 to 52 min as determined by liquid chromatography mass spectrometric (LCMS) analysis ($t_R$=48 min). These fractions were pooled and subjected to further purification by RPHPLC (YMC ODS-A 10×250 mm S-5 column; 40% to 70% acetonitrile in $H_2O$ over 30 min, flow rate of 2.5 ml/min) to yield 16.4 mg of the title compound ($t_R$=25 min).

B. Characterization of C9-Deoxomeridamycin

The compound prepared as described in Part A is characterized by having an apparent molecular formula: $C_{45}H_{77}NO_{11}$.

Molecular weight: Positive Ion Electrospray MS m/z=808.1 $(M+H)^+$; Negative Ion Electrospray MS m/z=806.5 $(M-H)^-$; High Resolution Fourier Transform MS m/z=830.53683 $(M+Na)^+$ Ultraviolet Absorption Spectrum: $\lambda_{max}$ nm (acetonitrile/water)=210 nm, end absorption A proton magnetic resonance spectrum: (400 MHz, $CD_3OD$) of FIG. 4.

Figure 5:
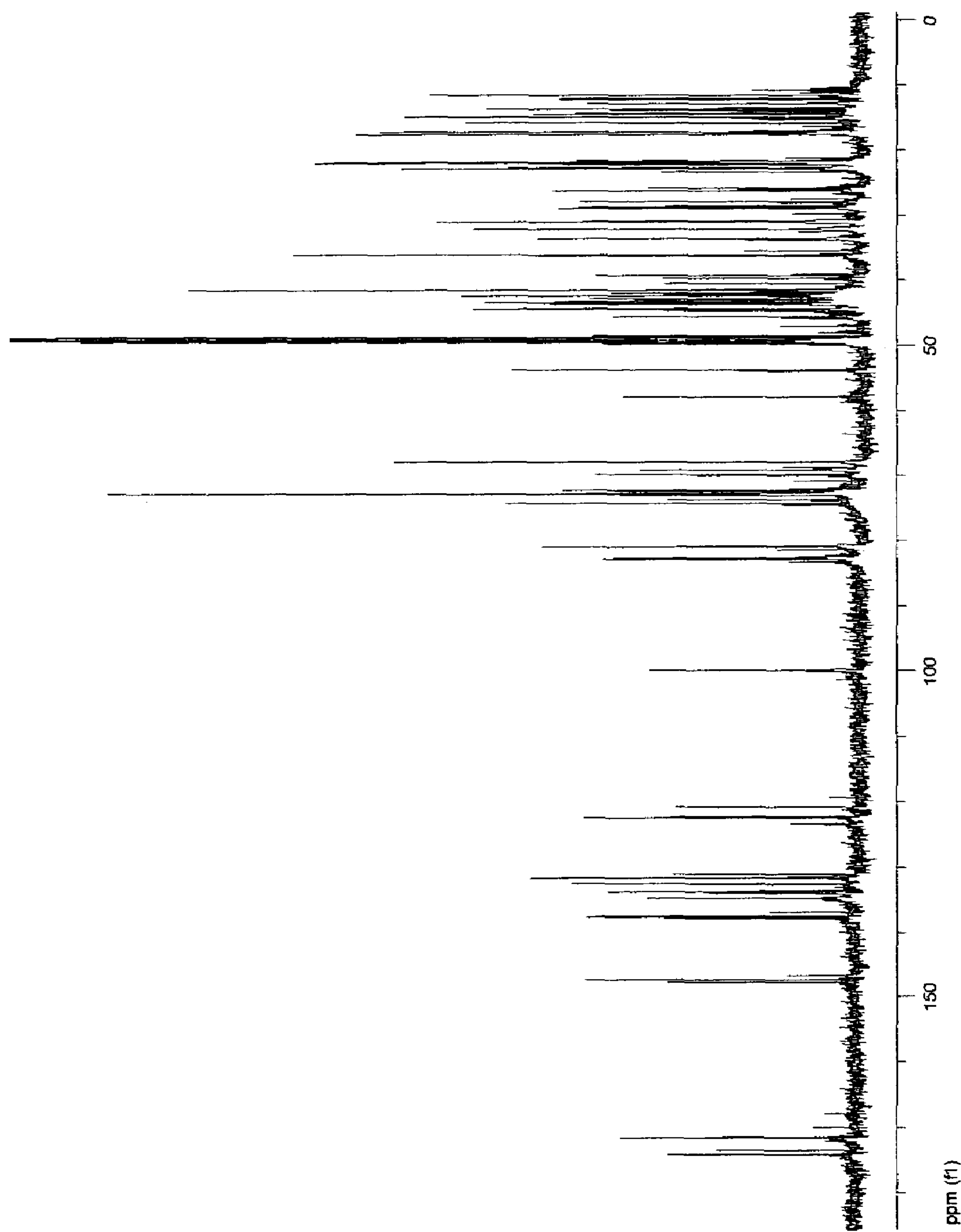
FIG. 5 is a carbon NMR spectrum of the compound of formula (III), wherein n=2, in $CD_3OD$ at 100 MHz.

A carbon magnetic resonance spectrum (100 MHz, $CD_3OD$) of FIG. 5

Example 10

The Compound of Formula (III), n=1

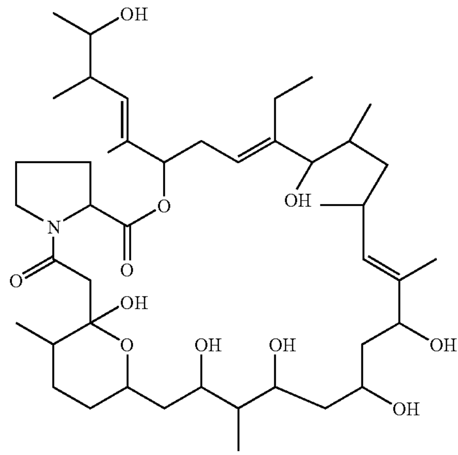

The 5-membered ring can be obtained through biosynthetic regulation including precursor feeding and inhibition of pipecolate biosynthesis in a manner analogous to that for the production of prolylrapamycin [Russo, R. J.; Howell, S. R.; Sehgal, S. N. U.S. Pat. No. 5,441,977, 1995; Nishida, H.; Sakakibara, T.; Aoki, F.; Saito, T.; Ichikawa, K.; Inagaki, T.; Kojima, Y.; Yamauchi, Y.; Huang, L. H.; Guadliana, M. A.; Kaneko, T.; Kojima, N. J. *Antibiot.* 1995, 48 (7), 657-666; Kojima, I.; Demain, A. L. *J. Ind. Microbiolo. Biotechnol.* 1998, 20, 309-316] and prolylimmunomycin. Nielsen, J. B.; Hsu, M. J.; Byrne, K. M.; Kaplan, L. *Biochemistry* 1991, 30, 5789-5796. Based on literature precedent for rapamycin, the 5-membered ring could be produced by fermentation of the *actinomycete* strain BB0005-MH1104-2 (Accession No. NRRL 30820) with the addition of proline and a known inhibitor of pipecolate biosynthesis such as nipecotic acid [Graziani, E. I.; Ritacco, F. V.; Summers, M. Y.; Zabriskie, M.; Yu, K.; Bernan, V. S.; Greenstein, M.; Carter, G. T. *Org. Lett.* 2003, 5, 2385-238], thiaproline (L-thiazolidine-4-carboxylic acid), or thiazolidine-2-carboxylic acid (T2CA).

The procedure previously outlined for the isolation of the compound in Example 9 can be used for the purification of the 5-membered ring.

Example 11

Neuroregenerative Properties of Compound of Formula III (n=2) in Neuronal Cell Culture Dissociated cortical neuron cultures were prepared as previously described [Pong et al, "Attenuation of staurosporine-induced apoptosis, oxidative stress, and mitochondrial dysfunction by synthetic superoxide dismutase and catalase mimetics, in cultured cortical neurons", *Exp Neurol.* 2001 September;171(1):84-97.] Briefly, embryonic day 15 rat fetuses were collected and dissected in ice-cold PBS. Dissected cortices were pooled together and transferred to an enzymatic dissociation medium containing papain. After 30 min, the tissue was mechanically triturated with a fire-polished glass Pasteur pipette. Single-cell suspensions in complete media were seeded on poly-L-ornithine and laminin coated 96-well plates. Twenty-four hours later, cultures were treated with various concentrations of compound of formula III for 72 hours. The cultures were then fixed and stained with an anti-tubulin antibody (TUJ-1) and a fluorescent-tagged secondary antibody. Neurite outgrowth was determined by using the Enhanced Neurite Outgrowth (ENO) algorithm with the Cellomics ArrayScan and expressed as average neurite length or neurite length per cell The compound prepared as described in Example 9 was active in the cortical neuron assay with an $EC_{50}$ of less than 1 μM.

Example 12

Neuroregenerative Properties of Compound (III) in Neuronal Cell Culture

Dissociated cortical neuron cultures were prepared as previously described [Pong et al., Exp Neurol. 2001 September; 171(1):84-97 (2001)]. Briefly, embryonic day 15 rat fetuses were collected and dissected in ice-cold PBS. Dissected cortices were pooled together and transferred to an enzymatic dissociation medium containing papain. After 30 min, the tissue was mechanically triturated with a fire-polished glass Pasteur pipette. Single-cell suspensions in complete media were seeded on poly-L-ornithine and laminin coated 96-well plates. 24 hours later, cultures were treated with various concentrations of compound of formula (III) for 72 hours. The cultures were then fixed and stained with a neurofilament primary antibody and a peroxidase-tagged secondary antibody. A peroxidase substrate (K-Blue Max) was added and the colorimetric change was measure on a colorimetric plate reader.

TABLE 4

NEUROFILAMENT CONTENT IN CULTURED CORTICAL NEURONS

| TREATMENT | NEUROFILAMENT CONTENT (FOLD-INCREASE ABOVE CONTROL) |
|---|---|
| 10 nM Compound | 1.9 |
| 100 nM Compound | 2.19 |
| 1 μM Compound | 2.24 |
| 10 μM Compound | 2.29 |

Example 13

Neuroregenerative Properties of Compound (III) in Cultured Cortical Neurons

Dissociated cortical neuron cultures were prepared as previously described (Pong et al., cited above, 2001). Briefly, embryonic day 15 rat fetuses were collected and dissected in ice-cold PBS. Dissected cortices were pooled together and transferred to an enzymatic dissociation medium containing papain. After 30 minutes, the tissue was mechanically triturated with a fire-polished glass Pasteur pipette. Single-cell suspensions in complete media were seeded on poly-L-ornithine and laminin coated 96-well plates. After 24 hours, cultures were treated with various concentrations of the compound of formula III for 72 hours. The cultures were then fixed and stained with an anti-tubulin primary antibody (TUJ-1) and a fluorescent-tagged secondary antibody. Neurite outgrowth was determined by using the Enhanced Neurite Outgrowth (ENO) algorithm with the Cellomics ArrayScan and expressed as total neurite length per cell.

TABLE 5

TOTAL NEURITE LENGTH IN CULTURED CORTICAL NEURONS

| TREATMENT | TOTAL NEURITE LENGTH (% ABOVE CONTROL) |
|---|---|
| 10 nM Compound | 10% |
| 100 nM Compound | 54% |
| 1 μM Compound | 86% |
| 10 μM Compound | 121% |

Example 14

Neuroregenerative Properties of Compound (III) in Cultured Dorsal Root Ganglia Dissociated dorsal root ganglia cultures were prepared as previously described [A. Wood et al., "Stimulation of neurite outgrowth by immunophilin ligands: quantitative analysis by Cellomics Array scan" Society for Neuroscience (2004), abstract 104.3]. Briefly, postnatal day 3-5 rat pups were euthanized. The spinal columns were removed and individual dorsal root ganglia (DRG) were dissected out. Dissected DRG were pooled together and transferred to an enzymatic dissociation medium containing papain. After 60 minutes, the tissue was mechanically triturated with a fire-polished glass Pasteur pipette. Single-cell suspensions in complete media were seeded on poly-L-ornithine and laminin coated 96-well plates. After 24 hours, cultures were treated with various concentrations of the compound of formula III for 72 hours. The cultures were then fixed and stained with an anti-tubulin primary antibody (TUJ-1) and a fluorescent-tagged secondary antibody. Neurite outgrowth was determined by using the Enhanced Neurite Outgrowth (ENO) algorithm with the Cellomics ArrayScan and expressed as total neurite length per cell.

TABLE 6

| TOTAL NEURITE LENGTH IN CULTURED DORSAL ROOT GANGLIA | |
|---|---|
| TREATMENT | TOTAL NEURITE LENGTH (% ABOVE CONTROL) |
| 10 nM Compound | 17% |
| 100 nM Compound | 24% |

TABLE 6-continued

| TOTAL NEURITE LENGTH IN CULTURED DORSAL ROOT GANGLIA | |
|---|---|
| TREATMENT | TOTAL NEURITE LENGTH (% ABOVE CONTROL) |
| 1 μM Compound | 36% |
| 10 μM Compound | 64% |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description. Patents, patent applications, publications, procedures, and the like are cited throughout this application, the disclosures of which are incorporated herein by reference in their entireties.

The invention claimed is:
1. A deoxomeridamycin compound of the structure:
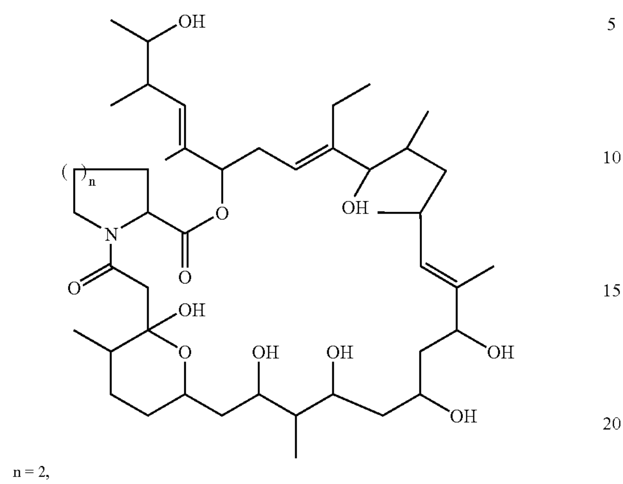
pharmaceutically acceptable salts thereof, or mixtures thereof.
2. The compound according to claim 1, wherein n =2.
* * * * *

UNITED STATES PATENT AND TRADEMARK OFFICE

CERTIFICATE OF CORRECTION

PATENT NO. : 7,507,752 B2
APPLICATION NO. : 11/143980
DATED : March 24, 2009
INVENTOR(S) : Min He and Melissa M. Wagenaar It is certified that error appears in the above-identified patent and that said Letters Patent is hereby corrected as shown below:

On the title page, item [75]:

Delete Inventor "Edmund Graziani"

Signed and Sealed this

Seventeenth Day of November, 2009

David J. Kappos

David J. Kappos
*Director of the United States Patent and Trademark Office*

UNITED STATES PATENT AND TRADEMARK OFFICE
CERTIFICATE OF CORRECTION

PATENT NO. : 7,507,752 B2
APPLICATION NO. : 11/143980
DATED : March 24, 2009
INVENTOR(S) : He et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 401 days Delete the phrase "by 401 days" and insert -- by 484 days --

Signed and Sealed this

Tenth Day of August, 2010

David J. Kappos
*Director of the United States Patent and Trademark Office*

SEQUENCE LISTING

```
<160> NUMBER OF SEQ ID NOS: 72

<210> SEQ ID NO 1
<211> LENGTH: 116856
<212> TYPE: DNA
<213> ORGANISM: Streptomyces sp.

<400> SEQUENCE: 1

ggttttccca gtcacgacgg atccccccat caccgtgagc agcggccact gccgggcggg      60

cgccggagcg gcaccgggcg cggcccggcc gccgccctcc ggacgcgcgg tgtcccgggt     120

gatcagcggg aagcggcgcg acctgcggat gaaccggccg ggccccgcgg gcggcgcggg     180

cggctcctgc ggctgctccc cggccgccgg cccgctcgcc tcagccgtca tggccggcac     240

cggcgtcggc ggccgccttc gcgtcccgct ccgcggcctc caccacgttg accagcagct     300

gggcgcgggt catcgggccg accccgcccg ggttcggcga gacccagccc gcgacctcgg     360

tcacaccggg gtgcacatcg ccggcgatct tgccgtgctc gtcccggctg acgcccacgt     420

cgagcaccgc cgcgcccggc ttgacgtcct ccggcttgac caggtgccgc accccggcgg     480

ccgccacgat gatgtcggcc tggcgcagga tcccgggcag gtcgcgggtg ccggtgtggc     540

agagggtgac cgtcgcgttc tccgaacggc gggtcagcag cagcccgatc gaccggccga     600

cggtgatgcc gcggccgacg accaccacat gcgcgccgtt gatctccaca ccgtggtggc     660

gcagcagctg gatgacgccc tggggcgtgc acggcagcgg gccgctctcg ttgagcacga     720

ggcggccgag gttcatcggg tgcagtccgt cggcgtcctt gaccgggtcg atcagctcca     780

gcacccggtt ggcgtcgatg cccttgggga gcggcagctg gacgatgtag cccgtgcagg     840

acgggtcctc gttgagctcc cggaccgccg cctcgatctc ctcctgggtg gcggtctcgg     900

gcaggtcgcg ccggatggag gcgatgccga cctcggcgca gtcgcggtgc ttgcccgcca     960

cgtaccactt gctgccgggg tcctcgccca ccagcacggt cccgaggccg ggatggatgc    1020

ccttggcctt cagcgcctcc acgcggctga cgagatcgga cttgatcgcg gctgcggttg    1080
```

-continued

```
ccttgccatc gagaatctgc gcggtcatgg cttcatcctc ccggatgcgg ggacgtcgga   1140
tccaatcagg ggccggtcgg ggccggaccg gcgaaggccg caccccgtga tccggtcggg   1200
atgcggcctc ctgtgctcgc tcagcgatcg cccggtgctc gctcgctggt cactcggtac   1260
tcgctcagtg gaagaagtgg cgcgtgcccg tgaagtacat ggtcacaccc gccttctggg   1320
cggcctccac cacggcctcg tcacggaccg agccgcccgg ctgcaccacg gccttcacgc   1380
ccgcctcggc cagcacctcg aagccgtccg ggaacgggaa gaaggcgtcg gaggcggcgt   1440
acgaaccggc ggcccgctcg gcaccggccc gctcgacggc cagcttcgcc gagtccacgc   1500
ggttgacctg gcccatgccg acgccgaccg tggcgccgcc cttggcgagc aggatcgcgt   1560
tggacttcac cgcgcggcag gagcgccagg cgaaggccag ctcggcgagg ccgtcggcgt   1620
ccagcgcctc gcccgtggcg agggtccagt tggccgggtc gtcgccctcg gcctggaggc   1680
ggtccttgac ctggacgagc gtgccgccct cgatggggcg ctgctcggcg gcctccaccg   1740
gcgactccgc gcagcgcagc acccggatgt tcttcttacg ggcgagcgcc tcgaccgcgc   1800
cgtcctcgta cgccggggcg acgatcacct cggtgaagat ctcggcgacc tgctcggcca   1860
tggcgaccga caccgggcgg ttgacggcga tcaccccgcc gaaggccgac agcgggtcgc   1920
aggcgtgcgc cttacggtgc gcttcggcga cgtccgcccc gactgcgatc ccgcacgggt   1980
tggcgtgctt gatgatcgcg acacagggct cggtgtggtc gtacgcggcc cggcgggcgg   2040
cctcggtgtc cgtgtagttg ttgaacgaca tctccttgcc gtgcagctgc tcggcctccg   2100
cgagcccctt accgctgcca tcggtgtaga gggcggcggg ctgatgcggg ttctcgccgt   2160
agcgcagcac gttcttacgg gtgatggtgg cgcccaggaa gtccgggaag gaggagtcgt   2220
ccgccgccgc gtagtcggcc gcgaaccagt tggccaccgc cacgtcgtag gcggcggtgt   2280
gctggaacgc ctcggccgcc agccgcttgc gccgctccag gtcgaaaccg ccctccgcgg   2340
cggcctcgag gacgtcgccg taccgctcgg ggttgacgac cacggccacg gacgggtgat   2400
tcttggcggc ggcccggacc atggaggggc cgccgatgtc gatctgctcg acgcactcgt   2460
ccggcgcggc gcccgaggcg accgtctcgc ggaacggata gaggttgacc acgaccagct   2520
cgaaggggtc cacgcccagc tcccggagct gctcgcggtg cgagtcgagc cgctggtcgg   2580
cgaggatgcc cgcgtggacg cgcgggtgca gcgtcttgac gcggccgtcg agacactcgg   2640
ggaagccggt cagctcctcg accttggtga ccgggacccc ggcggcggcg atcttcgcgg   2700
ccgtcgagcc ggtcgagacg agctggacac ccgccgcgtg cagccctcgg gccagctcct   2760
cgagacccgt cttgtcgtag acgctgacca gcgcgcggcg gatgggccgc ttggtacctt   2820
cggcggtcac gggatcctta cctttcgtcc ctctatgcgg tagccgtgac gggccagacg   2880
ccccacgacc tcgacgagca gcgagcgctc gacttccttg atccgctcat ggagagcgga   2940
ctcgtcgtcc tcgtcccgga cctcgaccac gccctgggcg atgatcgggc cggtgtcgac   3000
gccgtcgtcg acgaagtgga cggtgcatcc ggtcaccttc acaccgtgcg cgagcgcgtc   3060
gcgcacgcca tgggcgccgg gaaagctggg gagcagcgcg ggatgggtgt tgacgcagcg   3120
gccgccgaac cgggcgagga actcctggcc caggatcttc atgaacccgg ccgagacgac   3180
caggtccggc tcatgggcgg cggtggcctc cgccaaggcc gcgtcccact cggcgcggcc   3240
ggcgtggtcc ttgacccggc acacgaacgt ggggatcccg gcgcgctcgg cgcgcgtcag   3300
gccctcgatg ccgtcacggt cggcgcccac ggccaccacc tcggcgccgt atcgggccac   3360
gccctcggcg gcgatggcgt cgagcagcgc ctggagattc gtaccggagc cggagacgag   3420
gacgacgagg cggaccgggc gcccggggcg cgcagggctg gcgggggaag gcggggaggc   3480
```

-continued

```
cacggcgggg ctctttctcg cgggcggtgc tgccgtttgt gtggtcgtac aaggtcgcgg   3540
actcatcaat tccggggaac tctacgaagc cgccgaccgt cagcaacgat accggcacac   3600
gaagcggccc ccaggggacg gggcgggca cgggaggtag cgtctggact gcgaatgcaa   3660
ctgacgccac tgacgccgtg ggaacgaccg ccgcacccgc gcaccgagcc gtacggcacc   3720
ggccgtaccc gcgccgtacg gcaccaggcc gtacccgccc cggcgtgcag gacgacgaca   3780
caaggggaag acacactcca catgccggac cgacgccgcc gcgcggctca tcgcctcact   3840
ccgcccccg cccaggcccg ggggcggcga tgaggcgcgc ccgcatgtcg cgcacgacgc   3900
cgctgctccg ggagcagcag tcgtcatcct cctcgtcctc ctcgtcctcg tccgcccccg   3960
gcgggccgaa cggggaccag cacgaggaca atccgttcgc cccgccgccc gagggcaggc   4020
cggaccagcc ctggcggccc cgccaccggc cggacggctc cggcggggag agcggcgagg   4080
gccgccccgg cgcccagggc ggccaggacg ggccggacgg cgaccagagc ggtgagcagc   4140
cgcagcagcc cccggcctgg ggcagccagt ggagcagccg ccagcccggc cgccagaacg   4200
gcggcttcgg cggcaccccg ggctccaacc gcccctccgg ccccggcggg cccggcggcc   4260
cgcgctggga ccccaacgac ccggcccagc ggcgcgcccg gtacgcgctg ctctcgggca   4320
tgtgggcgtt cttcttcgcg ctcttcagcc tgccgcagat cgcgctgctg ctcggggtgc   4380
tggccctgta ctggggcatc agctcgctgc gggccaagcc gcgccgtacg gcgccgtccc   4440
cggccgcggc cgcgcccctg aacgccccgc ccccgcctcc gggcgccgcc cgggcagcgc   4500
tgcccgcgcc cggcagcggc ccggcgaagt cgcagtcgac ggcggcgatc agcggtctgg   4560
tgacgggcgg tctcgcgctc gccatcgtcg cggcgacgtt cagcttccag gtcgtctaca   4620
gcgactacta cacctgtgtg gacgacgccc tcacgcagac ctcgcgccac gactgcgaaa   4680
ccttgctccc cgagcagctc cgcccccctgc tgagcacgca ggactgacgg cgccgggccc   4740
gcacggcgga aggctcgcgc ccgcttgccg tccgccttac ggttcgcgtt tacggttcgc   4800
ggcgggcgtc gtccggcggc ggcgggggct ccgtgcgcga ggggtccggg gcggtcttgg   4860
actcggcggg cggctgcggc ccgggagcgc gcttccggct cagtgcccag cggcgtgggc   4920
gggcggcccc gggggcgccc ggggtgcccg cgggggtcgc gagtccggcc atcgtgccca   4980
caccggtttc gcgtccggtc tcccgtcccg tctccgcacc ggcgtcgggc gccgccttac   5040
ggttccgctt gcggtcggcg cccgacgcgc ccgggcgcag ccactgccac cacggctcgg   5100
ccatcgcctc gcgcacctcg gcggactcca tgggtgacac cgtgggcagc accgccgccc   5160
gcgcctccgc ctcggccgcg gcccgcgccg cgcgggcggc cttggcctcc gtacgggcct   5220
ccctggctgc cgtacgggcc tccccggccg ccgtacgggc ctgcgcgcgg gatgtccggc   5280
ggtccgcccg cgccgccttc cactccggcc aggaggccct ggtggggacg cacagccggt   5340
accagcgcag caccatcgcg ccgggcaccc cgatcactcc cgtccaggcc agcgtgatca   5400
cgcccgtgcg ccaccagctc gggccgaggt ccgcgagcat gccgatgccc agcggtccgc   5460
ccgagacccc ggccaggagc gccatcgcgg ccgcgcagcc gaccgccgcc agcgcggcga   5520
gcaccagcgt ctcggcccag ccccagggcg gcctgggctc gcccttgccg ggccgccgca   5580
ccgccgcgat cccgatgagc caggccaccg acgccccggc cgcgatcccc gtgagccaga   5640
ccagcggccc gccggagccg tccgtgggca gcgcggcgac cagggggaag tgcggcagct   5700
gggggtagga ggtgatgccc agcggcgcca ccacactgcc gccacccacc gtgaaccccg   5760
ccccgacccc gtacgccgcg ccccagacga tcgcgttcgg cagcagcgcc aggctcacca   5820
```

-continued

```
ggagcaccgc gaaccgcccc gaccacacat cgctgaggtt gaggaacgtc acctgcacgg   5880
cgcccgcgtg gctcagcatc gacgtcgccg taaggagcgc accgctgccg agcaggacga   5940
cgagaccgct ggtcccggcc cgtagcgcgg cggtcagccg gcggcgccgg caccagccgc   6000
gcgcggccag ggacgcggcc gtccttacgg tccgttcggc gccggggagc cgccgcagcc   6060
tctcgctcac ccgtccgggc aggcggagcg ggaaccgtcc gtcggccgtc cacacgccga   6120
cggcggcgat gaccccggcg acgaccggca gatgcagcag cgcgctcagc ggatcgacac   6180
gcagcggccc ggtcgaggcg tacaccgcgg cagcggtgcc caccagcaga tagccgccgg   6240
tcacccaggc gaaggcggtg cgcggatcga cgacggactc ctcgggcacc cactgcccgt   6300
cgccctcatc gggctccgcc tggtagacgg cgtgctgggc ggcccggtac agcagccagc   6360
acggcaccac gctgagcagc agcggggtca gcccgaccgg cgcggtgtgg ccggagagcg   6420
tctcggtgcg cacgaggtcg gcgccatggc cgagcagcca taggtcggcg gcgacatgca   6480
gggctccgtc ggggctgctc tcgggggagg aagaagtgat ccacaacagc agtacgacca   6540
cggcgagcgt gccgaggccg agccccgcgg cgaccacacc gccgaggaac gcctccctga   6600
tggcggagga acgccggggc gctgagcggt cgcgtgcgga caccgacggg ctgcgatcgg   6660
tcgtttgcgt cacatgacca tgctgccaat aacagccgtt tcatccctac atcaagggtt   6720
tggtcgccgt gtcgcggcta gtccgcttat gcgtctttta tagagtcgtg ggacggatga   6780
gtggcttgcc gcgttccgac cgggtatccg tcgcccggga acaccgcggg caccaccatg   6840
gggtggtgcg ggcccgcggc atcgggccgt ggcggcgtca gccggccagc gcggcgcgcg   6900
ccaggcgcgc ggtctcggac ggggtcttgc cgaccttcac gcccgcggcc tcgagggcct   6960
ccttcttcgc ctgggcggtg ccggaggagc cggagacgat ggcacccgcg tggcccatcg   7020
tcttgccctc gggggcggtg aagcccgcca catagccgac gaccggcttg gtgacgttgg   7080
ccttgatgaa gtccgcggcc cgctcctcgg cgtcgccacc gatctcgccg atcatcacga   7140
tcaggtcggt gtcggggtcg gcctggaagg cggcgagggc atcgatatgg gtggtgccga   7200
tgatcgggtc accgccgatg cccacacagg acgagaagcc gatgtcccgc agctcgtaca   7260
tcatctggta ggtcagcgtg ccggacttcg acaccagacc gatccggccg ggcttggtga   7320
tgtcggccgg gatgatgccc gcgttcgact gacccggcgt gatcagaccc gggcagttcg   7380
ggccgatgat gcgcgtcttg ttgcccttct tgcccgcgta ggcccagaag ttggcggagt   7440
cgtggaccgc gatgccctcg gtgatcacga cggcgagcgg aatctcggcg tcgatcgcct   7500
cgatgaccgc actcttggtg aacttctccg ggacgaagat gaccgtgaca tcggcgccgg   7560
tggcgtcgat ggcctccttg acggagccga agaccgggat ctcggtgccg tcgaagtcca   7620
cggtggtgcc ggccttgcgc gggttcacgc cgccgacgat gttggtgccc gaggcaagca   7680
tccgacgggt gtgcttctgc ccttcggacc cggtcatccc ctggacgatg accttgcttt   7740
ccttggtgag gaagatagcc atggtttctg gtgacctcgt cccttacttc gcagccagct   7800
cggcggcacg ctcggccgcg ccgtccatgg tgtccacctg ctgaacgagc gggtggttgg   7860
cgtcggtgag gatcttgcga cccagctccg cgttgttgcc gtcgaggcgc acgaccagcg   7920
gcttgctgac gtcctcgccc ttggacttca gcagctccag ggcctggacg atgccgttgg   7980
cgaccgcgtc acaggcggtg atgccaccga agacgttgac gaagaccgac ttgacgtccg   8040
ggtcgccgag gatgatctcg agaccgttgg ccatcacctc ggcggaggcg ccaccaccga   8100
tgtcgaggaa gttggcgggc ttgacgttgc cgtggttctc gcccgcgtag gcgacgacgt   8160
cgagggtgga catgaccaga cccgcgccgt tgccgatgat gccgacctcg ccgtcgagct   8220
```

-continued

```
tgacgtagtt gaggcccttg gccttggcgg ccgcctcgag cgggttggcc gcggccttgt   8280
cctcgagcgc ctcgtgctcc ggctgccgga aggcggcgtt ctcgtccagg gagaccttgc   8340
cgtccagcgc gatgaccttg ccgtcttcgg tcttgaccag cgggttgacc tcgacgagca   8400
gggcgtcttc cttgatgaag acggtccaca gcttctggag caccgcgacg acctggtccg   8460
cgatctcggc cgggaacttc gcggcggcga cgatctcggc ggccttctcc tcggtcacgc   8520
cctcgatggc gtccaccggg atcttggcga gcgcctcggg gttctgctcc gcgacgacct   8580
cgatctccac gccgccctcg acggaggcca tggcgaggaa ggtgcggttg gtgcggtcca   8640
gcaggaagga gacgtagtac tcctccttga tgtccgcggt ctcggcgagc atcaccttgt   8700
ggaccgtgtg gcccttgatg tccatgccca ggatctggcc ggccttctcg acggcgtcat   8760
ccgggtcgga ggccagcttg acgccgcccg ccttaccgcg gccgcccgtc ttgacctgcg   8820
ccttgacgac cgcgcggccg cccagccgct cggccacctc gcgcgccgcc ccaggcgtgt   8880
cgatgacttc accggccagc accggtacac cgtgcttggc gaagaggtcc ttcgcctggt   8940
attcgaacag gtccacgcgc gtccgtccct tttccatgga tttcgcggtc gttatcagcg   9000
cgggcgtgcc gcgggggcag cgtgacgacg cgatctgtaa cgagggcggc acacgttcgc   9060
cgggtacgcg gcatgtccgt ctcgcaggtt atctccgtgg gccgtgcggc cctaaatcgc   9120
agatcacact ggagcggtga ttacggtcac agatcgcgac cgtttccatc tatctccgta   9180
cgacaaccgg gcagcccccct ccccaacgag ggctgcccgg tcgatgacgc ttgccttacg   9240
gttttacggt ttcgcggcct gcatggcctt cacggcctga ctgtctgacg cccgccggag   9300
cgatcagacg gtcggaagcg tgcccggaac ggtcggcagc tggaccggaa cggagggcag   9360
gtcggcggga acctgcggga ggtcggccgg gagctgcggc aggtcggccg gaacggtggg   9420
cagctgcggc aggtcggtgg gcagctgcgg gaggtcggcc ggaacggtcg gcaggtccgc   9480
cgggagctgc ggcaggtcgg ccgggagctg cggcaggtcg gcgggaacct gcgggaggtc   9540
ggccgggagc tgcggcaggt ccgccggaac ggtgggcagc tgcggcaggt cggtgggcag   9600
ctgcgggagg tcggccggaa cggtcggcag gtccgccggg agctgcggga ggtcggccgg   9660
gagctgcggc aggtcggccg gcagcaccgg gagggccggg atgttggcga cgtcggtcag   9720
gtcggtgggc accgccggga gcaggctcag cgcaccgtcc ttggcgttac ccacggtggt   9780
ctgggcgttc gcggccacgc cggtggccag gccgtgggcg aacggcacgg tggtgcccgc   9840
cacgtcctgc gcgaacggaa cggcggtgga cggcacgctc accacgaccg gcaccaggcg   9900
gtcgacggtg tcctgggcgg ccggaaccac gttggaggcg gtgcccagcg cgaagccctc   9960
ggcgctgccg gtcacgacgt ccacgtacgg ggtggtgcgg gccacggcgt cgtcggccag  10020
cgcaccggtg tcacccacgg tgcgctcggc gaccgggacg accttgacca cgaggcggtg  10080
cacggcgggc ggcagcacgt cggaggccac accgtcgacg accggcttgg tggtgccgac  10140
ggcaccctgc accttgccgg tcagctcctc cgggcggatg ccggcgccgg agagggaggc  10200
gagcaggtca ttggccgaac ccggggcgga gggcagcttc ggggtcatca ccaccggtga  10260
ccacggctac gccaaggcgg tgctcgactc accgctccac cgcgacgtgg gcgcgctctt  10320
cccgcgcggc ggcggcatgt cgtgggcctc gaccgcgggc ctcggagccc tggacctggc  10380
caccgtcccc aacaagctca ccccgaagca gcgcgccgag gtgcgcgcga tggtgacgaa  10440
ggccgccgac cgctacgccg cggactccgc gaagtcggcc tacggcgtgc cgtacgcgcc  10500
gaaggacggc aagtacgagt ggggctccaa cagccaggtg ctcaacaaca tgatcgtgct  10560
```

-continued

```
cgccaccgca cacgacctga cggacaagcc ccgctacctc gacgcggtgc tccgcggcat  10620
ggactatctt ctgggcggca atccgctcaa ccagtcctat gtcaccggcc acggcgaacg  10680
ggactcgcac aaccagcacc accgtttctg ggcccaccag cgcgaccacc ggctgccgca  10740
tccggcgccc ggctcgctgg cgggcggccc gaactccggg ctgcaggacc cggtggccaa  10800
gaagaagctg aagggctgcg ccccggcgat gtgctacacc gacagcctga tggcgttctc  10860
caccaacgag atcaccatca actggaacgc cccgctggcc tggatcgcgt cgtacgtcga  10920
cggtctgggc ggcggcgcgg cggagcagtc cgtgcgctga cccggcccgg ccggaacacg  10980
ccgccgccca cccgcgctcg ggcgcgggtg ggcggcggac cagcggagcg gggaggtcag  11040
tcggcgccga actccatcgc ggcgcggtcg agcagcttgt cctgtccgga cacgtgcccg  11100
tccgaggcga tcgcctcgga ggcgccctgc ggcatcgcgc cgatcagccc ggtggacgcc  11160
gcctgcgcgg cgccgatcag cgccggatgc gagctgccga ccatgccgag accggcgtac  11220
tgctccagct tggcgcgtga gtcggcgatg tcgaggttgc gcatggtcag ctggccgatc  11280
cggtccaccg gaccgaaggc ggagtcctcg gtccgctcca tggagagctt gtccgggtgg  11340
tagctgaacg ccggtccgga ggtgtccagg atggagtagt cctcaccgcg ccgcagccgc  11400
agggtcacct cgccggtgat cgccgcgccg acccagcgct gcagcgactc gcgcaccatc  11460
agcgcctgcg ggtccagcca gcggccctcg tacatcagcc ggccgaggcg gcgcccctcg  11520
gtgtggtagg tggcgacggt gtcctcgttg tggatcgcgt tgaccagccg ctcgtaggcc  11580
gcgtgcagca gcgccatgcc cggtgcctcg tagatgcccc ggctcttggc ctcgatgacg  11640
cggttctcga tctggtcgga catgcccatg ccgtgccgac cgccgatggc gttggcctcc  11700
agcaccagat cgacggcgga ggcgaactcc ttgccgttga tcgttaccgg gcggccctgc  11760
tcgaagccga tcgtgacgtc ctcggccgct atctcgaccg acgggtccca gaaccgcacg  11820
cccatgatcg gctggacgat ctcgataccg gtgtcgaggt gctcgagcga ctttgcctcg  11880
tgggtggcgc cccagatgtt ggcatcggtg gagtacgcct tctccgcgct gtcccggtag  11940
ggcaggtcat gggcgagcag ccactccgac atctccttgc ggccgccgag ctcgctgacg  12000
aagtcggcgt ccagccacgg cttgtagatc cgcagggagg ggttggccag cagaccgtag  12060
cggtagaacc gctcgatgtc attgcccttg aaggtggagc cgtcgcccca gatctgcaca  12120
ttgtcctcga gcatggcgcg caccagcagg gtgccggtga ccgcccgccc gagcggggtg  12180
gtgttgaagt agctgcggcc gccggagcgg atgtggaacg ccccgcaggc gagggccgcg  12240
agcccctcct ccaccagggc cgcccggcag tccaccagac gggcgacctc cgcgccgtac  12300
gtcgtggcgc gcccggggac cgaggcgatg tcgggctcgt cgtactggcc gatgtcggcg  12360
gtgtaggtgc agggcaccgc gcccttgtcg cgcatccacg cgaccgctac cgaggtgtcg  12420
aggccgccgg agaaggcgat cccgacgcgt tcgccgacag ggagggaggt gagaactttg  12480
gacacagcag gagtatgcag ggttacgcat gatcatgcaa ggcctcctgg tgatcgccat  12540
gatccacacc tcgttccccg cgcttcgccg ggtcggggac cggggcgccc ggggcgcttc  12600
cggacggttt tggatgggtc cggacggctc caggcgggtc caggcggttc cggacggcga  12660
agcgcggggg tgaggatcat gaggtcagat acgcctccac ctcactgacc tgggccgcgg  12720
gccagccggt gttgccggtg acgctgagcc tcagatagcg cacattcgtg ctgtcgggca  12780
gggcgacggt gaccttgttg ccggacgccg ggtcgaagcg gtagccctgc gagcccacca  12840
ccgtggagta cgaggagccg tcggtgctgc ccagcacgga cagggtctgg gtgcgggcgc  12900
cccacgccga cgagggcggc agcttcagca ccagcctgcg gacggcctgg ccggcgccga  12960
```

-continued

```
ggtccacggt cagggcctgc ggaaaggcgt tgttggtcga ctcccagtag gtgttcgcgt  13020
cgccgtcgac cgccttgccg gggtgtaga cgtcccaaga gccggtcgcg gtggccgggc  13080
ggcccttggc gaggttgcgg cccgggtcgg gatccgggtt gccccggccg ggctggggcc  13140
agctggcaca gtccgaccag gtgctgctcc agccggagtt gccgccgccg tcgttgaggt  13200
cgaaggtgcc ggagcccgac gggtacgggc agttgtagac gcccgccgcg ccgacgctgg  13260
aggccgtgac atcgccgaac ttcaccgccc cctgcgcctc ggcctggacg acgaccgttc  13320
cggggttggt cacggtcgcg ccggacacat tgacgttctt gaccgcgtag cccctgccgc  13380
cgccggagac gaactcgaag gcgctgtacg ggctgtcggt gatggtcgtg ttggtgatgt  13440
tgacggtggc ctcgatcgcg ctgtcgtagg agtcgacgcg cagggcgccc atcgggtggc  13500
tccagttggg gttcatggcg cccgctcgga ccagcgtgtt gccgtcgacc gtgatcgtgc  13560
cggccagcgg gtggaacggg tccatgaact tctggttgga gatggcgatg ccactgccca  13620
gggcgttggt gtcggagatc aggttgttct tgaccgtgat gtccgtaccg ccgtagatgg  13680
cgatgccatt ggcgaggttc ggctgcgaga tggtgttgct ctcgaagctg ctgttggtgt  13740
ccggcgagtt cagcgaccac atggcgagcg cgtcgtcgcc ctggttgcgc aggaagttgt  13800
tccggacccg tacgttcttg gcgctgccgt tgaggttgag gccgtcggcc gtcatgtcca  13860
ggaagcggtt gttctcgacc acgaggttgt cgttgttgcc catcagccac agaccgacct  13920
tcaggtgctg cagccacatg ccggacacgc tggagcccgg gccgagcgag ccgttgacga  13980
agttgtcggg gttggagtcg acgcgctcgg tgacctcgcc gatgaccgcg aagtccttga  14040
tgtggacgtt gccggaggag ctggactggt cgatgaaccg cgaggtgtgc accacggagt  14100
gccagctgcc ggcgccctgg agggtgacgt tctggacgcc gttcagtgag gaggtcagcc  14160
tgtagtcacc cggcgggatc cagaccacac cgccctgggc tgcggcgatg gcgtcccgga  14220
acgcctgggt ggagtcgccc tgcccgctgg ggtcggcgcc cttggaggtg acggacaccg  14280
atccggcggg ctgggaggcg gccgccgcga cctgctcgaa gtcggccacg tccacggtga  14340
cctgggtgtt cgccgcctcg aaggcgatct tgtcaccggc ctggacgttc tggccgagca  14400
gcagccgggc gttgtcgtag aggtggtggg tcttcgaccc cgcgatccag ccggtgtcca  14460
cgtacgagta cttggacgtg accgcgatgg tcttggccag cttggtgccg ttgacataga  14520
cgttcaacgt gcccgactgg ccgtcgggca cgttgtaggc cacgttcacc gcgttcgccg  14580
cgcggggcgc ggtgaactcc acgcgctgcc cggcggcgag gcggacggcc tggcgcccgg  14640
atgcctcgga ggcgagcgtg ccctgggtga agtcggggcc gatcttcgtc cccgtggtgg  14700
tggccgactc ggcctcggcc gaggcgaagg gcagggaggc gcccgcggcc gcgtgtgccg  14760
ccgtgggggt cagggtgacg agcgtgccgg ccgcgagggc gacggccacg ccgatcgccg  14820
acaggcgttt ggtggatgcc gatgcggtac tgctgcggtg catgtgctga tcccttcatg  14880
gtgggggtgg tgggatagcg cggtgcgggg gtggcggctc agcggagcag ccaggccgcc  14940
gtgtcctgcg gaaggcggcc ccggtcgtcc agcgggccgc tgctgagcag aagccgggag  15000
gcgccgtcca gctcggtggg ggtgtccgcg aggttgacca cgcagaccag gccgtccgca  15060
cgggcgaagg ccaggacacc gtcggccgag gggagccagg tcagcggccc gtcgccgaag  15120
ccgggggtgg tgcggcggat gcggatcgcc gcgcggtaga ggccgagcat cgagcccggg  15180
gcctccgtct gcagatcggc cgcgtacgcc gcccagtgcg cgggctgcgg cagccacggc  15240
tcctcgcgcg agccgaaacc ggcgtacggc gcctccgccg cccacggcag cggcacccgg  15300
```

-continued

```
cagccgtccc ggcccgggtc ggtgccgccg gagcggaagt gcatcgggtc ctggatgcgg  15360
tcgcggggga tgtcggcctc gggcaggccc agttcctcgc cctggtagac gtagaccgcg  15420
ccgggcaggg ccagcgacag cagggcggcg gcccgtgccc gccgggtgcc gagggtgagg  15480
tcggtggggg tgccgaagac cttggtggcg aagtcgaaac cggtgtcctc gcgcccgtag  15540
cgggtcaccg tgcgggtcac atcgtggttg cacagcaccc aggtggccgg agctcccacc  15600
ggagcgtgtt cggcgagcgt ctcgtcgatc gacgtccgca gccgccgggc gtcccagggg  15660
caggccagaa acgagaagtt gaaggcggtg tgcagttcgt cggggcgcag atagcgggcg  15720
aagcgctcgc tgtccggcag ccacacctca ccgacgaaga caccgccgta ctcgtcggcc  15780
acgccgcgcc aggagcggta gatgtcatgg agctcatcgc ggtcgacgta cggatgggga  15840
tcgcggccct cgacgaagtc gggcagccgg ggatccttgg ccagcagggc ggccgagtcg  15900
atgcgcaccc ccgcgacacc ccgctccaac cagaagcgca ggatgtcctc gtgctcctgg  15960
cgtacggccg gatgggccca gttgaggtcc ggctgttcgg gggcgaacag atgcagatac  16020
cagtggccgt ccggcagccg ggtccacgcc gggccgccga actccgacgt ccagtcgttg  16080
ggcggcagtt caccgtgctc gccgcggccc gggcggacgt ggaagagctc gcgctcggcg  16140
ccgcccgcga gggcggcccg ccaccagggg tgctggtcgg agacgtggtt cgggacgatg  16200
tccacgatcg tgcggatgcc cagctcacgg gcctcggcga tgagtttctc cgcctcggcc  16260
agggtgccga aggccggatc gatggcgcgg tagtcggcga cgtcatagcc gccgtccttc  16320
atgggcgact ggtaccaggg gctgaaccac agcgcgtcga cgccgagttc ggcgagatac  16380
ggcagcctgg cgcggacgcc cgcgaggtcg ccggtgccat cgccgtcccc gtcggcgaag  16440
ctgcgcacat acacctggta gatgacggcg gagcgccacc agtcgttcgg cgtccgggca  16500
ggggtgggct gggccacggt gggagccttt ctgtcgaggg ggcggtgtca gcccttcgtg  16560
ctgcccgcgc tgatcccggc gatgatgtgc cgctggaaga cgaggaacag cgcgaccatc  16620
gggatgctgg cgatgaccat cgcggcgatg agcacggtca gctggatgtt ctgcgacagc  16680
tggacgagtg ccacgctgat cggctgcttg ccggtgtcgg agaagaccat cagcggccac  16740
aggaagtcct gccacaccgc caccagcgcg aagatcgaca caacgccgag caccgggcgc  16800
gacatgggca gcacgatcga ccacagggtg cgcagcttcc cggcgccgtc gatctcggcg  16860
gcctccagga catcgcgcgg gatctggtcg aagaaccgtt tgaggagata gaggttgaag  16920
gcgttggcga cggccggcag ccagatcgcg agcgggtcgt tgagcaggct ggtgtggatc  16980
agcggcaggt cggcgacggt caggtacttc ggcacgacca gcgcctgggc cggaaccatc  17040
agcgtggcca ggatgccacc gaggatcacc ttgccgaagg cgggcttcag cctggacagg  17100
gcataggcgg cggccgtgca gaagaccagc tggaacagcc aggcgccggc tgcctggacc  17160
accgtgttcc acaggtgctg cggcagctgc atcaggtccc aggcgtcgct gtagccgctg  17220
aggtgccact ctttcgggac gatggtgggc ggtgtccgcg ccacctcgtc gggcgacttc  17280
atcgcaccgg tcaccatcca gtagaccggg aagaggaagg cgatcgcgaa cagcaccacc  17340
acggtggtga agaccgtcca gtagacggcc cggccgcggg ggcgggccag ggcggcgggg  17400
gagacgaggg tccgggtgct catgcgtcgt cctccccgga gcgggtgagc cgcagataga  17460
gggcggagaa ggcgccgagc agcacgagca gcatcacgct cagcgcacag gcgccaccga  17520
agtcgttgta gaggaaggcg tacttgtaga tcaggtagag gaccgtgacc gtggcgttct  17580
ccgggccacc accggtgatc acgaacggct cggtgaagac ctgcatcgtc gcgatgatct  17640
gcagcagcat cagcatgagg atcacgaacc gcgtctgcgg gatcgtgacg tggcggacgc  17700
```

-continued

```
gctgcagcag gctcgcgccg tcgagttcgg ccgcctcgta cagctcaccg gggatggact  17760
gcagcgccgc caggtagatc aggacggtgc cgcccatatt ggcccaggtg gccacggcga  17820
cgagggagac cagagcggtg tcggcgccgt tggaccagtt cgaggtgggc aggtgcagga  17880
agcgcagcgc ctcgttggcc agcccggcgc ccgggtcgta gaaccacttc cacagcaggg  17940
cgctgaccac cggcgggatc atcaccggca gatagaccac gaccctgaag aacgccttgg  18000
cgtgccgcag ttcattgagc acgagggcga gcaggaacgg gatcgcgaag ccgatgagga  18060
gtgccagcag ggtgaaggtg agggtgttcc gccaggccgc ggtgaactcc gggtcgtgca  18120
ggacgcgggt gaagttggcg gtgccgaccc attcggggga cgagccgggc gtgtacttct  18180
ggaaggcgat cacgaccgcg cggatcgccg gataccagga gaacagcgcg aagcagatca  18240
ggccgccgag gaggaagcca taggcccgga cctggtcggc gagacggcgc cgcccccgac  18300
cccccgccgg gggcggcgcc tgcaccgggt ggacggcgat cgcctcggcg ggcggccgcg  18360
cggcggtctt ggtcatcggg tcagccccgg gccagaatgt tgtcgatctt gtcggaggct  18420
tcctccagga gctggtcgac atcggcgtcc ttcttggtga ggacggcgga gacggctccg  18480
tcgagcacgg agtagatctg ctgggcgtgc ggcggctcga tcctcatccg cagcttctgg  18540
ttgccgtcga ggaaggtctg gtagttgccc acggggacat tggcgttggc cttcttgacc  18600
tgctggtcct tggcgtcggc tgcgccggtg aacagccgtg gctcgggcag gcccaccggg  18660
gcgtttcgct tcttggcgcg gacgtagtcg ccgaggaagc catcgcccgg ggtgaggaac  18720
atgtggtcga gccacttgag accggcccgg atctgggcgg gcgtgtcctt cttctggaac  18780
atgtagccgt cgccgccgat gagcgtgccc ttgccaccgg gcatgggggc gatggcgagg  18840
tccttgtagt tgccgccctt ctccttcacc aggatcggga ggttgtcggg cgcggccagg  18900
tacatgccca gcttgccgga gcccatcagc tgctgggcgt cgttgatgac caggagctgc  18960
ttgctgccca tcgagtcgtc cacccagcgc atgtcgtgga ggttccgcag gacggcgcgc  19020
gcctcggggg tgtcgatggt ggccttcttg ccgtccgcgc tgacgacatc gccgccctgt  19080
gagtacagct cggccgtgaa gtgccagccg ccctggttct gggcgctgta gtccgcgtag  19140
ccgaccgtgc catcgcccag cttggcgatc ctcttggcgt cggcgcggac ctcctcccag  19200
gtcatcgggg gcttgtcggg gtcgagtccg gccttctcga agagcttgcg gttgtagatc  19260
agacccatcg agtagccggt gcgcgggatg ccgtagatct tgccgtcgac cgtgtagatg  19320
tcgcgcagct gcttctggag ggtggagtag ctcttcaact ccttgacgta cggcgtgaga  19380
tcggccgcct ggttgatgtc gaccacatgt ccggcgtcgg tgaagtacgt gtagaagacg  19440
ttctccatct ggcccccggc cagcttggcg tcgaacgtct tcgggtcctg gcaggggaac  19500
gcgtcatgcg cgacgacgtc gatgtccggg ttctgcttct cgaaggaggc gatgtcctcc  19560
tcgaagaacc tgcggtcgac cttggcgctc ttgggcggca tgcagttgac cgtgatgcgc  19620
gtctttccgc ccgccgagcc gtcgcccgac ccgccgcagg cggtgagggc gagggggaac  19680
gtgctgagcg cgatgagagt acgacggaac ccggtgcttc tcatgggtgg acccctctgt  19740
acaggagcag ggaagcccca cggccgtgag cggggcgcac acaaccgtga gtgcgccgca  19800
cactcaagca ccgacgacat cggcccgcaa gatgtcgcgt agattctgta attattcaac  19860
tgcgctgcga atcaggcgga ttgagcctgt cggtatctct cgaccgccct ttcgatcacc  19920
cctcgacggt cctccgcccg ctcactcccg tggcgcctgg gcggtggagc cgcggaccac  19980
cagctccggc tcgaacagca gctcctcgga cggtacggcc accccgccga tctgcgcgtt  20040
```

-continued

```
cagcacctcc accgccgccc tgcccatggc ctctatgggc tggcggacgg tggtcagcgg  20100
cggctcggtg cagttcatga acgcggagtc gtcgtagccg accacggaca cctgcgacgg  20160
cacgccgaac cccttgcggc gcgcggctcg tatcgcgccc agggccagcg ggtcgctggc  20220
gcagatgatg cccgtgacgc cccggtcgat cagccgggag gcagcggcgt ggccgccctc  20280
gatcgagaag atcgcccggg ccacgaactc atccggaagg tggcctgcga ccgcccgcgc  20340
ggcggtcagc ttgcgtgccg acggcatgtg gtcaccgggc ccgagcacca ggccgatccg  20400
ctcatggccg agggaggcca gatgccgcca cgcctgctcc acggccacgg cgtcgtcgca  20460
ggagacagcc gggaagccga ggtgctcgat ggccgcgttg accagcacca ccgggatgtt  20520
gcgctcggcg agcagccggt agtggtcatg cggcgcgtcg gcctgcgcgt acagcccgcc  20580
cgcgaacacc accccggaga cctgctgttg cagcagcagc gccacgtaat cggcctcgga  20640
gaccccgccc ttggtctggg tgcacagcac cggggtcagt ccaagctgtg ccagcgcccc  20700
accgatgacc tcggcgaacg ccgggaagat ggggttctgc agctcgggca gcaccagccc  20760
caccagccgg gcccggtcgc cccgcagctg cgtgggccgc tcgtagccga ggacgtccag  20820
ggcggacagc accgcctgcc gggtggctgc ggagaccccg ggcttaccgt tgagtacccg  20880
gctgaccgtg gcctcgctga caccgacctt cttcgccact tcagcaagtc gtcgcgtcat  20940
gcacgcaagc gtagcgcaag cactgcaagt ggcttgcgta agaggggtgg agaacgtgtg  21000
actccggcgg cggctcccgg ctcggattca ccctatttgc cgccctaaaa gtgtgggttg  21060
acagcggatc agccaacgat ctaggttccc ttcgaggggc tcgctggatg ggggacgggg  21120
gctgtagtga gtgttttgga gttgcgtgcg tccgatatca cccggaccgc gcggctggtc  21180
ggacgtgccg cattatcaga ccgaatgatc gaccaattga gctccgggat cgctgccttg  21240
gaccgcgcgg aaaatgacca ctcggcgcgg cgtggcggag ctatcggcga tatcgacgcc  21300
gagcacacca tcgatgccgg tcatacggcc cgcgtcgagg gcgagcgtcg gcggtcggcc  21360
gagcccaccg tattcgagtc cctcgactct cccggctcca gcgccgctac gggattcacg  21420
ctcgaagaaa cacttcgcat tcgatccctt tctcgggttt gccgccgaat gtaatcccgg  21480
ccgtactgcc gtttaagaag cgtttacgcc atcggttggc aagcgaaagc gacagcacca  21540
gcggaataac cgcgaaaagc aatttccatc agtcgtcggg gaaggctgtg ttgtggggaa  21600
ttcaggcgca cccaaatccc gtggtctcag cgcggccatg agcaatctct tcgagcggac  21660
caggagaaac gaatccaccg gcattgtgcc ggtcgaccgg ggccgggagc tgagggcgtc  21720
gttcgcccag caacggctgt ggtttctgga ccagttggaa cccggcaacg cctcgtacaa  21780
tctccccttc gcggtgcggg tgcgcggccg cttggacatc tctcatctct cccgggccct  21840
ctcgctcgtg gtcgcccggc acgaggcgct gcgcaccacc ttcggcgagg ccggcggtca  21900
gccggtgcag cggatcgagc cccccggccc cgtcccggtg cgccttgaag cggtgtccgg  21960
cggctcggag gaggagcggc tggccgaggt ccggcggctg gccggagccg agatcaccga  22020
gcccttcgac ctgagcaccg ggcccctgct gcgcgccaag gcgctgcgac tggacgaaca  22080
ggaccacgtc ctgctgctga cggtgcacca tgtggcgacg gacgcctggt cacaaggcat  22140
tgtggtgcgt gagctgtccg tcgcgtacgc gtcgctcgac gccgggcgcg agcccgtgct  22200
gcccccgctg cccgtgcagt acgcggacta cgcggagtgg gagcgcgact ggctgtccgg  22260
cccgaccctg cgccgccagc tggactactg gacgaagcgg ctcgacggca tggcgcccgc  22320
gctggagctg cccaccgacc ggcccaggcc ctcggtcgcc agccaggaag gcgacgcggt  22380
gcgctgggag ttgccgccgg aactgatccg ggcggcccgc cggctgggcg ccggtgagaa  22440
```

-continued

```
cgcgaccctc tacatgaccc tgctggccgc tttccagctg gtactgggcc ggtacgtgga  22500
cagcgacgac atcacggtgg gcaccccgt ggccaaccgg ggccgcgccg aggtcgaggg  22560
gctcatcggg ttcttcgtca acaccgtggt gctgcggacc gacctgtccg gcgaccccac  22620
cttccgccaa ctgctgggcc gggtccgcga cacggcggcg ggtgccttcg cccatggcga  22680
cctgcccttc gagtatctgg tggagcaggt gcaccccgag cgggacttgt cgcggaaccc  22740
gctggtccag gtgctcttcc agatgatcaa cgtaccggcg gagcggctcg agctgcccgg  22800
cgcgcggacc gagccctacg accacggcgg catcctcacg cgaatggatc tggaggtcca  22860
tctcgtcgag accggggacg gggttctggg gcacatcgtc ttcagcaagg ccctgttcga  22920
cacgagcacc atcgaacggc tgctgcacca cgtcaccgtc gtcctccggg gcgtcctggc  22980
cgagccggac cggcgcatct ccgagatctc gctgctcgac gaggcggagc gggcgaaggt  23040
cctggagaag ttcaacacga ccacgggccc cgtacccgcc ggatccctgc ccgcgctctt  23100
caccgcccag gccgagcgcc gccccgatgc ggtggccgtg atcagcggtg gtgaccgggt  23160
gacctacgcc gagctggatc agcgggcgaa ccagctcgcc catctgctgg agggccgggg  23220
ggtcggcccc gagaccctgg tcgggctctg cgtcgatcgc ggcatcgaga tgatcgtggc  23280
gatcctcgcg atcctcaagc tcggagcggc ctatgtgccg atcgatcccc accaccccg  23340
agaccgcgtc cagttcgtcc ttgccgactc cggggtgacc gtcgccgtca cccagcagcg  23400
cttcaccggc ctgctcgaaa ccccggaggc acccgggacg cccgatgcgt ccgggacgtc  23460
cgggatccgc ctcatcctgc tcgacgccga gcgcgagccg ctcgccgggc agccccggac  23520
cccgcccacg gcacggccca gcgcccagaa cctcgcctat gtcatttaca cctccggctc  23580
caccggagtc cccaagggca tcctcatgcc cgccacctgt gtgctcaacc tggtggcctg  23640
gcagaagcgg gccctgccga tcggtcccga cgccaagacg gcacagttcg ccacgctgac  23700
cttcgatatc tcgttgcagg agatcttctc cgcgctgctg tacggcgaga cgatcgtcgt  23760
ccccggcgag gaactgcgca tggaccccgc cgagttcgcc acatgggtcc acgccaacga  23820
gatcgaccag ctcttcgtcc cgaatgtgat gctgcgggcg atctccgagg aggtggatcc  23880
gcacggcacc gagctggccg cactgcgcca cctctcacag gccggcgaac ccctctccct  23940
ccaccacgat ctgcgcgagc tgtgcgcccg ccgccccgag ttgcggctgc acaaccacta  24000
cggtcccagc gaagcccatg tggtgacgtc gtactcgctc cccgccgagg tggccgagtg  24060
gccgctcacc gcacccatcg gccgccccgat cggcaacacc cgggtgtatg tggtcgaccg  24120
gcggctccgg cccgtcccgg tgggggtgcc aggtgagctg tgcgtggccg gagaggggct  24180
ggccaggggc tatctcggcc gcccggatct gaccgcttcc cggttcgtgg cggacccgtt  24240
ccgcggcgac ggatcgcgta tgtaccgctc cggcgacctg gtgcgctggc tgcccgacgg  24300
caacctggaa ttcctcggcc ggatcgatga ccaggtgaag atacgtggct tccggatcga  24360
accgggcgag atcgaggcga tcctcgcccg gcaccaggac gttctgcaca cggccgtgat  24420
ggtgcgcgag gacaccccg gcgacaagag gctggtggcc tatgtggtgg ccgatgccac  24480
cgccgcggac cggcacggcg ggctgaccga gaccctgcgc cggcacgtcg agtccgcggt  24540
gcccgaatac atggtgccct ccgcgttcgt cctgctggac accatgcccc tgacctccgg  24600
cggcaagatc gaccggaagg cgctgcccgc ccccgatctg cgcaccgtgc tcgaggtcgg  24660
ctacgtcgcc ccacgcaccc ccgaggaaga ggccgtctgc cgggtttacg cggatctgct  24720
cggcgcggcc aaggtcggca tcgacgacga cttcttcgca ctgggcggcc attccctcat  24780
```

-continued

```
cgccaccagg gtggtcgcca ggctccggtc cgccctcggt atcgccgtac cgctgaagac  24840
cgtcttccag cagcgcaccc cccgagagct ggcggccacg ctcaccgccg cggcccgctc  24900
cggtcccgaa cccgagctgc cgccgctggt tcccacgcgg cgcgaccagc ccgtccccct  24960
caccttcgca cagcagcaga cggacctctt cttcgacgat gtcctgaacg ccgggcactg  25020
gaacatcccc atggcggtgc gggtgtcggg cgaactggac ctcgactgcc tgcggcgggc  25080
gatggacctg ctgatcgacc gccacgaggc cctgcgcacc accttcgtca gggaagccga  25140
cggatacgtc caggtgatcc ggccgagcgc gccggtccag gtggaggtgg ccgagacgca  25200
cgacgagacc gaagcctcgg tactggccgg ccaggaggcc gcccgcccct tcgacctcac  25260
acgcggcccg ctggcgagac tgcgcgtgct gcggctgtcc cagtccgacc atgtgctggt  25320
gctcaccctg caccacctgg tcaccgacgg ctggtcccag ggagtgctgg tccgagatct  25380
gtccatcgtg tacgcggcac tgctgcacgg caccgaaccc gatctgccac ccgcacccgt  25440
ccagtacgcc gatgtcgcga gctgggagcg gaagtggttg cgcggtccgc tgctgcaacg  25500
ccaactcgag ttctggaagc ggcatttcga gggcatgacc cccgccgaac tgcccaccga  25560
ccggccccgc gccgcgtcgg cccgctacga gagtgacatc ttccactggc gactgccgac  25620
ggacgccgtc gagaccgccc gacggctggg cgaatcgtgc aacgccacct tgtacatgac  25680
gctgctgacc gccctgaagg tggtcatgtc cgcccgctcg gacaaccagg acgtcctcgt  25740
cggcgtgccc acggccaacc gtggccggga cgaactggag aacacggtgg gcctcgtctc  25800
caagatgctc gcgctgcgca ccgaagtgtc cggtgccacg gacttcggca cactgctggc  25860
cacggtgcgc gatgcgatgt ccgacgccca tacacaccag gacgtgccct tcgtgtccgt  25920
tctcaagcac atcggtgacc acaccgccgg ccccgccggt gacaccgccg gcggccgggc  25980
cgggacgcgg ctgtcggacg atccgccagt gaaggtgatc tttcagatcg tcaacacccc  26040
gccgcggcca ctccggctca ccggactgac ggccgagccg ttcccgatga cccacccgcc  26100
ggtcacggtc aacgtggaca tggagatcga cctgtacgag agcgcggagg acggcggcct  26160
cgccggcacc gtgctgttca gcaagtccct cttcgaccgt gccacgatcg agcggttctg  26220
cgacgacgtg gtggcggtcg tctccgcggc cgccgcggat cccggacggc cggtctcaca  26280
ggtgtggcag ggccggggcc gcgaccagtg aacgatcccg ccccgaggaa acgcatggaa  26340
ccggatgagg ccgtcgccgt tgtcggaatg tcctgccgct ttccgcaggc acccgatccc  26400
gaggcgttct ggcggctgct gagcgagggc atctcggcca tcggtgaggt gcccgcgggg  26460
cggtggaccg acgaccagcc cacgccgtcc gggaccgacg agcggtccac gccgcccgcc  26520
atccgccgcg gcggcttcat cgacgacgtc gaccgcttcg accccgcgtt cttcggcatc  26580
tcaccacggg aagccgcggc gatggacccc cagcagcggc tgatgctcga gctggcctgg  26640
gaagggctgg aggacgcggg catcgtgccc gccaccctgc ggggcgccac cgtcggagcg  26700
ttcatcggcg ccgggtccga cgactacgcc tcgctgatcc gcgcccgcgg ccgttcacac  26760
cacacgctga ccggcaccca gcggggcatg atcgcgaacc ggctctccca tgtgttcggc  26820
ctgagcggcc cgagcgtgac cgtggacgcg gcccaggcat cctccctggt cgcggtacac  26880
atggccgtgg agagcgtgcg ccgcggcgag tcacggctcg cgctggcggg cggggtcaac  26940
ctgaacctct ccgcggagac cgccgccgat atcgcggcgt tcggcgcact gtccccggac  27000
ggccgctgct tcaccttcga cgcacgcgcc aatggctatg tgcggggcga gggcggcgga  27060
ctcgtcgtcc tgaaaccgct ctccgacgct ctcgccgacg gcgacaccgt ctactgcgtg  27120
atcgagggca gcgcggtcaa caacgacggc ggcggtgcat cgctcaccgc acccgacccg  27180
```

-continued

```
gacggccagc gacgggtgct ccgactcgcc cagcggcggg ccgcgatctc ccccgaggcc  27240
gttcagtacg tggagctgca cggcaccgga acggcactcg gcgacccggc ggaagcggcg  27300
gccctgggcg ccgtcttcgg ccggagcgga gcgaggccgg tgcagctggg gtcggtgaag  27360
accaacatcg gccacctcga agccgccgcc ggtatcgccg gacttctgaa gaccgcactg  27420
gccatccacc accggcagct gccggccggc ctcaattacc gcacgccgaa tccccgtatc  27480
cccatgggcg aactcaacct ggagatgcgc ctcgcaccgg gggagtggcc gaagccggac  27540
gaccgcctgg tcgccggtgt cagctctttc gggatgggcg gcaccaactg ccatgtcctg  27600
ctcgccgaac cactcgtcgg cgtcccctcc cacgcctccg cgcatgcccc tgagcccgac  27660
tccctcccca gctcgatccc ggccccggtc ccggtcccgg tcccggtccc ggccccggtc  27720
ccggtcccgg ccccggcccc ggccccggcc ccggtcccgg tccccgtccc gcttccgttg  27780
tccggggtgt ccgctgccgc gcttcgcggc caggcgatgc ggctacggcc gtatctggag  27840
cgatcgccga acctcaccga cctctccttc tccctcgcca ccgcacgaac ctccttcgac  27900
caccgtgcgg tgctgatcac cgggcaggcg gccgacgcgg cacacggcct ggacgcgctc  27960
gtcgaaggcg gcacggtggc gggtttggtg acgggcacgg cgagggcggc gggaaagctc  28020
gccttcgcct tcgccggcca gggctcgcag cgtctcggca tgggacgtga actcggggcc  28080
gtcttccccg tctttgccca ggctcttgac gaagtgtgca cggcgctgga cgcacacctg  28140
gaccggccgc ttcgggacgt gatccacggt gacgacgccg aaccgctcaa ccggacggtg  28200
tacgcccagg ccggactctt cgcggtggag gtggcgctgt tccggctgct ggaggacttc  28260
ggcctcgtac cggacctgct gatcggccac tccctcggcg aggtgagcgc cgcccatgtc  28320
gccggtgtgc tgtccttggc ggacgccgcc accttcgtcg ccgcccgtgg gcggctgatg  28380
caggccgtga cggagccggg cgccatggtg tcgctcgaag ccaccgagga cgaggtcacc  28440
cggacgctca tggcgggcgg ggcatcggac gacggtgccc gggtgtgcgt ggcggcggtc  28500
aacggcccca ccgccacggt gatctcgggg gacgagcgcg ccgtactcga cctggcggtg  28560
gagtgggccg gtcgcggacg caagacgaag cggctccgga cgagccacgc cttccattcg  28620
ccccatctgg accccgtact ggacgagctt cggcacatcg ccgagagcct cacgtaccgg  28680
gcgccccgga tcccgctggt gtcgaatgtg accggccgac gtgccacggc ggaagagctg  28740
tgttctccgg agtactgggt ccggcatgtc cgccggaccg tacggttcct ggacggcgtc  28800
cgctgtctgg aggacgaagg cgtcaccacc atcctggaac tgggcccgga caaggcgctc  28860
accaccctgg cccgcgactg cctgaccggg cccgggacgc tggtgggcac ccttcgtcgc  28920
gaccggcccg agccgcaggc cctggtcacc gcgctggccg agctgtatgt ctcgggtgtc  28980
gaagtggcat ggagcccgct ggtgtccggt gggcggcgga ttccactgcc cacgtacgcc  29040
ttccagcggc agcggtactg gttctccgct cccgggcccg agagcggaac cacgcctggc  29100
catggggtca catccgggcg cgagcgcacg gacaccggcc tgagcggcga cgaggcgccc  29160
gacaccggcc cgagcggcgg cgagacgctt ggcatggtcc gggcgcacgc ggccgtcgtg  29220
ctcggatacg cgtcggcaac cgccatcggc gccgagcaca ccttcaagca actcgggttc  29280
gactcgatca ccgccgtcga actgtgcgaa cggctcggtg cggcgaccgc gcttccgctg  29340
cccggcacct tgctgttcga ctatccgacg cccgccgcgc tcgccgagca tctgcaccgc  29400
aggctccacg gccggacgga tgagcaggcc gcgcccgcga ccgtgccaac acctgacggc  29460
ggcgatccgg tggtgatcgt ggggatgggc tgccggttcc ccggccgggc ccactcgccg  29520
```

-continued

```
gaggacctgt ggcggatcgt ggccgacggt gaggacgcca tctccggctt tccgtccgac  29580
cggggctggg acctcgctgg tctctaccac cccgaccccg accaccccgg cacgtcatac  29640
gcacgcgacg gcggattcct ctacgacgcg gccgagttcg acgcggggtt cttcgggatc  29700
tcaccgcgtg aggccgaggc gatggacccg cagcagcggc tgctgctgga gacatcgtgg  29760
gaggcgttgg aacgggcggg tatccccgcg gaacacatca agggcagtag cacgggcgtg  29820
ttcatcggcg cctcgtcggt cggctacgcg gcggacgccg gagaggcggc cgagggctac  29880
cagctgaccg gcactgccgc gagcgtggcc tcgggcaggg tgtcctacac cctgggcctc  29940
gaaggcccgg cggtcaccgt ggacacggca tgctcgtcct cgctggtggc attgcacctg  30000
gccgtacagt cgctgagggc gggcgagtgc tcactggcat tggcgggcgg tgtgaccgtg  30060
atggccacac cggcgatgtt cgtggagttc tcccgtcagc gggggctggc catggacggt  30120
cggtgcaagg cgttcgcggc ggcggcggac ggcacggggt gggccgaagg cgtcggggtg  30180
ctggtggtcg agcggttgtc ggacgccgag cgcaatgggc atcgggtgtt ggcggtggtg  30240
cgtggttctg cggtgaatca ggatggtgcg tcgaatggtt tgacggcgcc gaatggtccg  30300
tcgcagcagc gggtgatccg gcaggcgttg gcgagtgcgg gtcttgtggc gtcggatgtg  30360
gatgcggtgg aggcgcatgg tacgggtacg acgctcggtg atccgattga ggcgcaggcg  30420
ttgttggcca cgtacggtca gggtcgggat gcggatcggc cgttgtggtt ggggtcggtg  30480
aagtcgaaca tcggtcatac gcaggcggcc gcgggtgtgg ctggtgtgat caagatggtg  30540
atggccatgc ggcacggggt gctgccgcga acgctgcacg tggatgagcc gtcgacccac  30600
gtcgactggt ccggcggccg ggtagagctg ctcaccggga caacgccatg gcccacgacg  30660
ggtggccttc gccgagcggg cgtctcctcg ttcggtgtga gtggcaccaa cgctcacgtc  30720
atcctggagc aggtcccgga gacggcccgg ccgaccgggc ccatcgggga agacgacggc  30780
gaagcggcgc ccgtcgcctg ggtgttgtcg ggacagggcg agactgggct gcgggcccag  30840
gccgagcggc tgtgcgcctt catggcggcc gatacccgcc ccaccccggc ggaagtggga  30900
tggtcactgg catcgacacg tgcgacgttg tcgcaccgcg cggtggtcgt gggtgctgga  30960
cgcgacgagt tgttgcgtgg tgtgaatgcg gtggcgaacg ggacacccgt gccgggagtg  31020
gtacggggca ccggagcctc cggggacgtg gtgttcgtct tcccggggca ggggtcgcag  31080
tgggttggga tggcgttgga gttggtggag tcgtcgccgg tgttcgcgcg gcggttgggt  31140
gattgtgcgg atgcgttggc gccgtttgtg gagtggtcgt tgttcgatgt gttgggtgat  31200
gaggtggcga tcggtcgggt tgatgtggtg cagccggtgt tgtgggcggt gatggtgtcg  31260
ttggcggagt tgtggcgttc gtttggtgtg gtgccgtcgg cggtggtggg gcattcgcag  31320
ggtgagatcg cggcggcgtg tgtggcgggt gcgttgactt tggaggatgg ggcgcgtgtg  31380
gtggccttgc ggagcagggc gttgctggct ctgtcgggtc ggggcggcat ggtgtccgta  31440
ccggtgtccg ccgatcggct ccgtgaccgt gtggggttgt cggtggcggc ggtgaatggt  31500
ccggcgtcga cggtcgtgtc cggggcggtt gaggtgctgg aggcggtgct ggcggagttc  31560
ccggaggcca aacggattcc ggtggattat gcctcgcatt cggtgcaggt ggaggggatc  31620
cgggaggggc tggcggaggc gttggcgccg gttcggccgc gtacgggtca ggtgccgttc  31680
tattcgacgg tgaccggccg gctgatggac accatcgagt tggacgcgga gtactggtac  31740
aggaacctgc gcgagacggt ggagttccag agcaccgtcg aacacctcat gcgccagggt  31800
catacggtgt ttgtcgaggc cagcccgcat ccggtgctga ccatcggcgt ccaggacacc  31860
gccgacacca ccgacactga catcgtcgtc accggatcgc tgcgccgcga tgatggcact  31920
```

-continued

```
gtccagcggt ttctgacctc cctggccgag ctccacgtgc gcggtgtccg gatcgactgg  31980
ggcccgctct tcgccggtgt ctcgcccgtt gagctgccga cgtacgcctt ccaacgggaa  32040
cggttctggc ttggggcgga catcgccgag tccgccgtgg acacgtggcg ataccagatc  32100
tcctggaagc cgctgccgga catggacccc ccggccctct ccggcacctg gctggccgtg  32160
gtccccgaag gggacgagtg ggccatggcg ggcgcacggg cgctgatcga gtcgggcacg  32220
gccagcgtcc gtaccctcca ggtgacctgc gacgcggacc gccggaccct ggccgggccg  32280
ctgacggatg tggcgggatc cgaagacatc gccggtgtcg tctcgttcct ggccgccgac  32340
gaagttccgc atccggccca ccccgcgctg tcccggggga tggcgcacac ggtcgagctg  32400
ctgtgctcgc tcaccactgc cgatgtcgag gccccgctgt ggtgtgtcac ccgggcggcc  32460
gtcacggcac tgcccgcgga cccggcgccg agccccgccc aggcggcggt atggggattc  32520
ggacgggtgg ccgggctgga gcgatccgag cggtggggcg gcctgatcga cctgcccgtc  32580
cactgcgacg cacacgtgct gcggcggttc gtcgccgtac tcgcgcaggc agccggtgag  32640
gaccaggtgg cggtgcggcc atcggcggcc ctgggccgac ggttggagcc ggcgcccagg  32700
accggaccgg ccggcgcatg gcgcccgcac ggcacggtgc tgatcaccgg tggcaccggc  32760
gtgctgggcg cacatgtggc acggtggctg gcgcggtccg gcgcggaaca cctggtgctg  32820
ctcagccgcc gtggcccgca ggcccctggg gcggccgtgc tcgacgacga actgaccgcg  32880
ctcggcgtac gagtgaccct gacggcctgc gatgtgaccg accgggccgc tctcgccggg  32940
gtgctggcat cggtgccgga cctcaccgcc gtggtccatc tcgcggggac cgtgcgattc  33000
ggcaattcca tcgacgcgga cctcgacgag tacgccggcg tcttcgacgc caaggtcacc  33060
ggtgccctgc atctggacga gctcctcgac cactcgtcac tggaggcgtt cgtcctcttc  33120
tcctcggcag cggccgtctg ggcggtgtc ggccaggccg gttacgcggc ggcgaacgcc  33180
ctgctcgacg cggtggcaca gcggcgtcgc gcacgcggtc tgccggccac ttcgatcggc  33240
tggggcacct ggggcggcag cctcgcgccc gaggacgagg agcggctgag ccgcatcggc  33300
ctgcgcccga tgcggccgga ggtggccgtc accgagctgc gccacgtcgt cggatcggcc  33360
gagccctgcc cggccatcgc ggacgtcgac tgggagacct tcggcccggc cttcacggca  33420
ggccggccca gccgcctgct cagcgagttg ccgcggctgc gaaacacctc cggcgccatg  33480
gcgatgaccg gcgaccacgc cgcattgcgg aggcgactgg ccggggtgtc cgcggccgac  33540
caggcccgga cgctggtgga cctggtacgt gaacacgcgg cggaactcct ggggcaccgc  33600
ggcccggcgg cgatcgaccc cacggtgcca ttccggcaac tgggcttcga ctcgctgacg  33660
gcggtcgagc tgcggacccg gctgaacgcg gccacgggac tgcgcctccc ggccaccttg  33720
ctgttcgacc acccgagctg ccgggcggtc gccgatctgc tgcgctcgga actgctcggc  33780
gaccggccgg gctccctcgc ggcgtcgtcc gccacggagg ctgtgcccgc cggcgtggtg  33840
gcctccgacg agccgatcgc catcgtcgcg atgagctgcc gcttcccggg aggcatcgga  33900
acccccgagg acttgtggcg ggtggtcagc gagggccggg acgtgctctc cgacttcccc  33960
gacgaccgcg gctgggacgt ggacgcgctg tacgacccgg acccggaccg gcccggcacc  34020
agctatgtgc gtaccggtgg attcctccac gacgccgcgg agttcgaccc ggaactcttc  34080
gggatctccc cgcgtgaggc gctggcgatg gatccccagc agcggctgct gctggagtcg  34140
gcgtggcagg tcctggagcg cgccaggatg gcgccgacct ccctgcgatc cagcaggacc  34200
ggtgtcttca tcggcggctg gggccagggc taccccctcgg cctcggacga ggggtatgcc  34260
```

-continued

```
ctgaccggcg ccgcgaccag cgtgatgtcc ggtcgtatcg cctacgcgct ggggctggag  34320
ggccccgccc tgaccgtgga cacggcatgt tcgtcctcgc tggtggcgct gcatctggcg  34380
agcgaggcgc tacggcgcgg cgagtgctcg ctggcgctcg ccggcggcgt gacggtgatg  34440
gcgacgccca gtacctttgt ggagttctcg cgccagcgtg ggctggcccc ggacgggcgc  34500
tgcaagccgt tcgccggggc ggcggacggc acggggtggg gcgagggcgt gggcatgctg  34560
ctggtggagc ggttgtcgga tgctgagcgg cttgggcatc cggtgctggc cgttgtctcc  34620
ggctctgcgg tgaatcaaga cggtgcgtcg aatggtttga cggcgccgaa tggtccgtcg  34680
cagcagcggg tgatccgtca ggcgttggcg agtgcgggtc ttgtggcgtc ggatgtggat  34740
gcggtggagg cgcacggtac gggtacgacg ctcggtgatc cgatcgaggc gcaggcgctg  34800
ctggccacct acggtcagga ccgggatgcg gatcggccgt tgtggttggg gtccctgaag  34860
tcgaacatcg gtcatacgca ggcggccgcg ggtgtggctg gtgtgatcaa gatggtgatg  34920
gccatgcggc acggggtgct gccgcgaacg ctgcacgtgg atgagccgac accgaaggtg  34980
gattggtccg ccggcgcggt gggactgctc accgagtcgg ccgagtggcg gcaggagggc  35040
cgaccgcgcc gagccggggt gtcggctttc ggggtgagcg gcaccaatgc ccatgtgatc  35100
ctggagcagg ccccgaagca cgcaccgggg gtggcggccg agggcaggaa ggggcgcggg  35160
gagccgccga cggtgccctg ggtgctgtcg ggcgcgagcg aggcgggtct gcgggcgcag  35220
atcgaaggct tgcgggcctt cgctgacgac aaccccacgc tcgatccggc ggatgtgggc  35280
tggtcgttgg cgtccacacg tgcgcttctg ccgtatcgca ctgtcgtcgt gggcaccgac  35340
ctcgacgagt tgcggcgtgg gttggacgcg gcggaggtgg tgggcgcggc cgagccggac  35400
cgtggcgccg tgttggtgtt cccggggcag ggtcgcagt gggttgggat ggcgttggag  35460
ttggtggagt cgtcgccggt gttcgcgggg cggatgcgtg attgtgcgga tgcgttggcg  35520
ccgttcgccg agtggtcgtt gttcggtgtg ttgggtgatg aggtggcgct tgggcgggtt  35580
gatgtggtgc agccggtgtt gtgggcggtg atggtgtcgt tggcggagtt gtggcgttcg  35640
tttggtgtgg tgccgtcggt ggtggtgggg cattcgcagg gtgagatcgc ggcggcgtgt  35700
gtggccgggg gtctgtcgtt ggaggacggt gcccgtgtgg tggccttgcg gagcagggcg  35760
ttgctggctc tgtcgggtcg gggtgggatg gtgtcggttc cggtttctgc tgaccggctg  35820
cggggtcgtg tggggttgtc ggtggcggcg gtgaatggtc cggtgtcgac ggtggtgtcg  35880
ggggctgttg aggtgctgga gggggtgctg gcggagttcc cgggggccaa gcggattccg  35940
gtggattatg cgtcgcattc ggtgcaggtg gaggggatcc gggaggggtt ggcggaggcg  36000
ttggcaccgg ttcggccgcg tacgggtgag gtgccgttct attcgacggt gaccgggcga  36060
ttgatggaca ccgtggggct ggatggggag tactggtatc ggaatctgcg tgagacggtg  36120
gagttccagt ccgcgatcga ggggctgctg gagcttggtc atacggtgtt cgtcgaggcc  36180
agcccgcatc cggtgctgac cgtcggcatc caggacaccg ccgagaccac ggacaccgac  36240
atcctcgtca ccggctcgct gcgccgtgac ggcggtggcc ttgcctcttt cctcaccgcg  36300
ctggcccggc tgcatgtccg gggtgtcgcg gtggagtggc gggaggcgtt cgccgggctg  36360
gacgcccacg ccgtggacct gccgacctac gcctttcagc gtcggcgctt ctgggcggcc  36420
tccctgcggc agactcccgg gacggccgag ttcgaccatc ccctcctggg cgcggtgctg  36480
cccttgcccg attccggcgg cggtctgctc acgggcgtgc tcacactggc cggacagccg  36540
tggctggccg aacactcggt ggccggtgtg gtgttgttcc cggggacggg gtttgtggag  36600
ttggtgttgc aggcggggtt gcggtggggg tgtggggtgg ttgaggagtt gactttggag  36660
```

-continued

```
gggccgttgg tgcttccgga gcggggtgag gttgaggttc aggtttcggt gggtggtgtg  36720
gatggggcgg ggtgtcggtc ggtgtcggtg ttttcgtgtc gtgggggtga gtgggttcgg  36780
catgcggtgg gtgtgcttgg ggtgggggat ggtgtggtgc cgggtgtgga ggtgtggccg  36840
ccggtgggtg cggagcgggt tggggtggag ggggtttatg aggttttggc ggagcggggg  36900
tatgtgtatg ggccggtgtt ccaggggttg cgggacgcct ggcgccgggg cgacgaaatc  36960
ttcgtggagg cggaggtacc ggcggaggcg cggggcgatg cggctcgctg tgccatccat  37020
cccgcgctgc tcgacgcagg gctgcacggc gtcggattgg gcggcctgat cagcgacgac  37080
ggccgggcgt acctgccgtt ctcctggagc ggggtcaggc tgcacgcggt cggcgcatcc  37140
gctgtccgga tgacgctgac gcccgccgga ccggacgcgg tgtcgctgag ggtgaccgat  37200
gaggcgggcg aggcggtgct gacggcggac tcccttgtgc tccgcccggt caccgaggga  37260
cagctcgccg aagccgagat cggcaaccgc gatgtgcttc atcgggtgga gtgggtggat  37320
gcgggggcgt gttcggtggg gtcgttcgtg gagtggggtg aggtggctgc tggtggggtg  37380
gtgccggatt gtgtggtgtt ggccggggct gatgtggcgg gtgtgttgga ggttttgcgg  37440
acgtgggtgg tggaggagcg gtttgagggt tcgcggttgg tggtggtgac gaggggtgcg  37500
gtgtcggtcg gtggtgaggg tttggaggat gtgagtggtg gtgcggtgtg ggggttggtg  37560
cggtcggcgc agtcggagca tccgggggcgg tttgtgctgg tggacgccga tgtagatacg  37620
gatgtggttc cggatgtggt ggggctgggg gagtggcagg tggcggtgcg tgcgggtcgg  37680
gtgtgggtgc cgcgtctggt ggatgtggat gtgagtgtgg gtggtgctgt ggtgcgtggg  37740
ggcttgggtt cgggtgtggc gttggtgacg ggtgggacgg ggttgctggg tgggttggtg  37800
gcgcgtcatc tggtgtcggc gtatggggtg ggtgagttgg tgttggtgag tcgtcggggg  37860
gtggctgcgc cgggcgtgga ggagttggtg ggggagttgg aggggttggg cgcgcgggtg  37920
cgggtggtgg cgtgtgatgt ggcggatcgg ggtgcggtgg cggagttggt ggggtcgatc  37980
gaggggttgc gggtggtggt gcacgcggcg ggtgtcgtgg atgacggggt gatcggttcg  38040
ttggacgcgg agcggttgtg tggggtgatg gggccgaagg cgtggggtgc ctggcatctg  38100
catgagctga cgcgtgggtt ggatctgtcg gcgttcgtgt tgttctcgtc ggcggcgggt  38160
gtgttgggca acgcgggcca gggcggctac gcggccgcga atgggttcct ggacgcgctg  38220
gcggttcacc gtcgggggcg gggactcccc gcggtgtcga tcgcgtgggg cttctgggag  38280
gaacgcagcg aactgaccgc cgacctggcc gaggtgcagc tgtcgaggat ctcccggtcc  38340
gtaggggcca gcatcagcag cgcacaagga ctggatctgt tcgacgcggc gcttgccgcc  38400
gacgagccga tggtgctggc cacacccctg aacctgcccg cgttgcggga ccaggccgcc  38460
gcgggcacgt tgccctcgat cctgagcgga ctggtcaccg ctcccgtccg caggacggcc  38520
ggcaccgggc gcactccggc cggactgcgg caccaactcg ccggggtgac agaggccgaa  38580
aggcagcacc agatcatgcg cctggtgcag gaacatgtgg ccggcgttct gggacatgcc  38640
tccgcggagt tggtcgacgc ctcgcggacg ttccaggaga tcgggttcga ctcgctgacc  38700
gccgtggaac tgcgcaaccg gatcagcgcc gccaccggca tacggctgcc cgccaccgcg  38760
gtcttcgacc accccacgcc caggctgctg gccgagcggg tgctggccga ggtagggggc  38820
tccttgccga ccgccgcccc gatcgcgccg gtgtcggccg tcgatgacga gccgatcgtg  38880
atcgtgggca tgagttgccg cttccccggc ggcgtcgagt cccccgagga cctgtggcgc  38940
ctggtccact cggccaccga cgcggtctcc gcgctgccca cggaccgggg ctgggacctg  39000
```

-continued

```
gccaccttgt ccggtgccaa gggcggcgcc ggtgcctcgt acgcccggga cggcggattc  39060
ctttacgacg cggctgagtt cgacgccgga ttcttcggga tctcgccgcg cgaggcgacc  39120
gcgatggatc cgcagcagcg gctgctgctg gaggcggcct gggaggtgtt cgagcgggcc  39180
ggaatcgccc cggacacgct caaaggcagc cggacgggcg tcttcacagg cgtgatgtac  39240
cacgactacg gctcgtggct caccgatgtc ccggaggacg tcgagggcta tctgggcaca  39300
ggcatcgcgg gcagtgtggc gtcggggcga ctcgcctata cgttcggcct tgaggggcct  39360
gccctgacgg tggacacggc ctgctcctca tcactggtgg cgctgcatct ggcggccgag  39420
tcgctgcggc gcggggagtg ctcgctggca ctcgcgggcg gcgtcaccgt actggcgact  39480
ccgcaggtct tcgtggagtt cacacgccag ggcggactcg caccggatgg ccggtgcaag  39540
cccttcgccg ctggtgcgga tgggacgggc tggtcggagg gtgttgggct gctgctggtg  39600
gagcggttgt cggatgccga gcggaacggg catccggtgc tggccgttgt ctccggctcc  39660
gcggtgaatc aagacggtgc gtcgaatggt ttgacggcgc cgaatggtcc gtcgcagcag  39720
cgggtgatcc gtcaggcgtt ggcgaacgcc gggctcgccg ccagggatgt cgatgcggtg  39780
gaggcgcatg gtacggggac gacgctgggt gatccgatcg aggcgcaggc gttgctggcc  39840
acgtacggtc agggccggga tgtgggtcag ccgttgtggt tggggtcggt gaagtcgaac  39900
atcggtcata cgcaggcggc tgcgggtgtg gctggtgtga tcaagatggt gatggctatg  39960
cggcacgggg tgctgccgcg aacgctgcac gtcgatgagc cgtcgccgca tgtggattgg  40020
tctgctgggg cggtggagct cctgggggag cacatgggct ggccggaggt cgggcggccc  40080
cgtcgggcgg gtgtctcgtc gttcggggcg agtggcacca acgcccatgt gattcttgag  40140
caggcccccg acatggcggg tgaacctgag caaaggccgg agcgtaacga actaccggcg  40200
attccctggg tgttctccgc tggcgacgag gcgggtttgc gggcacaggc cgtacggcta  40260
cgggccttcg cggaccggaa tccggatctg gatccggtgg atgtggggtg gtctttggcg  40320
actggtcgtg cggggttgtc gcatcgtgcg gtggtggtgg gtgcgggtcg tggtgagttg  40380
ttgggggctt tggagggtgt gccggtggtg ggtgtgccgg tggtgggtgg gttgggtgtg  40440
ttgtttgcgg gtcaggggtc gcagcggttg ggatgggtc gtgggttgta tgaggggtat  40500
ccggtgttcg ctgcggtgtg ggatgaggtg tgcgcgcagc tggaccagca tttggatagg  40560
ccggtgggtg aggtggtgtg gggtgatgat gccgggttgg tcggggagac ggtgtatgcg  40620
caggcggggt tgttcgcgct tgaggtggcg ctgtatcggc tgatcgcttc gtggggtgtg  40680
agggggatt atctgctggg tcattcgatt ggtgagttgg ctgcggcgta tgtggcgggt  40740
gtgtggtcgt tggaggatgc ggggagggtg gtggtggcgc ggggtcgttt gatgcaggcg  40800
ttgccgtcgg gtggtgcgat ggttggggtg gcggcgtcgg agggtgtggt gcggccgctg  40860
ctgggcgagg gtgtggtggt tgcggcggtg aatggtcccg agtcggtggt gctgtcgggt  40920
gatgaggatg cggttgaggc ggttgtggat gtgttggctg ggcgtggggt gcggacgcgg  40980
cggttgcggg tgagtcatgc gtttcattcg gctcgtatgg acgggatgct ggcggagttc  41040
ggtgaggtgc ttcggggggt ggagttccgt gccccgagcg tgcccgtggt gtcgaacgtg  41100
tccggtgcgg tggcgggtga ggagttgtgt tcgccggagt attgggtgcg gcatgtgcgg  41160
gagacggtcc ggttcgccga tgggctggat actctccgtg agctgggtgt gggttcgttc  41220
ctggagttgg ggccggacgg gacgttgacc gccttggcgg atggcgatgg tgtgcctgtc  41280
ttgcgtcggg atcgtccgga gcctctgacc gctatggcgg ctttgggcgg gctgtacgtc  41340
cggggtgtcc agatcgactg ggatgcggtg ttcccgggtg ctcggcgggt tgatttgccg  41400
```

-continued

```
acgtatgcct tccagcgtga gcggttctgg ttggagccgt cccctgagcg gcccacgacg  41460
agcgtggttg acgcggcgtt ctgggatgcg gttgagcgtg gggatctcgg ttcgttcggc  41520
atcgatgccg agcagccgct cagcaccgcc ctgcccgccc tctcgtcctg gcggagggcg  41580
cggcaggagc agtcggtgat tgatggctgg cgttaccggc tcggttggat gccgattccg  41640
gcggtgtccg gggaggtggg cctcaccggt acctggctgg ttgtggtcga gccgggtgcg  41700
gacggtactg atgtggctgt cgcgttgcgg tcggccgggg ccggtgtcga ggttgtgacg  41760
tcggcggagc tgagcgctgg tccggttgcg ggtgtggtgt cgttggtgtc ggtcgaggcg  41820
acggtgtcgt tgctgcacgt ccttgtggcg gccggggtcg atgcgccgtt gtggtgtgtg  41880
actcgtggtg cggtctcggt ggtcgacggt gacttggtgg atcctggcca ggcgggagtc  41940
tggggtctgg gccgtgtgat cggtctggag catccggatc gttggggcgg gctgatcgac  42000
ttgcctggcg aactggacga tcgcgcgggg aatgcgctgg taggcatcct tgccgggggc  42060
accggtgagg atcaggtggc catccgtgtc accggcatat ggggtgcccg gctggtgcgg  42120
gcgacgccgg tcccgatcgg tgacgcgggt ggtgaggctg cggccgcgtg gcgtgggcgt  42180
ggtaccgcgc tggtcaccgg tggtacgggg gcgctggggc gccaggtggc gcgctggctg  42240
gtggacagtg gtctggagcg ggtcgtgctg acgagccgtc ggggggggcga ggcgcccggt  42300
gccgtcgagc tggtggctga gttggggagc cgagtgcgtg tcgtggcctg tgatgtcggc  42360
gatcgtgagg agcttgcggc tcttttggcg atgctcccgg atgtgcggac catcgtgcat  42420
gcggcgggtg tcctcgacga cggggtgctc gaatcgctga cgcccgagcg gatccgtgag  42480
gtgatgcggg ccaaggccga cggcgcgcgg catctccacg agttgacccg tgacatcgac  42540
ctcgacgcct tcgtgttgtt ctcgtcggct gccgggaccg tgggtaatgc gggtcagggg  42600
agctatgcgg cggccaacgc cgtcctggac gggctggcgt ggcgtcgccg ggccgagggc  42660
ttggtggcca catcggtggc ctggggagcc tgggccgaca gcggcatggg ggctgggcac  42720
gcacgggcca tggcaccacg gctggcgctg gcagcccttc agcgagcgtt ggacgacgac  42780
gagaccgcac tcatggtcgc ggacgtggat tggtcgagct tcggctcccg gttcaccgcc  42840
gtacggccga gcccgctgct gagcgaactg ctgccccgct ccagcgcgcc ggtggaaccg  42900
gtcgaggcac tcgccacccg gttgcggggc atgtcgcgga tcgagcgcga tcgggcggtg  42960
ctggagctgg tccgtgccca agtggcggcc gtgctgggac atgcgaagcc cgcttcggtc  43020
gacccctcgc ggaccttcca ggaagtcggc ttcgactcgc tgaccgcggt ggagctgcgg  43080
aaccggctgg ccactgccac cggcgtaccg ttcccggggt cggtcatctt cgactatccg  43140
actcccacgg cgctcgccga ccatgtccgg gcccggttcg ttccggacac ggacaacgac  43200
gaggacgggg gcggcgcgac gtccgtgctc gacgagctga ccaggctgga agccgtgctg  43260
tccgacctgt ccccgagcga cgtggccggt gccgaggtcg ccgcgaagat caagagcctg  43320
ctgtcccact ggggagcggc caccaacagt gacatcgaca tggattccgc gacggacgag  43380
gagatgttcg acctcctcgg caaggagttc gggatctcgt gaacctgccg tcgagttcgt  43440
ctccgagtga gtccagcacc gcgttgagag ggccgtcctg tggagaatga agagaaactt  43500
cgtcattacc tcaaagaggt cacgaaggat ctgcggcaga cccgccagcg cttgcaggac  43560
gtcgaggcga agagccgcga gcccatcgcg atcgtcggca tgagctgccg tttccccggt  43620
ggcatcgcaa cgccggaagc gctgtgggac ctggtgcgcg agggcggcga cgcggtgtcg  43680
gagttcccgg ccgaccgcgg atgggacacg gagggcctct acgaccccgc gggcggctcc  43740
```

-continued

```
gggaagtcgg tcacccgcta cggcggattc ctgcgcggcg tcgccgattt cgacgccgcg  43800
ctcttcggga tctctccccg tgaggcgatc gcgatggacc cgcagcagcg gctgatgctg  43860
gagacctcct gggaagcgtt cgagcgggcc ggtgtcaacc gtgacgcggt gcggggcagc  43920
cggaccgggg tgttcatcgg caccaacggc caggactacg cgacactgct cagcgctgcc  43980
cgggacgatg tgcaaggcca cctcggcacg ggcagcgcgg ccagtgtgct ctcgggacgg  44040
gtcgcctaca ccttcggtct cgaagggccg acggtcaccg tggacaccgc gtgctcgtcc  44100
tcactgatcg ccctgcacct ggccgtccag gcactgcgca acggcgagtg cgagctggcg  44160
ctggcgggcg gcgtcacggt gatgacgacg acgaacacct tcgtcgagct gtccaagcag  44220
ggcgggctgg cgccggacgg ccggtccaag gcgttcgcgg cggcggcgga cggcaccggc  44280
tggggtgagg gcgccgggat gctgctggtg gagcggctgt ccgacgccga acggcacggt  44340
caccccgtgc tggcggtggt gcgtggcacc gccgccaacc aggacggcgc gtcgaatggg  44400
ctgaccgcgc cgaacgggcc ctcccagcgc cgggtcatcc gcgcggcgct gtccaacgcc  44460
cagctgtcca cgggcgatgt cgacgtggtg gaggcacacg gcaccggcac ccggctcggc  44520
gacccgatcg aggcacaggc cctgctcgac acctacggtc aggaccggga ccggccgctg  44580
tggctcggat cggtcaagtc gaacctggga cacacccagg ccgccgcggg tgtcgccggg  44640
gtcatcaaga tggtgctcgc catgcgccac ggtgtgctgc cgcgcaccct gcacgtggat  44700
gaaccgaccc cgcatgtgga ctggtccgcc ggggcggtgc ggctgctcac cgagcggacc  44760
ccgtggccgg aggccgaccg gccgcgcagg gcgggcgtct ccgccttcgg agtgagcggc  44820
accaacgccc atgtgatcgt ggagcaggca tcggaggccg agcccgtcga gccgccccgg  44880
gccgaaccgg tgacggtgcc ctgggtgctc tcgggccagg gcgaggccgg tctgcgggcc  44940
ttcgcggccc ggctcgccga tgtggccacc gaagcgcacc ccggcgacct cggatggacc  45000
ctggccacca cccgctcggc gctgccgcac cgtgcggtgg tgatcggatc cacaccagag  45060
gaactgcgga gcggcctcgc ggcggtggcc gccggagagc cggcctcgaa cgtggtggag  45120
ggagtggccg gctccgacac cggcgtggtc ttcgtcttcc cgggacaggg ctcgcagtgg  45180
gccggtatgg ccgtggaact gctggactcc tccccggcct tcgcccgccg gttcgccgaa  45240
tgcgcccgtg ccctggagac acacctcgac tggtccatcg aggacgtggt gcgttccgcg  45300
cccggtgcgc cctcgctcga cctcatcgag gtcgtccagc cggtcctgtt caccatgatg  45360
gtgtccctcg ctgagctgtg ggcctcctac gggatcactc catcggccgt ggtcggccac  45420
tcccagggcg agatcgcggc ggcctgtgtg gccggggcgc tgtcgctgga ggacgcggcc  45480
aaggtggtgg tgttgcgcag ccgcctcttc gccgaaacgc tggtgggcaa cggcgccatc  45540
gcctcggtcg ccctgcccgc ggaacaactg gccacccgga tcgagccgtg gggcgagcgc  45600
ctcgtggtgg ccggggtgaa cgggcccgcg gccgccacgg tggccggcga tccccagagc  45660
ctcgaggagt tcgtcgccgc atgcgcggcg gacggcgtac gcgcccgcgt cgtgcccgcc  45720
accgtggcct cccacggccc gcaggtggaa ccgctgcggg aacggctgct cgccctgctg  45780
gccgacgtgg cgccacgcca gtccaccgtt ccgttctact ccacggtgac cggcggactc  45840
ctggacacca ccgaactcga cgcggactac tggttctgga acgcccgtaa gccgatcgac  45900
ttcctcggcg cgctccgggc gctgttcgcc gacggccacc gcgtcttcgt ggagtcgagc  45960
acccaccccg ccctgaccat gggggtccag gacaccgcgg atgcctccgg cgagtccgtg  46020
gaggtcaccg gctcgttgcg gcgtggcgag ggcgggctcg accagttcca ctcggccgtg  46080
gcgcggctgc atgtgcacgg cgtacgggtg gactggtccg cggccttcgg ggcggcgcgg  46140
```

-continued

```
cgggtggagc tgccgaccta ccccttccag cgggagcgtt actggctgac gccccggccc  46200
ggccagggtg acgcctccgc cctggggctg ggtgcgctcg accacccccct gctgggggcc  46260
acggtcgtgc tgcccgagtc cggcggttgc ctgctcaccg gtcggctgtc cctggccgga  46320
cagccgtggc tggccgatca cgccctctcc ggtgtggtgt tgctgccggg gacggggttt  46380
gtggagttgg tgttgcaggc ggggttgcgg tgggggtgtg gggtggttga ggagttgact  46440
ttggaggggc cgttggttct tccggagcgg ggtgaggttg aggttcaggt ttcggtgggt  46500
ggtgtggatg gggccgggtg tcggtcggtg tcggtgtttt cgtgtcgtgg gggtgagtgg  46560
gttcggcatg cggtgggtgt gcttggggtg ggggatggtg cggtgccggt ggcggaggtg  46620
tggccgccgg tgggtgcgga gcgggttggg gtggaggggg tttatgaggc gttggcggag  46680
cgggggtatg cgtacggccc ggtgttccag gggctgcggg acgcctggcg ccggggagac  46740
gaaatcttcg tcgaggtggc ggtggcccag gaggcacggg cggacgcggc gcggtgcgcg  46800
atccatcccg cgctgctcga cgccgcgctc cacggggtgc gattcggtga cttcgtatcc  46860
gacgacgacc aggcttatgt gccgttctcc tggaccggcg tcacgctgca cgcggtcggt  46920
gcgacggtcc tgcgcgtcac actgtccccg gcaggacgcg acgcgatcgc cctccgggcc  46980
acggacacca ccggtgcgcc ggtcctgtcg gcacgctcac tggccctgcg accggtctcc  47040
gcccagcagt tgaacgacac gcgggggagc aggactgacg ccctccatcg ggtggagtgg  47100
gtggacgcgt ccggaaccgt ggcggtgggg ggtgaggtgg cgccgcggac tgaggtggtg  47160
cgggtcgtct ccgagggtcc ggatgtggtg ggtgaggcgt acgggcatgt gcttgaggtt  47220
ctggagcggg tgcaggcgtg ggtggcggat gaggacctgg cgggtgagcg gttggtggtg  47280
gtgacgcggg gcgctgtcga cacgggtgat ggtgtggcgg acgtggctgg ggccgcggtg  47340
tggggcctgg tgcggtccgc gcagtcggag aacccggggc gtctggtgct ggtggacacc  47400
gatgacctgg acggcgtcga cagtctgctt cccgggatgc tggctctgga tgaggagcag  47460
gtgctggtgc ggtcgggtgc ggtgcgggtg ccgcgtctgg ctcgggtgcc ggcgccgggt  47520
gaggtatcgg gagggtttgg ttccggtgcg gtgttggtga cgggtggcac tggtgtgctg  47580
ggcggtctgg tgtcacggca tctggtggcg cggcatgggg tgagcaggct ggtgctgctg  47640
tcgcgtcgcg gtgcggaggc cgaaggtgcg gcggagttgc gggaggagct ggaggccgcg  47700
ggcgccgagg tggtgatcgc ggcgtgtgat gccgcggatc gtgaggctct ggccggggtg  47760
ttgtcggggt tgtcggcgga cttcgccttg agcggtgtgg tgcatgcggc gggtgtgctg  47820
gacgacgggt tgctcacgtc gttgacgcgt gagcgggtcg agccggtgtt gcgggcgaag  47880
gtggacgcgg cgtggaacct gcatgagctg accacgggca tggatctgtc ggcgtttgtg  47940
ctgttctcat cggcggcggg tattctgggc aacgcgggcc agggcagtta tgcggcggcg  48000
aacgggttcc tggacgcgct ggcggctcat cggcgggcgc ggggactgcc cgcggtgtcg  48060
atcgcgtggg gcttctggga agcacgcagc gagctgaccc agcacctgtc ggccgacgat  48120
ctggcgcgtg cccacgcggt gccgatgccc acctcccagg cactggatct gttcgacgcg  48180
acgctcgccg ccgacgagcc gatggtgctg gccgcacccc tgaacccgca ggcatggtcg  48240
gacgccggcc acctgcctcc cgtcctgcgc gatctggtcc ggccgcggat ccggcgcgcg  48300
gcggagacaa ccggcgcccc cgaatcggcc tccgcgctcg gacaccggct ggccgccgtc  48360
gaccgctccg agtgggacca ggtcgtacgc gaactcgtgc gcaatcacat cgcggcggtg  48420
ctgcgccatg cctccgggga gtcggtggac acctcgcgga cgttccagga gatcggcttc  48480
```

-continued

```
gactcgctga ccgccgtgga actgcgcaac cggatcagcg ccgccaccgg cgtacggctg  48540
cccgccaccg ccgtgttcga ctacccgaca ccgcaagcgc tggccgagta cctgctcgcc  48600
gaagtcctcg ggaaggacag cgccgccgcc gcgacacccg tcggaaccgc cctcgtcgcc  48660
gacgatccca tcgtcatcgt cggaatgagc tgccgctacc ccggcgggat cacctcgccg  48720
gaagcgctgt gggacctggt gcgctcggac ggcgatgcca tatccgtcct gccggccgac  48780
agaggatggg acctggacgg cctctacgac ccggatccgg accgcaccgg tacgtcgtac  48840
gcccgcagcg gtggattcgt ctacgacgcg gccgagttcg acgccgcctt cttcgggatc  48900
tcgccgcgcg aggccgccgc catggacccg cagcagcggc tgctactgga aacctcatgg  48960
gaggcgttcg aacgcgcggg catccccgcc acctccgtca agggtgagcg gatcggcgtg  49020
ttcaccgggg tgatgcacca cgactacctc acccgcctgt cgaccacacc ggacgccgtt  49080
gagggctatc tgggcacggg cgcggcagcg ggcgtcgcct cgggccgcgt ggcctacacc  49140
ttcggactcg agggcccggc ggtcaccgtg gacaccgcct gctcgtcgtc gctggtggcc  49200
ctgcacctcg ccgtacaggc gctgcgcctc ggcgagtgct cgctcgcgct ggccggtggt  49260
gtgacggtga tgtccacgcc caccgtcttc gtcgagttct cccgccagcg cgggctcgcg  49320
ccggacggca ggtgtaaggc gttcgcggga gcggcggacg gcaccggctt cgccgaaggc  49380
atcggcatgc tgctggtcga acggctctcg gacgcacggc gcaacggaca ccccgtcctg  49440
gccgtggtgc ggggcagtgc ggtgaatcag gatggtgcgt cgaatgggtt gacggccccg  49500
aatggtccgt cgcagcagcg ggtgatccgg caggcgctgg cgagcgcggg gctgtccacg  49560
gtggatgtgg acgcggtgga ggcgcacggt acgggtacga cgctgggtga tccgatcgag  49620
gcgcaggcgt tgctggccac gtacggtcag ggccgggatt cggaccggcc gttgctgctg  49680
gggtcgatca agtcgaacat cggtcacact caggcggccg ccggtgtggc tggtgtgatc  49740
aagatggtga tggcgatgcg ccacggcgtg ctgccgcaga gcctgcacat cgatgagccc  49800
actccccacg tcgactggtc caccggcgcg gtggagctcc tgagcgaaca gacggcatgg  49860
ccggaggccg ggcggccccg ccgggccggg gtgtcgtcgt tcggcatcag cgggacgaac  49920
gcgcacctga tccttgagca ggctccgctg ccgacggcag cggagcggcc cggtgacgcc  49980
gagcccgttc cggtcgagcc tgccgcggtg gtcccgtgga tcgtctcggg gcgcgaccgg  50040
catgccgtgc gcgcgcaggc ggaacgactg cgcgcacacg tggtgagcca ccctgaccgg  50100
agggtggcgg acatcggttt ctcgctgctg accagccgcg ccgtgctgga gcaccgagcg  50160
gtggtactcg gcggtgacca tgccgaactg ctggccgggc tgacggccct ggcacgggac  50220
gaacccgcac cgggcgtggt ggaggccctg gacgcggccg agccggggcg caaggtggtg  50280
ttcgtcttcc ccggtcaggg gtcgcagtgg gccgggatgg cgctggaact gatggagtcc  50340
tcgcccgtgt tcgcacggcg gatgggcgag tgcgccgatg cgctggctcc gctggtggag  50400
tggtcgctgc cggacgtgct ggcggatgag cgagcgctgg cccgtgtcga tgtggtgcag  50460
ccggtgctgt gggcggtgat ggtgtcgctg gccgagctgt ggcgttcgta cggtgtggtg  50520
ccgtcggcgg tggtgggtca ctcgcagggt gagatcgcgg cggcgtgtgt cgcgggtggc  50580
ctgtccctgg cggacggggc aagggtggtc gtgctgcgcg gcaaggcgct gctcgccttg  50640
tcgggccggg gcggaatggt gtccgttccg gtgcccgccg accggctgcg ggaccggccc  50700
ggggtctcca tcgcggcggt gaacggccca tcctcgacag tggtgtccgg cggcgacgag  50760
gtgctggacg cggtgctggc ggagttcccg gccgccaagc gcatcccggt ggactacgcc  50820
tcccactcgc cccagatcga cgacatccgg gacgaactgc tgaaggccct ggcgccgatc  50880
```

-continued

```
gagccgcgca ccgcggcgat ccccttccac tccacggtga ccggacggcc catcgacacc  50940
gccgacctgg acgcggacta ctggtatcgc aatctgcgcg agaccgtgga gctcgagcgg  51000
gtcatccgta cggcggtcga ggacggccac cacaccttca tcgagatcag cccccacccg  51060
gtgctgacca cgggcctgcg cgaaacactc gacgacgcgg acgcgcacgg cggcctcgta  51120
ctggcctcac tgcgccggga cgacggtggc cctacccgct tcctcaccgc cttggccgag  51180
gcgtacgcac acggcgtcga ggtcgactgg ctgccgctgt tcccgggcgc ccgccgggtg  51240
gatctgccga cgtacgcctt ccagcgcgag cgctactggc tggacgcgcc caccgccgag  51300
gcccccacca gcgcgatcga cgcggaattc tgggccgccg tcgagcgcga ggacctcgag  51360
tcgctcgccg cgacgctgcg cgtcgacggg cagccgctgc gcgaagtgct gcccgccctg  51420
tcccagtggc ggcgcgaacg ccgtgacgtc tccaccatcg actcatggcg ttacacgatc  51480
cggtggaagc cgctcacccc gcccgccact tcaccgaccg gcacctggct ggtcgtggtc  51540
tgccatgccg aggccgggca cgagtgggtc gcgggggtga ccgacgcgct gacccgtcac  51600
ggtgccgagc cgctcgtggt cgttctcggc gagcccgaac tggaccgtgc cgcgctggcc  51660
gcccggctgg gcggcgtact ggccgacacc cccaggatca gcggtgtggt gtcgctgacc  51720
gcgctggacg agagcccgca cccggcgtac ccctcggtcc cccagggata cgcgatgacg  51780
ctgctgctct cgcaggcgct cggggacgcc agggtggaag ctccgctgtg gtgcctcacc  51840
cagcgcggcg tctcgctcgg cgatgccgga ggcagtggca gtggcagtgg cactggcgac  51900
ggcaggggca agggcaaggg tgatgtggcc gtcagccgga agcaggccct gacctggggt  51960
ctcggcaagg tgatcgctct ggaacagccc ctgcgctggg gcggtttgat cgacctgccg  52020
gagggcgtgg ccccgcatac ccaggactac cttgccggtg tgctgtccgg cacctcggac  52080
gaggaccagg tggcgatccg cccgacgggg ctcttcggcc gtaggctggc ccacgcgccg  52140
gcccgcgagc gcggcggggg ctggcaaccc cgcggcaccg tactggtcac cggtggcacc  52200
ggagcgctgg gcggccatgt cgcccggtgg ctggccggcc agggggctga acacgtggtg  52260
ctgaccagtc gccggggcat ggccgcgccc ggcgccgagc ggctggccgg ggagctggag  52320
gcgctcggcg cccgggtgac ggtggcggcg tgcgacgtcg gtgaccggga cgccctggcc  52380
gggttgctgg ccgaggtcgg cccgctgacc gctgtggtgc acaccgcggc ggtgctcgac  52440
gacggcacgc tgaactcgct caccaccgac cagctgcaac gcgtgctgcg cgtcaagacc  52500
gacggcgcgg tgcatctgca cgaactgacg cgggacatgg agctgtccgc gttcgtgctc  52560
ttctcctcgc tgtccggcac tctgggcgca cccggtcagg gcaactacgc acccggccat  52620
gtcttcgtgg acacgctggc cgagcagcgg cgggccgagg gcctggtggc cacctccatc  52680
gcctgggggc tgtgggccgg tgacggcatg ggcgagggcg gtgtgggcga cgtggcccgc  52740
cgccatggcg taccggagat ggcgccggag atggcggtcg ccgccatggc acgcgccgtc  52800
gagcaggacg acaccgtcgt cacggtggcc gagatcgact gggaccggca ctacgtcgcg  52860
ttcaccgcga cccgccccag cccgctgctg tccgacctcc ccgaggtgcg tgcgctggtc  52920
gacgccggag tcggccagga gagcgccgag ccgggccacg agcgctcgga attcgcggag  52980
cggctcgccg ggatggccga gaccgaccgg aaccacgcgt tgctggacct ggtccggcgc  53040
catgtcgccg tcgtactcgg acacaccggt ccggacgcga tcgaccccgg ccgggccttc  53100
cacgagatcg gcttcgactc ggtcaccgcg gtcgaactgc gcaaccggct caaccgggcc  53160
accggcctac ggctgcccgc caccgtgacg ttcgaccagc ccaccccgct ggcgatggcg  53220
```

-continued

```
cagtacctcc gcggcgaact gctgcacgac ggccaaggcc gatcggcccc cgccctcccg  53280
gtccgcgcga ccggcgcggt ggacgacgag cctatcgcga tcgtggggat gagctgccgc  53340
ttccccgggg acgtcgcgtc ccccgaggac ctgtggcggc tgctcgccga cggttccgac  53400
gccatcggcg agttccccga gaaccggggc tgggacaccg cgcacctctt ccacccggac  53460
cccgaccacc gaggcacctc ctccacccga gcggccgcgt tcgtctccgg ggccggtgag  53520
ttcgacgccg gattcttcgg gatctccccg cgggaagcgg tggcgatgga cccgcaacag  53580
cggctgctgc tcgaagtgtc atgggaggcg ctggagcggg ccgggatcga ccccacgacc  53640
ctgcggggca gcgagaccgg cgtgttcacg gggacgaacg gtcaggacta cgcgtcgttg  53700
ctgaaggcgg acgagacggg tgacttcgag ggccgggtgg gcaccggcaa ctcggcatcg  53760
gtcatgtccg gccggatctc ctacgtcctc ggtctcgaag gccccgcgct gaccgtggat  53820
acggcgtgct cgtcgtcgct ggtggcattg cacctggcgg tgcgggccct gcggtcgggc  53880
gagtgctcac tggccctggc gggaggcgcg agtgtcatga cgaccgccgg catcttcgtg  53940
gagttctccc gtcagcgcgc gttggcggcc gatggacgct gcaaggcgtt cgcggcggcg  54000
gcggacggta ccggctgggg tgagggtgcc ggaatgctgg tggtggagcg gttgtcggat  54060
gctgagcggc ttgggcatcg ggtgttggcg gtggtgcgtg gttctgcggt gaatcaggat  54120
ggtgcgtcga atggtttgac ggcgccgaat ggtccgtcgc agcagcgggt gatccggcag  54180
gcgctggcga gcgcggggct gtccacggtg gatgtggacg cggtggaggc gcacggtacg  54240
ggtacgacgc tgggtgatcc gatcgaggcg caggcgttgc tggccacgta cggtcagggc  54300
cgggattcgg accggccgtt gctgctgggg tcgatcaagt cgaacatcgg tcacactcag  54360
gcggccgccg gtgtggctgg tgtgatcaag atggtgatgg cgatgcgcca cggtgtgctg  54420
ccgcagagcc tgcacatcga tgagcccact ccccacgtcg actggtccac cggcgcggtg  54480
gagctcctga gcgaacagac ggcatggccg gagaacacac ggccccgccg cgccggggtg  54540
tccgccttcg gagtgagcgg caccaacgcg catgtgattc tggagcaggc ccccgagccg  54600
accgccgccc agcccgaact ctcgccggaa cgcgacgaaa tgagggccgt gccgtgggtg  54660
gtgacgggtg cgagcgaggc cggagtccgc gcacaggccg cgcgcctcat ggcctttgtc  54720
gacgaccggc cggaactccg cccggtgaac atcggctggt cgctggcctc gacccgcgcg  54780
gccctgtcac accgtgccgt ggtcgtaggt gctgaacgta cggaactgct gcgtgagctg  54840
gaggccgtgg ccagtggcag cgtcacggtc ggcgaggccc gcacgcattc cggggtggtg  54900
ttcgtcttcc cggggcaggg gtcgcagtgg gttgggatgg cgttggagtt ggtggagtcg  54960
tcgccggtgt tcgcggggcg gatgcgtgat tgtgcggatg cgttggcccc gtttgtggag  55020
tggtcgttgt tcgatgtgtt gggtgatgag gtggcgcttg ggcgggttga tgtggtgcag  55080
ccggtgttgt gggcggtgat ggtgtcgttg gcggagttgt ggcgttcgtt tggtgtggtg  55140
ccgtcggtgg tggtggggca ttcgcagggt gagatcgcgg cggcgtgtgt ggccgggggt  55200
ctgtcgttgg aggacggtgc ccgtgtggtg gccttgcgga gcagggcgtt gctggctctg  55260
tcgggtcggg gcggcatggt gtcggttccg gtttctgctg accggctgcg ggtcgtgtg  55320
gggttgtcgg tggcggcggt gaatggtccg gtgtcgacgg tggtgtcggg ggctgttgag  55380
gtgctggatg gggtgctggc ggagttcccg gaggcgaggc ggattccggt ggattatgcg  55440
tcgcattcgg tgcaggtgga ggggatccgg gagggtttgg cggaggcgtt ggcgccggtt  55500
cggccgcgta cgggtgaggt gccgttctat tcgacggtga ccggccggct gatggacacc  55560
atcgagttgg acgcggagta ctggtaccgg aacctgcgcg agacggtgga gttccagagc  55620
```

-continued

```
gcgatcgagg ggctgctgga gcttggccat acggtgttcg tcgaggccag cccgcatccg  55680
gtgctgacca ttggcatcca ggacaccgcc gacaccaccg acaccgacat cgtcgtaagc  55740
gggtcactgc gccgcgacga cggcggtcct gtccgcttcc tcagcaccgt cgggcgactg  55800
ttcaccgagg gcgtgccggt ggagtggcag ccgctgttcg ccgcggccgg ggcgcgaaag  55860
gtcgatctcc cgacctatgc gttccagcat gagtggttct ggctggatcc ggtgcgcggc  55920
gcgagtgatg tgggcggcgc gggccttgcc ggtctcgctc accccttggt gagcgcggtg  55980
ttgccgctgc ccgaatccga tggctgtgtg ctgaccggct cgctctcctc ggccacccat  56040
ccttggctgc gtgaccacgc cgtgctggac aaggtgttgc tgccgggcac cgggttcgtg  56100
gaactggccc ttcaggccgg gctgcacctg ggctgccgga cgctggatga gctgaccctg  56160
caggcgccgc tcatgctgcc cgcgcacgga gacgtacaga tccaggtggc ggtcggcgga  56220
ccggacgaca gcggccgccg gccggtcacg gtgtactcca ggccgggcaa ggaccggacc  56280
tggatgcggc acgccaccgg cagcatcagc cccgtcggtg aaacggccac cgtggaccgg  56340
gcggtgtggc ccccggtcgg cgccacaccg gtcgagctca ccgatgtcta cgccgagatg  56400
agcacgcacg gttacgcgta tgggcccgtc ttccaggggc tgcgcgccgc atggcgacgt  56460
ggcgacgagg tgttcgccga ggtggtcctg cccgagacgg ccgagagcga cgcgggtcgt  56520
tgcgccatcc accccgccct cctcgacgcc gccctgcacg gtgccggact gggcacgttc  56580
gtgaccgaac caggccgacc gcaccttccg ttcacctgga ccggtgtcac cctgcacgcc  56640
gtcggtgcca ccaccttgcg ggtcgtcctg tcgcccgccg ggccggacgc catctcgctc  56700
ctggccatgg acggcacggg agcgccggtg ctgacggcgg actctctggc cctgcgcccg  56760
gtgtccgagg gcgggctcgg cggctcccac gacgactcgc tgttccgcgt ggactggacc  56820
gagctcaccc tggacgcctc ggacgcctcg gacgcaccgg aggtgtcgga tgaagcggcc  56880
ttcccggtcg tcgagtccgt ggcccagctg gccggggtgg cggcggcccg gagcgggcgc  56940
ggggccgtgg tgttcaggct ttccaccacg gagaccacag gaggcgccgc cgaggagagc  57000
ccggaggacg tctacgcgct caccagccgt gtcctcaagg tcgcgcaggc gtggttggcg  57060
gacgaccggt tcggggacgc ccgcctcgtc gtggtgacgc ggggcgcggt cgcgaccacg  57120
cccggagaga acccggagag ccttgccgcc gccgcggtct ggggcctcat ccgcaccgcg  57180
cagaccgaga accccggccg tttcgtcctc gtggacacgg tggacgagga tccgtcggcg  57240
ttgccggggg tgctcgccac cgatgagcca caggtggcga tccgggcggg gaaggcgctg  57300
gtgcccaggc tggtacgggc cacctcgtcg gcgttgccgg taccagctga gacggacacc  57360
tggcggctgg agaccgacgg tcagggcact ctggagaacc tggtcctctc gccccgcgcc  57420
gaggcgtcca ggccacttgc cgcacatgag atccgggtgg ccgtgcacgc ggccggggtc  57480
aacttccgcg atgtactgct cgctttgggg atgtacccgg acaaggccgg tctgctgggc  57540
agcgaagccg ccgggacggt gctggagatc ggctccggag tagtgggagt ggcaccggga  57600
gaccgggtga tgggtctgtt ctccggtgcc ttcgcgccgg tggcgatcac cgatcaccga  57660
ctggtggcac cgatcccgga ggggtggtcc ttcccgcagg ccgccgccac cccgatcgcc  57720
ttcctcacgg cgatgtacgc cttgatcgac ctggccgaag tgcggagcgg cgagtcggtg  57780
ctggtgcacg cggcggccgg tggcgtcggg atggcggcag tgcaggtggc gcgctggctg  57840
ggcgccgagg tgttcgccac cgcgagcccg gccaagtggg atgcggtgcg cgcatgcggg  57900
gtcgccccgc ggcggatcgc ttcctcccgc tcgccggagt tcgcggaccg cttccgctcg  57960
```

-continued

```
gacgcaccgg acggtgtgga tgtcgtactc aactcgctga ccggtgaact cctcaacgcg  58020
tcgctcggac tgctgcgtcc cggtggacgg ctgatcgaga tgggcaggac cgaactccgg  58080
gacgcacagg aggtgatggc gcgccacggt gtgtcgtacc gggccttcga actgctcgac  58140
gccggtcccg accgtatcgg ccgactgctc accgagctgc tcgccctgtt ccaccagggc  58200
gtgttcaccc cgctgccact gcgcgtccag gacgtacggc aggcgagtga cgctttccgc  58260
cacctctccc aggcgcgcca catcggcaag ctggccctca ccatcccgcg accgttgtcc  58320
ggcggcaccg cactgatcac cgggggcacc gggacactgg gcggtctggt ggctcgccaa  58380
ctggtgcggg agcacggcgt gacggagctg gtgctggcca gccgtcgtgg tgacaccgct  58440
ccgcaggcgg cggagctgct caccgagctg gaggccgccg gggcgcgggt gcgggtggcc  58500
gcatgcgatg tgtcggaccg ggacgccatc gccgcactcg tcgcctcgct gccgaacctg  58560
cggagcgtgg tgcacacggc cggtgtcctc gacgacgccg tgatcgggtc gctcaccccg  58620
gagcggctgc ggacggtact gcgtcccaag gcggacgccg catggcatct gcatgaactg  58680
acccgggacc gggaccttgc cgagttcgtg ttgttctcct cggcggccgg agtactcggt  58740
ggcccagggc agggcaatta cgcggcggcc aacgccttcc tggacgcgct ggccgcgcgc  58800
cgccgggcac agggactgcc cgcgacctcg ctggcctggg gcttctggga gcagcgcagc  58860
ggactgaccg aacacctgac caccgatcgg ctcgcccggg ccggcgtcct gccgctgtcc  58920
accgacgagg ggctggtcct cttcgacgac gcccgcgcga ccggcgacac cctgctggtg  58980
ccgatgcgtt acgaaccgtc ctcgccgggc cctgagccgg tacccgccct gctgcgtggc  59040
ctcgtacgcg ctccgctcgc ccgcgccctt ccgggcccgg ccgatggtgt gggcagcggt  59100
gtggcggagg gcctcacagg gctggcggcg gacgaacgcc tcggcgcact gctcgacctg  59160
gtccgccggg aggcggcggc cgtgctcggc cacggcggtc cggaatcggt gacaccccag  59220
cgtccgttca aggaactcgg cttcgactcg ctctccgccg tggaactgcg caaccggctg  59280
cgcgcggcga ccggccgacg gctggaggcc acccttgtct tcgaccaccc cactccggcc  59340
gtgctcgcac gccacctcga cgccgagctg ttcggcgcca ccgacgtggc ggcgcccgta  59400
ccagcaccgg cggtcgcgca cccggccgac gagccgatcg ccatcgtcgg catgagctgt  59460
cggctcccgg ccggggtgga ctccccggag gcgctgtgga agctgctggt gagcggcacg  59520
gacgcgatat cggagctgcc ccccgaccgc ggctgggacc ttgacaggct ctacgaccag  59580
gatccgagcc ggcccggtac gacatacgcc aagaccggtg gcttcctgaa gaacgcggcg  59640
gacttcgacg cgggattctt cacgatctcc ccccgagagg cgctggccgc ggatccccag  59700
caacggctgt ggctcgaggc gtgctgggaa gccttcgaac gcgccggtat cgatccgctc  59760
gccctgaagg gcacccgaac cggggtgttc gcgggtgccg tttcgacgac gtacggcgcg  59820
ggtcaggccg ccactccgga cggctccgag gggtacctgc tcaccggcaa ctccacctcc  59880
gtgatctccg gccgcgtggc ctacaccctc ggcctcgaag gccccgccgt caccgtggac  59940
accgcgtgct cgtcctcgct ggtcagcgtg cactgggcgt gtgagtccct gcgccggggc  60000
gaaagcacac tggcgctggc gggcggtgtg gcggtgatga cgacaccgga cctgctggtc  60060
gaattctccc gccagcgcgg actcgcaccg gacgggcggt gcaagtcgtt cgccgccgcc  60120
gctgacggca cagggttcgc cgaaggcgtc ggggtgctcg tcctggaacg gctgtccgac  60180
gccacgcgga acggccacca ggtgctggcg gtgatccgcg gctccgccgt caaccaggac  60240
ggcgcgtcca acggtctgac cgcgccgaac ggcccctcgc agcagcgggt gatccggcag  60300
gcgctggtga acgccggact cgcctcccag gatgtcgacg tggtggaggc gcacggtacg  60360
```

-continued

```
ggtacgacgc tgggcgaccc catcgaggcg caggctctgc tggccaccta cggccaggac  60420
cgggatccgg atcggccgct gctgctgggc tccgtgaagt ccaacatcgg gcacacccag  60480
gcggccgcag gtgccgccgg actcatcaag atggttctgg cgctgcgcaa cggcgtactg  60540
ccgcgcaccc tgcacgtcga cgagccctcc ccgcacgtcg actggtccgc cggggccatg  60600
gagctgctga ccgagcagac cgcgtggccc gaccgggacc acctgcgccg ggccggggtg  60660
tccgcgttcg gagtgagcgg caccaacgcc catgtgatcc tcgaacaggc cccggagccg  60720
gatgagaacg gcgaaccgga caccgtccgg tcgtggttgc ccgcggtgcc ctgggtgctg  60780
tcgggcgcgg gagcggccgg gcttcgggcc caggcccagc ggttggcgtc cttcgtgcgg  60840
gagaaccccg ggctcgaccc cgtggacgtg ggctggtccc tggtcgcgac ccgcgccgcc  60900
ctgtcgcacc gagccgtcgt cgtgggcgcg gaccgcacgg aactgctgcg cgagctggcc  60960
gcggtggaat ccgtgggcgc cgccgaggcg gagcgcgacg tggtgttcgt cttcccgggg  61020
caggggtcgc agtgggttgg gatggcgttg gagttggtgg agtcgtcgcc ggtgttcgcg  61080
gggcggatgc gtgaatgtgc cgatgcgctc gccccgtttg tggagtggtc gttgttcggt  61140
gtgttgggtg atgaggtggc gctcggtcgg gttgatgtgg tgcagccggt gttgtgggcg  61200
gtgatggtgt cgctggcgga gttgtggcgt tcgtttggtg tggtgccgtc ggtggtggtg  61260
gggcattcgc agggtgagat tgcggcggcg tgtgtggcgg gtgcgttgac tttggaggat  61320
ggggcgcgtg tggtggcctt gcggagcagg gcgttgctgg ctctgtcggg tcggggcggc  61380
atggtgtcgg ttccggtgtc cgctgatcgg ctgcggggtc gtgtggggtt gtcggtggcg  61440
gcggtgaatg gtccggtgtc gacggtggtg tcgggggctg ttgaggtgct ggatggggtg  61500
ctggcggagt tcccggaggc gaggcggatt ccggtggatt atgcgtcgca ttcggtgcag  61560
gtggagggga tccgggaggg tttggcggag gcgttggcgc cggttcggcc gcgtacgggt  61620
gaggtgccgt tctattcgac ggtgaccggt cggttgatgg acaccgtggg gctggacggg  61680
gagtactggt atcggaatct gcgtgagacg gtggagttcc agagcaccgt cgaagctctg  61740
atcggccagg gccacacggt gttcgtcgag gccagcccgc atccggtgct gaccgtcggc  61800
gtccaggaca ccgccgacgc gatggagacc cccatagtgg ccaccggttc gcttcgccgg  61860
gacgagggag gcgtacgacg gttcctgacg tcactggctg aggtatccgt ccatggcatc  61920
gaggtcaact ggcagacggt cttcgacggc accggcgctc ggcgagtcga cttgcccacc  61980
tacgcgttcc agcgtgagcg gttctggctg gtgccatcga cgggcacggg cgacgcgtcc  62040
gggctgggcc tgggcgccgt tgaccatccg ctgctgggcg cggcggtgcc gcttccggac  62100
gcggacggct gtgtgctgac cggtgcgctg tcgctggccg ggcagccatg gctggccgac  62160
cactccgtcc tcggcatggt ccttctgccg ggcaccgcgt tcgtggagct cgcgttgcag  62220
gcgggggcgc ggttcggctg cggcactctg gaagagctga cgttgcatga gccgctcgtc  62280
ctgcccgagc gggagaccgt gcagctccag gtgtcggtcg gaggctcgga cgacttcgga  62340
ggccgcccct tcacggtgtt ctcccgctgt gagggtgagt ggatacgcca cgccgggggc  62400
accctgcgtg tgggcgagcg tggcgatccg cccgcgaacc cgtcggtctg gccaccggcc  62460
gatgcccggc cggtcgatgt cgccgagttg cacacgacga tggccgagcg gggctatcag  62520
tacgggcccg ccttccaggg cctgcggaag gcatggatcc gtgacagcga agtgtttctc  62580
gacgtcgcgt tgcccgagca ggtgaggggc gacgcggccc gctgcggagt gcatcccgcg  62640
ttgctggacg cggccctgca aggcatcggc ctcggcgcct tcgtcaacga accgggccag  62700
```

-continued

```
gcccatctcc ccttctcctg gagcggggtg accctgcacg cggtgggcgc cactgccgtg  62760
cgggtgacac tcagcccggc cggaccggac acggtggcca tccggatggc ggacaccatc  62820
ggggcgcccg tgctgtccat cgacgcgctg gcgatgcgtc cgctcgcgga gcagcggctg  62880
ctcgaggcgg gtggcagccg cggcgatgcg ctgttccggc tggagtggaa ggagcttccc  62940
gtccccacgg gggccaccgg cccacgggcg cagtcctggg gcctgctggg cggccacgac  63000
gagcctcgac tgaccgcggc gctgaccgcg gccggtgtgt cgccacaacg ccatcgggac  63060
ctcgcctcca tcgaccaggt gccggatgtg ctggtcctgt cgtgtccgcc cgaggcggat  63120
ggcggcccgg ccccggaagc cacctcgtcc gccctccgcc gagtgctgga agtggtgcgg  63180
gagtggctcg gggacgcgcg gtacaccgat gcccgactga tggtgctcac ccgccgcgcg  63240
gtggccacat ccaccggtga cgacgtggag gatctggcgg cggccgctgt acggggactc  63300
ctgcgcaccg cacaacagga gaaccccgac cggctcgtcg tgatcgacca tgacgactcg  63360
gaccttgagg tgctccccgt ggtgctcggg acaggggagc ccgaagcggc catccgggcc  63420
ggtaaggtgc tggtgcccag gctggtcaag gcggccgtat cggaagggaa ggcccctgcc  63480
tgggacgccg gcaccgtgct gatcaccggc gggacgggga cactcggcgg cctggtcgcc  63540
cgccatctgg tgaccaccca tggcgcgcgt gacctggtgc tggccagtcg cggaggtgac  63600
accgcgcccg gcgccgtgga actggccacc gaactggagg cgctcggtgc ccgcatccgc  63660
gtcgccgcct gcgatgtggc cgatcgtgcc cagctgaccg cgctgctcga caccattccg  63720
gcgctgcgtg ctgtcgtcca caccgcaggt gtggtggacg acggtgtcat cggctcgatg  63780
accgccgaac gcgtggagac cgtcctacgg ccgaaggcga acgcggcgtg gcacctgcac  63840
gcgctgaccc gccacctgga cctggacgcg ttcgtactgt tctcctccgc caccggagtg  63900
ctgggcagcg cgggacaggg caactacgcc gcggccaacg ccttcctcga cgcgctggcc  63960
gtgcaccggc gcgcccaggg gctccccgcg gtgtcggtgg catggggcct gtgggagcgg  64020
cgcagtggcc tgaccgcaca tctgtcggag caggacgtgg cccgtatgac cagcacgggc  64080
gccgttcccc tctccgacga acgcggtctc gagctgttcg acgccgcgtg ccggagtggc  64140
gaacccacac tcgtggccac cccgttgcac cttcgtgcgg tggcggccac cggtacggtg  64200
ccccacgtgc tcagcgcgct ggcaccgacc ccgccacgcc gggccgccga ggccggtgac  64260
ggtggagtgg ctctacggca gagccttgcc gagatgtcgg gcgcggaaca gagccagacc  64320
gtcctggggc tggtacgcgg gcaggtcgcc gccgtgctgc ggcacccgga cccgtcggcg  64380
atcgacacgg cgcggacgtt ccaggagatc ggcttcgact cgctgaccgc ggtggagctg  64440
cgcaaccggc tgggcgccac caccgggatc aggctggccg cgaccgcgat cttcgactat  64500
ccgacacctg ccacgctggc acagcacctg ctcgccgaga tcgtgccgga gaccgccgac  64560
ccggtcgcgg cccggctcgg cgagctggac aaggtggccg ccatgatttc ggcgatggcc  64620
gaggacgaca ccctgcgcga gcagttgtcc tcgcggatgg agaccatcgt cgcgatgtgg  64680
gccgacctgc accgtccgga gcggccgggc acggttgagc gggacctcga atccgcctcg  64740
ctcgacgaca tgttcggaat catcgaccag gaactcgatg ggtcatgagc agcgagaacg  64800
tccgaccgga aatcgagggg actggcacgc ggatgtcgaa cgacgaaaag gtactcgagt  64860
acctcaagaa gctcaccgcc gatctgcgcc agacgcgtca gcgtctccag gacgtcgagg  64920
ccaagagccg cgagccgatc gcgatcgtcg gtatgagctg ccgtttcccg ggtggggtga  64980
gctccccgga agacctgtgg cggctgacgg agtctgcggt ggacgcggtc tccggtttcc  65040
ccacggaccg aggctgggac ctggacggtc tgtacgaccc cgacccggat cgcgcgggcc  65100
```

-continued

```
ggtcgtacgc ccgagagggc gcgttcatcc ccgatgcagg ccacttcgac cccggcctct  65160
tcgggatctc gccacgtgag gcgctggcga tggatccgca gcagcggctg ctgctggagg  65220
catcgtggga ggccctggag cgggcgggta ttcccaccga ttccctgaag ggcagccgga  65280
ccggggtgtt cgccggactg atgtcttccg actatgtctc gcggctgtcc gcggtcccgg  65340
acgaactcga ggggtacgtc ggaatcggaa gcgcggcgag cgtcgcctcc ggccgcgtgt  65400
cgtacaccct ggggcttgag ggcccggcgg tcaccgtgga cacggcgtgt tcgtcgtcgt  65460
tggtggcgtt gcatctggcg gtgcaggcat tgcggtcggg tgagtgctcg ctggcgctcg  65520
cgggcggtgt cacggtgatg gcgacacccg gcaccttcgt ccagttctcc cgccagcgcg  65580
gcctggccgc cgacggccgg tgcaaggcgt tcgcggcggg ggccgacggt accggctggg  65640
gcgaaggcgt cggcatgctg gtggtggagc ggttgtcgga tgctgagcgg cttgggcatc  65700
gggtgttggc ggtggtgcgt ggttctgcgg tgaatcagga tggtgcgtcg aatggtttga  65760
cggcgccgaa tggtccgtcg cagcagcggg tgatccgtca ggcgttggcg aatgcccgtt  65820
tgtcggcggt ggatgtggat gcggtggagg cgcatggtac gggtacggcg ttgggtgatc  65880
cgattgaggc gcaggcgttg ttggccacgt atggtcaggg tcgggatgtg ggtcggccgt  65940
tgtggttggg gtcggtgaag tcgaacatcg gtcatacgca ggcggctgcg ggtgtggctg  66000
gtgtgatcaa gatggtgatg gcgatgcggc atggggtgtt gccgcggacg ttgcatgtgg  66060
atgagccgtc gccgcatgtg gattggtctg ctggtgcggt tgagttgttg acggggcagg  66120
tggcgtggcc ggaggtggat cggccgcgtc gggcgggtgt gtcggcgttc ggggtgagtg  66180
ggacgaatgc gcatgtgatt gtggagcagg cgcctgaagt ggcggagtct gaggctgaag  66240
gtgtggtgtt gcctgctgtg ccgtgggtgg tgtcgggtgt gggtgaggtg gcggtgcggg  66300
cgcaggtgga gcggttgcgg gcctttgcgg accggaatcc gggtctggat ccggtggatg  66360
tggggtggtc tttggcgact ggtcgtgcgg ggttgtcgca tcgtgcggtg gtggtgggtg  66420
cgggtcgtgg tgagttgttg gggcctttgg agggtgtgcc ggtggtgggt gttccggtgg  66480
tgggtgggtt gggtgtgttg tttgcgggtc aggggtcgca gcggttgggg atggggcgtg  66540
ggttgtatga ggggtatccg gtgttcgctg cggtgtggga tgaggtgtgc gcgcagctgg  66600
atcggtattt ggataggccg gtgggtgagg tggtgtgggg tgatgatgcc gggttggtcg  66660
gggagacggt gtatgcgcag gcggggttgt tcgcgcttga ggtggcgttg tatcggctga  66720
tcgcttcgtg ggtgtgtgagg gcggattatc tgctgggtca ttcgattggt gagttggctg  66780
cggcgtatgt ggcgggtgtg tggtcgttgg aggatgcggt gagggtggtg gtggcgcggg  66840
ggcgtttgat gcaggcgttg ccgtcgggtg gtgcgatggt tgcggtgggg gcgtcggagg  66900
gtgtggtgcg gccgctgctg ggcgagggtg tggtggttgc ggcggtgaat ggtcccgagt  66960
cggtggtgct gtcgggtgat gaggatgcgg ttcaggttgt ggtggatgtg ttggctgggc  67020
gtggggtgcg gacgcggcgg ttgcgggtga gtcatgcgtt tcattcggct cgtatggacg  67080
gcatgctggc ggagttcggt gaggtgcttc ggggcgtgga gttccgtgcc ccgagcgtgc  67140
ccgtggtgtc gaacgtgtcc ggtgtggtgg cgggcgagga gttgtgttcg ccggagtatt  67200
gggtgcggca tgtgcgggag acggtccggt tcgccgatgg gctggagacg ctgcgcgagc  67260
tgggtgtggg ttcgttcctg gagttgggac cggacgggac attgaccgcg ctggccgacg  67320
gcgatggtgt gtcggcgctg cgccgggacc gtccggaacc gactgcggta atggctgctt  67380
tgggtgggtt gtatgtccgg ggtgtggagg tcgactggga cgcggtgttc ccgggtgctc  67440
```

-continued

```
ggcgggtcga tttgccgacg tatgccttcc agcgtgagcg gttctggctg gaaccggccg  67500
ctgagcagcc tgcgacgagc gcggtggacg cggcgttctg ggacgcggtc gagcggggcg  67560
atgcggagat tctcggggtt gacgttgagc agccgttgag tgccgcgttg cccgcattgg  67620
cgtcgtggcg acgggcgcgg caggaagagt cggtcatcga cgcatggcgg tatcggctga  67680
cctggacccc ggtcgcgggt ctctcttcgc agctctccgg cgtgtggttg gtggtggtcg  67740
agccggacga ggcggagccg gacgtcgtcg ccgcgctgcg gggcgccggc gccgaggtgc  67800
gtgtcgtaac gatcgatgag ctggacgcgg gcccggtcgc gggcgtggtg tctttgttgt  67860
cggtcgagac gacggtgtca ttgctccagg cccttgtggc agaggggggc gatgcgccgt  67920
tgtggtgtgt cactcggggt gcggtctccg tggtggacgg ggatgtggtg gatccgcatg  67980
cgtcggccgt ctggggtttg ggccgtgtga tcggtctgga gcatccggac cgttggggcg  68040
ggctgatcga tctgcccacc gcatggggtg agcgaacctc cggcatgttg tgctcggtgc  68100
tttcgggcgc cacgggtgag gaccacacag cgatccgtgg cgacgaggtg ttgggttgtc  68160
gtctgagccg tgcgacgacg tcggcaccgg ggccgtccac tgcctgggaa gcgtcgggga  68220
ccgcgctgat caccggtgga acgggtgcct tggggagcca tgtcgcccga tggctcgcgg  68280
ataccggcgt cgaagagatc gtgctgacga gccgacgagg cgcggacgct cccggagcac  68340
gggaactggt cgccgaactg tcggccatgg gcgtatcggc ccgcgtcgtg gcgtgtgatg  68400
tggccgatcg ggacgcggtt gcggagctga tcgagaccat tccggacctc cgcgtggtcg  68460
tccacgccgc gggagtaccg agctggggtg cgttgagcac acttaccgca cagggccttc  68520
aggatgggat gcgggcgaag gtcgcgggag ccatccacct ggatgagctg acgcgcgata  68580
tgcgcttgga cgcctttgtg ttgttctcgt cggtggcggg ggtgtggggg agcggtagtc  68640
agtcggcgta tgcggcggcg aacgcgtttc tggatgggtt ggcgtggcgg cgtcgtggtg  68700
ttgggttggt ggcgacgtcg gtggcgtggg ggatgtgggg tggcggtggt atggcggttg  68760
ggggtgagga gtttctggtt gagcgtggtg tgtcggggat ggctccgggg tcggcggtgg  68820
ctgcgttgcg gcgggcgctg tgtgatggtg agacggcgct tgtggtggcg gatgtggatt  68880
gggagcggtt cgggccgagg ttcaccgcgt tgcgtccgag cccactgctg agcgagctga  68940
tccccgacac cgtcggctcg ggggttccgc tgggtgaatt cgcggcccgt ttccagacca  69000
tgtccgaggg cgagcgcatg cgcgcggccg tcgagctggt gcgtgtttcg gccgcggccg  69060
tgctggggca ccagggcccg gaggccatcg atcccgtcag gacgttccag gagatcggct  69120
tcgactcgct gaccgcggtg gaactgcgca accggatcgc cacggctacc ggtatccgcc  69180
cgccggccac gatggtcttc gactatccga ctcctgtggc cctcgccgaa tatctgagcg  69240
tggaattgct cggttcgccg caggacagtg tgccgccgtt gcaggtggcc gcgccggacg  69300
acggtgatcc cattgtcatc gtcggcatga gctgccgctt ccccggggac gtcgagtctc  69360
ccgaggatct gtggcggttg atcgactccg acggcgatgc cataacggcc tttccgacgg  69420
accgtggatg ggacctgacc ggcctcttcg acacggctgt gggggagtcg gggacgtcgt  69480
atgcgcgtgt tggtggcttc gtccacgacg cgggtgagtt cgatccggcc ttcttcggta  69540
tctcgccgcg tgaggcgacc gcgatggatc cgcagcagcg gctgctgctg cacgcggcat  69600
gggaggcgtt cgagcgggcc ggtatcccgg ccgcctcggt caggggcagc aggactggag  69660
tgttcgtcgg agcctcgccg cagggctatg gcgccgccga agcgtcggaa ggctatttcc  69720
tcaccggtag ttcgggcagt gtcatttcgg gtcgcgtgtc gtacacgctg ggtcttgagg  69780
gcccggcggt cacggtggat acggcgtgtt cgtcgtcgtt ggtggcgttg catctggcgg  69840
```

-continued

```
tgcaggcgtt gcggtcgggc gagtgttcgc tggcgctcgc gggcggtgtc acggtgatgg  69900
cgacacccac tgctttcgtg gagttctcgc gtcagcgtgg gctggccgcc gatggccgct  69960
gcaagtcctt tgccgctggt gcggatggga caggttggtc ggagggtgtt gggctgctgc  70020
tggtggagcg gttgtcggat gcggagcggc ttgggcatcg ggtgctggcg gtggtgcgtg  70080
gttctgcggt gaatcaggat ggtgcgtcga atggtttgac ggcgccgaat ggtccgtcgc  70140
agcagcgggt gatccgtcag gcgttggcga atgcccgttt gtcggcggtg gatgtggatg  70200
cggtggaggc gcatggtacg ggtacggcgt tgggtgatcc gatcgaggcg caggccctgt  70260
tggccacgta tggtcagggt cgggatgtgg gtcggccgtt gtggttgggg tcggtgaagt  70320
cgaatattgg tcatacgcag gcggctgcgg gtgtggctgg tgtgatcaag atggtgatgg  70380
cgctgcggca tggggtgctg ccgcgaacgt tgcacgtcga tgaaccctcc ccgcatgtgg  70440
actggtcgtc cggggcggtc gagttgttga gcgagagggc tgcttggccg gagatgggcc  70500
gaccgcgtcg ggcgggcgtg tcgtcgttcg gggtgagcgg gacgaacgcg catgtggtgt  70560
tggagcaggc tcctggggcg gtggaggagt ctcggggcga gggtgttgcg ttgcctgctg  70620
tgccgtgggt ggtgtcgggt gcgggtgagg tggcggtgcg ggcgcaggtg gagcggttgc  70680
gggccttcgc ggaccggaat ccgggtctgg atccggtgga tgtggggtgg tctttggtgg  70740
ccactcgttc tgggttgtcg catcgtgcgg tggtggtggg tgcggatcgt gaggagttgc  70800
tgggtgggtt gggttcggtg gtggtgggtg ttccggttgc gggtgggttg ggtgtgttgt  70860
ttgcgggtca ggggtcgcag cggttgggga tgggtcgtgg gttgtatgag gggtatccgg  70920
tgttcgctgc ggtgtgggat gaggtgtgcg gggagctgga tcggtatctg gataggccgg  70980
tgggtgaggt ggtgtggggt gatgatgccg ggttggtcgg ggagacggtg tatgcgcagg  71040
cggggttgtt cgcgctggag gtgtcgctgt atcggctgat cgcttcgtgg ggtgtgaggg  71100
gggattatct gctgggtcat tcgattggtg agttggctgc ggcgtatgtg gcgggtgtgt  71160
ggtcgttgga ggatgcgggg agggtggtgg tggcgcgggg gcgtttgatg caggcgttgc  71220
cgtcgggtgg tgcgatggtt gcggtggcgg cgtcggaggg tgaggtgcgg ccgctgctgg  71280
gcgagggtgt ggtggttgcg gcggtgaatg gtcccgagtc ggtggtggtc tcgggggatg  71340
aggatgcggt tgaggcggtt gtggatgtgt tggctgggcg tggggtgcgg acgcggcggt  71400
tgcgggtgag tcatgcgttt cattcggctc gtatggacgg gatgctcgcg gagttcggtg  71460
aggtgcttcg gggcgtggag ttccgtgccc cgagcgtgcc cgtggtgtcg aacgtgtccg  71520
gtgcggtggc cggtgaagag ctctgctcgc cggagtattg ggtgcgtcat gtgcgggaga  71580
cggtccgatt cgcggatggg ctggagacgc tccgtgagct gggtgttggt tcgttcctgg  71640
agttggggcc tgacgggacg ttgaccgcct tggcggatgg cgatggtgtg cctgtcttgc  71700
gtcgggatcg tccggagcct ctgaccgtta tggcggcttt gggtgggctg tacgtccggg  71760
gtgtccagat cgactgggat gcggtgttcc cgggtgctcg gcgggttgat ttgccgacgt  71820
atgccttcca gcgtgagcgg ttctggttgg agccgtcccc tgagcagccc acgacgagcg  71880
cggcggacgc ggcgttctgg gatgcggttg agcgtgggga tctcggttct ttcggtatcg  71940
atgccgaaca gccgctcagc gccgcactgc ccgccctctc gtcctggcgc cgccgtcacc  72000
aggagaggtc actcgtcgag tcctggcggt accgcctcga ctggtccccg atcggcaccg  72060
cttccgagca gccgagtctg cgcggcacgt ggctggtggt gggcgagggc ggagacgacg  72120
tggtcgccgt gctgcgggct gcgggggccg atgcgcgagt tgtgacaatg gcggagctgg  72180
```

-continued

```
gcgaggtcgc ggctgcgggt gtggtgtcgt tgttgccggt cgaggcgacg gtgtcactgg  72240
tgcaggcact ggggacggcc ggggccgatg cgccgttgtg gtgtgtgact cggggtgcgg  72300
tgtcggtggt cgatggtgat gtggtggatc cggggcagtc gggggtgtgg ggtcttggcc  72360
gggtgatccg tttggagcat ccggatcgtt ggggtggtct gatcgatgtg ccggtggtgg  72420
tggatgagga ggccggggct tggttgtgcc gggtgttggg tgggggtacg ggggaggacc  72480
aggttgcggt tcgtggtggt ggggcgtggg gtgctcggct ggtgcgggtg tcgggctcgg  72540
gttcgggatc gggtggggcg gttgtgtggc ggggtcgagg ggcggcgttg gtgacgggcg  72600
gtacgggtgc gttgggtggt catgtggcgc ggtggttggc cggtgctggt gtggagactg  72660
ttgtgctggc gagtcgtcgg gggatggctg cgccggatgc ggagcagctg gtcgcggagt  72720
tggaggggtt gggtgttgcg gtgcgggtgg tggcgtgtga tgtggcggat cggggtgcgg  72780
tggcggagtt gttggagggg attggggatt tgcgtgtggt ggtgcatgcg gcgggtgtgc  72840
tggatgacgg tgtgttggag tcgctgacgt ctgagcgggt tcgtgaggtg atgcgggtca  72900
aggcggaggg tgcgcggtat ctggatgagt tgacgcgggg ttgggatctg gatgcgtttg  72960
tgttgttttc ttcggctgcg gggactgtgg gtaatgcggg tcaggggagt tatgcggcgg  73020
cgaatgcggt gttggacggg ttggcttggc ggcgtcgggc ggaggggttg gtggccacgt  73080
cggtggcttg gggagcctgg gccgacagcg gcatgggggc tgggcacgca cgggccatgg  73140
caccacggct ggcgttggca gcccttcagc gagcgttgga cgacgacgag accgcactga  73200
tgatcgcgga cgtggattgg tcgagcttcg gctcccggtt caccgccgtg cggcccagcc  73260
cgctgctcgg tgaattgctg ggtggcgccg ctcatcccgc gcccgcggtg ggcgggttcg  73320
tcgaccggct acgggacctc cccccggccg agcgggaacg gacggtcctt gagctcgtac  73380
gtggccaggt ggccgtcgtt ctgggacatg ccaccccggg ggcgatcgac accgcagcga  73440
cattccagtc agccggtttc gactccctga ccgcgatcga actccgcaat cggctcatgg  73500
cggccaccgg agtgcagaca cctgcctcgg tcgtcttcga ctaccccact ccggaacttc  73560
tcgccggcca cctgcgggag caactgctcg gggcagggtc ggcagcactc tcgacgacgg  73620
tcgccacggc tccggtcgat gacgacccga ttgcgatcat cggcatgagc tgccgattcc  73680
ctggtggtgt cgactcgccc gaagagctgt ggcggctcct ggagtcgggg acggatgcca  73740
tttccgcctt tccacaagac cgcggctggg acctcgtggg cggagtcgat ggcgcgtcgg  73800
tccgggcggg tggcttcctc tacacggcgg ccgagttcga ccccgcgttc ttcgggatct  73860
cgccgcgcga ggcgatcgcg atggatccgc agcagcggct gctgctcgag gcctcgtggg  73920
aggtcttcga gcgggccggg atcgccgcgg acgcgttgcg ggacagcccc accggagtgt  73980
tcgtcggcac caacggccag gattacgccg ccctcgtcgg taacgcgcca cagcgtgcgg  74040
acggccatct ggccaccggc agcgcggcga gcgtggcatc cggccgactg tcctacacct  74100
tcgggctcga gggcccggcc atcaccgtgg acaccgcgtg ttcgtcgtcg ctggtggcca  74160
tgcacctggc cgcgcaggcg ctgcgctcgg gcgaatgccg tatggccctt gcgggcggcg  74220
ccacggtaat ggccacgccc accgcgttcg ccgagttctc ccggcaaggc gcgttggccg  74280
ctgatggccg gtgcaaggcg ttcgcggcgg gcgcggacgg caccggctgg ggcgaaggcg  74340
taggcattct gctgttggag cggctgtccg acgccgagcg gaacggccac cgggtgctgg  74400
cggtgatgcg tggctccgcc gtcaaccagg atggtgcgtc gaatggtttg acggcgccga  74460
atggtccgtc gcagcagcgg gtgatccggc aggcgctggc gaacgcacgt ctgtccacag  74520
tagacgtgga cgcggtggag gcgcacggta cgggtacgac gctgggcgac cccatcgagg  74580
```

-continued

```
cgcaggctct gctggccacc tacggccagg accgggatcc ggatcggccg ctgctgctgg  74640
gctccgtgaa gtccaacatc ggccatacgc aggccgcggc cggtgtggct ggtgtgatca  74700
agatggtgat ggcgatgcgc cacggcgtgc tgccgcggag cctacacatc gacgagccca  74760
ctccccacgt ggactggacg gccggacgga tcgcactgct caccgaaccg tccccctggc  74820
ctctgacggg agcgccgcga cgcgccgccg tctcctcgtt cggtgtgagt ggcaccaacg  74880
cgcatgtgat cctcgaacag gcatctgcgg tggccgaacc cgaggaaacc gacacggcgc  74940
gaacacccga accgccagct gttccgtggg tgctctcggc acggagcgag gcggggctac  75000
gggcgcatgc cctcaggctt cggtccttcg tgaacgccga tgctgatctg cgtccagtcg  75060
atgtcggctg gtcgctggcg tcggctcgct cggtgttgtc acaccgtgcg gtggtcgtgg  75120
gcgcggaccg cgatgaactc ctccgtgaac tggaggccgt ggccagtggc agcgtcacgg  75180
tcggcgaggc ccgcacgcat tccggggtgg tgtttgtctt cccggggcag gggtcgcagt  75240
gggttgggat ggcgttggag ctcctggagc attcgccggt gttcgcgggg cggatgcgtg  75300
attgtgcgga tgcgttggcg ccgtttgtgg agtggtcgtt gttcgatgtg ttgggtgatg  75360
aggtggcgct cggtcgggtt gatgtggtgc agccggtgtt gtgggcggtg atggtgtcgc  75420
tggccgagtt gtggcgttcg tttggtgtgg tgccgtcggc ggtggtgggg cattcgcagg  75480
gtgagatcgc ggcggcgtgt gtggccgggg gtctgtcgtt ggaggacggt gcccgtgtgg  75540
tggccttgcg gagcagggcg ttgctggctc tgtcgggtag gggcggcatg gtgtcggttc  75600
cggtttctgc tgaccggctg cggggtcgtg tggggttgtc ggttgcggcg gtgaatggtc  75660
cggtgtcgac ggtggtgtcg ggggcggttg aggtgctgga gggggtgctg gcggagttcc  75720
cggaggccaa gcggattccg gtggattatg cgtcgcattc ggtgcaggtg gaggggatcc  75780
gggagggttt ggcggaggcg ttggcgccgg ttcggccgcg tacgggtgag gtgccgttct  75840
attcgacggt gaccggccgg ctgatggaca ccatcgagtt ggacggggag tactggtacc  75900
ggaatctgcg tgagacggtg gagttccaga gcaccgtcga agctctgatc ggccagggtc  75960
atacggtgtt cgtcgaggcc agcccgcatc cggtgctgac cgtcggcgtc caggacaccg  76020
ccgacaccac cgacaccgcc accgacatcg tcgtcaccgg atcgctgcgc cgcgacgacg  76080
gcggtccggc gcgcttcctc accgcgctgg ccgagctgtc cgtacgaggg gtggcgacgg  76140
actggcggca ggcgttcgaa gggaccggcg cccgacatgt cgacttgccg acctacccct  76200
tccagcggca gcgcttttgg atcgaaccca ctgccccgga cgtggcccgg gaggacgctc  76260
gcgtcaccac tgcggacggc gagttctggg cggccgtcga gcgcgaagac gccgcatccc  76320
tggcaacagc cctggaggtc gacgacgcct cactgggcaa cctgctgccc gccttgtcgg  76380
cctggcgccg ccggcggcac gagtggtccg cattggaggc cgtccggtac caggtcaact  76440
ggaagcggct cgtcgatgac cgacccgcga tgttgtcagg tgcctggctg gtcgtggttt  76500
cccaggccga cgccgaccat gagtgggtct ccggcgtaag cgagacgctc gccgagtacg  76560
gggccgagcc agtggtgtgc ccggtggacg agcgacacct ggatcgtgcc gtgctggccg  76620
accggctggc gagcatgacc ggtacgagca gcacgacgag cacggcgagt atcagcggcg  76680
tggtgtcgct ggtcgccctg gaccagcgcc cgcacccgga cttcgcctcc gtgcccattg  76740
gtttcgcgat gacggtgctg ctgactcagg cgttgggcga cacgggggtg gaggccccgc  76800
tgtggagtct gacccaacac gccgtgtcca ccgggcccgc tgacaccctc ctcgcgtccg  76860
catcggcgca ggcactggtg tggggcgtcg gccgagtgat cgcactcgag cagcccctgc  76920
```

-continued

```
gctggggtgg tctcatcgac ctgccgaccg aggtgaacgc gagggcgcgg gaacggctgg 76980
caagggtcct gtcaggcgtt tcgggcgagg accaggtcgc gatccggacg gtgggggcct 77040
tcggacgcag gctcgtccat gcacccgcgt tgcggaccga cctgccgtcc tggcagccga 77100
gcgggaccgt actggtcacc ggaggcactg gagcgctggg cggtcatatc gcgcggtggc 77160
tggcgcatca gggcgcggag cacctcgtgc tgaccagccg acgcggtatg gccgcgcccg 77220
gggcgtccgc actcgtggcg gacctggaag cggccggagc ggcggtgacg gtggccgtgt 77280
gcgacgtggc cgagcgtgcc caactggccg acctggtggc ggatgtcggc ccgctgacgg 77340
ctgttgtgca cacggccgcc ctgctggacg acgcgacggt cgagtccctg accaccgagc 77400
aactgcaccg ggtgctccgc gtcaaggtcg acggtgcgac gcatctgcac gagttgaccc 77460
gtgacatgga actctccgcg ttcgtgctct tctcctcctt gtccgggacg gtcggcacac 77520
cggggcaggg caactacgca ccgggcaacg ccttcctcga cgcgctggcc gagtaccgca 77580
ggacccaagg cctggtggcg acatcggtgg cctggggcct gtgggccggt gacgggatgg 77640
gagagggcga agccggcgag gtggcccggc ggcatggtgt tcccgcgctg tcgccggagc 77700
tggcggtggc cgctctgcgt gcggccgtcg aacagggcga cgcggtggtc acggttgccg 77760
acatcgaatg ggaacgccat tacgccgcct tcaccgcgac gcgccccagc cccttgctcg 77820
ccgaccttcc agaggtacgg cgactcatcg acgcgggcgc cgcttcggcc gtcgaggaga 77880
cggaccggga ccgatccgga ctcagcgggc gcttggcagg gctcgacggg gccgaacagc 77940
ggcgactgct gctcgatttg gtacgccgca atgtcgcggt ggtgctcggg cacaccgacc 78000
cagaagccgt gtcgtcccac cgcgccttcc aggagctcgg cttcgactcc gtgacggcgg 78060
tcgagttccg caaccggctg ggtgccgcga ccggtctgcg gctcccggcc actgccgtat 78120
tcgactaccc gaccccgctg gccctggcgg agtacgcgct gtcggaactg ctggggacgg 78180
tcggggagcc ccttcgcgtc gagtcgagcg gctccccgt ggacgacgat ccgatcgtga 78240
tcgtgggaat gagctgccgc ttccccggcg gggtgagctc gccggaggac ctgtgggacc 78300
tcctcaccga gggcggggac gcgatgtcgg cgttccccgg ggaccgtggc tgggacctgg 78360
ccgggctctt ccacagcgac cccggccacc cgggtacctc gtacacccgg acaggtggtt 78420
tcctccatga cgcgaccgcg ttcgacgccg acttcttcgg catctcgcca cgtgaagcgc 78480
tggcgatgga cccgcagcag cggctgctgc tggaggcgtc atgggaggcg ttcgagcggg 78540
cggggatcga tcctcggtcg ctgcggggca gcgagaccgg ggtgttcgcc ggcaccaatg 78600
gtcaggacta cgtcagcctt ttgggcggag atcagccgca ggagttcgag ggctatgtcg 78660
gaacgggcaa ttcggcatcg gtgatgtccg gccggatcgc ctacgtcctg ggccttgagg 78720
gcccggcgct gacggtggat acggcgtgtt cgtcgtcgtt ggtggcgttg catctggcgg 78780
tgcaggcgtt gcggtcgggt gagtgttcgc tggcgctcgc gggcggtgtc acggtgatgg 78840
cgacaccggg tctgttcgtg gagttctccc gtcagcgtgg cctggccgcc gatggtcggt 78900
gcaaggcgtt cgcgggggcg gctgatggca ccggtttctc cgagggtgtg gggatgctgg 78960
tggtggagcg gttgtcggat gctgagcggc ttgggcatcg ggtgttggcg gtggtgcggg 79020
gcagtgcggt gaatcaggat ggtgcgtcga atggtttgac ggcgccgaat ggtccgtcgc 79080
agcagcgggt gatccgtcag gcgttggcga gcgcgggtct tgtggcggtg gatgtggatg 79140
cggtggaggc gcatggtacg ggtacggcgt tgggtgatcc gattgaggcg caggcgttgt 79200
tggccacgta tggtcagggt cgggatgtgg gtcggccgtt gtggttgggt tcggtgaagt 79260
cgaatattgg tcatacgcag gcggccgcgg gtgtggctgg tgtgatcaag atggtgatgg 79320
```

-continued

```
cgctgcggca tggggtgttg ccgcagagtc tgcacatcga tgagccgaca ccgcatgtgg  79380
actggtccac cggcgcggtg gagctcctgg gggagcacac gggctggccg gaggtggatc  79440
ggccgcgtcg ggcgggtgtg tcggcgttcg gggtgagtgg gacgaatgcg catgtgattg  79500
tggagcaggc gcctgaagtg gtggagcctg aggctgaagg tgtggtgttg cctgctgtgc  79560
cgtgggtggt gtcgggtgtg ggtgaggtgg cggtgcgggc gcaggtggag cggttgcggg  79620
cctttgcgga ccggaatccg ggtctggatc cggtggatgt ggggtggtct ttggcgactg  79680
gtcgtgcggg gttgtcgcat cgtgcggtgg tggtgggtgc ggatcgtggt gagttgttgg  79740
gggctttgga gggtgtgccg gtggtgggtg ttccggtggt gggtgggttg ggtgtgttgt  79800
ttgcggggca ggggtcgcag cggttgggga tgggtcgtgg gttgtatgag ggtatccgg   79860
tgttcgctgc ggtgtgggat gaggtgtgcg cgcagctgga ccagcatttg gataggccgg  79920
tgggtgaggt ggtgtggggt gatgatgccg agctaattgg cgagacggtg tatgcgcagg  79980
cggggttgtt cgcgcttgag gtggcgctgt atcggctgat cgcttcgtgg ggtgtgaggg  80040
gggattatct gctgggtcat tcgattggtg agttggctgc ggcgtatgtg gcgggtgtgt  80100
ggtcgttgga ggatgcggcg agggtggtgg tggcgcgggg tcgtttgatg caggcgttgc  80160
cgtcgggtgg tgcgatggtt gcggtggccg tttcggaggg tgtggtgcgg ccgctgctgg  80220
gcgagggtgt ggtggttgcg gcggtgaatg gtcccgagtc ggtggtgctg tcgggtgatg  80280
aggatgcggt tcaggttgtg gtggatgtgt tggctgggcg tggggtgcgg acgcggcggt  80340
tgcgggtgag tcatgcgttc cattcggctc gtatggacgg gatgctggcg gagttcggtg  80400
aggtgcttgg gggcgtggag ttccgtgccc cgagcgtgcc cgtggtgtcg aacgtgtccg  80460
gtgcggtggc gggtgaggag ttgtgttcgc cggagtattg ggtgcggcat gtgcgggaga  80520
cggtccggtt cgccgatggg ctggagacgc tgcgcgagct gggtgtgggt tcgttcctgg  80580
agttggggcc tgacgggacg ttgactgcct tggcggatgg cgatggtgtg cctgtcttgc  80640
gtcgggatcg tccggagcct ctgaccgcta tggcggcttt gggcgggctg tacgtccggg  80700
gtgtccagat cgactggggg gcggtgttcc cgggtgctcg gcgggtcgat ttgccgacgt  80760
atgccttcca gcgtgagcgg ttctggttgg agccatccgc tgagcagcct gcgacgagcg  80820
tggtggacgc ggcgttctgg gacgcggtcg agcggggcga tgcggaggct cttgggggcg  80880
atgccgagca gtcgttgagt gccgcgttgc ctgctttggc gtcgtggcgg cgggcgcagc  80940
aggaagagtc ggttatcgac gggtggcgtt accggctcgg ctggacgccg atcccggtgg  81000
tgctggggga gccatgcctc actggcactt ggcgggttgt ggtcgaaccg ggtgcggacg  81060
gtaccgatgt ggctgccgcg ctgcggtcgg ccggggctga tgccgaggtc gtgacgtcgg  81120
cggaactgag cgcggggccg gtcgcgggtg tggtgtcatt gttgtcggtc gaggcgacgg  81180
tggcgctggt gcaggctctc gggacggtcg ggatcgatgc gccgttgtgg tgtgtgacgc  81240
ggggtgcggt ctccgtggtg gacggggatg tggtggaacc gtacgcgtcg gccgtctggg  81300
gtctgggccg tgtgatcggt ctggagcatc cggaccgttg ggcgggcgctg atcgacctgc 81360
ccacggaggc ggacgcacgt gtgggtgcgt tgttggccgg ggttctcgcc gggcgcaccg  81420
gggaggatca ggtggcaatc cgggccgccg gggcgtgggg tgcccggctg agccgggcga  81480
caccgattgc ggacacgtct ggcgggtggc gtggtcgggg agctgccttg atcaccgggg  81540
gtacgggtgc gctgggcggc catgtggcgc gctggctggc ggggaccggg gtggagcgca  81600
tcgtgctgac gagccgccgg gggatcgaga ccccgggtgc ggccgagctg gtgaccgagt  81660
```

-continued

```
tggaggagtt cggagtccag gtgacggtgg tcgcgtgcga tgtcgccgat cgggaggcgg  81720
tcgcgacgct gctggtcacc atccccgatc tccgggtcgt cgtacacgcc gcaggggtgc  81780
cgagctggag tgcggtggac agcctgacac ccgaggagtt cgaggagagc gcgcggtcga  81840
aggttgccgg ggcggcgaac ctggacgcgc tcctggcgga cgctgagctg gacgcctttg  81900
tgttgttctc gtcggtggcg ggggtgtggg ggagcggtag tcagtcggcg tatgcggcgg  81960
cgaacgcgtt tctggatggg ttggcgtggc ggcgtcgtgg tgttgggttg gtggcgacgt  82020
cggtggcgtg ggggatgtgg ggtggcggtg gtatggcggt tgggggtgag gagtttctgg  82080
ttgagcgtgg tgtgtcgggg atggctccgg ggttggcggt ggctgcgttg cggcgggcgc  82140
tgtgtgatgg tgagacggcg cttgtggtgg cggatgtgga ttgggagcgg ttcgggccga  82200
ggttcaccgc gttgcgtccg agcccactgc tgagcgagct gatccccgat acgtccgaac  82260
cactcgcgtc gacggtgggt gagttcgcgg tcgagctgcg cggattgtcg cgcgaggacc  82320
gggaccgtgc cgtcgtggag ctcgtacgga cacatgccgc cgaggtgttg ggccaccaga  82380
acccgagcgc gatcgacctg gaccggacgt tccaggagct gggctttgac tcgctgaccg  82440
ccgtggaatt gcgggaccgg ctcggcacgg ctactcagct gcgattccca gcgtccgtga  82500
tcttcgacta cccgactccg gcggcactcg ccgagcatgt gtgcggggcg gccctcggac  82560
tggccgaaga gatacaggta gcgcacacgc ccagcgcggt ggccgacgat ccgatcgtga  82620
tcatcggcat gagctgccga ttcccgggcg gtgtggactc tccggaggcg ctgtggcggc  82680
tggtcagcgc cggtggcgac gccgtatcgt ccttcccgtc cgaccgtggc tgggacctgg  82740
ccggtgtgta cgacgccgac gccactcgct cgggccggtc gtacgtccgc acgggtggat  82800
tcctccatga cgcggctgag ttcgacgccg gattcttcgg gatctcgccg cgcgaggcga  82860
ccgcgatgga tccgcagcag cggctgctgc tggaggcgtc ctgggaggcg ttcgagcggg  82920
ccggaatccc ggcctcgacg ctcaagggca gccagaccgg cgtcttcgtg ggcgcgtccg  82980
cacagggcta tggcggcggg gacgggcagg cgccggaagg atccgaagga taccttctga  83040
ccggcaacgc gggcagcgtg gtgtccggtc gggtggccta tacgtttggg ctggagggcc  83100
cggcggtcac cgtggacacg gcgtgctcgt cctcgttggt ggcgctgcac tgggcggtgc  83160
gggcccttcg gtcgggcgag tgctccctcg cgctggccgg cggagtgacg gtgatggcga  83220
cacccgccac ctttgtggag ttctcacgtc agcgtgggct ggccgccgat ggccgctgca  83280
agtccttcgc cgccggtgcg gatgggacgg gctggtcgga gggtgttggg ctgttgctgg  83340
tggagcggtt gtcggatgcc gagcggaacg ggcatccggt gctggccgtt gtctccggct  83400
ctgcggtgaa tcaagacggt gcgtcgaatg gtttgacggc gccgaatggt ccgtcgcagc  83460
agcgggtgat ccgtcaggcg ttggcgaatg cgggtcttgt ggcgtcggat gtggatgcgg  83520
tggaggcgca cggtacgggt acgacgctgg gtgatccgat cgaggcgcag gcgttgttgg  83580
ccacgtacgg tcagggtcgg gatgcgggtc ggccgttgtg gttggggtcg gtgaagtcga  83640
acatcggtca tacgcaggcg gctgcgggtg tggctggtgt gatcaagatg gtgatggcca  83700
tgcggcatgg ggtgttgccg cggacgttgc atgtggatga gccgtcgccg catgtggatt  83760
ggtctgctgg tgcggtggag ttgttgacgg ggcaggtggc gtggccggag gtggatcggc  83820
cgcgtcgggc gggtgtgtcg gcgttcgggg tgagtgggac gaatgcgcat gtgattgtgg  83880
agcaggcgcc tgaagtggtg gagcctgagg ctgaaggtgt ggtgttgcct gctgtgccgt  83940
gggtggtgtc gggtgtgggt gaggtggcgg tgcgggcgca ggtggagcgg ttgcgggcct  84000
tcgcggaccg gaatccgggt ctggatccgg tggatgtggg gtggtctttg gtggccaccc  84060
```

-continued

```
ggtctgggtt gtcgcatcgt gcggtggtgg tggttgcgga tggtgaggag ttgttggggg  84120
ctttggaggg tgttccggtg gtgggtgggt tgggtgtgtt gtttgcgggt caggggtcgc  84180
agcggttggg gatgggtcgt gggttgtatg aggggtatcc ggtgttcgct gcggcgtggg  84240
atgaggtgtg cgcccagctg gaccagcatc tggataggcc ggtgggtgag gtggtgtggg  84300
gtgatgatgc cgagctaatt ggcgagacgg tgtatgcgca ggcggggttg ttcgcgcttg  84360
aggtggcgct gtatcggctg gtcgcctcgt ggggtgtgag ggcggattac ctgctgggtc  84420
attcgattgg tgagttggct gcggcgtatg tggcgggtgt gtggtcgttg gaggatgcgg  84480
cgagggtggt ggcggcgcgg ggacgtttga tgcaggcgtt gccgtcgggt ggcgcgatgg  84540
tcgcggtggc ggcgtcggag ggtgaggtgc ggccgctgct gggcgagggt gtggtggttg  84600
cggcggtgaa cggtcccgag tcggtagtgg tctcgggtga tgaggatgcg gtgcatgcca  84660
tcgaggagac gttcgccatg ggtggggtgc ggacgcggcg gttgcgggtg agtcatgcgt  84720
tccattcggc tcgtatggac gggatgctcg cggagttcgg tgaggtgctt cggggcgtgg  84780
agttccgtgc cccgagcgtg cctgtcgtgt cgaacgtgtc cggtgcggtg gccggtgagg  84840
agctctgctc gccggagtat tgggtgcggc atgtgcggga aacggtccgg ttcgccgatg  84900
ggctggatac tctccgtgag ctgggtgtgg gttcgttcct ggagttgggg ccggacggga  84960
cgttgaccgc cttggcggat ggcgatggtg tgcctgtctt gcgtcgggat cgtccggagc  85020
ccctgaccgc tatggcggct ctgggcgggc tgtacgtccg ggtgtggag gtggactggg  85080
acgcggtgtt ccccggcggt cggcgggtcg atctccccac ctacgcgttc caacggcagc  85140
ggttctggtt ggagtcggcc tcggaccagc ctgcgaccag cgcggtggac gcggcgttct  85200
gggacgcggt cgagcgcggg gatgcgcggg cgctgggcat tgacgaggaa cagccgttga  85260
gtgccgtact gcccgccctc tcgtcgtggc ggagggcgcg gcaggagcag tcggtgattg  85320
atggctggcg ttatcggctc ggttggatgc cgattccggc ggtgttgggg gaggtgggcc  85380
tcatcggtac ctggctggtt gtggtcgagc cgggtgtgga cggtactgat gtggccgcag  85440
tgttgcggtc ggccggggct ggtgtcgagg ttgtgacgtc ggcggagctg agcgctggtc  85500
cggttgcggg tgtggtgtcg ttggtgtcgg tcgaggcgac ggtgtcgttg ctgcaagtcc  85560
ttgtggcggc cggggtcgat gcgccgttgt ggtgtgtgac tcgtggtgcg gtctcggtgg  85620
tcgacggtga cctggtggat cctggccagg cgggaatctg ggtctgggc cgtgtgatcg  85680
gtctggagtg tccggaccgt tggggcgggc tgatcgactt gcctggcgaa ctggacgatc  85740
gcgcggggaa tgcgctggta ggcatccttg ccgggggcac cggtgaggat caggtggcca  85800
tccgtgtcac cggcatatgg ggtgcccggc tggtgcgggc gacgccggtc ccgatcggtg  85860
acgcgggtgg tgaggctgcg gccgcgtggc gtgggcgtgg taccgcgctg gtcaccggtg  85920
gtacgggggc gttggggcgt caggtggcgc ggtggctggt gggcagtggt ctggagcggg  85980
tcgtgctgac gagccgtcgg ggggttgagg cgcccggtgc cgtcgagctg gtggctgagt  86040
tggggagccg agtgcgtgtc gtggcctgtg atgtcggcga tcgtgaggag cttgcggctc  86100
ttttggtgac gcttccggat gtgcggacca tcgtgcatgc ggcgggtgtc ctcgacgacg  86160
gggtgctcga atcgctgacg cccgagcgga tccgtgaggt gatgcgggcc aaggccgacg  86220
gcgcgcggca tctccacgag ttgacccgtg acatcgacct cgacgccttt gtgttgttct  86280
cctcggctgc cgggaccgtg ggtaatgcgg gtcaggggag ctatgcggcg gccaacgccg  86340
tcctggacgg gctggcgtgg cgtcgccggg ccgagggctt ggtggccaca tcggtggcct  86400
```

-continued

```
ggggagcctg ggccgaatcc ggtatggccg cggagatggc gcggtcgcag ggcatggatc  86460
cgaggtcggc gctcgccgcc ctggggctgg tgctggccgc tgacgagacc acggtgatgg  86520
tggccgacat cgactgggcg accttcgggg cccggttcac cgcctcacgg ccgagcccgc  86580
tgctcagcga gttgctcggc gacggatccg tgtcgaccga ggcagccgac ggcgaaccgg  86640
ccgacgcgtt cgccacccgc ctggaggcca tggccgagcg ggaacgggcg gccaccgtgc  86700
tggacctcgt ccgtacgcat gtggccgctg tcctgggaca cacggcatcc gaggcgatcg  86760
acccggcccg gcccttccag gagatcggtt tcgactcgct caccgcggtg gagctgcgga  86820
accggctcac cgcggccacc ggggtacggt tcccggcttc cgtgatctac gactacccga  86880
ccccggccgc gctcgccgag cacgtgtgcc gggaggcgct gggtccgggc ggacggacac  86940
cggctccggt ggtgccacgc ccggtggacg acgaaccgat cgccatcatc gggatgagct  87000
gccgtttccc cggcggggtg agctcgccgg aggacctgtg gggctgctg gccgagggcc  87060
gtgacgccgt gtcggacttc ccggcggacc gtggctggaa cctggccgag ctgtacgacc  87120
cggatcccga ccaccccggc tcctcgtacg tccgggcggg cggattcctt gatgacgcgg  87180
ccgcgttcga ccccggcttc ttcgggatat cgccgcgcga ggcgctcgcg atggacccgc  87240
agcagcggct attgctggag gtcgcctggg aggcgttcga gcgcgcccat atgtccccccg  87300
ccaccctcaa gggcagccgg accggggtgt tcgtcgggac caacggccag gattacgccg  87360
ctctggcgag cggggccccg cggagcgcgg aagggtatct gggcacgggc agcgccgcca  87420
gtgtcgcctc gggccggctg gcgtacacct tcggcctcga gggcccggcg gtcaccgtgg  87480
acaccgcctg ctcgtcgtcg ctggtcgcgc tgcacctcgc cgcacaggcc ctgcgctccg  87540
gtgaatgctc cttggccttg gccggtggtg cgaccgtcat ggccactccg gcggccttcc  87600
tggaattctc ccgccagcgt gcgttggcgg ccgatgggcg ctgcaaggcg ttcgcggcgg  87660
cggcggacgg caccggctgg ggcgagggcg tcggcatgct cctggtggag cggctctccg  87720
acgcggagcg caacggccac cgggtgctgg cggtgatgcg tggctccgcc gtcaatcagg  87780
acggcgcgtc caacgggctc acggcgccga acggcccgtc gcagcagcga gtgatccgtc  87840
aggccctggc gaacgcccgg ctgtccgcca cggacatcga cgtggtggag gcgcacggca  87900
ccggcaccag tctcggcgac ccgatcgagg cgcaggcact gctcgccacg tacggtcagg  87960
gccggtccca gaacaagcca ctgtggctcg gctcggtgaa gtccaacatc gggcacaccc  88020
aggcggccgc cggcgtggcc ggtgtgatca agatggtcat ggccatgcga cacggtgtac  88080
tgccgcggac cctgcatgtc gactcgccct cgccccatgt ggactgggcg gcggcccggg  88140
tcgagttgct cgtcgaagcg agggagtggc cgcggaccgg cgctcctcgc cgggcgggtg  88200
tgtcctcgtt cggggtcagt ggcaccaacg cccatgtcat cgtcgagcag gggccggtgg  88260
tggcccggcc cgatcgggag tcggcgcgcg agccgtcacc ctccgtgccg tgggtgctgt  88320
caggtgcggg gggaggccgg gctgagggcc caggtcgagc gcctggcgtc cttcatcgac  88380
gcccatccgg gcctggatcc cgccgatgtc gggtggacgc tggtggccgg ccgttcgtgt  88440
cagtcgcacc gcgccgtagt ggtgggtgca gacctcgcgg agcttcgacg tggactggac  88500
gcagtctcga ccggtggcgc cgcccggtcc ggccgcaagg tggtgttcgt cttccccggc  88560
caggggtcgc agtgggccgg aatggcgttg gaactgttgg agcattcgcc ggtgttcgcg  88620
gagcggatgc gtgcatgcgc cgatgcgctc accccgttcg ccgagtggtc gctgttcgat  88680
gtgctgggtg atgaggtggc gctcggtcgg gttgatgtgg tgcagccggt gttgtgggcg  88740
gtgatggtgt cgctggccga gttgtggcgt tcgtttggtg tggtgccgtc ggcggtggtg  88800
```

-continued

```
gggcattcgc agggtgagat cgcggcggcg tgtgtggccg ggggtctgtc gctggaggac  88860
ggtgcccgtg tggtggcctt gcggagcagg gcgttgctgg ctctgtcggg tcggggtggg  88920
atggtgtccg taccggtgtc cgccgatcgg ctccgtgacc gtgcggggtt gtcggtggcg  88980
gcggtgaacg gtccggcgtc gacggtggtg tcgggggctg ttgaggtgct ggatggggtg  89040
ctggcggagt ttccggaggc caaacggatt ccggtggatt acgcctcaca ctccccgcag  89100
gtggccgaga tccagcggga gctggcggac gtgctggcgc cggtccggcc gcgcggtgga  89160
cagatcgcgt tccactcgac ggtgaccgga cggctcaccg acacctccga actcgacgcc  89220
gactactggt accgcaacct ccggcacacc gtggaattcc agagcaccgt cgaagccctg  89280
atgaaccagg gccacaccgt gttcgtcgag gtgagcccgc accccgtgct gaccatcggc  89340
atccaggaca ccgccgagac cccaggcacc cccgacaccc caggcacccc cgacaccgcg  89400
gacgccaccg acgctcacga ggccaccggc gcccccgacg tcgccaacac cgccgacgtc  89460
accggcgctc ccgacgtcac cggcgccgac atcgtcatca ccggatcgct gcgccgcgac  89520
gacggtggcc ccgcccgctt cctcaccgcc ctcggcgacc tccacacccg gggcgtggac  89580
gtggactgga gcccggtctt caccggagcc cggacggtgg accttcccac ctacgccttc  89640
caacgggaac gcttctggct gaagcccgcg cgggcggtga cccaggcgtc cgggctgggc  89700
ctcggcgata tcgagcaccc cctgctgggc gcggtactgc ccctgcccgg ggacgagggc  89760
ggtgtgctga ccggactgct ctccctggac ggacagccct ggctggccca ccacatggtg  89820
cgggacacgg ttgtcttccc cggcacggga ttcgtcgaac tcgccctgca ggccggtcag  89880
cacttcggcc actcggtgat cgaggagctg accctgcatg ccccgctggt ggtgccggac  89940
cagggcgggg tccaggtaca ggtggccgta tcggcggcgg acgaacgggg ccggaggccg  90000
gtcacggtgc actcgtgccg tgccggggag tggctgctgc acgcctcggg cactctcggc  90060
gccaccggag gcctcgacgt caccgagccg cgcccccgccg acgtggcccg gcccctggag  90120
gtctggccgc ccgagggcgc gcggagcctc gatgtctcgg ggatgtacga ggcgatggcg  90180
gagcgcggct acgggtacgg tcccgctttc caagggctgc gcgccgcgtg gacacgggac  90240
gatgagatct acgccgaagt ggctctggag ccggaggcac aggacgtggc ggcgcggtgc  90300
ggtgcgcatc cggccctgct cgacgccgcg ctccacggag tggggctcgg ccgcttcctc  90360
accgaccccg gccaggcgta tctgccgttc tcctggagcg gggtcgcgct gcacgcggta  90420
ggcgcctccg ccatccgcgt ggtgctctcc ccggccggta cggacgcggt gtcgctggag  90480
gtgacggacc cgacgggagc gccggtgctg tcggtggcgt cgctctcgtt gcgtccgctg  90540
tccagcgggc ggatcgcgga cacccgaggg gtggaccagg actcgctgta ccgcgtggac  90600
tgggtcgaga tgccgctgcc gactgccccg gcaggctcgg ccccggccga gtacgacgcg  90660
ccggcgatgt tcgacgccct ggtattcgac gccccggtcg agtacgacgt tctcgcctcc  90720
gacgcctccg acgcctccga cgcctccgac gcccccggca cccccgacgc ctccagtgcc  90780
ccggtgcccg acatgcccga catggtggtg ctgccgtgtg agtcggccgg tgacgcggtg  90840
tccaccgtcg tgtgccgggc gctggcggcg gtacggcgat ggctcgccga cgagcgctgt  90900
gcccggtcgc ggctggccgt gctgacgcgc ggcgcgatgg ccaccgctcc cggcgagagc  90960
gtcgaagacc tcggcgcggc agcggtctgg ggcctgctcc gcagcgccca ggccgagcac  91020
ccggaccgct tcgtcctcgt cgaccacgac ggccaccagg attcccgtgc ggtgctcgcc  91080
gccgcgctgg ccgccgcggt cgacggtggc catgcgcatc tcgcgctgcg ccgtggccgt  91140
```

-continued

```
gtcctgacgc ctcagctcgc tccgctcacc ccgtccgcga ccgccctgtc caccaccgca  91200
ccgcccgccg ccaccccaac cccggaggcc ggggcaccgt ggcggatgga cgtcaccagt  91260
cagggcacgc tggagaacct ggccgccgtc ccctgcccgg aggccgccgg tgtcctcggc  91320
gccggacagg tgcgggtggc gatgcacgcg gccggggtga acttccggga cgtcgtcgtc  91380
gccctcggca tgatccccgg tcaggacgtc atcggcagcg agggtgccgg agtggtgctc  91440
gacatcggcc ccggtgtgtc cggcctggcg cccggtgacc gggtgatggg tctgttctcc  91500
ggggcgttcg gccccgtggc ggtgaccgat caccgactgt tggcgcggct gccggaaggc  91560
tggtcgttcg ccgacgccgc ggccacgccg gtggtgttcc tgaccgccat gtacgggctg  91620
atggacctgg ccggtctgcg acccggtgaa tcggtgctgc tgcactcggc cgccggcggg  91680
gtgggcatgg ccgcgacaca ggtggcccgc tggctcggcg ctgaggtgta cgccaccgcg  91740
agcccaggga agtgggacgc gctgcgcgcc ggaggagtgg cggacgaccg gatcgcctcg  91800
tcccgctcct tggagttcgc cgaccgcttc ggccgggtgg acgtggtgct gaactcgctg  91860
gcgggcgagt acgtggacgc ctcgctcggc ctgctcgccg acggtggccg tttcctggag  91920
atgggcaaga ccgacatccg cgacggtgag cgcgtggccg cggagcacgg ggtgcggtac  91980
caggcgttcg acctcatgga cgcggggccc gaccgggtcg gggaactgct caggctgctg  92040
gtgtcgctct tcgagcgagg gatcttcacg gcactgccga cccgcgtctg ggacgtccgg  92100
caggcgggtg acgcgctgcg cttcctctcg caggcacgcc acatcggcaa gctggtgctg  92160
tccattccgc agccgctgcg ggagggggac accgtgctca tcaccggcgg caccggcaca  92220
ctgggcgggc tggtcgcccg tcacctggtc gaacggcacg gagtacggga tgtcgtcctg  92280
gccggccggc gggggccgga cgccccggac gcggccgaac tcgccgccgc cctgcgcgaa  92340
tacggcgccc gggtgcgggt ggtggcctgt gacgtggccg accgggacca gctggcacgg  92400
ctgctggaca ccgtctccgg cctgcggatg gtggtgcaca ccgcgggtgt gctcgacgac  92460
ggggtgatcg agtcgctcac cccggagcgg gtgcgcgagg tcctgaggcc gaaagtggac  92520
gccgcctggt atctgcacga gctgacggcc ggtcgtgagc tggcggaatt cgtggtgttc  92580
tcctcggccg cgggtgttct gggaagcccc gggcagggcg cctacgcggc ggcgaacgcc  92640
tggctggacg cgctgatggc gcatcgccgg gccgccgggc tgccgggtct ctccgtggcc  92700
tgggggctgt gggccgagcg cagcgggatg accggccatc tgtcggaccg ggatctcgcc  92760
cggatggcca gggccggtgc cacgcctctc gccaccgatc aggggctccg gctcctggac  92820
agtgccaggg cggccaccga ggcgctcgtg ctggccacac cgctggacgc cgcggcgctg  92880
cgggcacaag ccgacgccgg ggcgctgccc gcgctcttcc gcggtctggt ccgtgcgccg  92940
atccgccgcg cgaccggcgc gggcccggtg gaggacgagt cgtcgctgcg gggccggatg  93000
gccgcgatgc cggtcgccga gcgcgaacag ctggtgctgg acctggtccg tacgcaggtg  93060
gcgaccgtgc tggggcacgg caccgccacc gcggtcgacc cggcgcgtac gttcgcggag  93120
accggcttcg actcgctcac ggccgtcgag ctgcgcaacc ggctgcgcac cgccaccggg  93180
gtcaggctgt cggccaccgc gatcttcgac tatccgacac ccgcggtcct ggccggtcat  93240
ctcctccggg agctggacgg caccgtcggc gaggccgtga cacggcccgc cgccccggcc  93300
gccgccaccg accgggaccc gatcgtgatc gtcggaatgg cctgccgcta tccgggcgga  93360
gtggcgtcgc ccgaggagtt gtgggagctg ctcgccaccg ggcgcgacgc ggtcgcggat  93420
ctgccggacg accggggctg ggacctggac ggcctgtaca gcgccgatcc ggacagctcg  93480
ggcacctcgt acgtccgctc cggtggcttc gtgtacgacg cgggcgagtt cgacgccgac  93540
```

-continued

```
ttcttcggca tctcgccgcg cgaggcgctc gcgatggatc cgcagcagcg gttgctgctg  93600
gaagtggcct gggagacggt ggagcgggcc ggtgtcccgg cggcgtcgct gaaggggagc  93660
cagaccgggg tgttcgtcgg tgccgcggca cagggctacg gcacgggggc cgggcaggcg  93720
gcggagggat ccgagggcta cttcctgacc ggtggcgcgg gcagcgtggt ctccggccgg  93780
ctctcgtaca ccttcggcct ggagggggccg gcggtcaccg tggacaccgc ctgctcgtcg  93840
tcgctggtcg cgctgcacct ggcggcgcag gccctgcggt ccggcgagtg ctcgctggca  93900
ctggccggcg gggtgacggt gatggccacc ccgggcatct tcgtggagtt ctcccgacag  93960
cgcggactgg ccgccgacgg ccgctgcaag gcgttcgccg acgcggcgga cggcaccggc  94020
tggggcgagg gcgtcggcat gctgctgctg gagcggctgt ccgacgcccg ccgcaacggc  94080
caccgggtcc tggcggtcgt acggggctcc gccgtcaacc aggacggcgc ctcgaacggc  94140
ctgacggcgc cgaacgggcc ctcgcagcag cgggtgatcc gggccgcgct ggcgaacgcc  94200
gggctggccg cgtcggacgt ggacgcggtg gaggcacacg gcaccggcac cagcctgggc  94260
gacccgatcg aggcacaggc gctgctggcc acctacgggc agcaacgcga acggccgctg  94320
ctgctgggct cgatcaagtc gaacatcggg cacacccagt cggccgcggg agtggccggt  94380
gtgatcaaga tggtgctggc gatgcggcac ggggcgctgc cccgcaccct gcacgtggac  94440
cagccgtcga cccatgtgga ctggtcggcc ggtgcggtgg agctgctgac cgagcccgcc  94500
gagtggccgg ggacctcccg cccccgccgg gccggggtgt cctcgttcgg ggtgagcggg  94560
accaacgccc atgtgatcct cgaacagcca cccgcggagg cggagtccgg gcccgctccg  94620
gagtcggcac ccgggcccgt cccggcggtg gtgcccgggc ccgtcccggc ggtggtgcca  94680
tgggtgctct ccggccaggg cgagcgcgga ctgcgggcgc aggccgcccg gttgcggtcc  94740
ttcctggccg cgcgccccga gtccggcccg gccgacgtgg gctggtcgct ggccgccacc  94800
cgttcggcgc tctcccaccg ggccgcggtg gtcggggcgg accgggcgga actgctggac  94860
ggactggccg cgcttgcggc cggcgagccc gccccgggcg tggtcttggg caccgcggac  94920
ccgggccggg tgggcgtgct gttcgcgggc cagggtacgc aacggcccgg tatggggcgt  94980
gagttgtacc agtcgttccc ggttttcgcg gcggcgtggg acgaggtgtg cgccgcgctc  95040
gacccgcatc tggaccgtcc gctcggcgag gtggtgaccg atgccaccgg cgcgctggac  95100
gccaccacgt acacgcaggc gggcctgttc gccctcgaag tgtcgctgtt ccggctggtg  95160
tcctcctggg gcgtgcggcc ggactatctg ctgggccact ccatcggcga gctggcggcc  95220
gcgcaggtgg ccggtctgtg gtcgctggag gacgccgcca aggtggtggc ggcccggggc  95280
cggctcatgg gcgcgctgcc gccgggcggg gcgatggtgg ccctggccgc gccggaggac  95340
caggtacggc cgttcctgac cgaccgggtc gccctcgcgg ccgtgaacgg gccgtcgtcg  95400
gtcgtggtgt ccggggacga ggacgcggtg tgcggtgtgg ccgaggcgtt cgccgcccgt  95460
ggggtgaaga cgcggcggct gcgggtcggc cacgccttcc actcgccgct gatggacgag  95520
atgctcatcg cgttcgccga ggtactcgac acggtggact tccgcacccc gcggataccg  95580
gtggtgtcga acctctccgg tgcggtggcg ggggaggagc tgtgctcccc cgcttactgg  95640
gtgcggcagg tgcgggagac ggtgcggttc gccgccgggc ttgagcgtct gcgggagctc  95700
ggcacgggca ccttcctcga actcgggccg gacggcaccc tcaccgcctt ggcccaggcc  95760
cagatcaccg ggcggacgc cgagttcatc cccactctgc gcgccgaccg gcccgagccg  95820
gtcacggtca ccaccgccct cgcccagttg cacacacacg gtgtggagcc ggactggtcc  95880
```

-continued

```
gcggtcttcc ccggcgccca ccgggccgag ctgccgacct acgccttcca gcgctcccgc  95940
ttctggctgg agccctcccg tacacccggt gacgcgggcg acttcgggct cggcgcgctg  96000
gaccatccgc tggtcggcgc gagggtgccg ctgcccgacg cggacggcgt tctgctcacc  96060
ggccgcatct ccgccgaggc ccactcgtgg ctgatcggtc agcgggcgct gggcgtgccc  96120
ctgttcccgg cgaccggctt cctggaactg gtgctccagg cggggctcca gtgcgacagc  96180
cggacggtgg acgaactcac catccatgaa ccactcgtcc tccccgagcg gggcggggtc  96240
gaggtgcagg tgtccgtccg tggcgccgac gagtccggcc gccgcccggc caccgtgtac  96300
tgccgccgcg accagcggtg ggtccggcat gccacggccg tcctcggcgc ggaccggccg  96360
cccgcgccgg agccgcgccc cgagccctgg ccgcccaccg gcgcccggcc gctggagtcc  96420
ggcgggacac cggcgtggcg ccgtgacgac gaggtcttcc tggacatcga gctgcccgag  96480
gtggccgggg ccgaggccga acgctggacg ctgcatcccg ccctgctcga acaggcgttg  96540
cgcggggagg cgctggcagg gctggtcacg gcggccgagg ggacccatct gccgttctcc  96600
tggacgggga tcaccctgca cacgacgggt gccacgagac tgcgagccac cctcgcgccc  96660
gtcggcccgg acacggtctc gctccacgtg gccgacgccg ccggaacacc cgtgctgtcg  96720
gtggactcgc tggcgctccg cccggtgtcc ggacagcggc tgcgccaggc caacgcggcg  96780
ctgttccggc cggtgtgggc ggcttgccgc acgcgggccg aaccggacac cggctctgtc  96840
cgatgggggc tcgtcggcga cccggacgcc tggaaaccgg acacgctcgg cgcgccggtc  96900
gcgctgtacc cggacctgtc ggccatcgag gacgtaccgg acgtcatcct cctcccgtgc  96960
gtatccgagg gcggaacggc gtccgaggtg gccgtccgcg tatccgagac cgtgcggacg  97020
tggttggccg gggagcggtt cgccgcctcg cgtctggtgc tggtgacccg gggcgcgctc  97080
gccacggcgg ccggtgagga gctcgaggac ctggccgcgg ccgcggtgtg gtcgctggtc  97140
gagcccctcc aggcggccgt ggcgggacgg ctgacactcg tcgacaccga tacgtccgat  97200
ctgcgcatgc tgcccgccgc ggtggccgtg ggggaggacc gggtcgcggt ccgggcggga  97260
gcggtgctgg taccggacct ggtcacgccg ccggccaccg agcaggatcc gcccgcctgg  97320
ggcccgggga cggtgctggt caccggtggg tcggccatgg ctgtctcccg gcatctggtc  97380
gccgaacgcg gtgtgcgtga cctggtcctg gccggggacg gcgacatggc cgaactggcg  97440
gccctcggag ccacggttcg gctcgccccg tgtgatccgg cggacggtca ggcgctggcg  97500
gcgctggtgg cggagattcc cgggctgcgg agcgtggtgc acaccgcggc cgacgccccg  97560
gagcggaccc ggtccctctt gccggaatcc ctgcggccac agctgcggtc gggagtggcg  97620
gcggcctgga acctgcacct ggccacgcgg ggcctggaac tggaccgctt tgtgctgttc  97680
acctccgccg acgggacact gggcccccgcg tacgccgacg cgctggccgc acaccggcgg  97740
gctcgcggac tgcccgcggt gtccgtctcc accgatctgg gtctcgccct gttcgacgag  97800
gcatgcgccg ggcccgggga ggcgatccgg gtcaccaccg ccacgccggc ccccgcaccc  97860
accgaggcgg accggcagcc ggtggaacaa cccccggcgg ccgaggcctc cgcgaccacg  97920
ttgctggagc ggctggccgg gcggacggag gacgagcagg acgagatcct gctggagctg  97980
gtccgtggcc aggtcgccat ggtgctcggc catcccgacg ccaccatggt cgacccggac  98040
cgaggcttcg tggaactggg cttcgactcg gtggcggccg tgaagctccg caaccaactg  98100
gccggagcca cccggctcga cctgcccgcc agcctcacct tcgaccaccc cacggctgtc  98160
gatctcgccc gccatctgcg cgccgaaatg ctgcccgacg acgcggcggc cgccattctc  98220
gtgctcgaag agctcaacaa gctcgacgat tcgatcctcg tgctcgaccc ggcaagcgcg  98280
```

-continued

```
gcacgggtgc ggatctcgac cctgctccag gacctggccg cgaaatgggt cgagcggacg  98340
gatcggccat gaccacacac gatcagttga tgcgcgaacg agggagtcaa cagtgagcga  98400
gaccttgtcc cttcccggga ccgtgaaggc cgaacggcgt tgtccgtacg acccgccgga  98460
ggcgcaccgc cgactgcggg acaagggcga actgggcaaa ctggagctgc ccggcggtct  98520
ggtgatgtgg ttcctgacca agcacgacga catcagggcc atgctggccg actcccggtt  98580
cagcggtgcg agggtgccgt ttccggcgat gaacccggag atacccgcgg gcttcttctt  98640
ctccatggac ccgccggacc acacccgcta ccgccgcaca ctcaccgccg agttctcggt  98700
gcgcggcgca cgcgaactga ccggccggat cgagcggctg gccgaccggc acctcgatgc  98760
gatggaggcg gcgggcacga gcgcggacct cgtggcggcc tacgccagtc cggtgcccgc  98820
gatggtgatc tccgaaatcc tcggcgtgcc gtacacctac caccagaagt tcgaccacga  98880
ggtacgcacg ctccgggaga ccggcggcga cgatcaggcc gtcggcgcga tggcgaccgc  98940
gtggtgggac gagatgcgcg gattcgtgcg tgccaaacgg gccgagcccg gggacgacat  99000
gatcagcagg ctgctgcatg atgaggtcga gggcggtgcg ctgaccgacg aggaggtggt  99060
cggcattgcg atgaccatca ttttcgccgg tcatgaaccc gtggagaacc tgatcggcct  99120
cggcatgctg gcgctgttcc aggacggtga gcagctgacc cggttgcggg agaaccccga  99180
cctcattgac agcgccgtgg aggagttcct tcgctacttc cccgtcaaca acttcggcac  99240
cgtgcgcacc gccaccgagg atgcagtgat caatggtcac cccatcgcga agggcgagat  99300
cgtggccggt ctggtgtcca ccgccaaccg ggaccccgag cggttcgccg atcccgaccg  99360
ccttgtcctc gaccggtcgc acacctccca cctcgcgttc gggcacggtg tgcaccagtg  99420
tctgggccag cagctggcga gggtggaact gaaggtgctc ctacagcggc tgctcgtcag  99480
gttccccgct ctgcggctgg cggtggcccc ggaggagatc aggtaccggg agaacacctc  99540
gttctacggt gtccacgagc tcccggtgac ctgggcggcc gagtagccgc agccggggcc  99600
ggaagacacg gcgcgggcgg tggccgcggg gtccggcgcg agcggtggcc ggatacccgg  99660
ccaccggctc agccggcccg ggtgacgccc actgccgccc tgagatccgc ccagaactcc  99720
ggccgaccgc ggatctcaag agccgagccg gccgccggtc aggcgtgcca gcgggcggcg  99780
gcgacgagcc gcgcgcctgc gcaggacgac cgcggcggtg gcgcccgccg cggcggcacc  99840
cgcaccggcg acggctgcca ggaccttccg ggccttgatc atcatccagg ccgaacccgc  99900
cgccgcggca gccttcttgg gcgcctcagc ggccacggta cgaccggtgg tcacggcctt  99960
cccggcggcc acttgagcct tgtcggcggc gacatgagcg gtgtgcgccg cggtcgtcgc 100020
cgcgccggcc gcggcggtct tcgccgtggt ctccgccttg cccgcggtgt ccttggccct 100080
ttccgcggtc tccttggcct tggtggcggt ggccttcgcg ttcacgttgg tgctccgggt 100140
agtgtgtgcg ttcttcttct cggtcatgtt caccgcgtta ccactcgacc cgacaacaaa 100200
cccgcgtcct cggggccggc cgccacggcg tgacgatccg agggggcggc acaccgggag 100260
gcgcgccgcc catcggctca ttcgatgtct gagccgcccg aaccacccga gccgcgccgc 100320
tgctggaaca gcacaaaccc tccggccagg gcgaacagac agacgccgat gatgatgccc 100380
acggcgggcc aagcggatcc gccgtcggat gtcgcggcct tcgaaggctc cagcgatgtg 100440
gcatcgggca actgtcttac gacgaaactg tgttcggcgt tctcgccggg tgcgagcgcc 100500
gggccgccga ccgagtagcc gtcatcggtg ggcttcagct tccagccctt cggggcctgc 100560
ttcagcctca catcgccggg gtcgatgccc gtgggcaaca cggtccggat ctcggtgaaa 100620
```

-continued ccggccctcc cgtcctccgc ctccgactcg aacgtcagcg tgacgtcctt cgccagggcg 100680
cgggagtcgg aggcgctcac ctcggtgtgg gccagggcgg gggtcgccgt ggcgaggacg 100740
agcgccgagg tggcgacggc cagggcgccg atccgtcgcg gccgcgggtg ggacggcgga 100800
cgatgtgctt tcacggtatc tctcctcgtc catggggtgg tcacccgagc cctcctcacc 100860
ggtcacccgg cgcgctcacc aggtgcgttc acattccccg gtacgtacgg cccgggcgcg 100920
atgttcatcc tcgcccagac cggaagcccg cttgccacgc gggggagcaa ggagttccgg 100980
cgtcttcgtg gcccgcgcaa ggcggaccga gggggtcgcc gcgtcccagt gcggtgatgt 101040
gcccggtggt caggtggtcc gctggtcccg cagggtccgg gacagctcct cctcggtgag 101100
cacccggggc gcgggtccgg caccgggctt cgtctcggcg ccgttcgccg ggctcttgtt 101160
ctcggtcgtc gtcatgaggg tgcacctttc gctggtggtg gcggaggacg ggatcaggcg 101220
gtggcgaccg gtgtggcggg cggattggcg ttccgcggca cagcgggggg cttgcgcgca 101280
ggtcctcgca gtacggtgaa cgccaccgcg aaggccgcca cgatgagccc cgttccgacg 101340
gcgaaggcca ggtggtagcc gccggtcagc gcctcggccc gacccttgcc ccgggagagc 101400
agggcatccg tgcgggaggc ggccagggtg gacagcaccg cgacgcccag cgccatgccg 101460
atctgctggg tggtgttgaa cagcccggag acgagcccgg cctcgtcctc cttcgcaccg 101520
gacattccca ggctggtcag cgcagggagc gccagcccga aaccggcggc gagcagcatc 101580
accgggagga ggtcggggag gtaccgggcg tgcacgggga cgcggacgag caggccgaga 101640
acgccggtca ggagggccag cccggtcagc agcaccgcgc ggtcgccgaa gcgtgcgctg 101700
agccgtgcgg agacgccgag ggacaccgcg ccgatggcga tggcggccgg gagcatggcc 101760
agaccggttc cggtggcgtc gtaccccagc acattgcgca gatagagggc gaccaggatc 101820
tggaacgaga agagcgcggc caccatcagg agctggacca gattggcccc cgccaccccg 101880
cgcgaccgca ggatccgcag gggcatcagc ggggtgcggg cggtggtctg gcggaccagg 101940
aacagggcga tcaggaggat cgagacggcg ccgaggccga gtgtgcgcgc cgccgtccag 102000
ccgtagtccg ccaccttgac cacggtgtag atgcccagca tcagcccggt cgtgaccagc 102060
agggcgccga ggacatcggc gccggccgcg aggcccggcc cgcggtcggc gggcaggacg 102120
ggtatggcga ccgcgagcgt cagcagcccg atcggcagat tgatcaggaa gatccagtgc 102180
cagctgagcg cgtcggtgag gaggccgccg agcacctggc cgatcgacgc tccggcggcg 102240
ccggtgaagc tgaacacggc gatcgccttc gaccgttcgg cgcgttcggt gaagagcgtg 102300
acgaggatgc ccaggctgac cgccgaggcc atcgcgctgc cgaccccctg gaggaaccgt 102360
gcggcgatca gcacagcggg ggaggtggcc acggccgcga gcaacgaggc cgcggtgaac 102420
accgcggtac cggtcaggaa cacccgcttg cggccgatga gatcgccgat acggccgccg 102480
agcagcagca gaccgccgaa cgcgatcagg taggcgttga cgacccagct gagcccggcg 102540
ggggagaacc gcagatcgct ctggatggcg ggcatggcca cggtcacgat gctgccgtcg 102600
aggatcacca tcagcatgcc ggtggcgatg accccgaggg ccagtcgacg tgtcgggggg 102660
acacggggag acgtcgggtc ggaagaggcg gcggacatgc ggacactcct gtcagtaggc 102720
gcgacaggag tgaccgtagc agatggtttt gttgcagact atttgtttcg gctctacttg 102780
tggcgcatga cgggcggccg cgcggatgtc tccgctctac ttctcgcgct gccgcgccct 102840
ccgcgccggg cgggggctct cggcgggcgt ggccagatgc ccctcggaca gccgggtcaa 102900
cgcctttagc agcgcggcgc gttgggtctc ggggagtgtc gccaacgcct cgcgatggac 102960
gcggtccacg atctcctggc tccgttcggc gatccgcgcg ccctcctcgg tgaccgcgat 103020

-continued gatccgggcc cggcgatcgt gggtcgaggc gcgccgctcc gcgaggcccg ccttctccag 103080
ggcgtccacc gtcaccacca tcgtggtctt gtccatgtcg ccgatctcgg cgagctgggc 103140
ctgggtgcgc tcttcctcca gggcgtggac cagtacgcag tgcatccgcg ccgtcagccc 103200
gatttcggcg agcgcggccg acatctgggt gcggaggacg tggctggtgt ggtcgaggag 103260
gaacgacagg tcgggttcgg tcttggtggg cgccatggcg gtcatgcggc ccagggtaac 103320
aattcgatcc gtactggatt atccggaaca gtccataggg aggggtgggg tcaggggtca 103380
gccgttgcgg tagagggcgg tgagcagctc gaccgcggtc tgggtggcgg ggtgcgggtc 103440
gtcccgccac caggcgaggc gtaccgcgat gggctcggcg tcgcggaccg gccggtaggc 103500
gattccgggc ctcggatact ggttggccgt ggactccgcc gtcatgccga cgcagcggcc 103560
cgcggagatc acggtgagcc agtcctccac gtcgtgggtc tcctccgtgg ccggccggga 103620
gtcgggcggc cacagctccg tggtggtggt accggtcctg cggtcgacca gcagggtgcg 103680
cccgctgagg tcggccagcc ggaccgagcg gcgcctggcg agcgggtcgt cggcggccac 103740
ggcgcacagc cgccgctcca gtccgacgat ggcggagtcg aagcggcgct cgtcgagcgg 103800
tctgcgcacc acggccaggt cgcaggcgcc ctccgtcagc cccgcggtgg cggaattgac 103860
gcggacgagg tgcagctccg tctcgggata cgcctgcgcc cagcggcgct ggaaggcggg 103920
ggtgtgacgg cccagcgcgg accaggcgta gccgatccgc agatgggcgt ggcccgatac 103980
ggcctcccgg atcagcccgt ccacctcggc cagcacccgc cgggcgtgtg ccaccacccg 104040
cagcccggtg cccgtcgggg tcacctcgcg ggaggtccgc cgcaacagcc ttgtccccag 104100
ggcgcgttcg agcgctgcca gggtgcggga cacggccgcc tgggagacgc cgagcgcgat 104160
ggcggcgtcg gtgaaggtgc cctcgtcgac gatcgcgacg aggcagcgca gttgccgtag 104220
ctccacatcc atacgtccag cgtatagata gaaccccgaa cgcattttgc gcatgcatga 104280
gccgggcgca cgatcgacgc atgcgactcg cccccgcgtc acgcaccccg tccccacgag 104340
cgatggacac cgcacaccgg accgcgccga cccctgccga ctacgacctg ggacagggcc 104400
tggagcgggg cctggcccct gaccctgatc agcggccgac cggacggcgg ttcgccggtg 104460
tggccacgat gatcggcagt gggctgtcca accagaccgg cgccgcgatc ggatcccagg 104520
ccttccccgt catcggcccg gtcggggtcg tcgccgtccg ccagtacgtg gccgcgatcg 104580
tcctgctggc cgtcggcagg ccccggttgc ggagcttcac ctggtggcag tggcggccgg 104640
tggtggggct cgccgtggtg ttcggcacca tgaatctgtc cctgtacagc gccatcgacc 104700
gcatcggcct cgggctggcg gtgaccctgg agttcctcgg cccgctgtgc atcgcgctcg 104760
ccggctcacg gcgccgcgtg gacgcctgct gtgcgctggt cgcggcggcc gccgtggtga 104820
ccctcatgcg cccgcgcccc tcggccgact atctgggtat ggggctgggg ttgctggccg 104880
ccgtgtgctg ggcgtcgtac atcctgctca accgcaccgt ggggcggcgg gtccccggcg 104940
cccaggggtc ggcggcggcc gcggggatct ccgcgctgat gttcctgccg gtcgggatcg 105000
ccgtcgccgt ccaccagccg ccgaccgtga gcgccgcggc gtacgccatc atcgcgggcg 105060
tcctctcctc ggccgtgccg tacctcgcgg acctgttcac gctgcgccgc gtgcccgccc 105120
aggcgttcgg gctcttcatg agcgtcaacc ccgtcctcgc cgcactggtc ggctgggtcg 105180
gcctggggca gagcctgggg tggacggagt ggatcagcgt gggcgccatc gtcgcggcca 105240
acgcgctgag catcctcacc cggcgcggct gaaggaccag cgggggtggc ccggtgactt 105300
ggctgacctg gacccggggg tggacccggg gacggagggc cgcgccgccc ccaggccacc 105360

-continued

```
gctccgcccc cgggccaccg ctcagcccgc ggcctcgaac agcgcctccg cggcggcgat 105420
cgcctcggcc agggcggtgg gctccggccg cagccccgcc acgatcgtgt cgatggcgcg 105480
caggtccgcc cgctggagga gccgcttctc gttggtgacc cactcaccgc gcgccgccag 105540
caccgcgtgc gccgtctgga gggcggcggt cgccaccgcc cccgcgacct cggtggcctg 105600
gccacgtccc acgtacgcgg ccgaggcgta ccgcagggtc aaggccgccc gcccgcgcca 105660
cgccgggggt gccgcctcac gcagcgccgc cgggtactcg gggcggggca gggtgccccg 105720
cagcacctgg ttcagggcga gttcggccac caccagatag ctggggatgc ccgcgaggtg 105780
gaacatcagc ggctcccagt ggaagcggcc ccgtcgcgac tcggcgagtt cgtgttccac 105840
cacctcgagg tcgcggtagt ggacgtccac gcgccgtccg tcgatcgtca gccaggcgcc 105900
cccgttgaag acaccaccgc cccactcgcc gagctcggag acctcgccct cccagcccac 105960
ggcccgcagc gcggccgggt cgaagccgcc tcggtagtac agggccaggt cccagtcgct 106020
ctccggggtg tgggtcccct gcgcacgcga gcccccgagg gcgacggcgt gcacggcggg 106080
cagggcggcg agtcgctctg cgacatcgtc gaggaacgtg tcgtcggtca tgaggaacat 106140
gtcgtcggtc atacggatcc gatcgtgtga agtggatgac gggtgccgcg ggcacaccga 106200
acgcacgccg gagcacaggc tcgaacggcg gcgtccatac ggatcggtgt gccgggtcat 106260
cactccatga cgccgacctt accgcccccg tcagagggcg gcagcggcca gcggcggatc 106320
agtccttcac caggcccagg cggaacaggc tctccgcggt gtcgaggatg gtcgtcaccg 106380
ggtcgcgcgg ggtccagccg aacacggaac gcgccttctc ggtgcgcagg atcggcaccc 106440
gctccgtcac gccgaccgct tcccgcgctc gttcgtcgtc gaactcccgc gtgggcaccc 106500
gggcggcgcg ctcgccgagg tgctcggcca gcacctgggc gatccacagg aagctgacgg 106560
tccggtcgcc gctggcgagg aagcgctctc cggccgcggc ggggtgtgcc atggcccgga 106620
ggtggagctc ggcgacatcg cgcacgtcca ccatgccgaa gtgtgcgcgg gggacggccg 106680
acatcgcccc ctccagcatc gcccggacgt gttccgtcga ggcggacagc cgggggccga 106740
gtgccggacc gaagatcccg gtcgggttga tcaccgtcag ttcgaggccg tccccctcct 106800
tcgccacgaa gtcccaggcg gccagctccg cgatggtctt cgagcggatg tagggcgggt 106860
tgtcgtcctc ggggtcggtc cagtcgctct cgtcgtactc gtcaccgtcc ttgtggctgt 106920
atcccaccgc ggcgaacgag gacgtcatca cgacccgttt cacaccctgg tcccgtgcgg 106980
ccctcagcac acgaagggtg ccgtcccgcg cggggacgat cagctcgtcg gcgttgtccg 107040
gctggacggc ggggaacggt gacgcgacgt ggtggacgcg ggtgcacccc gccatcgcgt 107100
cgtcccagcc gtcgtccgtg gtcaggtcgg cgctgacgat atcgagccgc ccgccgggat 107160
cgacaccgga ggccgcgatg gccgaccgga cactcgcggc ggcgccggtg gccgggccgt 107220
gtgaacggac cgtggtgcgg acccgatggc cgctccgcag caggccgctg atcacatggg 107280
tgccgagata gccgctgcct cctgtcacca ggacgagttc gccactaacg gtgtcgccac 107340
gggcgtcggc gccggcatca gcggacacgg gggttgcctt gctttccatg gggtacttcg 107400
gatcccttcc caagtgtgtt tctcgcagct gtgtctctca cggccgcagc gcgtcgatga 107460
cgtccgtcag ttcgtcgatc gcccggcgct ccgcatcggc gtcggcgcgc tcccgcgcgt 107520
cccacatgtc cgccttgagc cgcagatagc gcagccggac ctccatgagc gcgatctccc 107580
gctccaggcg gtccgcgttg cgttggaaga ggtcacgcag gggagccgca ccctgatcgc 107640
cttcgtcgag gtggccgagg taggcgcgca tgtcctgcat gctcatgccg gtggatctca 107700
ggcaccccag cgacctgatc gtctccacca cggagggggg atagcgccgg tggccactgt 107760
```

-continued cccggtcgcg gtccacggcg gggatcaagc cgatcttctc gtagtagcgc agtgtcggct 107820
ccgagaggcc actcagcctc gacacctgct ggatggtcat cggggagccc cggacctctg 107880
tcctcgtcgt tgtcatagga cgagcatccg atacttgaag cgcttgaggt caagcgagcc 107940
gatcggcctt tgcggggacg gcggtcccgg aagtgggcgc gcccgggcgc ttcccggccg 108000
tggcgatgga gatgtcccgc atgaggagca gcgccccgag ggcgaggagc ccggcggcgc 108060
cgccgctcca ggagacggtg gagccgatgg ccgtggcggt gggcgcggcc gcgccggagt 108120
ggccgatcag ggactgggcg ctggccaggc cgaccgcgcc accgagctgc ttggtgagcg 108180
cggaacccgc ggtggcggtg cccatgtccg cacgcgggac ggcgctctgg gtggcgatgg 108240
tgagcccgcc catggccggt cccgcgccga gcccgacgag cagcagcaga acggacgtca 108300
gcgcgagagg ggtcgtggcc cgcagggcga cgaaggcggc ggtaccggcg gtgagcagcc 108360
ccgcgccgat cagcaggacc ggcttgacgt gcccgctgcg cagcacggtg gcggcggtga 108420
gccggttgcc cagggtcatg ccgatgagca gggggagcag cagcagaccg gaggcggtgg 108480
ccgaatggcc gcggatgtgc tggaagtaca gcggcaggaa gattcccacc ggcgccgcgg 108540
cgacctggaa gaagaaaccg gcggtcagca gggcggtgta ggtgcggtgc cggaacagcc 108600
gcaggggcag gacggggacg gcggcccgcc gctcgaccgg tatgagcgtg gtgagcagcg 108660
ccagaccgcc gagcagacag cccagcacgg ccgggtccgt ccaggagggc gcgtgtccgg 108720
cggtcgcgtt cccettgagg ctgaggccgg tcagcgcgag ggcgagcccc gcggcgagca 108780
ggaggatccc cgccacgtcg agccggccgg acggcggggt ggcgggacgg cggtcgggca 108840
gggccaggac gatgacggcg cccgcggcca gcccgagcgg gaggttgagc cagaacgccc 108900
agcgccagcc gatgtgatcg gcgagtaacc cgccgaggag cgggccgccc accatgccca 108960
ggatcatcat ggcggccatc gccgtctgca tccggatgag gccctggggg cgggacggcg 109020
ggtggaggtc gcggaccagt gccatgccga gggtcagcag ggatccggca cccaggccct 109080
ggagcgcgcg ggagaggatc agggcgggca tcgaggcgga caggccgcag gcgatggagc 109140
cgatcaggaa gacgccgagc ccgccgatca gcagccggcg gcggccgtgg aggtcggaga 109200
agcggccgta gaccggcacg ctgaccgagg aggtcagcag ataggcggtg acgagccaga 109260
cgtaccagga gtcccctccg ccgatctgct cgacgatgcg gggcagcgcg gtgccgacca 109320
cggtgccgtc cagcatggcc aggaaggcgc agcccagcag ggcgatggtg accagggccc 109380
ggcggcggtg cgggagcgct tcgtacccgt cgggtccggt caccgggcct ccccgggcgc 109440
cacgagcgcg ccgtgcagga agaggtccac gacttcctcg gtggtcagcg gctcgggggc 109500
gcccaggcgc ccggccgaca tcagcgtcag ctggaaggcg tcggcgagcc gttccggggc 109560
gagtcgcagg cggtcccggt cgggctcgaa cagcgcggcc agcgcggcgc gcggccggac 109620
caggctcgcc tcgcggtccg ggaggcgccc gtccttgccg ggcttgggcg ccatgcgctc 109680
cagccgcccg gccgccgcga gcgccccggc gaccgcgccg atgcgcgcca tgtgtccgcg 109740
caccacatcg gccgcctcgg cgagccggtc cgcaagcggc tggtcaaggg cgatcgactc 109800
cagatgggcc acggtgtcat cgggccgcac ggcctccgcc atacaggccg cgagcagggc 109860
gtccttgtcc tcgaagacgc ggaagatagt gccttccccg atgcccgcgg cccgggcgat 109920
cttcgcggtc gtcacggtgg cgccgtattc gacgacgagg gggagcgcgg cggcgacgat 109980
catcgcgcgg cgctggtcgg gatccatggc cggagcgcgg cggcgggtcg gagtggaggg 110040
gttctctgcc ttctctgtca tgcgggatac ggtacggagt gagtactcac tccgtcaatg 110100

-continued cacggtgcgc ggccacaagg cgagtggcgg ttcggcttcg acgttgtcgg tcagcgcgcg 110160
gcgagcaggg cccggcgcag ggcgcggccc gcctcggacg ggggatggtt gcgcgaggcg 110220
gcgaggccga gaccgtgcag cggcggtgga tcggcgagat cgacctgggt caggccgggc 110280
cgcgaggcga tggtctcctc ggccacgaag gcgagcccga gacgccgccg gaccatggtc 110340
agggcggtcg tggtgtcgac gacctccagt gccacggtgc gctgaactcc ggcggtgccg 110400
aagaggctgt cgacgatggt gcggtcgccc caccccgtgg ggaagtcgat gaagcggcgg 110460
tcggcgaggt cggcgtaggt cacgccgtgc gcctcggcga gggggtcgtc ggtgcggcag 110520
gccagcccga ggcgtatccg cgacacatca tcgatgatca gatccgggcc gaggacggcg 110580
gggccgtgcg ggggcaccgg cagcagcatc aggtcgaacc tgccctcgcg cagggcggtg 110640
gcgtgtccgg ccagcggacc ggtcgagtgg cgcagccgca ccacgacatc ggggtgctcg 110700
gcctgaaacg tgctcagcgc cccgatcagg tcgaacgagc cggtggacag gaccgtcccg 110760
agggtgaccg taccgctgag ccccccggtg agacggccca tgtcatcgcg cgcccgctgc 110820
gcctccgcga gcaggatccg ggcccgggcc agcagggtgc gccccgcggt ggtcagctcc 110880
agggtgcggt gcgagcggtc gaagagcgcg gtctggaact cctgctccag ccgggccacg 110940
gcggcggagg ccgccgactg gacgacgtgt tcccgctggg cgccgcgggt gaagctgcgc 111000
tcctcggcca ccgcgacgaa gtacgccagc tgccggagct ccaccatcat ctccattcgc 111060
gatgccacac agcacacatc atcgttggac acgataccta tgggaccgcc accgtggagg 111120
ggaagcggaa cgccccggcc ggacggcccg gttcggcgcc acgcccccca acttccccgt 111180
gtgccagcac acttcaccac ggaaggcatc catcgtcatg agcgtctcag ccatccagat 111240
cgggctccac cccgatgcca tcgactacga ggcgccggag ttcgccgcct tcgccggtct 111300
gagccgggag acgttgcgcg ccgccaacga cgacaacctc gccctgctgc tcgacgccgg 111360
atacgaggcg gacggctgtc agatcgactt cggggagacc gccctcgaca ccatccgcgc 111420
catgctcggc cgcaagcgct acgacgcggt cctcatcggc gccggggtac ggctcaccgc 111480
gggcaataca ctgctcttcg aatccatcgt caacctcgtc cacaccgcgt tgccccacgc 111540
gcggttcatc ttcaaccact ccgccgcggc cacccccgac gacatccgcc gccactaccc 111600
cgacccggcc tccaccgttc ccctcgacgt cccccgcgac ctcgaggagg ccgcgctgaa 111660
gaaccccggc aacgccgccc gccccgaagc cgcccacggc ccgcgggaga cgcggtgacc 111720
gccccggccc ggccccacgg tgaggcgaac ccggaccttc acaccacgga tgtgctcgtc 111780
gtcggcggcg ggccgaccgg aatgaccctg gccggggatc tggcacgggc cggacgcgcg 111840
gtcaccgtgc tggaacgccg gccggcgatc catccgtcca gccgtgcctt cgtcaccatg 111900
ccccgcaccc tggaagtcct cgacagccgt ggtctggccg acgacctcct ggccggggcg 111960
aacaccaccg aagcggtcca cctgttcgcg ggcgccacgc tcgatctgac acatctgccc 112020
tcccgccacc gatacgggat gatcaccccg cagaccaatg tggaccaggc gctcgaacgc 112080
tacgcccgcg accagggcgc ccgggtgctg cgcggcaccg aggtcaccgg cctcgcccag 112140
gacgccgacg cggtcaccgt caccgcccgc gccgacggcg gcggacccgc ttccacgtgg 112200
cgagcccggt acgtcgtggg ggcggacggg gcgcacagca ccgtccgcgg cctcctcggc 112260
gccgacttcc ccggaaggac ggttctgacc tccgtggtgc tggccgatgt ccgcctcgcc 112320
gacggcccca ccgggaacgg gctcaccctg ggcaacaccc ctgaggtctt cggcttcctc 112380
gtgccgtacg ggaaggcgcg ccccggctgg taccggtcga tgacctggga ccgccgccac 112440
caactgcccg acaaggccgc cgtggaggag gcggaggtca cccgcgtact ggccgaggcc 112500

-continued

```
atgggacgtg acgtcggggt ccgtgagatc ggctggcact cccggttcca ctgcgatgaa 112560
cgccaggtcc gctcctaccg gcacggccgg gtcttcctcg ccggggacgc cgcccacgtg 112620
cactccccga tgggcggcca gggcatgaac accggcgtcc aggacgcggc caacctcgcc 112680
tggaagctcg acctcgccct cggcggcgcc gacccggcca tcctggacac ctaccaccgg 112740
gagcgccacc ccgtcggccg ccgtgtcctg ctccagagcg gtgccatgat gcgcgccgtc 112800
accctcgggc cgcgcccggc gcggtggctg cgcgaccatc tggccccggc cctgctgggc 112860
gtcggccggg tgcgcgacac catcgccgga agcttcaccg gcgtcacccc gcgctatccg 112920
cgcggacggc gacagcacgc actggtgggc acccgcgcca ccgaagtccc gctcgccgag 112980
ggccggttga ccgaactgca gcgggccggt ggctttctgc tgatccgcga gcggggcgcg 113040
gcgcgcgtcg acaccacggt ggcccaggcc gagcgcaccg actccggccc cgccctgctg 113100
gtccgccccg acggctatat cgcctgggcc ggacccggtg tccgtacgga cggccccgac 113160
ggctggcaca ccacatggcg ggcctggacc ggcccggcca ccgatgcggt gcgcgccggg 113220
cgctgaacag gagacgggga gacggcgccg ggcgggcggc ccggcgccga cgccctcatc 113280
cgttccccgt cgcctgcccg gcggacaggg agtcggggag ggcagcggcg gccggttcct 113340
cgggtcgtcc cttgcggaag aaccggagca gcgacgggcc gccccggaaa caccacagcg 113400
cgatgaccgg atcgcagatc gcacagccca gcgacgagcc atgcgcgaac gggacgatgg 113460
ggttgccctt gatgtgatgc acgatgtccc acgcggtgtg cagcagccag ccgatgccga 113520
tgaaggtcca cgactccagg ccacggtagg ccacataggt ggcgaccacg gtgaaggcga 113580
actcccagcc gtccaggccg ccgccgctga ggtaggccgc acccgctccg ccgaccatga 113640
tcgcgttgaa gcgccggcgg tgcggttcgc gaatcaggga catcaggagc gcgtagagga 113700
caccgatgaa gaccggagcg atgtattgga tcatgcggaa gaacttcctg cgggtgacgg 113760
aacgttggcc gcccggcggg gcgacggttc atcacgctag atccgccccc ggccgcccca 113820
cagggccatt cccgacacgc tccaacggat aatcgccggg gccggatcat cgccgtggcc 113880
acggcctcca cccggccacc acgctcaggg cccgatcaca gcagccgcca caggtggtca 113940
tcggttccgt tgtcgtcgta ctgcaccacc tgggcgctgt tggcggtgga catgccgtcg 114000
acacccagca ccttctggct gttcttgttg aggacgcgga accagccgtc gccgttgtcc 114060
accttccgcc agaggtgatc ggccgtgccg ttgtcctcgt actggacgac gatggcgctg 114120
ttcgcggtgg acatccggtc gacgcccagg accttgccgc tgtggccgtt gcggatcagg 114180
aaccagccgt cgccccggtc gatccactgc caggcgtggt cgcccgtcgg tgtgttgtcg 114240
tactgcacca cgcgggcgct gttggccgtg gacatctcgt cgacggcgag caccttgccg 114300
ctgtgcttgt tgagcagtcg gcggaagggc ggctccgggg tccacgcccg gccgtccggc 114360
gcggccgtgg gaaagcaggt gatacgcagc cgggcggcgc ccatggggat gagggtgacc 114420
gtctccgccg gtgcgtcggc ccgggccggg ctctgctgaa gcggggtgac cacatgctcg 114480
tcgtccgaga cccactcggc gatacggcgc gcctgggcgg tcatgcggac cggggtggtc 114540
tcgtgggtga agggattggc ggcgagcgga ccgtcgtcgc gggtgagcac ggggagggct 114600
ccgggggcga ggccgtagtt ccacggagtg gtggcgtgca cttcgtactc ggggaaggtg 114660
tcggtgccgg cgtagcgcac gaagtcctcg ccgatgcgca gggagtacgt cagcgggccg 114720
tggtcgacgc tgaccgcgcc gtgctgcgcc gaccaggtcc gcagggcggt gcgctgcggc 114780
aggcggatcg tcaccacatc gccgtccgtc cagctccggt cgaccttgac gaaggccgga 114840
```

-continued

```
ccgccgcgcg tggccaccgc ccggccgttg acctcgatcc gggggttctt gcaccagccg 114900

gggacccgca gatggagcgg gaaggccacc ttctcggggg tggacagcgt gagtgtgatg 114960

gtctcgtcga acggatagtc ggtgtcctcg gtgacggtga ccgtcgtacc gcccgccacc 115020

ttcgcggaca cctggcttgc ggcgtacagg gaggcggcga gccccttgtc gggcgtggcc 115080

agccacagct cctcgctgaa gtacggccag cccatgccgt agttgtgcgg acagcagcgg 115140

tactggtcga cgcccggctg gtacgactgc atcgcgaagc cgttctggaa ctgcccctgc 115200

gacttcaccg cgttgttcag atcgatgctg ttcgcgctgg tgatgtagtg ggtgccggtg 115260

ccctgggggt cgagggcggc gggcagcatg ttgaacgcca ggtcctcgca ccggtcggcc 115320

cacaccggat cgccggtgat ccgggtcagc agctcatggc tggccatgaa ttcgacgatg 115380

ccgcaggtct cgaagccctg ccgggggtct ccgaaacccg ggcggtagtt ctcgtccccg 115440

gcgaagccac cgcccgggaa ctggccgtat gcgccgagca ccgacgtata gccgcggtag 115500

gtcgcctgcc tgagctcggc ggagccggtc agctgggcgt actgggcggg ctcgcggaag 115560

ccctgggcga tattgacgtt gtgcggggtc gggatgttgt cgacccaatt ggcgccgtac 115620

gtgtgcatct tctggacgag gtcgaggagg aacgcctcgc cggtgcggcg gtggagccac 115680

atcgcggtgt cgattccgtc gccccagcgg taggagaccc agctggagtc gaaggcgccc 115740

gggccctgcg cgttcatgaa gcgcaggaag cgggtgagga aggggacgat gcgctggtcg 115800

ccggtgaact cctcatgggt gcgcagggcc atgaggaggg ggaggaacgg ccagaagtcg 115860

gggccgccgt tcagctttgt ccgcagggag cgcggcccga agaagccgtc gctctgctgg 115920

gtggcgagga tggcgtcgat ccatccgcgg gcgttggcga gcgccgcctg gtcgcgcgtc 115980

gccaccgcca gcgggacata gccacgcagc cagtacggca cctcctccca gccgtcccgg 116040

tccgggtggg tccacccggt ggcgttgatg tcgaggaagt gcgagcgctc ctggtaccgg 116100

ccgcagaggc cgtggagttg gaggcgcagc tgctcggcca gccagccacg cggggtgatg 116160

ctcccggacg ggagccggtc gaaggcgtcg gacagcgggg cccttggccg ccgggccggg 116220

gatgccacgg cgtccgtggc caggtgcccg gcgagtgcgg gggcgccgag ggtgagggcg 116280

ctggtgcgga ggaagcgacg tcggtcgagg ggcatcgtgc ggctcctgtc ggtggggtgc 116340

cgaggaagac gggtggcgcc tgacatcgtt gtcgcgcatc acagcacgcc atcggcgcgc 116400

tgtctataag ttcgacaggc cgccctgccc cggtgggctc tatgctgagc gtgatgtccg 116460

cacctcaggg ccagggcccc accttccgtg aactcgtcgt ccaggcgctg tcctccgtcg 116520

agcgcggcta cgatctgctg gccccgaagt tcgaccacac cgggtaccgg acgtcggcct 116580

cggtgctgga ctccgtgacc ggcgccctgc gcccgctcgg gcccttcgac agcggcctcg 116640

acgtgtgctg cggaaccggc gccggcatgg gcgtgctgcg ccaggtgtgc cgggagcgga 116700

tcaccggcgt cgacttcagc gcgggcatgc tggccgtggg ccgggagcgt acgcggacgg 116760

tgccggacgc cccgcgcacg gactgggtac gcgccgacgc gcgcgccctc ccgttcgagc 116820

cggtcttcga cctggcggtg agcttcgggg cgttcg                         116856
```

<210> SEQ ID NO 2
<211> LENGTH: 28
<212> TYPE: DNA
<213> ORGANISM: Streptomyces sp.

<400> SEQUENCE: 2

```
gagcctgcgg gctctgcgac tccgctac                                  28
```

<210> SEQ ID NO 3
<211> LENGTH: 27
<212> TYPE: DNA
<213> ORGANISM: Streptomyces sp.

<400> SEQUENCE: 3
gcgagcgaag cagcgcgcgt gtcgcac 27

<210> SEQ ID NO 4
<211> LENGTH: 32
<212> TYPE: DNA
<213> ORGANISM: Streptomyces sp.
<220> FEATURE:
<221> NAME/KEY: misc_feature
<222> LOCATION: (24)..(24)
<223> OTHER INFORMATION: n is inosine

<400> SEQUENCE: 4
acgctcgcgg ctacgcaccg gccngccgca ag 32

<210> SEQ ID NO 5
<211> LENGTH: 42
<212> TYPE: DNA
<213> ORGANISM: Streptomyces sp.

<400> SEQUENCE: 5
agctcgcatc gccggctaga gccgccggca tccttgcacc tg 42

<210> SEQ ID NO 6
<211> LENGTH: 888
<212> TYPE: DNA
<213> ORGANISM: Streptomyces sp.

<400> SEQUENCE: 6
atgaccgcgc agattctcga tggcaaggca accgcagccg cgatcaagtc cgatctcgtc 60
agccgcgtgg aggcgctgaa ggccaagggc atccatcccg gcctcgggac cgtgctggtg 120
ggcgaggacc ccggcagcaa gtggtacgtg gcgggcaagc accgcgactg cgccgaggtc 180
ggcatcgcct ccatccggcg cgacctgccc gagaccgcca cccaggagga gatcgaggcg 240
gcggtccggg agctcaacga ggacccgtcc tgcacgggct acatcgtcca gctgccgctc 300
cccaagggca tcgacgccaa ccgggtgctg gagctgatcg acccggtcaa ggacgccgac 360
ggactgcacc cgatgaacct cggccgcctc gtgctcaacg agagcggccc gctgccgtgc 420
acgccccagg gcgtcatcca gctgctgcgc caccacggtg tggagatcaa cggcgcgcat 480
gtggtggtcg tcggccgcgg catcaccgtc ggccggtcga tcgggctgct gctgacccgc 540
cgttcggaga acgcgacggt caccctctgc cacaccggca cccgcgacct gcccgggatc 600
ctgcgccagg ccgacatcat cgtggcggcc gccggggtgc ggcacctggt caagccggag 660
gacgtcaagc cgggcgcggc ggtgctcgac gtgggcgtca gccgggacga gcacggcaag 720
atcgccggcg atgtgcaccc cggtgtgacc gaggtcgcgg gctgggtctc gccgaacccg 780
ggcggggtcg gcccgatgac ccgcgcccag ctgctggtca acgtggtgga ggccgcggag 840
cgggacgcga aggcggccgc cgacgccggt gccggccatg acggctga 888

<210> SEQ ID NO 7
<211> LENGTH: 1566
<212> TYPE: DNA
<213> ORGANISM: Streptomyces sp.

<400> SEQUENCE: 7

-continued

```
gtgaccgccg aaggtaccaa gcggcccatc cgccgcgcgc tggtcagcgt ctacgacaag      60

acgggtctcg aggagctggc ccgagggctg cacgcggcgg gtgtccagct cgtctcgacc     120

ggctcgacgg ccgcgaagat cgccgccgcc ggggtcccgg tcaccaaggt cgaggagctg     180

accggcttcc ccgagtgtct cgacggccgc gtcaagacgc tgcacccgcg cgtccacgcg     240

ggcatcctcg ccgaccagcg gctcgactcg caccgcgagc agctccggga gctgggcgtg     300

gaccccttcg agctggtcgt ggtcaacctc tatccgttcc gcgagacggt cgcctcgggc     360

gccgcgccgg acgagtgcgt cgagcagatc gacatcggcg gcccctccat ggtccgggcc     420

gccgccaaga atcacccgtc cgtggccgtg gtcgtcaacc ccgagcggta cggcgacgtc     480

ctcgaggccg ccgcggaggg cggtttcgac ctggagcggc gcaagcggct ggcggccgag     540

gcgttccagc acaccgccgc ctacgacgtg gcggtggcca actggttcgc ggccgactac     600

gcggcggcgg acgactcctc cttcccggac ttcctgggcg ccaccatcac ccgtaagaac     660

gtgctgcgct acggcgagaa cccgcatcag cccgccgccc tctacaccga tggcagcggt     720

aaggggctcg cggaggccga gcagctgcac ggcaaggaga tgtcgttcaa caactacacg     780

gacaccgagg ccgcccgccg ggccgcgtac gaccacaccg agccctgtgt cgcgatcatc     840

aagcacgcca acccgtgcgg gatcgcagtc ggggcggacg tcgccgaagc gcaccgtaag     900

gcgcacgcct gcgacccgct gtcggccttc ggcggggtga tcgccgtcaa ccgcccggtg     960

tcggtcgcca tggccgagca ggtcgccgag atcttcaccg aggtgatcgt cgccccggcg    1020

tacgaggacg gcgcggtcga ggcgctcgcc cgtaagaaga acatccgggt gctgcgctgc    1080

gcggagtcgc cggtggaggc cgccgagcag cgccccatcg agggcggcac gctcgtccag    1140

gtcaaggacc gcctccaggc cgagggcgac gacccggcca actggaccct cgccacgggc    1200

gaggcgctgg acgccgacgg cctcgccgag ctggccttcg cctggcgctc ctgccgcgcg    1260

gtgaagtcca acgcgatcct gctcgccaag ggcggcgcca cggtcggcgt cggcatgggc    1320

caggtcaacc gcgtggactc ggcgaagctg gccgtcgagc gggccggtgc cgagcgggcc    1380

gccggttcgt acgccgcctc cgacgccttc ttcccgttcc cggacggctt cgaggtgctg    1440

gccgaggcgg gcgtgaaggc cgtggtgcag ccgggcggct cggtccgtga cgaggccgtg    1500

gtggaggccg cccagaaggc gggtgtgacc atgtacttca cgggcacgcg ccacttcttc    1560

cactga                                                              1566
```

<210> SEQ ID NO 8
<211> LENGTH: 657
<212> TYPE: DNA
<213> ORGANISM: Streptomyces sp.

<400> SEQUENCE: 8

```
gtggcctccc cgccttcccc cgccagccct gcgcgccccg ggcgcccggt ccgcctcgtc      60

gtcctcgtct ccggctccgg tacgaatctc caggcgctgc tcgacgccat cgccgccgag     120

ggcgtggccc gatacggcgc cgaggtggtg gccgtgggcg ccgaccgtga cggcatcgag     180

ggcctgacgc gcgccgagcg cgccgggatc cccacgttcg tgtgccgggt caaggaccac     240

gccggccgcg ccgagtggga cgcggccttg gcggaggcca ccgccgccca tgagccggac     300

ctggtcgtct cggccgggtt catgaagatc ctgggccagg agttcctcgc ccggttcggc     360

ggccgctgcg tcaacaccca tcccgcgctg ctccccagct ttcccggcgc ccatggcgtg     420

cgcgacgcgc tcgcgcacgg tgtgaaggtg accggatgca ccgtccactt cgtcgacgac     480

ggcgtcgaca ccggcccgat catcgcccag ggcgtggtcg aggtccggga cgaggacgac     540
```

-continued

```
gagtccgctc tccatgagcg gatcaaggaa gtcgagcgct cgctgctcgt cgaggtcgtg    600

gggcgtctgg cccgtcacgg ctaccgcata gagggacgaa aggtaaggat cccgtga       657
```

<210> SEQ ID NO 9
<211> LENGTH: 1854
<212> TYPE: DNA
<213> ORGANISM: Streptomyces sp.

<400> SEQUENCE: 9

```
gtgtccgcac gcgaccgctc agcgccccgg cgttcctccg ccatcaggga ggcgttcctc     60

ggcggtgtgg tcgccgcggg gctcggcctc ggcacgctcg ccgtggtcgt actgctgttg    120

tggatcactt cttcctcccc cgagagcagc cccgacggag ccctgcatgt cgccgccgac    180

ctatggctgc tcggccatgg cgccgacctc gtgcgcaccg agacgctctc cggccacacc    240

gcgccggtcg ggctgacccc gctgctgctc agcgtggtgc cgtgctggct gctgtaccgg    300

gccgcccagc acgccgtcta ccaggcggag cccgatgagg gcgacgggca gtgggtgccc    360

gaggagtccg tcgtcgatcc gcgcaccgcc ttcgcctggg tgaccggcgg ctatctgctg    420

gtgggcaccg ctgccgcggt gtacgcctcg accgggccgc tgcgtgtcga tccgctgagc    480

gcgctgctgc atctgccggt cgtcgccggg gtcatcgccg ccgtcggcgt gtggacggcc    540

gacggacggt tcccgctccg cctgcccgga cgggtgagcg agaggctgcg gcggctcccc    600

ggcgccgaac ggaccgtaag gacggccgcg tccctggccg cgcgcggctg gtgccggcgc    660

cgccggctga ccgccgcgct acgggccggg accagcggtc tcgtcgtcct gctcggcagc    720

ggtgcgctcc ttacggcgac gtcgatgctg agccacgcgg gcgccgtgca ggtgacgttc    780

ctcaacctca gcgatgtgtg gtcggggcgg ttcgcggtgc tcctggtgag cctggcgctg    840

ctgccgaacg cgatcgtctg gggcgcggcg tacggggtcg ggcgggggtt cacggtgggt    900

ggcggcagtg tggtggcgcc gctgggcatc acctcctacc cccagctgcc gcacttcccc    960

ctggtcgccg cgctgcccac ggacggctcc ggcgggccgc tggtctggct cacggggatc   1020

gcggccgggg cgtcggtggc ctggctcatc gggatcgcgg cggtgcggcg gcccggcaag   1080

ggcgagccca ggccgccctg ggctgggcc  gagacgctgg tgctcgccgc gctggcggcg   1140

gtcggctgcg cggccgcgat ggcgctcctg gccggggtct cgggcggacc gctgggcatc   1200

ggcatgctcg cggacctcgg cccgagctgg tggcgcacgg gcgtgatcac gctggcctgg   1260

acgggagtga tcggggtgcc cggcgcgatg gtgctgcgct ggtaccggct gtgcgtcccc   1320

accagggcct cctggccgga gtggaaggcg gcgcgggcgg accgccggac atcccgcgcg   1380

caggcccgta cggcggccgg ggaggcccgt acggcagcca gggaggcccg tacggaggcc   1440

aaggccgccc gcgcggcgcg ggccgcggcc gaggcggagg cgcgggcggc ggtgctgccc   1500

acggtgtcac ccatggagtc cgccgaggtg cgcgaggcga tggccgagcc gtggtggcag   1560

tggctgcgcc cgggcgcgtc gggcgccgac cgcaagcgga accgtaaggc ggcgcccgac   1620

gccggtgcgg agacgggacg ggagaccgga cgcgaaaccg gtgtgggcac gatggccgga   1680

ctcgcgaccc ccgcgggcac cccgggcgcc cccggggccg cccgcccacg ccgctgggca   1740

ctgagccgga agcgcgctcc cgggccgcag ccgcccgccg agtccaagac cgccccggac   1800

ccctcgcgca cggagccccc gccgccgccg gacgacgccc gccgcgaacc gtaa         1854
```

<210> SEQ ID NO 10
<211> LENGTH: 885
<212> TYPE: DNA

<213> ORGANISM: Streptomyces sp.

<400> SEQUENCE: 10

```
atggctatct tcctcaccaa ggaaagcaag gtcatcgtcc aggggatgac cgggtccgaa     60
gggcagaagc acacccgtcg gatgcttgcc tcgggcacca acatcgtcgg cggcgtgaac    120
ccgcgcaagg ccggcaccac cgtggacttc gacggcaccg agatcccggt cttcggctcc    180
gtcaaggagg ccatcgacgc caccggcgcc gatgtcacgg tcatcttcgt cccggagaag    240
ttcaccaaga gtgcggtcat cgaggcgatc gacgccgaga ttccgctcgc cgtcgtgatc    300
accgagggca tcgcggtcca cgactccgcc aacttctggg cctacgcggg caagaagggc    360
aacaagacgc gcatcatcgg cccgaactgc ccgggtctga tcacgccggg tcagtcgaac    420
gcgggcatca tcccggccga catcaccaag cccggccgga tcggtctggt gtcgaagtcc    480
ggcacgctga cctaccagat gatgtacgag ctgcgggaca tcggcttctc gtcctgtgtg    540
ggcatcggcg gtgacccgat catcggcacc acccatatcg atgccctcgc cgccttccag    600
gccgaccccg acaccgacct gatcgtgatg atcggcgaga tcggtggcga cgccgaggag    660
cgggccgcgg acttcatcaa ggccaacgtc accaagccgg tcgtcggcta tgtggcgggc    720
ttcaccgccc ccgagggcaa gacgatgggc cacgcgggtg ccatcgtctc cggctcctcc    780
ggcaccgccc aggcgaagaa ggaggccctc gaggccgcgg gcgtgaaggt cggcaagacc    840
ccgtccgaga ccgcgcgcct ggcgcgcgcc gcgctggccg gctga                    885
```

<210> SEQ ID NO 11
<211> LENGTH: 1119
<212> TYPE: DNA
<213> ORGANISM: Streptomyces sp.

<400> SEQUENCE: 11

```
gtgctggccg gtgaagtcat cgacacgcct ggggcggcgc gcgaggtggc cgagcggctg     60
ggcggccgcg cggtcgtcaa ggcgcaggtc aagacgggcg gccgcggtaa ggcgggcggc    120
gtcaagctgg cctccgaccc ggatgacgcc gtcgagaagg ccggccagat cctgggcatg    180
gacatcaagg gccacacggt ccacaaggtg atgctcgccg agaccgcgga catcaaggag    240
gagtactacg tctccttcct gctggaccgc accaaccgca ccttcctcgc catggcctcc    300
gtcgagggcg gcgtggagat cgaggtcgtc gcggagcaga accccgaggc gctcgccaag    360
atcccggtgg acgccatcga gggcgtgacc gaggagaagg ccgccgagat cgtcgccgcc    420
gcgaagttcc cggccgagat cgcggaccag gtcgtcgcgg tgctccagaa gctgtggacc    480
gtcttcatca aggaagacgc cctgctcgtc gaggtcaacc cgctggtcaa gaccgaagac    540
ggcaaggtca tcgcgctgga cggcaaggtc tccctggacg agaacgccgc cttccggcag    600
ccggagcacg aggcgctcga ggacaaggcc gcggccaacc cgctcgaggc ggccgccaag    660
gccaagggcc tcaactacgt caagctcgac ggcgaggtcg gcatcatcgg caacggcgcg    720
ggtctggtca tgtccaccct cgacgtcgtc gcctacgcgg gcgagaacca cggcaacgtc    780
aagcccgcca acttcctcga catcggtggt ggcgcctccg ccgaggtgat ggccaacggt    840
ctcgagatca tcctcggcga cccggacgtc aagtcggtct tcgtcaacgt cttcggtggc    900
atcaccgcct gtgacgcggt cgccaacggc atcgtccagg ccctggagct gctgaagtcc    960
aagggcgagg acgtcagcaa gccgctggtc gtgcgcctcg acggcaacaa cgcggagctg   1020
ggtcgcaaga tcctcaccga cgccaaccac ccgctcgttc agcaggtgga caccatggac   1080
ggcgcggccg agcgtgccgc cgagctggct gcgaagtaa                          1119
```

<210> SEQ ID NO 12
<211> LENGTH: 1341
<212> TYPE: DNA
<213> ORGANISM: Streptomyces sp.

<400> SEQUENCE: 12
gtgccctgca cctacaccgc cgacatcggc cagtacgacg agcccgacat cgcctcggtc 60
cccgggcgcg ccacgacgta cggcgcggag gtcgcccgtc tggtggactg ccgggcggcc 120
ctggtggagg aggggctcgc ggccctcgcc tgcggggcgt tccacatccg ctccggcggc 180
cgcagctact tcaacaccac cccgctcggg cgggcggtca ccggcaccct gctggtgcgc 240
gccatgctcg aggacaatgt gcagatctgg ggcgacggct ccaccttcaa gggcaatgac 300
atcgagcggt tctaccgcta cggtctgctg gccaacccct ccctgcggat ctacaagccg 360
tggctggacg ccgacttcgt cagcgagctc ggcggccgca aggagatgtc ggagtggctg 420
ctcgcccatg acctgcccta ccgggacagc gcggagaagg cgtactccac cgatgccaac 480
atctggggcg ccacccacga ggcaaagtcg ctcgagcacc tcgacaccgg tatcgagatc 540
gtccagccga tcatgggcgt gcggttctgg gacccgtcgg tcgagatagc ggccgaggac 600
gtcacgatcg gcttcgagca gggccgcccg gtaacgatca acggcaagga gttcgcctcc 660
gccgtcgatc tggtgctgga ggccaacgcc atcggcggtc ggcacggcat gggcatgtcc 720
gaccagatcg agaaccgcgt catcgaggcc aagagccggg gcatctacga ggcaccgggc 780
atggcgctgc tgcacgcggc ctacgagcgg ctggtcaacg cgatccacaa cgaggacacc 840
gtcgccacct accacaccga ggggcgccgc ctcggccggc tgatgtacga gggccgctgg 900
ctggacccgc aggcgctgat ggtgcgcgag tcgctgcagc gctgggtcgg cgcggcgatc 960
accggcgagg tgaccctgcg gctgcggcgc ggtgaggact actccatcct ggacacctcc 1020
ggaccggcgt tcagctacca cccggacaag ctctccatgg agcggaccga ggactccgcc 1080
ttcggtccgg tggaccggat cggccagctg accatgcgca acctcgacat cgccgactca 1140
cgcgccaagc tggagcagta cgccggtctc ggcatggtcg gcagctcgca tccggcgctg 1200
atcggcgccg cgcaggcggc gtccaccggg ctgatcggcg cgatgccgca gggcgcctcc 1260
gaggcgatcg cctcggacgg gcacgtgtcc ggacaggaca agctgctcga ccgcgccgcg 1320
atggagttcg gcgccgactg a 1341

<210> SEQ ID NO 13
<211> LENGTH: 2133
<212> TYPE: DNA
<213> ORGANISM: Streptomyces sp.

<400> SEQUENCE: 13
gtggccgtcg ccctcgcggc cggcacgctc gtcaccctga cccccacggc ggcacacgcg 60
gccgcgggcg cctccctgcc cttcgcctcg gccgaggccg agtcggccac caccacgggg 120
acgaagatcg gccccgactt cacccagggc acgctcgcct ccgaggcatc cgggcgccag 180
gccgtccgcc tcgccgccgg gcagcgcgtg gagttcaccg cgccccgcgc ggcgaacgcg 240
gtgaacgtgg cctacaacgt gcccgacggc cagtcgggca cgttgaacgt ctatgtcaac 300
ggcaccaagc tggccaagac catcgcggtc acgtccaagt actcgtacgt ggacaccggc 360
tggatcgcgg ggtcgaagac ccaccacctc tacgacaacg cccggctgct gctcggccag 420
aacgtccagg ccggtgacaa gatcgccttc gaggcggcga acacccaggt caccgtggac 480

-continued

```
gtggccgact tcgagcaggt cgcggcggcc gcctcccagc ccgccggatc ggtgtccgtc     540

acctccaagg gcgccgaccc cagcgggcag ggcgactcca cccaggcgtt ccgggacgcc     600

atcgccgcag cccagggcgg tgtggtctgg atcccgccgg gtgactacag gctgacctcc     660

tcactgaacg gcgtccagaa cgtcaccctc cagggcgccg gcagctggca ctccgtggtg     720

cacacctcgc ggttcatcga ccagtccagc tcctccggca acgtccacat caaggacttc     780

gcggtcatcg gcgaggtcac cgagcgcgtc gactccaacc ccgacaactt cgtcaacggc     840

tcgctcggcc cgggctccag cgtgtccggc atgtggctgc agcacctgaa ggtcggtctg     900

tggctgatgg gcaacaacga caacctcgtg gtcgagaaca accgcttcct ggacatgacg     960

gccgacggcc tcaacctcaa cggcagcgcc aagaacgtac gggtccggaa caacttcctg    1020

cgcaaccagg gcgacgacgc gctcgccatg tggtcgctga actcgccgga caccaacagc    1080

agcttcgaga gcaacaccat ctcgcagccg aacctcgcca atggcatcgc catctacggc    1140

ggtacggaca tcacggtcaa gaacaacctg atctccgaca ccaacgccct gggcagtggc    1200

atcgccatct ccaaccagaa gttcatggac ccgttccacc cgctggccgg cacgatcacg    1260

gtcgacggca acacgctggt ccgagcgggc gccatgaacc ccaactggag ccacccgatg    1320

ggcgccctgc gcgtcgactc ctacgacagc gcgatcgagg ccaccgtcaa catcaccaac    1380

acgaccatca ccgacagccc gtacagcgcc ttcgagttcg tctccggcgg cggcaggggc    1440

tacgcggtca agaacgtcaa tgtgtccggc gcgaccgtga ccaaccccgg aacggtcgtc    1500

gtccaggccg aggcgcaggg ggcggtgaag ttcggcgatg tcacggcctc cagcgtcggc    1560

gcggcgggcg tctacaactg cccgtacccg tcgggctccg gcaccttcga cctcaacgac    1620

ggcggcggca actccggctg gagcagcacc tggtcggact gtgccagctg gccccagccc    1680

ggccggggca acccggatcc cgacccgggc cgcaacctcg ccaagggccg cccggccacc    1740

gcgaccggct cttgggacgt ctacaccccc ggcaaggcgg tcgacggcga cgcgaacacc    1800

tactgggagt cgaccaacaa cgcctttccg caggccctga ccgtggacct cggcgccggc    1860

caggccgtcc gcaggctggt gctgaagctg ccgccctcgt cggcgtgggg cgcccgcacc    1920

cagaccctgt ccgtgctggg cagcaccgac ggctcctcgt actccacggt ggtgggctcg    1980

cagggctacc gcttcgaccc ggcgtccggc aacaaggtca ccgtcgccct gcccgacagc    2040

acgaatgtgc gctatctgag gctcagcgtc accggcaaca ccggctggcc cgcggcccag    2100

gtcagtgagg tggaggcgta tctgacctca tga                                 2133
```

<210> SEQ ID NO 14
<211> LENGTH: 1599
<212> TYPE: DNA
<213> ORGANISM: Streptomyces sp.

<400> SEQUENCE: 14

```
gtggcccagc ccaccccctgc ccggacgccg aacgactggt ggcgctccgc cgtcatctac      60

caggtgtatg tgcgcagctt cgccgacggg gacggcgatg gcaccggcga cctcgcgggc     120

gtccgcgcca ggctgccgta tctcgccgaa ctcggcgtcg acgcgctgtg gttcagcccc     180

tggtaccagt cgcccatgaa ggacggcggc tatgacgtcg ccgactaccg cgccatcgat     240

ccggccttcg gcaccctggc cgaggcggag aaactcatcg ccgaggcccg tgagctgggc     300

atccgcacga tcgtggacat cgtcccgaac cacgtctccg accagcaccc ctggtggcgg     360

gccgccctcg cgggcggcgc cgagcgcgag ctcttccacg tccgcccggg ccgcggcgag     420

cacggtgaac tgccgcccaa cgactggacg tcggagttcg gcggcccggc gtggacccgg     480
```

-continued

```
ctgccggacg gccactggta tctgcatctg ttcgccccg aacagccgga cctcaactgg    540

gcccatccgg ccgtacgcca ggagcacgag gacatcctgc gcttctggtt ggagcggggt   600

gtcgcggggg tgcgcatcga ctcggccgcc ctgctggcca aggatccccg gctgcccgac   660

ttcgtcgagg gccgcgatcc ccatccgtac gtcgaccgcg atgagctcca tgacatctac   720

cgctcctggc gcggcgtggc cgacgagtac ggcggtgtct tcgtcggtga ggtgtggctg   780

ccggacagcg agcgcttcgc ccgctatctg cgccccgacg aactgcacac cgccttcaac   840

ttctcgtttc tggcctgccc ctgggacgcc cggcggctgc ggacgtcgat cgacgagacg   900

ctcgccgaac acgctccggt gggagctccg gccacctggg tgctgtgcaa ccacgatgtg   960

acccgcacgg tgacccgcta cggcgcgcag gacaccggtt tcgacttcgc caccaaggtc  1020

ttcggcaccc ccaccgacct caccctcggc acccggcggg cacgggccgc cgccctgctg  1080

tcgctggccc tgcccggcgc ggtctacgtc taccagggcg aggaactggg cctgcccgag  1140

gccgacatcc cccgcgaccg catccaggac ccgatgcact tccgctccgg cggcaccgac  1200

ccgggccggg acggctgccg ggtgccgctg ccgtgggcgg cggaggcgcc gtacgccggt  1260

ttcggctcgc gcgaggagcc gtggctgccg cagcccgcgc actgggcggc gtacgcggcc  1320

gatctgcaga cggaggcccc gggctcgatg ctcggcctct accgcgcggc gatccgcatc  1380

cgccgcacca cccccggctt cggcgacggg ccgctgacct ggctcccctc ggccgacggt  1440

gtcctggcct tcgcccgtgc ggacggcctg gtctgcgtgg tcaacctcgc ggacaccccc  1500

accgagctgg acggcgcctc ccggcttctg ctcagcagcg gcccgctgga cgaccggggc  1560

cgccttccgc aggacacggc ggcctggctg ctccgctga                          1599
```

<210> SEQ ID NO 15
<211> LENGTH: 876
<212> TYPE: DNA
<213> ORGANISM: Streptomyces sp.

<400> SEQUENCE: 15

```
atgagcaccc ggaccctcgt ctcccccgcc gccctggccc gcccccgcgg ccgggccgtc    60

tactggacgg tcttcaccac cgtggtggtg ctgttcgcga tcgccttcct cttcccggtc   120

tactggatgg tgaccggtgc gatgaagtcg cccgacgagg tggcgcggac accgcccacc   180

atcgtcccga aagagtggca cctcagcggc tacagcgacg cctgggacct gatgcagctg   240

ccgcagcacc tgtggaacac ggtggtccag gcagccggcg cctggctgtt ccagctggtc   300

ttctgcacgg ccgccgccta tgccctgtcc aggctgaagc ccgccttcgg caaggtgatc   360

ctcggtggca tcctggccac gctgatggtt ccggcccagg cgctggtcgt gccgaagtac   420

ctgaccgtcg ccgacctgcc gctgatccac accagcctgc tcaacgaccc gctcgcgatc   480

tggctgccgg ccgtcgccaa cgccttcaac ctctatctcc tcaaacggtt cttcgaccag   540

atcccgcgcg atgtcctgga ggccgccgag atcgacggcg ccgggaagct gcgcaccctg   600

tggtcgatcg tgctgcccat gtcgcgcccg gtgctcggcg ttgtgtcgat cttcgcgctg   660

gtggcggtgt ggcaggactt cctgtggccg ctgatggtct tctccgacac cggcaagcag   720

ccgatcagcg tggcactcgt ccagctgtcg cagaacatcc agctgaccgt gctcatcgcc   780

gcgatggtca tcgccagcat cccgatggtc gcgctgttcc tcgtcttcca gcggcacatc   840

atcgccggga tcagcgcggg cagcacgaag ggctga                             876
```

<210> SEQ ID NO 16

-continued

<211> LENGTH: 1023
<212> TYPE: DNA
<213> ORGANISM: Streptomyces sp.

<400> SEQUENCE: 16

```
atgtcgacca gctcctggag gaagcctccg acaagatcga caacattctg gcccggggct     60
gacccgatga ccaagaccgc cgcgcggccg cccgccgagg cgatcgccgt ccacccggtg    120
caggcgccgc ccccggcggg gggtcggggg cggcgccgtc tcgccgacca ggtccgggcc    180
tatggcttcc tcctcggcgg cctgatctgc ttcgcgctgt tctcctggta tccggcgatc    240
cgcgcggtcg tgatcgcctt ccagaagtac acgcccggct cgtcccccga atgggtcggc    300
accgccaact tcacccgcgt cctgcacgac ccggagttca ccgcggcctg gcggaacacc    360
ctcaccttca ccctgctggc actcctcatc ggcttcgcga tcccgttcct gctcgccctc    420
gtgctcaatg aactgcggca cgccaaggcg ttcttcaggg tcgtggtcta tctgccggtg    480
atgatcccgc cggtggtcag cgccctgctg tggaagtggt tctacgaccc gggcgccggg    540
ctggccaacg aggcgctgcg cttcctgcac ctgcccacct cgaactggtc caacggcgcc    600
gacaccgctc tggtctccct cgtcgccgtg gccacctggg ccaatatggg cggcaccgtc    660
ctgatctacc tggcggcgct gcagtccatc cccggtgagc tgtacgaggc ggccgaactc    720
gacggcgcga gcctgctgca gcgcgtccgc cacgtcacga tcccgcagac gcggttcgtg    780
atcctcatgc tgatgctgct gcagatcatc gcgacgatgc aggtcttcac cgagccgttc    840
gtgatcaccg gtggtggccc ggagaacgcc acggtcacgg tcctctacct gatctacaag    900
tacgccttcc tctacaacga cttcggtggc gcctgtgcgc tgagcgtgat gctgctcgtg    960
ctgctcggcg ccttctccgc cctctatctg cggctcaccc gctccgggga ggacgacgca   1020
tga                                                                  1023
```

<210> SEQ ID NO 17
<211> LENGTH: 1431
<212> TYPE: DNA
<213> ORGANISM: Streptomyces sp.

<400> SEQUENCE: 17

```
gtgcttgagt gtgcggcgca ctcacggttg tgtgcgcccc gctcacggcc gtggggcttc     60
cctgctcctg tacagagggg tccacccatg agaagcaccg ggttccgtcg tactctcatc    120
gcgctcagca cgttccccct cgccctcacc gcctgcggcg ggtcgggcga cggctcggcg    180
ggcggaaaga cgcgcatcac ggtcaactgc atgccgccca agagcgccaa ggtcgaccgc    240
aggttcttcg aggaggacat cgcctccttc gagaagcaga acccggacat cgacgtcgtc    300
gcgcatgacg cgttccccctg ccaggacccg aagacgttcg acgccaagct ggccgggggc    360
cagatggaga acgtcttcta cacgtacttc accgacgccg gacatgtggt cgacatcaac    420
caggcggccg atctcacgcc gtacgtcaag gagttgaaga gctactccac cctccagaag    480
cagctgcgcg acatctacac ggtcgacggc aagatctacg gcatcccgcg caccggctac    540
tcgatgggtc tgatctacaa ccgcaagctc ttcgagaagg ccggactcga ccccgacaag    600
cccccgatga cctgggagga ggtccgcgcc gacgccaaga ggatcgccaa gctgggcgat    660
ggcacggtcg gctacgcgga ctacagcgcc cagaaccagg gcggctggca cttcacggcc    720
gagctgtact cacagggcgg cgatgtcgtc agcgcggacg gcaagaaggc caccatcgac    780
acccccgagg cgcgcgccgt cctgcggaac ctccacgaca tgcgctgggt ggacgactcg    840
atgggcagca agcagctcct ggtcatcaac gacgcccagc agctgatggg ctccggcaag    900
```

-continued

```
ctgggcatgt acctggccgc gcccgacaac ctcccgatcc tggtgaagga gaagggcggc    960
aactacaagg acctcgccat cgcccccatg cccggtggca agggcacgct catcggcggc   1020
gacggctaca tgttccagaa gaaggacacg cccgcccaga tccgggccgg tctcaagtgg   1080
ctcgaccaca tgttcctcac cccgggcgat ggcttcctcg gcgactacgt ccgcgccaag   1140
aagcgaaacg ccccggtggg cctgcccgag ccacggctgt tcaccggcgc agccgacgcc   1200
aaggaccagc aggtcaagaa ggccaacgcc aatgtccccg tgggcaacta ccagaccttc   1260
ctcgacggca accagaagct gcggatgagg atcgagccgc cgcacgccca gcagatctac   1320
tccgtgctcg acggagccgt ctccgccgtc ctcaccaaga aggacgccga tgtcgaccag   1380
ctcctggagg aagcctccga caagatcgac aacattctgg cccggggctg a            1431
```

<210> SEQ ID NO 18
<211> LENGTH: 978
<212> TYPE: DNA
<213> ORGANISM: Streptomyces sp.

<400> SEQUENCE: 18

```
gtggcgaaga aggtcggtgt cagcgaggcc acggtcagcc gggtactcaa cggtaagccc     60
ggggtctccg cagccacccg gcaggcggtg ctgtccgccc tggacgtcct cggctacgag    120
cggcccacgc agctgcgggg cgaccgggcc cggctggtgg ggctggtgct gcccgagctg    180
cagaacccca tcttcccggc gttcgccgag gtcatcggtg ggcgctggc acagcttgga    240
ctgaccccgg tgctgtgcac ccagaccaag ggcggggtct ccgaggccga ttacgtggcg    300
ctgctgctgc aacagcaggt ctccggggtg gtgttcgcgg gcgggctgta cgcgcaggcc    360
gacgcgccgc atgaccacta ccggctgctc gccgagcgca acatcccggt ggtgctggtc    420
aacgcggcca tcgagcacct cggcttcccg gctgtctcct gcgacgacgc cgtggccgtg    480
gagcaggcgt ggcggcatct ggcctccctc ggccatgagc ggatcggcct ggtgctcggg    540
cccggtgacc acatgccgtc ggcacgcaag ctgaccgccg cgcgggcggt cgcaggccac    600
cttccggatg agttcgtggc ccgggcgatc ttctcgatcg agggcggcca cgccgctgcc    660
tcccggctga tcgaccgggg cgtcacgggc atcatctgcg ccagcgaccc gctggccctg    720
ggcgcgatac gagccgcgcg ccgcaagggg ttcggcgtgc cgtcgcaggt gtccgtggtc    780
ggctacgacg actccgcgtt catgaactgc accgagccgc cgctgaccac cgtccgccag    840
cccatagagg ccatgggcag ggcggcggtg gaggtgctga acgcgcagat cggcggggtg    900
gccgtaccgt ccgaggagct gctgttcgag ccggagctgg tggtccgcgg ctccaccgcc    960
caggcgccac gggagtga                                                  978
```

<210> SEQ ID NO 19
<211> LENGTH: 519
<212> TYPE: DNA
<213> ORGANISM: Streptomyces sp.

<400> SEQUENCE: 19

```
gtgtgccgcc ccctcggatc gtcacgccgt ggcggccggc cccgaggacg cgggtttgtt     60
gtcgggtcga gtggtaacgc ggtgaacatg accgagaaga agaacgcaca cactacccgg    120
agcaccaacg tgaacgcgaa ggccaccgcc accaaggcca aggagaccgc ggaaagggcc    180
aaggacaccg cgggcaaggc ggagaccacg gcgaagaccg ccgcggccgg cgcggcgacg    240
accgcggcgc acaccgctca tgtcgccgcc gacaaggctc aagtggccgc cgggaaggcc    300
```

```
gtgaccaccg gtcgtaccgt ggccgctgag gcgcccaaga aggctgccgc ggcggcgggt    360

tcggcctgga tgatgatcaa ggcccggaag gtcctggcag ccgtcgccgg tgcgggtgcc    420

gccgcggcgg gcgccaccgc cgcggtcgtc ctgcgcaggc gcgcggctcg tcgccgccgc    480

ccgctggcac gcctgaccgg cggccggctc ggctcttga                           519
```

```
<210> SEQ ID NO 20
<211> LENGTH: 1485
<212> TYPE: DNA
<213> ORGANISM: Streptomyces sp.

<400> SEQUENCE: 20

atgtccgccg cctcttccga cccgacgtct ccccgtgtcc ccccgacacg tcgactggcc      60

ctcggggtca tcgccaccgg catgctgatg gtgatcctcg acggcagcat cgtgaccgtg     120

gccatgcccg ccatccagag cgatctgcgg ttctccccccg ccgggctcag ctgggtcgtc    180

aacgcctacc tgatcgcgtt cggcggtctg ctgctgctcg gcggccgtat cggcgatctc     240

atcggccgca agcgggtgtt cctgaccggt accgcggtgt tcaccgcggc ctcgttgctc     300

gcggccgtgg ccacctcccc cgctgtgctg atcgccgcac ggttcctcca gggggtcggc     360

agcgcgatgg cctcggcggt cagcctgggc atcctcgtca cgctcttcac cgaacgcgcc     420

gaacggtcga aggcgatcgc cgtgttcagc ttcaccggcg ccgccggagc gtcgatcggc     480

caggtgctcg gcggcctcct caccgacgcg ctcagctggc actggatctt cctgatcaat     540

ctgccgatcg ggctgctgac gctcgcggtc gccataccccg tcctgcccgc cgaccgcggg    600

ccgggcctcg cggccggcgc cgatgtcctc ggcgccctgc tggtcacgac cgggctgatg     660

ctgggcatct acaccgtggt caaggtggcg gactacggct ggacggcggc gcgcacactc     720

ggcctcggcg ccgtctcgat cctcctgatc gccctgttcc tggtccgcca gaccaccgcc     780

cgcaccccgc tgatgcccct gcggatcctg cggtcgcgcg gggtggcggg ggccaatctg     840

gtccagctcc tgatggtggc cgcgctcttc tcgttccaga tcctggtcgc cctctatctg     900

cgcaatgtgc tggggtacga cgccaccgga accggtctgg ccatgctccc ggccgccatc     960

gccatcggcg cggtgtccct cggcgtctcc gcacggctca gcgcacgctt cggcgaccgc    1020

gcggtgctgc tgaccgggct ggccctcctg accggcgttc tcggcctgct cgtccgcgtc    1080

cccgtgcacg cccggtacct ccccgacctc ctcccggtga tgctgctcgc cgccggtttc    1140

gggctggcgc tccctgcgct gaccagcctg ggaatgtccg gtgcgaagga ggacgaggcc    1200

gggctcgtct ccgggctgtt caacaccacc cagcagatcg gcatggcgct gggcgtcgcg    1260

gtgctgtcca ccctggccgc ctcccgcacg gatgccctgc tctcccgggg caagggtcgg    1320

gccgaggcgc tgaccggcgg ctaccacctg gccttcgccg tcggaacggg gctcatcgtg    1380

gcggccttcg cggtggcgtt caccgtactg cgaggacctg cgcgcaagcc ccccgctgtg    1440

ccgcggaacg ccaatccgcc cgccacaccg gtcgccaccg cctga                    1485
```

```
<210> SEQ ID NO 21
<211> LENGTH: 480
<212> TYPE: DNA
<213> ORGANISM: Streptomyces sp.

<400> SEQUENCE: 21

atggcgccca ccaagaccga acccgacctg tcgttcctcc tcgaccacac cagccacgtc      60

ctccgcaccc agatgtcggc cgcgctcgcc gaaatcgggc tgacggcgcg gatgcactgc     120

gtactggtcc acgccctgga ggaagagcgc acccaggccc agctcgccga gatcggcgac     180
```

-continued

```
atggacaaga ccacgatggt ggtgacggtg gacgccctgg agaaggcggg cctcgcggag    240

cggcgcgcct cgacccacga tcgccgggcc cggatcatcg cggtcaccga ggagggcgcg    300

cggatcgccg aacggagcca ggagatcgtg gaccgcgtcc atcgcgaggc gttggcgaca    360

ctccccgaga cccaacgcgc cgcgctgcta aaggcgttga cccggctgtc cgaggggcat    420

ctggccacgc ccgccgagag cccccgcccg gcgcggaggg cgcggcagcg cgagaagtag    480
```

<210> SEQ ID NO 22
<211> LENGTH: 945
<212> TYPE: DNA
<213> ORGANISM: Streptomyces sp.

<400> SEQUENCE: 22

```
gtgacgcggg ggcgagtcgc atgcgtcgat cgtgcgcccg gctcatgcat gcgcaaaatg     60

cgttcggggt tctatctata cgctggacgt atggatgtgg agctacggca actgcgctgc    120

ctcgtcgcga tcgtcgacga gggcaccttc accgacgccg ccatcgcgct cggcgtctcc    180

caggcggccg tgtcccgcac cctggcagcg ctcgaacgcg ccctggggac aaggctgttg    240

cggcggacct cccgcgaggt gaccccgacg ggcaccgggc tgcgggtggt ggcacacgcc    300

cggcgggtgc tggccgaggt ggacgggctg atccgggagg ccgtatcggg ccacgcccat    360

ctgcggatcg gctacgcctg gtccgcgctg ggccgtcaca cccccgcctt ccagcgccgc    420

tgggcgcagg cgtatcccga gacggagctg cacctcgtcc gcgtcaattc cgccaccgcg    480

gggctgacgg agggcgcctg cgacctggcc gtggtgcgca gaccgctcga cgagcgccgc    540

ttcgactccg ccatcgtcgg actggagcgg cggctgtgcg ccgtggccgc cgacgacccg    600

ctcgccaggc gccgctcggt ccggctggcc gacctcagcg ggcgcaccct gctggtcgac    660

cgcaggaccg gtaccaccac cacggagctg tggccgcccg actcccggcc ggccacggag    720

gagacccacg acgtggagga ctggctcacc gtgatctccg cgggccgctg cgtcggcatg    780

acggcggagt ccacggccaa ccagtatccg aggcccggaa tcgcctaccg gccggtccgc    840

gacgccgagc ccatcgcggt acgcctcgcc tggtggcggg acgacccgca ccccgccacc    900

cagaccgcgg tcgagctgct caccgccctc taccgcaacg gctga                    945
```

<210> SEQ ID NO 23
<211> LENGTH: 825
<212> TYPE: DNA
<213> ORGANISM: Streptomyces sp.

<400> SEQUENCE: 23

```
gtgcgttcgg tgtgcccgcg gcacccgtca tccacttcac acgatcggat ccgtatgacc     60

gacgacatgt tcctcatgac cgacgacacg ttcctcgacg atgtcgcaga gcgactcgcc    120

gccctgcccg ccgtgcacgc cgtcgccctc gggggctcgc gtgcgcaggg gacccacacc    180

ccggagagcg actgggacct ggccctgtac taccgaggcg gcttcgaccc ggccgcgctg    240

cgggccgtgg gctgggaggg cgaggtctcc gagctcggcg agtggggcgg tggtgtcttc    300

aacgggggcg cctggctgac gatcgacgga cggcgcgtgg acgtccacta ccgcgacctc    360

gaggtggtgg aacacgaact cgccgagtcg cgacggggcc gcttccactg ggagccgctg    420

atgttccacc tcgcgggcat ccccagctat ctggtggtgg ccgaactcgc cctgaaccag    480

gtgctgcggg gcaccctgcc ccgccccgag tacccggcgg cgctgcgtga ggcggcaccc    540

ccggcgtggc gcgggcgggc ggccttgacc ctgcggtacg cctcggccgc gtacgtggga    600
```

-continued

```
cgtggccagg ccaccgaggt cgcgggggcg gtggcgaccg ccgccctcca gacggcgcac    660

gcggtgctgg cggcgcgcgg tgagtgggtc accaacgaga agcggctcct ccagcgggcg    720

gacctgcgcg ccatcgacac gatcgtggcg gggctgcggc cggagcccac cgccctggcc    780

gaggcgatcg ccgccgcgga ggcgctgttc gaggccgcgg gctga                    825
```

<210> SEQ ID NO 24
<211> LENGTH: 1050
<212> TYPE: DNA
<213> ORGANISM: Streptomyces sp.

<400> SEQUENCE: 24

```
gtgtccgctg atgccggcgc cgacgcccgt ggcgacaccg ttagtggcga actcgtcctg      60

gtgacaggag gcagcggcta tctcggcacc catgtgatca gcggcctgct gcggagcggc     120

catcgggtcc gcaccacggt ccgttcacac ggcccggcca ccggcgccgc cgcgagtgtc     180

cggtcggcca tcgcggcctc cggtgtcgat cccggcgggc ggctcgatat cgtcagcgcc     240

gacctgacca cggacgacgg ctgggacgac gcgatggcgg ggtgcacccg cgtccaccac     300

gtcgcgtcac cgttccccgc cgtccagccg gacaacgccg acgagctgat cgtccccgcg     360

cgggacggca cccttcgtgt gctgagggcc gcacgggacc agggtgtgaa acgggtcgtg     420

atgacgtcct cgttcgccgc ggtgggatac agccacaagg acggtgacga gtacgacgag     480

agcgactgga ccgaccccga ggacgacaac ccgccctaca tccgctcgaa gaccatcgcg     540

gagctggccg cctgggactt cgtggcgaag gagggggacg gcctcgaact gacggtgatc     600

aacccgaccg ggatcttcgg tccggcactc ggcccccggc tgtccgcctc gacggaacac     660

gtccgggcga tgctggaggg ggcgatgtcg gccgtccccc gcgcacactt cggcatggtg     720

gacgtgcgcg atgtcgccga gctccacctc cgggccatgg cacaccccgc cgcggccgga     780

gagcgcttcc tcgccagcgg cgaccggacc gtcagcttcc tgtggatcgc ccaggtgctg     840

gccgagcacc tcggcgagcg cgccgcccgg gtgcccacgc gggagttcga cgacgaacga     900

gcgcgggaag cggtcggcgt gacggagcgg gtgccgatcc tgcgcaccga gaaggcgcgt     960

tccgtgttcg gctggacccc gcgcgacccg gtgacgacca tcctcgacac cgcggagagc    1020

ctgttccgcc tgggcctggt gaaggactga                                     1050
```

<210> SEQ ID NO 25
<211> LENGTH: 408
<212> TYPE: DNA
<213> ORGANISM: Streptomyces sp.

<400> SEQUENCE: 25

```
gtgtcgaggc tgagtggcct ctcggagccg acactgcgct actacgagaa gatcggcttg      60

atccccgccg tggaccgcga ccgggacagt ggccaccggc gctatccccc ctccgtggtg     120

gagacgatca ggtcgctggg gtgcctgaga tccaccggca tgagcatgca ggacatgcgc     180

gcctacctcg gccacctcga cgaaggcgat cagggtgcgg ctcccctgcg tgacctcttc     240

caacgcaacg cggaccgcct ggagcgggag atcgcgctca tggaggtccg gctgcgctat     300

ctgcggctca aggcggacat gtgggacgcg cgggagcgcg ccgacgccga tgcggagcgc     360

cgggcgatcg acgaactgac ggacgtcatc gacgcgctgc ggccgtga                  408
```

<210> SEQ ID NO 26
<211> LENGTH: 1494
<212> TYPE: DNA
<213> ORGANISM: Streptomyces sp.

-continued

<400> SEQUENCE: 26
gtgaccggac ccgacgggta cgaagcgctc ccgcaccgcc gccgggccct ggtcaccatc 60
gccctgctgg gctgcgcctt cctggccatg ctggacggca ccgtggtcgg caccgcgctg 120
ccccgcatcg tcgagcagat cggcggaggg gactcctggt acgtctggct cgtcaccgcc 180
tatctgctga cctcctcggt cagcgtgccg gtctacggcc gcttctccga cctccacggc 240
cgccgccggc tgctgatcgg cgggctcggc gtcttcctga tcggctccat cgcctgcggc 300
ctgtccgcct cgatgcccgc cctgatcctc tcccgcgcgc tccagggcct gggtgccgga 360
tccctgctga ccctcggcat ggcactggtc cgcgacctcc acccgccgtc ccgcccccag 420
ggcctcatcc ggatgcagac ggcgatggcc gccatgatga tcctgggcat ggtgggcggc 480
ccgctcctcg gcgggttact cgccgatcac atcggctggc gctgggcgtt ctggctcaac 540
ctcccgctcg ggctggccgc gggcgccgtc atcgtcctgg ccctgcccga ccgccgtccc 600
gccaccccgc cgtccggccg gctcgacgtg gcggggatcc tcctgctcgc cgcggggctc 660
gccctcgcgc tgaccggcct cagcctcaag ggaacgcga ccgccggaca cgcgccctcc 720
tggacggacc cggccgtgct gggctgtctg ctcggcggtc tggcgctgct caccacgctc 780
ataccggtcg agcggcgggc cgccgtcccc gtcctgcccc tgcggctgtt ccggcaccgc 840
acctacaccg ccctgctgac cgccggtttc ttcttccagg tcgccgcggc gccggtggga 900
atcttcctgc cgctgtactt ccagcacatc cgcggccatt cggccaccgc ctccggtctg 960
ctgctgctcc ccctgctcat cggcatgacc ctgggcaacc ggctcaccgc cgccaccgtg 1020
ctgcgcagcg ggcacgtcaa gccggtcctg ctgatcggcg cggggctgct caccgccggt 1080
accgccgcct tcgtcgccct gcgggccacg acccctctcg cgctgacgtc cgttctgctg 1140
ctgctcgtcg ggctcggcgc gggaccggcc atgggcgggc tcaccatcgc cacccagagc 1200
gccgtcccgc gtgcggacat gggcaccgcc accgcgggtt ccgcgctcac caagcagctc 1260
ggtggcgcgg tcggcctggc cagcgcccag tccctgatcg gccactccgg cgcggccgcg 1320
cccaccgcca cggccatcgg ctccaccgtc tcctggagcg gcggcgccgc cgggctcctc 1380
gccctcgggg cgctgctcct catgcgggac atctccatcg ccacggccgg gaagcgcccg 1440
ggcgcgccca cttccgggac cgccgtcccc gcaaaggccg atcggctcgc ttga 1494

<210> SEQ ID NO 27
<211> LENGTH: 642
<212> TYPE: DNA
<213> ORGANISM: Streptomyces sp.

<400> SEQUENCE: 27
atgacagaga aggcagagaa cccctccact ccgacccgcc gccgcgctcc ggccatggat 60
cccgaccagc gccgcgcgat gatcgtcgcc gccgcgctcc ccctcgtcgt cgaatacggc 120
gccaccgtga cgaccgcgaa gatcgcccgg gccgcgggca tcggggaagg cactatcttc 180
cgcgtcttcg aggacaagga cgccctgctc gcggcctgta tggcggaggc cgtgcggccc 240
gatgacaccg tggcccatct ggagtcgatc gccccttgacc agccgcttgc ggaccggctc 300
gccgaggcgg ccgatgtggt gcgcggacac atggcgcgca tcggcgcggt cgccggggcg 360
ctcgcggcgg ccgggcggct ggagcgcatg gcgcccaagc ccggcaagga cgggcgcctc 420
ccggaccgcg aggcgagcct ggtccggccg cgcgccgcgc tggccgcgct gttcgagccc 480
gaccgggacc gcctgcgact cgccccggaa cggctcgccg acgccttcca gctgacgctg 540

-continued

```
atgtcggccg ggcgcctggg cgcccccgag ccgctgacca ccgaggaagt cgtggacctc    600

ttcctgcacg gcgcgctcgt ggcgcccggg gaggcccggt ga                        642
```

<210> SEQ ID NO 28
<211> LENGTH: 1047
<212> TYPE: DNA
<213> ORGANISM: Streptomyces sp.

<400> SEQUENCE: 28

```
gtgaagtgtg ctggcacacg gggaagttgg ggggcgtggc gccgaaccgg gccgtccggc     60

cggggcgttc cgcttcccct ccacggtggc ggtcccatag gtatcgtgtc caacgatgat    120

gtgtgctgtg tggcatcgcg aatggagatg atggtggagc tccggcagct ggcgtacttc    180

gtcgcggtgg ccgaggagcg cagcttcacc cgcggcgccc agcgggaaca cgtcgtccag    240

tcggcggcct ccgccgccgt ggcccggctg gagcaggagt tccagaccgc gctcttcgac    300

cgctcgcacc gcaccctgga gctgaccacc gcggggcgca ccctgctggc ccgggcccgg    360

atcctgctcg cggaggcgca gcgggcgcgc gatgacatgg gccgtctcac cggggggctc    420

agcggtacgg tcaccctcgg gacggtcctg tccaccggct cgttcgacct gatcggggcg    480

ctgagcacgt ttcaggccga gcaccccgat gtcgtggtgc ggctgcgcca ctcgaccggt    540

ccgctggccg gacacgccac cgccctgcgc gagggcaggt tcgacctgat gctgctgccg    600

gtgcccccgc acggccccgc cgtcctcggc ccggatctga tcatcgatga tgtgtcgcgg    660

atacgcctcg ggctggcctg ccgcaccgac gacccccctcg ccgaggcgca cggcgtgacc    720

tacgccgacc tcgccgaccg ccgcttcatc gacttcccca cggggtgggg cgaccgcacc    780

atcgtcgaca gcctcttcgg caccgccgga gttcagcgca ccgtggcact ggaggtcgtc    840

gacaccacga ccgccctgac catggtccgg cggcgtctcg ggctcgcctt cgtggccgag    900

gagaccatcg cctcgcggcc cggcctgacc caggtcgatc tcgccgatcc accgccgctg    960

cacggtctcg gcctcgccgc ctcgcgcaac catccccgt ccgaggcggg ccgcgccctg    1020

cgccgggccc tgctcgccgc gcgctga                                        1047
```

<210> SEQ ID NO 29
<211> LENGTH: 408
<212> TYPE: DNA
<213> ORGANISM: Streptomyces sp.

<400> SEQUENCE: 29

```
atgtccctga ttcgcgaacc gcaccgccgg cgcttcaacg cgatcatggt cggcggagcg     60

ggtgcggcct acctcagcgg cggcggcctg gacggctggg agttcgcctt caccgtggtc    120

gccacctatg tggcctaccg tggcctggag tcgtggacct tcatcggcat cggctggctg    180

ctgcacaccg cgtgggacat cgtgcatcac atcaagggca accccatcgt cccgttcgcg    240

catggctcgt cgctgggctg tgcgatctgc gatccggtca tcgcgctgtg gtgtttccgg    300

ggcggcccgt cgctgctccg gttcttccgc aagggacgac ccgaggaacc ggccgccgct    360

gccctccccg actccctgtc cgccgggcag gcgacgggga acggatga                 408
```

<210> SEQ ID NO 30
<211> LENGTH: 2451
<212> TYPE: DNA
<213> ORGANISM: Streptomyces sp.

<400> SEQUENCE: 30

```
atgtcaggcg ccacccgtct tcctcggcac cccaccgaca ggagccgcac gatgcccctc     60
```

-continued

```
gaccgacgtc gcttcctccg caccagcgcc ctcaccctcg gcgcccccgc actcgccggg    120
cacctggcca cggacgccgt ggcatccccg gcccggcggc caagggcccc gctgtccgac    180
gccttcgacc ggctcccgtc cgggagcatc accccgcgtg gctggctggc cgagcagctg    240
cgcctccaac tccacggcct ctgcggccgg taccaggagc gctcgcactt cctcgacatc    300
aacgccaccg ggtggaccca cccggaccgg gacggctggg aggaggtgcc gtactggctg    360
cgtggctatg tcccgctggc ggtggcgacg cgcgaccagg cggcgctcgc caacgcccgc    420
ggatggatcg acgccatcct cgccacccag cagagcgacg gcttcttcgg gccgcgctcc    480
ctgcggacaa agctgaacgg cggccccgac ttctggccgt tcctccccct cctcatggcc    540
ctgcgcaccc atgaggagtt caccggcgac cagcgcatcg tccccttcct cacccgcttc    600
ctgcgcttca tgaacgcgca gggcccgggc gccttcgact ccagctgggt ctcctaccgc    660
tggggcgacg gaatcgacac cgcgatgtgg ctccaccgcc gcaccggcga ggcgttcctc    720
ctcgacctcg tccagaagat gcacacgtac ggcgccaatt gggtcgacaa catcccgacc    780
ccgcacaacg tcaatatcgc ccagggcttc cgcgagcccg cccagtacgc ccagctgacc    840
ggctccgccg agctcaggca ggcgacctac cgcggctata cgtcggtgct cggcgcatac    900
ggccagttcc cgggcggtgg cttcgccggg gacgagaact accgcccggg tttcggagac    960
ccccggcagg gcttcgagac ctgcggcatc gtcgaattca tggccagcca tgagctgctg   1020
acccggatca ccggcgatcc ggtgtgggcc gaccggtgcg aggacctggc gttcaacatg   1080
ctgcccgccg ccctcgaccc ccagggcacc ggcacccact acatcaccag cgcgaacagc   1140
atcgatctga acaacgcggt gaagtcgcag gggcagttcc agaacggctt cgcgatgcag   1200
tcgtaccagc cgggcgtcga ccagtaccgc tgctgtccgc acaactacgg catgggctgg   1260
ccgtacttca gcgaggagct gtggctggcc acgcccgaca aggggctcgc cgcctccctg   1320
tacgccgcaa gccaggtgtc cgcgaaggtg gcgggcggta cgacggtcac cgtcaccgag   1380
gacaccgact atccgttcga cgagaccatc acactcacgc tgtccacccc cgagaaggtg   1440
gccttcccgc tccatctgcg ggtccccggc tggtgcaaga acccccggat cgaggtcaac   1500
ggccgggcgg tggccacgcg cggcggtccg gccttcgtca aggtcgaccg gagctggacg   1560
gacggcgatg tggtgacgat ccgcctgccg cagcgcaccg ccctgcggac ctggtcggcg   1620
cagcacggcg cggtcagcgt cgaccacggc ccgctgacgt actccctgcg catcggcgag   1680
gacttcgtgc gctacgccgg caccgacacc ttccccgagt acgaagtgca cgccaccact   1740
ccgtggaact acggcctcgc cccccggagcc ctccccgtgc tcacccgcga cgacggtccg   1800
ctcgccgcca atcccttcac ccacgagacc accccggtcc gcatgaccgc ccaggcgcgc   1860
cgtatcgccg agtgggtctc ggacgacgag catgtggtca ccccgcttca gcagagcccg   1920
gcccgggccg acgcaccggc ggagacggtc accctcatcc ccatgggcgc cgcccggctg   1980
cgtatcacct gctttcccac ggccgcgccg gacggccggg cgtggacccc ggagccgccc   2040
ttccgccgac tgctcaacaa gcacagcggc aaggtgctcg ccgtcgacga gatgtccacg   2100
gccaacagcg cccgcgtggt gcagtacgac aacacaccga cgggcgacca cgcctggcag   2160
tggatcgacc ggggcgacgg ctggttcctg atccgcaacg gccacagcgg caaggtcctg   2220
ggcgtcgacc ggatgtccac cgcgaacagc gccatcgtcg tccagtacga ggacaacggc   2280
acggccgatc acctctggcg gaaggtggac aacggcgacg gctggttccg cgtcctcaac   2340
aagaacagcc agaaggtgct gggtgtcgac ggcatgtcca ccgccaacag cgcccaggtg   2400
```

-continued

```
gtgcagtacg acgacaacgg aaccgatgac cacctgtggc ggctgctgtg a            2451


<210> SEQ ID NO 31
<211> LENGTH: 295
<212> TYPE: PRT
<213> ORGANISM: Streptomyces sp.

<400> SEQUENCE: 31

Met Thr Ala Gln Ile Leu Asp Gly Lys Ala Thr Ala Ala Ala Ile Lys
1               5                   10                  15

Ser Asp Leu Val Ser Arg Val Glu Ala Leu Lys Ala Lys Gly Ile His
            20                  25                  30

Pro Gly Leu Gly Thr Val Leu Val Gly Glu Asp Pro Gly Ser Lys Trp
        35                  40                  45

Tyr Val Ala Gly Lys His Arg Asp Cys Ala Glu Val Gly Ile Ala Ser
    50                  55                  60

Ile Arg Arg Asp Leu Pro Glu Thr Ala Thr Gln Glu Glu Ile Glu Ala
65                  70                  75                  80

Ala Val Arg Glu Leu Asn Glu Asp Pro Ser Cys Thr Gly Tyr Ile Val
                85                  90                  95

Gln Leu Pro Leu Pro Lys Gly Ile Asp Ala Asn Arg Val Leu Glu Leu
            100                 105                 110

Ile Asp Pro Val Lys Asp Ala Asp Gly Leu His Pro Met Asn Leu Gly
        115                 120                 125

Arg Leu Val Leu Asn Glu Ser Gly Pro Leu Pro Cys Thr Pro Gln Gly
    130                 135                 140

Val Ile Gln Leu Leu Arg His His Gly Val Glu Ile Asn Gly Ala His
145                 150                 155                 160

Val Val Val Val Gly Arg Gly Ile Thr Val Gly Arg Ser Ile Gly Leu
                165                 170                 175

Leu Leu Thr Arg Arg Ser Glu Asn Ala Thr Val Thr Leu Cys His Thr
            180                 185                 190

Gly Thr Arg Asp Leu Pro Gly Ile Leu Arg Gln Ala Asp Ile Ile Val
        195                 200                 205

Ala Ala Ala Gly Val Arg His Leu Val Lys Pro Glu Asp Val Lys Pro
    210                 215                 220

Gly Ala Ala Val Leu Asp Val Gly Val Ser Arg Asp Glu His Gly Lys
225                 230                 235                 240

Ile Ala Gly Asp Val His Pro Gly Val Thr Glu Val Ala Gly Trp Val
                245                 250                 255

Ser Pro Asn Pro Gly Gly Val Gly Pro Met Thr Arg Ala Gln Leu Leu
            260                 265                 270

Val Asn Val Val Glu Ala Ala Glu Arg Asp Ala Lys Ala Ala Ala Asp
        275                 280                 285

Ala Gly Ala Gly His Asp Gly
    290                 295


<210> SEQ ID NO 32
<211> LENGTH: 521
<212> TYPE: PRT
<213> ORGANISM: Streptomyces sp.

<400> SEQUENCE: 32

Val Thr Ala Glu Gly Thr Lys Arg Pro Ile Arg Arg Ala Leu Val Ser
1               5                   10                  15

Val Tyr Asp Lys Thr Gly Leu Glu Glu Leu Ala Arg Gly Leu His Ala
```

-continued

```
            20                  25                  30

Ala Gly Val Gln Leu Val Ser Thr Gly Ser Thr Ala Ala Lys Ile Ala
        35                  40                  45

Ala Ala Gly Val Pro Val Thr Lys Val Glu Glu Leu Thr Gly Phe Pro
    50                  55                  60

Glu Cys Leu Asp Gly Arg Val Lys Thr Leu His Pro Arg Val His Ala
65                  70                  75                  80

Gly Ile Leu Ala Asp Gln Arg Leu Asp Ser His Arg Glu Gln Leu Arg
                85                  90                  95

Glu Leu Gly Val Asp Pro Phe Glu Leu Val Val Val Asn Leu Tyr Pro
            100                 105                 110

Phe Arg Glu Thr Val Ala Ser Gly Ala Ala Pro Asp Glu Cys Val Glu
        115                 120                 125

Gln Ile Asp Ile Gly Gly Pro Ser Met Val Arg Ala Ala Ala Lys Asn
    130                 135                 140

His Pro Ser Val Ala Val Val Val Asn Pro Glu Arg Tyr Gly Asp Val
145                 150                 155                 160

Leu Glu Ala Ala Ala Glu Gly Gly Phe Asp Leu Glu Arg Arg Lys Arg
                165                 170                 175

Leu Ala Ala Glu Ala Phe Gln His Thr Ala Ala Tyr Asp Val Ala Val
            180                 185                 190

Ala Asn Trp Phe Ala Ala Asp Tyr Ala Ala Ala Asp Asp Ser Ser Phe
        195                 200                 205

Pro Asp Phe Leu Gly Ala Thr Ile Thr Arg Lys Asn Val Leu Arg Tyr
    210                 215                 220

Gly Glu Asn Pro His Gln Pro Ala Ala Leu Tyr Thr Asp Gly Ser Gly
225                 230                 235                 240

Lys Gly Leu Ala Glu Ala Glu Gln Leu His Gly Lys Glu Met Ser Phe
                245                 250                 255

Asn Asn Tyr Thr Asp Thr Glu Ala Ala Arg Arg Ala Ala Tyr Asp His
            260                 265                 270

Thr Glu Pro Cys Val Ala Ile Ile Lys His Ala Asn Pro Cys Gly Ile
        275                 280                 285

Ala Val Gly Ala Asp Val Ala Glu Ala His Arg Lys Ala His Ala Cys
    290                 295                 300

Asp Pro Leu Ser Ala Phe Gly Gly Val Ile Ala Val Asn Arg Pro Val
305                 310                 315                 320

Ser Val Ala Met Ala Glu Gln Val Ala Glu Ile Phe Thr Glu Val Ile
                325                 330                 335

Val Ala Pro Ala Tyr Glu Asp Gly Ala Val Glu Ala Leu Ala Arg Lys
            340                 345                 350

Lys Asn Ile Arg Val Leu Arg Cys Ala Glu Ser Pro Val Glu Ala Ala
        355                 360                 365

Glu Gln Arg Pro Ile Glu Gly Gly Thr Leu Val Gln Val Lys Asp Arg
    370                 375                 380

Leu Gln Ala Glu Gly Asp Asp Pro Ala Asn Trp Thr Leu Ala Thr Gly
385                 390                 395                 400

Glu Ala Leu Asp Ala Asp Gly Leu Ala Glu Leu Ala Phe Ala Trp Arg
                405                 410                 415

Ser Cys Arg Ala Val Lys Ser Asn Ala Ile Leu Leu Ala Lys Gly Gly
            420                 425                 430

Ala Thr Val Gly Val Gly Met Gly Gln Val Asn Arg Val Asp Ser Ala
        435                 440                 445
```

-continued

```
Lys Leu Ala Val Glu Arg Ala Gly Ala Glu Arg Ala Ala Gly Ser Tyr
    450                 455                 460

Ala Ala Ser Asp Ala Phe Phe Pro Phe Pro Asp Gly Phe Glu Val Leu
465                 470                 475                 480

Ala Glu Ala Gly Val Lys Ala Val Val Gln Pro Gly Gly Ser Val Arg
                485                 490                 495

Asp Glu Ala Val Val Glu Ala Ala Gln Lys Ala Gly Val Thr Met Tyr
            500                 505                 510

Phe Thr Gly Thr Arg His Phe Phe His
        515                 520


<210> SEQ ID NO 33
<211> LENGTH: 218
<212> TYPE: PRT
<213> ORGANISM: Streptomyces sp.

<400> SEQUENCE: 33

Val Ala Ser Pro Pro Ser Pro Ala Ser Pro Ala Arg Pro Gly Arg Pro
1               5                   10                  15

Val Arg Leu Val Val Leu Val Ser Gly Ser Gly Thr Asn Leu Gln Ala
            20                  25                  30

Leu Leu Asp Ala Ile Ala Ala Glu Gly Val Ala Arg Tyr Gly Ala Glu
        35                  40                  45

Val Val Ala Val Gly Ala Asp Arg Asp Gly Ile Glu Gly Leu Thr Arg
    50                  55                  60

Ala Glu Arg Ala Gly Ile Pro Thr Phe Val Cys Arg Val Lys Asp His
65                  70                  75                  80

Ala Gly Arg Ala Glu Trp Asp Ala Ala Leu Ala Glu Ala Thr Ala Ala
                85                  90                  95

His Glu Pro Asp Leu Val Val Ser Ala Gly Phe Met Lys Ile Leu Gly
            100                 105                 110

Gln Glu Phe Leu Ala Arg Phe Gly Gly Arg Cys Val Asn Thr His Pro
        115                 120                 125

Ala Leu Leu Pro Ser Phe Pro Gly Ala His Gly Val Arg Asp Ala Leu
    130                 135                 140

Ala His Gly Val Lys Val Thr Gly Cys Thr Val His Phe Val Asp Asp
145                 150                 155                 160

Gly Val Asp Thr Gly Pro Ile Ile Ala Gln Gly Val Val Glu Val Arg
                165                 170                 175

Asp Glu Asp Asp Glu Ser Ala Leu His Glu Arg Ile Lys Glu Val Glu
            180                 185                 190

Arg Ser Leu Leu Val Glu Val Val Gly Arg Leu Ala Arg His Gly Tyr
        195                 200                 205

Arg Ile Glu Gly Arg Lys Val Arg Ile Pro
    210                 215


<210> SEQ ID NO 34
<211> LENGTH: 280
<212> TYPE: PRT
<213> ORGANISM: Streptomyces sp.

<400> SEQUENCE: 34

Met Ser Arg Thr Thr Pro Leu Leu Arg Glu Gln Gln Ser Ser Ser Ser
1               5                   10                  15

Ser Ser Ser Ser Ser Ser Ser Ala Pro Gly Gly Pro Asn Gly Asp Gln
            20                  25                  30
```

```
His Glu Asp Asn Pro Phe Ala Pro Pro Pro Glu Gly Arg Pro Asp Gln
        35                  40                  45

Pro Trp Arg Pro Arg His Arg Pro Asp Gly Ser Gly Gly Glu Ser Gly
    50                  55                  60

Glu Gly Arg Pro Gly Ala Gln Gly Gly Gln Asp Gly Pro Asp Gly Asp
65                  70                  75                  80

Gln Ser Gly Glu Gln Pro Gln Gln Pro Pro Ala Trp Gly Ser Gln Trp
                85                  90                  95

Ser Ser Arg Gln Pro Gly Arg Gln Asn Gly Gly Phe Gly Gly Thr Pro
            100                 105                 110

Gly Ser Asn Arg Pro Ser Gly Pro Gly Gly Pro Gly Gly Pro Arg Trp
        115                 120                 125

Asp Pro Asn Asp Pro Ala Gln Arg Arg Ala Arg Tyr Ala Leu Leu Ser
    130                 135                 140

Gly Met Trp Ala Phe Phe Phe Ala Leu Phe Ser Leu Pro Gln Ile Ala
145                 150                 155                 160

Leu Leu Leu Gly Val Leu Ala Leu Tyr Trp Gly Ile Ser Ser Leu Arg
                165                 170                 175

Ala Lys Pro Arg Arg Thr Ala Pro Ser Pro Ala Ala Ala Ala Pro Leu
            180                 185                 190

Asn Ala Pro Pro Pro Pro Pro Gly Ala Ala Arg Ala Ala Leu Pro Ala
        195                 200                 205

Pro Gly Ser Gly Pro Ala Lys Ser Gln Ser Thr Ala Ala Ile Ser Gly
    210                 215                 220

Leu Val Thr Gly Gly Leu Ala Leu Ala Ile Val Ala Ala Thr Phe Ser
225                 230                 235                 240

Phe Gln Val Val Tyr Ser Asp Tyr Tyr Thr Cys Val Asp Asp Ala Leu
                245                 250                 255

Thr Gln Thr Ser Arg His Asp Cys Glu Thr Leu Leu Pro Glu Gln Leu
            260                 265                 270

Arg Pro Leu Leu Ser Thr Gln Asp
        275                 280


<210> SEQ ID NO 35
<211> LENGTH: 617
<212> TYPE: PRT
<213> ORGANISM: Streptomyces sp.

<400> SEQUENCE: 35

Val Ser Ala Arg Asp Arg Ser Ala Pro Arg Arg Ser Ser Ala Ile Arg
1               5                   10                  15

Glu Ala Phe Leu Gly Gly Val Val Ala Ala Gly Leu Gly Leu Gly Thr
            20                  25                  30

Leu Ala Val Val Val Leu Leu Leu Trp Ile Thr Ser Ser Ser Pro Glu
        35                  40                  45

Ser Ser Pro Asp Gly Ala Leu His Val Ala Ala Asp Leu Trp Leu Leu
    50                  55                  60

Gly His Gly Ala Asp Leu Val Arg Thr Glu Thr Leu Ser Gly His Thr
65                  70                  75                  80

Ala Pro Val Gly Leu Thr Pro Leu Leu Leu Ser Val Val Pro Cys Trp
                85                  90                  95

Leu Leu Tyr Arg Ala Ala Gln His Ala Val Tyr Gln Ala Glu Pro Asp
            100                 105                 110

Glu Gly Asp Gly Gln Trp Val Pro Glu Glu Ser Val Val Asp Pro Arg
```

```
        115                 120                 125

Thr Ala Phe Ala Trp Val Thr Gly Gly Tyr Leu Leu Val Gly Thr Ala
    130                 135                 140

Ala Ala Val Tyr Ala Ser Thr Gly Pro Leu Arg Val Asp Pro Leu Ser
145                 150                 155                 160

Ala Leu Leu His Leu Pro Val Val Ala Gly Val Ile Ala Ala Val Gly
                165                 170                 175

Val Trp Thr Ala Asp Gly Arg Phe Pro Leu Arg Leu Pro Gly Arg Val
            180                 185                 190

Ser Glu Arg Leu Arg Arg Leu Pro Gly Ala Glu Arg Thr Val Arg Thr
        195                 200                 205

Ala Ala Ser Leu Ala Ala Arg Gly Trp Cys Arg Arg Arg Arg Leu Thr
    210                 215                 220

Ala Ala Leu Arg Ala Gly Thr Ser Gly Leu Val Val Leu Leu Gly Ser
225                 230                 235                 240

Gly Ala Leu Leu Thr Ala Thr Ser Met Leu Ser His Ala Gly Ala Val
                245                 250                 255

Gln Val Thr Phe Leu Asn Leu Ser Asp Val Trp Ser Gly Arg Phe Ala
            260                 265                 270

Val Leu Leu Val Ser Leu Ala Leu Leu Pro Asn Ala Ile Val Trp Gly
        275                 280                 285

Ala Ala Tyr Gly Val Gly Ala Gly Phe Thr Val Gly Gly Gly Ser Val
    290                 295                 300

Val Ala Pro Leu Gly Ile Thr Ser Tyr Pro Gln Leu Pro His Phe Pro
305                 310                 315                 320

Leu Val Ala Ala Leu Pro Thr Asp Gly Ser Gly Gly Pro Leu Val Trp
                325                 330                 335

Leu Thr Gly Ile Ala Ala Gly Ala Ser Val Ala Trp Leu Ile Gly Ile
            340                 345                 350

Ala Ala Val Arg Arg Pro Gly Lys Gly Glu Pro Arg Pro Pro Trp Gly
        355                 360                 365

Trp Ala Glu Thr Leu Val Leu Ala Ala Leu Ala Ala Val Gly Cys Ala
    370                 375                 380

Ala Ala Met Ala Leu Leu Ala Gly Val Ser Gly Gly Pro Leu Gly Ile
385                 390                 395                 400

Gly Met Leu Ala Asp Leu Gly Pro Ser Trp Trp Arg Thr Gly Val Ile
                405                 410                 415

Thr Leu Ala Trp Thr Gly Val Ile Gly Val Pro Gly Ala Met Val Leu
            420                 425                 430

Arg Trp Tyr Arg Leu Cys Val Pro Thr Arg Ala Ser Trp Pro Glu Trp
        435                 440                 445

Lys Ala Ala Arg Ala Asp Arg Arg Thr Ser Arg Ala Gln Ala Arg Thr
    450                 455                 460

Ala Ala Gly Glu Ala Arg Thr Ala Ala Arg Glu Ala Arg Thr Glu Ala
465                 470                 475                 480

Lys Ala Ala Arg Ala Ala Arg Ala Ala Ala Glu Ala Glu Ala Arg Ala
                485                 490                 495

Ala Val Leu Pro Thr Val Ser Pro Met Glu Ser Ala Glu Val Arg Glu
            500                 505                 510

Ala Met Ala Glu Pro Trp Trp Gln Trp Leu Arg Pro Gly Ala Ser Gly
        515                 520                 525

Ala Asp Arg Lys Arg Asn Arg Lys Ala Ala Pro Asp Ala Gly Ala Glu
    530                 535                 540
```

-continued

```
Thr Gly Arg Glu Thr Gly Arg Glu Thr Gly Val Gly Thr Met Ala Gly
545                 550                 555                 560

Leu Ala Thr Pro Ala Gly Thr Pro Gly Ala Pro Gly Ala Ala Arg Pro
                565                 570                 575

Arg Arg Trp Ala Leu Ser Arg Lys Arg Ala Pro Gly Pro Gln Pro Pro
            580                 585                 590

Ala Glu Ser Lys Thr Ala Pro Asp Pro Ser Arg Thr Glu Pro Pro Pro
        595                 600                 605

Pro Pro Asp Asp Ala Arg Arg Glu Pro
    610                 615


<210> SEQ ID NO 36
<211> LENGTH: 294
<212> TYPE: PRT
<213> ORGANISM: Streptomyces sp.

<400> SEQUENCE: 36

Met Ala Ile Phe Leu Thr Lys Glu Ser Lys Val Ile Val Gln Gly Met
1               5                   10                  15

Thr Gly Ser Glu Gly Gln Lys His Thr Arg Arg Met Leu Ala Ser Gly
            20                  25                  30

Thr Asn Ile Val Gly Gly Val Asn Pro Arg Lys Ala Gly Thr Thr Val
        35                  40                  45

Asp Phe Asp Gly Thr Glu Ile Pro Val Phe Gly Ser Val Lys Glu Ala
    50                  55                  60

Ile Asp Ala Thr Gly Ala Asp Val Thr Val Ile Phe Val Pro Glu Lys
65                  70                  75                  80

Phe Thr Lys Ser Ala Val Ile Glu Ala Ile Asp Ala Glu Ile Pro Leu
                85                  90                  95

Ala Val Val Ile Thr Glu Gly Ile Ala Val His Asp Ser Ala Asn Phe
            100                 105                 110

Trp Ala Tyr Ala Gly Lys Lys Gly Asn Lys Thr Arg Ile Ile Gly Pro
        115                 120                 125

Asn Cys Pro Gly Leu Ile Thr Pro Gly Gln Ser Asn Ala Gly Ile Ile
    130                 135                 140

Pro Ala Asp Ile Thr Lys Pro Gly Arg Ile Gly Leu Val Ser Lys Ser
145                 150                 155                 160

Gly Thr Leu Thr Tyr Gln Met Met Tyr Glu Leu Arg Asp Ile Gly Phe
                165                 170                 175

Ser Ser Cys Val Gly Ile Gly Gly Asp Pro Ile Ile Gly Thr Thr His
            180                 185                 190

Ile Asp Ala Leu Ala Ala Phe Gln Ala Asp Pro Asp Thr Asp Leu Ile
        195                 200                 205

Val Met Ile Gly Glu Ile Gly Gly Asp Ala Glu Glu Arg Ala Ala Asp
    210                 215                 220

Phe Ile Lys Ala Asn Val Thr Lys Pro Val Val Gly Tyr Val Ala Gly
225                 230                 235                 240

Phe Thr Ala Pro Glu Gly Lys Thr Met Gly His Ala Gly Ala Ile Val
                245                 250                 255

Ser Gly Ser Ser Gly Thr Ala Gln Ala Lys Lys Glu Ala Leu Glu Ala
            260                 265                 270

Ala Gly Val Lys Val Gly Lys Thr Pro Ser Glu Thr Ala Arg Leu Ala
        275                 280                 285

Arg Ala Ala Leu Ala Gly
```

290

<210> SEQ ID NO 37
<211> LENGTH: 372
<212> TYPE: PRT
<213> ORGANISM: Streptomyces sp.

<400> SEQUENCE: 37

Val Leu Ala Gly Glu Val Ile Asp Thr Pro Gly Ala Ala Arg Glu Val
1               5                   10                  15

Ala Glu Arg Leu Gly Gly Arg Ala Val Val Lys Ala Gln Val Lys Thr
            20                  25                  30

Gly Gly Arg Gly Lys Ala Gly Gly Val Lys Leu Ala Ser Asp Pro Asp
        35                  40                  45

Asp Ala Val Glu Lys Ala Gly Gln Ile Leu Gly Met Asp Ile Lys Gly
    50                  55                  60

His Thr Val His Lys Val Met Leu Ala Glu Thr Ala Asp Ile Lys Glu
65                  70                  75                  80

Glu Tyr Tyr Val Ser Phe Leu Leu Asp Arg Thr Asn Arg Thr Phe Leu
                85                  90                  95

Ala Met Ala Ser Val Glu Gly Gly Val Glu Ile Glu Val Val Ala Glu
            100                 105                 110

Gln Asn Pro Glu Ala Leu Ala Lys Ile Pro Val Asp Ala Ile Glu Gly
        115                 120                 125

Val Thr Glu Glu Lys Ala Ala Glu Ile Val Ala Ala Ala Lys Phe Pro
    130                 135                 140

Ala Glu Ile Ala Asp Gln Val Val Ala Val Leu Gln Lys Leu Trp Thr
145                 150                 155                 160

Val Phe Ile Lys Glu Asp Ala Leu Leu Val Glu Val Asn Pro Leu Val
                165                 170                 175

Lys Thr Glu Asp Gly Lys Val Ile Ala Leu Asp Gly Lys Val Ser Leu
            180                 185                 190

Asp Glu Asn Ala Ala Phe Arg Gln Pro Glu His Glu Ala Leu Glu Asp
        195                 200                 205

Lys Ala Ala Ala Asn Pro Leu Glu Ala Ala Ala Lys Ala Lys Gly Leu
    210                 215                 220

Asn Tyr Val Lys Leu Asp Gly Glu Val Gly Ile Ile Gly Asn Gly Ala
225                 230                 235                 240

Gly Leu Val Met Ser Thr Leu Asp Val Val Ala Tyr Ala Gly Glu Asn
                245                 250                 255

His Gly Asn Val Lys Pro Ala Asn Phe Leu Asp Ile Gly Gly Gly Ala
            260                 265                 270

Ser Ala Glu Val Met Ala Asn Gly Leu Glu Ile Ile Leu Gly Asp Pro
        275                 280                 285

Asp Val Lys Ser Val Phe Val Asn Val Phe Gly Gly Ile Thr Ala Cys
    290                 295                 300

Asp Ala Val Ala Asn Gly Ile Val Gln Ala Leu Glu Leu Leu Lys Ser
305                 310                 315                 320

Lys Gly Glu Asp Val Ser Lys Pro Leu Val Val Arg Leu Asp Gly Asn
                325                 330                 335

Asn Ala Glu Leu Gly Arg Lys Ile Leu Thr Asp Ala Asn His Pro Leu
            340                 345                 350

Val Gln Gln Val Asp Thr Met Asp Gly Ala Ala Glu Arg Ala Ala Glu
        355                 360                 365

```
Leu Ala Ala Lys
    370


<210> SEQ ID NO 38
<211> LENGTH: 546
<212> TYPE: PRT
<213> ORGANISM: Streptomyces sp.

<400> SEQUENCE: 38

Val Pro Gly Thr Val Gly Ser Trp Thr Gly Thr Glu Gly Arg Ser Ala
1               5                   10                  15

Gly Thr Cys Gly Arg Ser Ala Gly Ser Cys Gly Arg Ser Ala Gly Thr
            20                  25                  30

Val Gly Ser Cys Gly Arg Ser Val Gly Ser Cys Gly Arg Ser Ala Gly
        35                  40                  45

Thr Val Gly Arg Ser Ala Gly Ser Cys Gly Arg Ser Ala Gly Ser Cys
    50                  55                  60

Gly Arg Ser Ala Gly Thr Cys Gly Arg Ser Ala Gly Ser Cys Gly Arg
65                  70                  75                  80

Ser Ala Gly Thr Val Gly Ser Cys Gly Arg Ser Val Gly Ser Cys Gly
                85                  90                  95

Arg Ser Ala Gly Thr Val Gly Arg Ser Ala Gly Ser Cys Gly Arg Ser
            100                 105                 110

Ala Gly Ser Cys Gly Arg Ser Ala Gly Ser Thr Gly Arg Ala Gly Met
        115                 120                 125

Leu Ala Thr Ser Val Arg Ser Val Gly Thr Ala Gly Ser Arg Leu Ser
    130                 135                 140

Ala Pro Ser Leu Ala Leu Pro Thr Val Val Trp Ala Phe Ala Ala Thr
145                 150                 155                 160

Pro Val Ala Arg Pro Trp Ala Asn Gly Thr Val Val Pro Ala Thr Ser
                165                 170                 175

Cys Ala Asn Gly Thr Ala Val Asp Gly Thr Leu Thr Thr Thr Gly Thr
            180                 185                 190

Arg Arg Ser Thr Val Ser Trp Ala Ala Gly Thr Thr Leu Glu Ala Val
        195                 200                 205

Pro Ser Ala Lys Pro Ser Ala Leu Pro Val Thr Thr Ser Thr Tyr Gly
    210                 215                 220

Val Val Arg Ala Thr Ala Ser Ser Ala Ser Ala Pro Val Ser Pro Thr
225                 230                 235                 240

Val Arg Ser Ala Thr Gly Thr Thr Leu Thr Thr Arg Arg Cys Thr Ala
                245                 250                 255

Gly Gly Ser Thr Ser Glu Ala Thr Pro Ser Thr Thr Gly Leu Val Val
            260                 265                 270

Pro Thr Ala Pro Cys Thr Leu Pro Val Ser Ser Ser Gly Arg Met Pro
        275                 280                 285

Ala Pro Glu Arg Glu Ala Ser Arg Ser Leu Ala Glu Pro Gly Ala Glu
    290                 295                 300

Gly Ser Phe Gly Val Ile Thr Thr Gly Asp His Gly Tyr Ala Lys Ala
305                 310                 315                 320

Val Leu Asp Ser Pro Leu His Arg Asp Val Gly Ala Leu Phe Pro Arg
                325                 330                 335

Gly Gly Gly Met Ser Trp Ala Ser Thr Ala Gly Leu Gly Ala Leu Asp
            340                 345                 350

Leu Ala Thr Val Pro Asn Lys Leu Thr Pro Lys Gln Arg Ala Glu Val
        355                 360                 365
```

-continued

```
Arg Ala Met Val Thr Lys Ala Ala Asp Arg Tyr Ala Ala Asp Ser Ala
    370                 375                 380

Lys Ser Ala Tyr Gly Val Pro Tyr Ala Pro Lys Asp Gly Lys Tyr Glu
385                 390                 395                 400

Trp Gly Ser Asn Ser Gln Val Leu Asn Asn Met Ile Val Leu Ala Thr
                405                 410                 415

Ala His Asp Leu Thr Asp Lys Pro Arg Tyr Leu Asp Ala Val Leu Arg
            420                 425                 430

Gly Met Asp Tyr Leu Leu Gly Gly Asn Pro Leu Asn Gln Ser Tyr Val
        435                 440                 445

Thr Gly His Gly Glu Arg Asp Ser His Asn Gln His His Arg Phe Trp
    450                 455                 460

Ala His Gln Arg Asp His Arg Leu Pro His Pro Ala Pro Gly Ser Leu
465                 470                 475                 480

Ala Gly Gly Pro Asn Ser Gly Leu Gln Asp Pro Val Ala Lys Lys Lys
                485                 490                 495

Leu Lys Gly Cys Ala Pro Ala Met Cys Tyr Thr Asp Ser Leu Met Ala
            500                 505                 510

Phe Ser Thr Asn Glu Ile Thr Ile Asn Trp Asn Ala Pro Leu Ala Trp
        515                 520                 525

Ile Ala Ser Tyr Val Asp Gly Leu Gly Gly Gly Ala Ala Glu Gln Ser
    530                 535                 540

Val Arg
545


<210> SEQ ID NO 39
<211> LENGTH: 446
<212> TYPE: PRT
<213> ORGANISM: Streptomyces sp.

<400> SEQUENCE: 39

Val Pro Cys Thr Tyr Thr Ala Asp Ile Gly Gln Tyr Asp Glu Pro Asp
1               5                   10                  15

Ile Ala Ser Val Pro Gly Arg Ala Thr Thr Tyr Gly Ala Glu Val Ala
            20                  25                  30

Arg Leu Val Asp Cys Arg Ala Ala Leu Val Glu Glu Gly Leu Ala Ala
        35                  40                  45

Leu Ala Cys Gly Ala Phe His Ile Arg Ser Gly Gly Arg Ser Tyr Phe
    50                  55                  60

Asn Thr Thr Pro Leu Gly Arg Ala Val Thr Gly Thr Leu Leu Val Arg
65                  70                  75                  80

Ala Met Leu Glu Asp Asn Val Gln Ile Trp Gly Asp Gly Ser Thr Phe
                85                  90                  95

Lys Gly Asn Asp Ile Glu Arg Phe Tyr Arg Tyr Gly Leu Leu Ala Asn
            100                 105                 110

Pro Ser Leu Arg Ile Tyr Lys Pro Trp Leu Asp Ala Asp Phe Val Ser
        115                 120                 125

Glu Leu Gly Gly Arg Lys Glu Met Ser Glu Trp Leu Leu Ala His Asp
    130                 135                 140

Leu Pro Tyr Arg Asp Ser Ala Glu Lys Ala Tyr Ser Thr Asp Ala Asn
145                 150                 155                 160

Ile Trp Gly Ala Thr His Glu Ala Lys Ser Leu Glu His Leu Asp Thr
                165                 170                 175

Gly Ile Glu Ile Val Gln Pro Ile Met Gly Val Arg Phe Trp Asp Pro
```

-continued

```
            180                 185                 190

Ser Val Glu Ile Ala Ala Glu Asp Val Thr Ile Gly Phe Glu Gln Gly
        195                 200                 205

Arg Pro Val Thr Ile Asn Gly Lys Glu Phe Ala Ser Ala Val Asp Leu
    210                 215                 220

Val Leu Glu Ala Asn Ala Ile Gly Gly Arg His Gly Met Gly Met Ser
225                 230                 235                 240

Asp Gln Ile Glu Asn Arg Val Ile Glu Ala Lys Ser Arg Gly Ile Tyr
                245                 250                 255

Glu Ala Pro Gly Met Ala Leu Leu His Ala Ala Tyr Glu Arg Leu Val
            260                 265                 270

Asn Ala Ile His Asn Glu Asp Thr Val Ala Thr Tyr His Thr Glu Gly
        275                 280                 285

Arg Arg Leu Gly Arg Leu Met Tyr Glu Gly Arg Trp Leu Asp Pro Gln
    290                 295                 300

Ala Leu Met Val Arg Glu Ser Leu Gln Arg Trp Val Gly Ala Ala Ile
305                 310                 315                 320

Thr Gly Glu Val Thr Leu Arg Leu Arg Arg Gly Glu Asp Tyr Ser Ile
                325                 330                 335

Leu Asp Thr Ser Gly Pro Ala Phe Ser Tyr His Pro Asp Lys Leu Ser
            340                 345                 350

Met Glu Arg Thr Glu Asp Ser Ala Phe Gly Pro Val Asp Arg Ile Gly
        355                 360                 365

Gln Leu Thr Met Arg Asn Leu Asp Ile Ala Asp Ser Arg Ala Lys Leu
    370                 375                 380

Glu Gln Tyr Ala Gly Leu Gly Met Val Gly Ser Ser His Pro Ala Leu
385                 390                 395                 400

Ile Gly Ala Ala Gln Ala Ala Ser Thr Gly Leu Ile Gly Ala Met Pro
                405                 410                 415

Gln Gly Ala Ser Glu Ala Ile Ala Ser Asp Gly His Val Ser Gly Gln
            420                 425                 430

Asp Lys Leu Leu Asp Arg Ala Ala Met Glu Phe Gly Ala Asp
        435                 440                 445


<210> SEQ ID NO 40
<211> LENGTH: 710
<212> TYPE: PRT
<213> ORGANISM: Streptomyces sp.

<400> SEQUENCE: 40

Val Ala Val Ala Leu Ala Ala Gly Thr Leu Val Thr Leu Thr Pro Thr
1               5                   10                  15

Ala Ala His Ala Ala Ala Gly Ala Ser Leu Pro Phe Ala Ser Ala Glu
            20                  25                  30

Ala Glu Ser Ala Thr Thr Thr Gly Thr Lys Ile Gly Pro Asp Phe Thr
        35                  40                  45

Gln Gly Thr Leu Ala Ser Glu Ala Ser Gly Arg Gln Ala Val Arg Leu
    50                  55                  60

Ala Ala Gly Gln Arg Val Glu Phe Thr Ala Pro Arg Ala Ala Asn Ala
65                  70                  75                  80

Val Asn Val Ala Tyr Asn Val Pro Asp Gly Gln Ser Gly Thr Leu Asn
                85                  90                  95

Val Tyr Val Asn Gly Thr Lys Leu Ala Lys Thr Ile Ala Val Thr Ser
            100                 105                 110
```

-continued

```
Lys Tyr Ser Tyr Val Asp Thr Gly Trp Ile Ala Gly Ser Lys Thr His
        115                 120                 125

His Leu Tyr Asp Asn Ala Arg Leu Leu Leu Gly Gln Asn Val Gln Ala
    130                 135                 140

Gly Asp Lys Ile Ala Phe Glu Ala Ala Asn Thr Gln Val Thr Val Asp
145                 150                 155                 160

Val Ala Asp Phe Glu Gln Val Ala Ala Ala Ala Ser Gln Pro Ala Gly
                165                 170                 175

Ser Val Ser Val Thr Ser Lys Gly Ala Asp Pro Ser Gly Gln Gly Asp
            180                 185                 190

Ser Thr Gln Ala Phe Arg Asp Ala Ile Ala Ala Ala Gln Gly Gly Val
        195                 200                 205

Val Trp Ile Pro Pro Gly Asp Tyr Arg Leu Thr Ser Ser Leu Asn Gly
    210                 215                 220

Val Gln Asn Val Thr Leu Gln Gly Ala Gly Ser Trp His Ser Val Val
225                 230                 235                 240

His Thr Ser Arg Phe Ile Asp Gln Ser Ser Ser Ser Gly Asn Val His
                245                 250                 255

Ile Lys Asp Phe Ala Val Ile Gly Glu Val Thr Glu Arg Val Asp Ser
            260                 265                 270

Asn Pro Asp Asn Phe Val Asn Gly Ser Leu Gly Pro Gly Ser Ser Val
        275                 280                 285

Ser Gly Met Trp Leu Gln His Leu Lys Val Gly Leu Trp Leu Met Gly
    290                 295                 300

Asn Asn Asp Asn Leu Val Val Glu Asn Asn Arg Phe Leu Asp Met Thr
305                 310                 315                 320

Ala Asp Gly Leu Asn Leu Asn Gly Ser Ala Lys Asn Val Arg Val Arg
                325                 330                 335

Asn Asn Phe Leu Arg Asn Gln Gly Asp Asp Ala Leu Ala Met Trp Ser
            340                 345                 350

Leu Asn Ser Pro Asp Thr Asn Ser Ser Phe Glu Ser Asn Thr Ile Ser
        355                 360                 365

Gln Pro Asn Leu Ala Asn Gly Ile Ala Ile Tyr Gly Gly Thr Asp Ile
    370                 375                 380

Thr Val Lys Asn Asn Leu Ile Ser Asp Thr Asn Ala Leu Gly Ser Gly
385                 390                 395                 400

Ile Ala Ile Ser Asn Gln Lys Phe Met Asp Pro Phe His Pro Leu Ala
                405                 410                 415

Gly Thr Ile Thr Val Asp Gly Asn Thr Leu Val Arg Ala Gly Ala Met
            420                 425                 430

Asn Pro Asn Trp Ser His Pro Met Gly Ala Leu Arg Val Asp Ser Tyr
        435                 440                 445

Asp Ser Ala Ile Glu Ala Thr Val Asn Ile Thr Asn Thr Thr Ile Thr
    450                 455                 460

Asp Ser Pro Tyr Ser Ala Phe Glu Phe Val Ser Gly Gly Gly Arg Gly
465                 470                 475                 480

Tyr Ala Val Lys Asn Val Asn Val Ser Gly Ala Thr Val Thr Asn Pro
                485                 490                 495

Gly Thr Val Val Val Gln Ala Glu Ala Gln Gly Ala Val Lys Phe Gly
            500                 505                 510

Asp Val Thr Ala Ser Ser Val Gly Ala Ala Gly Val Tyr Asn Cys Pro
        515                 520                 525

Tyr Pro Ser Gly Ser Gly Thr Phe Asp Leu Asn Asp Gly Gly Gly Asn
```

-continued

```
    530                 535                 540

Ser Gly Trp Ser Ser Thr Trp Ser Asp Cys Ala Ser Trp Pro Gln Pro
545                 550                 555                 560

Gly Arg Gly Asn Pro Asp Pro Asp Pro Gly Arg Asn Leu Ala Lys Gly
                565                 570                 575

Arg Pro Ala Thr Ala Thr Gly Ser Trp Asp Val Tyr Thr Pro Gly Lys
            580                 585                 590

Ala Val Asp Gly Asp Ala Asn Thr Tyr Trp Glu Ser Thr Asn Asn Ala
        595                 600                 605

Phe Pro Gln Ala Leu Thr Val Asp Leu Gly Ala Gly Gln Ala Val Arg
    610                 615                 620

Arg Leu Val Leu Lys Leu Pro Pro Ser Ser Ala Trp Gly Ala Arg Thr
625                 630                 635                 640

Gln Thr Leu Ser Val Leu Gly Ser Thr Asp Gly Ser Ser Tyr Ser Thr
                645                 650                 655

Val Val Gly Ser Gln Gly Tyr Arg Phe Asp Pro Ala Ser Gly Asn Lys
            660                 665                 670

Val Thr Val Ala Leu Pro Asp Ser Thr Asn Val Arg Tyr Leu Arg Leu
        675                 680                 685

Ser Val Thr Gly Asn Thr Gly Trp Pro Ala Ala Gln Val Ser Glu Val
    690                 695                 700

Glu Ala Tyr Leu Thr Ser
705                 710


<210> SEQ ID NO 41
<211> LENGTH: 532
<212> TYPE: PRT
<213> ORGANISM: Streptomyces sp.

<400> SEQUENCE: 41

Val Ala Gln Pro Thr Pro Ala Arg Thr Pro Asn Asp Trp Trp Arg Ser
1               5                   10                  15

Ala Val Ile Tyr Gln Val Tyr Val Arg Ser Phe Ala Asp Gly Asp Gly
            20                  25                  30

Asp Gly Thr Gly Asp Leu Ala Gly Val Arg Ala Arg Leu Pro Tyr Leu
        35                  40                  45

Ala Glu Leu Gly Val Asp Ala Leu Trp Phe Ser Pro Trp Tyr Gln Ser
    50                  55                  60

Pro Met Lys Asp Gly Gly Tyr Asp Val Ala Asp Tyr Arg Ala Ile Asp
65                  70                  75                  80

Pro Ala Phe Gly Thr Leu Ala Glu Ala Glu Lys Leu Ile Ala Glu Ala
                85                  90                  95

Arg Glu Leu Gly Ile Arg Thr Ile Val Asp Ile Val Pro Asn His Val
            100                 105                 110

Ser Asp Gln His Pro Trp Trp Arg Ala Ala Leu Ala Gly Gly Ala Glu
        115                 120                 125

Arg Glu Leu Phe His Val Arg Pro Gly Arg Gly Glu His Gly Glu Leu
    130                 135                 140

Pro Pro Asn Asp Trp Thr Ser Glu Phe Gly Gly Pro Ala Trp Thr Arg
145                 150                 155                 160

Leu Pro Asp Gly His Trp Tyr Leu His Leu Phe Ala Pro Glu Gln Pro
                165                 170                 175

Asp Leu Asn Trp Ala His Pro Ala Val Arg Gln Glu His Glu Asp Ile
            180                 185                 190
```

-continued

```
Leu Arg Phe Trp Leu Glu Arg Gly Val Ala Gly Val Arg Ile Asp Ser
        195                 200                 205

Ala Ala Leu Leu Ala Lys Asp Pro Arg Leu Pro Asp Phe Val Glu Gly
    210                 215                 220

Arg Asp Pro His Pro Tyr Val Asp Arg Asp Glu Leu His Asp Ile Tyr
225                 230                 235                 240

Arg Ser Trp Arg Gly Val Ala Asp Glu Tyr Gly Gly Val Phe Val Gly
                245                 250                 255

Glu Val Trp Leu Pro Asp Ser Glu Arg Phe Ala Arg Tyr Leu Arg Pro
            260                 265                 270

Asp Glu Leu His Thr Ala Phe Asn Phe Ser Phe Leu Ala Cys Pro Trp
        275                 280                 285

Asp Ala Arg Arg Leu Arg Thr Ser Ile Asp Glu Thr Leu Ala Glu His
    290                 295                 300

Ala Pro Val Gly Ala Pro Ala Thr Trp Val Leu Cys Asn His Asp Val
305                 310                 315                 320

Thr Arg Thr Val Thr Arg Tyr Gly Arg Glu Asp Thr Gly Phe Asp Phe
                325                 330                 335

Ala Thr Lys Val Phe Gly Thr Pro Thr Asp Leu Thr Leu Gly Thr Arg
            340                 345                 350

Arg Ala Arg Ala Ala Ala Leu Leu Ser Leu Ala Leu Pro Gly Ala Val
        355                 360                 365

Tyr Val Tyr Gln Gly Glu Glu Leu Gly Leu Pro Glu Ala Asp Ile Pro
    370                 375                 380

Arg Asp Arg Ile Gln Asp Pro Met His Phe Arg Ser Gly Gly Thr Asp
385                 390                 395                 400

Pro Gly Arg Asp Gly Cys Arg Val Pro Leu Pro Trp Ala Ala Glu Ala
                405                 410                 415

Pro Tyr Ala Gly Phe Gly Ser Arg Glu Glu Pro Trp Leu Pro Gln Pro
            420                 425                 430

Ala His Trp Ala Ala Tyr Ala Ala Asp Leu Gln Thr Glu Ala Pro Gly
        435                 440                 445

Ser Met Leu Gly Leu Tyr Arg Ala Ala Ile Arg Ile Arg Arg Thr Thr
    450                 455                 460

Pro Gly Phe Gly Asp Gly Pro Leu Thr Trp Leu Pro Ser Ala Asp Gly
465                 470                 475                 480

Val Leu Ala Phe Ala Arg Ala Asp Gly Leu Val Cys Val Val Asn Leu
                485                 490                 495

Ala Asp Thr Pro Thr Glu Leu Asp Gly Ala Ser Arg Leu Leu Leu Ser
            500                 505                 510

Ser Gly Pro Leu Asp Asp Arg Gly Arg Leu Pro Gln Asp Thr Ala Ala
        515                 520                 525

Trp Leu Leu Arg
    530
```

<210> SEQ ID NO 42
<211> LENGTH: 291
<212> TYPE: PRT
<213> ORGANISM: Streptomyces sp.

<400> SEQUENCE: 42

```
Met Ser Thr Arg Thr Leu Val Ser Pro Ala Ala Leu Ala Arg Pro Arg
1               5                   10                  15

Gly Arg Ala Val Tyr Trp Thr Val Phe Thr Thr Val Val Val Leu Phe
            20                  25                  30
```

-continued

```
Ala Ile Ala Phe Leu Phe Pro Val Tyr Trp Met Val Thr Gly Ala Met
        35                  40                  45

Lys Ser Pro Asp Glu Val Ala Arg Thr Pro Pro Thr Ile Val Pro Lys
    50                  55                  60

Glu Trp His Leu Ser Gly Tyr Ser Asp Ala Trp Asp Leu Met Gln Leu
65                  70                  75                  80

Pro Gln His Leu Trp Asn Thr Val Val Gln Ala Ala Gly Ala Trp Leu
                85                  90                  95

Phe Gln Leu Val Phe Cys Thr Ala Ala Ala Tyr Ala Leu Ser Arg Leu
            100                 105                 110

Lys Pro Ala Phe Gly Lys Val Ile Leu Gly Gly Ile Leu Ala Thr Leu
        115                 120                 125

Met Val Pro Ala Gln Ala Leu Val Val Pro Lys Tyr Leu Thr Val Ala
    130                 135                 140

Asp Leu Pro Leu Ile His Thr Ser Leu Leu Asn Asp Pro Leu Ala Ile
145                 150                 155                 160

Trp Leu Pro Ala Val Ala Asn Ala Phe Asn Leu Tyr Leu Leu Lys Arg
                165                 170                 175

Phe Phe Asp Gln Ile Pro Arg Asp Val Leu Glu Ala Ala Glu Ile Asp
            180                 185                 190

Gly Ala Gly Lys Leu Arg Thr Leu Trp Ser Ile Val Leu Pro Met Ser
        195                 200                 205

Arg Pro Val Leu Gly Val Val Ser Ile Phe Ala Leu Val Ala Val Trp
    210                 215                 220

Gln Asp Phe Leu Trp Pro Leu Met Val Phe Ser Asp Thr Gly Lys Gln
225                 230                 235                 240

Pro Ile Ser Val Ala Leu Val Gln Leu Ser Gln Asn Ile Gln Leu Thr
                245                 250                 255

Val Leu Ile Ala Ala Met Val Ile Ala Ser Ile Pro Met Val Ala Leu
            260                 265                 270

Phe Leu Val Phe Gln Arg His Ile Ile Ala Gly Ile Ser Ala Gly Ser
        275                 280                 285

Thr Lys Gly
    290


<210> SEQ ID NO 43
<211> LENGTH: 340
<212> TYPE: PRT
<213> ORGANISM: Streptomyces sp.

<400> SEQUENCE: 43

Met Ser Thr Ser Ser Trp Arg Lys Pro Pro Thr Arg Ser Thr Thr Phe
1               5                   10                  15

Trp Pro Gly Ala Asp Pro Met Thr Lys Thr Ala Ala Arg Pro Pro Ala
            20                  25                  30

Glu Ala Ile Ala Val His Pro Val Gln Ala Pro Pro Pro Ala Gly Gly
        35                  40                  45

Arg Gly Arg Arg Arg Leu Ala Asp Gln Val Arg Ala Tyr Gly Phe Leu
    50                  55                  60

Leu Gly Gly Leu Ile Cys Phe Ala Leu Phe Ser Trp Tyr Pro Ala Ile
65                  70                  75                  80

Arg Ala Val Val Ile Ala Phe Gln Lys Tyr Thr Pro Gly Ser Ser Pro
                85                  90                  95

Glu Trp Val Gly Thr Ala Asn Phe Thr Arg Val Leu His Asp Pro Glu
```

-continued

```
            100                 105                 110

Phe Thr Ala Ala Trp Arg Asn Thr Leu Thr Phe Thr Leu Leu Ala Leu
        115                 120                 125

Leu Ile Gly Phe Ala Ile Pro Phe Leu Leu Ala Leu Val Leu Asn Glu
    130                 135                 140

Leu Arg His Ala Lys Ala Phe Phe Arg Val Val Val Tyr Leu Pro Val
145                 150                 155                 160

Met Ile Pro Pro Val Val Ser Ala Leu Leu Trp Lys Trp Phe Tyr Asp
                165                 170                 175

Pro Gly Ala Gly Leu Ala Asn Glu Ala Leu Arg Phe Leu His Leu Pro
            180                 185                 190

Thr Ser Asn Trp Ser Asn Gly Ala Asp Thr Ala Leu Val Ser Leu Val
        195                 200                 205

Ala Val Ala Thr Trp Ala Asn Met Gly Gly Thr Val Leu Ile Tyr Leu
    210                 215                 220

Ala Ala Leu Gln Ser Ile Pro Gly Glu Leu Tyr Glu Ala Ala Glu Leu
225                 230                 235                 240

Asp Gly Ala Ser Leu Leu Gln Arg Val Arg His Val Thr Ile Pro Gln
                245                 250                 255

Thr Arg Phe Val Ile Leu Met Leu Met Leu Leu Gln Ile Ile Ala Thr
            260                 265                 270

Met Gln Val Phe Thr Glu Pro Phe Val Ile Thr Gly Gly Gly Pro Glu
        275                 280                 285

Asn Ala Thr Val Thr Val Leu Tyr Leu Ile Tyr Lys Tyr Ala Phe Leu
    290                 295                 300

Tyr Asn Asp Phe Gly Gly Ala Cys Ala Leu Ser Val Met Leu Leu Val
305                 310                 315                 320

Leu Leu Gly Ala Phe Ser Ala Leu Tyr Leu Arg Leu Thr Arg Ser Gly
                325                 330                 335

Glu Asp Asp Ala
            340


<210> SEQ ID NO 44
<211> LENGTH: 476
<212> TYPE: PRT
<213> ORGANISM: Streptomyces sp.

<400> SEQUENCE: 44

Val Leu Glu Cys Ala Ala His Ser Arg Leu Cys Ala Pro Arg Ser Arg
1               5                   10                  15

Pro Trp Gly Phe Pro Ala Pro Val Gln Arg Gly Pro Pro Met Arg Ser
            20                  25                  30

Thr Gly Phe Arg Arg Thr Leu Ile Ala Leu Ser Thr Phe Pro Leu Ala
        35                  40                  45

Leu Thr Ala Cys Gly Gly Ser Gly Asp Gly Ser Ala Gly Gly Lys Thr
    50                  55                  60

Arg Ile Thr Val Asn Cys Met Pro Pro Lys Ser Ala Lys Val Asp Arg
65                  70                  75                  80

Arg Phe Phe Glu Glu Asp Ile Ala Ser Phe Glu Lys Gln Asn Pro Asp
                85                  90                  95

Ile Asp Val Val Ala His Asp Ala Phe Pro Cys Gln Asp Pro Lys Thr
            100                 105                 110

Phe Asp Ala Lys Leu Ala Gly Gly Gln Met Glu Asn Val Phe Tyr Thr
        115                 120                 125
```

-continued

```
Tyr Phe Thr Asp Ala Gly His Val Val Asp Ile Asn Gln Ala Ala Asp
    130                 135                 140

Leu Thr Pro Tyr Val Lys Glu Leu Lys Ser Tyr Ser Thr Leu Gln Lys
145                 150                 155                 160

Gln Leu Arg Asp Ile Tyr Thr Val Asp Gly Lys Ile Tyr Gly Ile Pro
                165                 170                 175

Arg Thr Gly Tyr Ser Met Gly Leu Ile Tyr Asn Arg Lys Leu Phe Glu
            180                 185                 190

Lys Ala Gly Leu Asp Pro Asp Lys Pro Pro Met Thr Trp Glu Glu Val
        195                 200                 205

Arg Ala Asp Ala Lys Arg Ile Ala Lys Leu Gly Asp Gly Thr Val Gly
    210                 215                 220

Tyr Ala Asp Tyr Ser Ala Gln Asn Gln Gly Gly Trp His Phe Thr Ala
225                 230                 235                 240

Glu Leu Tyr Ser Gln Gly Gly Asp Val Val Ser Ala Asp Gly Lys Lys
                245                 250                 255

Ala Thr Ile Asp Thr Pro Glu Ala Arg Ala Val Leu Arg Asn Leu His
            260                 265                 270

Asp Met Arg Trp Val Asp Asp Ser Met Gly Ser Lys Gln Leu Leu Val
        275                 280                 285

Ile Asn Asp Ala Gln Gln Leu Met Gly Ser Gly Lys Leu Gly Met Tyr
    290                 295                 300

Leu Ala Ala Pro Asp Asn Leu Pro Ile Leu Val Lys Glu Lys Gly Gly
305                 310                 315                 320

Asn Tyr Lys Asp Leu Ala Ile Ala Pro Met Pro Gly Gly Lys Gly Thr
                325                 330                 335

Leu Ile Gly Gly Asp Gly Tyr Met Phe Gln Lys Lys Asp Thr Pro Ala
            340                 345                 350

Gln Ile Arg Ala Gly Leu Lys Trp Leu Asp His Met Phe Leu Thr Pro
        355                 360                 365

Gly Asp Gly Phe Leu Gly Asp Tyr Val Arg Ala Lys Lys Arg Asn Ala
    370                 375                 380

Pro Val Gly Leu Pro Glu Pro Arg Leu Phe Thr Gly Ala Ala Asp Ala
385                 390                 395                 400

Lys Asp Gln Gln Val Lys Lys Ala Asn Ala Asn Val Pro Val Gly Asn
                405                 410                 415

Tyr Gln Thr Phe Leu Asp Gly Asn Gln Lys Leu Arg Met Arg Ile Glu
            420                 425                 430

Pro Pro His Ala Gln Gln Ile Tyr Ser Val Leu Asp Gly Ala Val Ser
        435                 440                 445

Ala Val Leu Thr Lys Lys Asp Ala Asp Val Asp Gln Leu Leu Glu Glu
    450                 455                 460

Ala Ser Asp Lys Ile Asp Asn Ile Leu Ala Arg Gly
465                 470                 475


<210> SEQ ID NO 45
<211> LENGTH: 325
<212> TYPE: PRT
<213> ORGANISM: Streptomyces sp.

<400> SEQUENCE: 45

Val Ala Lys Lys Val Gly Val Ser Glu Ala Thr Val Ser Arg Val Leu
1               5                   10                  15

Asn Gly Lys Pro Gly Val Ser Ala Ala Thr Arg Gln Ala Val Leu Ser
            20                  25                  30
```

```
Ala Leu Asp Val Leu Gly Tyr Glu Arg Pro Thr Gln Leu Arg Gly Asp
        35                  40                  45

Arg Ala Arg Leu Val Gly Leu Val Leu Pro Glu Leu Gln Asn Pro Ile
    50                  55                  60

Phe Pro Ala Phe Ala Glu Val Ile Gly Gly Ala Leu Ala Gln Leu Gly
65                  70                  75                  80

Leu Thr Pro Val Leu Cys Thr Gln Thr Lys Gly Gly Val Ser Glu Ala
                85                  90                  95

Asp Tyr Val Ala Leu Leu Leu Gln Gln Gln Val Ser Gly Val Val Phe
            100                 105                 110

Ala Gly Gly Leu Tyr Ala Gln Ala Asp Ala Pro His Asp His Tyr Arg
        115                 120                 125

Leu Leu Ala Glu Arg Asn Ile Pro Val Val Leu Val Asn Ala Ala Ile
    130                 135                 140

Glu His Leu Gly Phe Pro Ala Val Ser Cys Asp Asp Ala Val Ala Val
145                 150                 155                 160

Glu Gln Ala Trp Arg His Leu Ala Ser Leu Gly His Glu Arg Ile Gly
                165                 170                 175

Leu Val Leu Gly Pro Gly Asp His Met Pro Ser Ala Arg Lys Leu Thr
            180                 185                 190

Ala Ala Arg Ala Val Ala Gly His Leu Pro Asp Glu Phe Val Ala Arg
        195                 200                 205

Ala Ile Phe Ser Ile Glu Gly Gly His Ala Ala Ala Ser Arg Leu Ile
    210                 215                 220

Asp Arg Gly Val Thr Gly Ile Ile Cys Ala Ser Asp Pro Leu Ala Leu
225                 230                 235                 240

Gly Ala Ile Arg Ala Ala Arg Arg Lys Gly Phe Gly Val Pro Ser Gln
                245                 250                 255

Val Ser Val Val Gly Tyr Asp Asp Ser Ala Phe Met Asn Cys Thr Glu
            260                 265                 270

Pro Pro Leu Thr Thr Val Arg Gln Pro Ile Glu Ala Met Gly Arg Ala
        275                 280                 285

Ala Val Glu Val Leu Asn Ala Gln Ile Gly Gly Val Ala Val Pro Ser
    290                 295                 300

Glu Glu Leu Leu Phe Glu Pro Glu Leu Val Val Arg Gly Ser Thr Ala
305                 310                 315                 320

Gln Ala Pro Arg Glu
                325


<210> SEQ ID NO 46
<211> LENGTH: 1572
<212> TYPE: PRT
<213> ORGANISM: Streptomyces sp.

<400> SEQUENCE: 46

Val Gly Asn Ser Gly Ala Pro Lys Ser Arg Gly Leu Ser Ala Ala Met
1               5                   10                  15

Ser Asn Leu Phe Glu Arg Thr Arg Arg Asn Glu Ser Thr Gly Ile Val
            20                  25                  30

Pro Val Asp Arg Gly Arg Glu Leu Arg Ala Ser Phe Ala Gln Gln Arg
        35                  40                  45

Leu Trp Phe Leu Asp Gln Leu Glu Pro Gly Asn Ala Ser Tyr Asn Leu
    50                  55                  60

Pro Phe Ala Val Arg Val Arg Gly Arg Leu Asp Ile Ser His Leu Ser
```

-continued

```
65                  70                  75                  80

Arg Ala Leu Ser Leu Val Val Ala Arg His Glu Ala Leu Arg Thr Thr
                85                  90                  95

Phe Gly Glu Ala Gly Gly Gln Pro Val Gln Arg Ile Glu Pro Pro Gly
            100                 105                 110

Pro Val Pro Val Arg Leu Glu Ala Val Ser Gly Gly Ser Glu Glu Glu
        115                 120                 125

Arg Leu Ala Glu Val Arg Arg Leu Ala Gly Ala Glu Ile Thr Glu Pro
    130                 135                 140

Phe Asp Leu Ser Thr Gly Pro Leu Leu Arg Ala Lys Ala Leu Arg Leu
145                 150                 155                 160

Asp Glu Gln Asp His Val Leu Leu Leu Thr Val His His Val Ala Thr
                165                 170                 175

Asp Ala Trp Ser Gln Gly Ile Val Val Arg Glu Leu Ser Val Ala Tyr
            180                 185                 190

Ala Ser Leu Asp Ala Gly Arg Glu Pro Val Leu Pro Pro Leu Pro Val
        195                 200                 205

Gln Tyr Ala Asp Tyr Ala Glu Trp Glu Arg Asp Trp Leu Ser Gly Pro
    210                 215                 220

Thr Leu Arg Arg Gln Leu Asp Tyr Trp Thr Lys Arg Leu Asp Gly Met
225                 230                 235                 240

Ala Pro Ala Leu Glu Leu Pro Thr Asp Arg Pro Arg Pro Ser Val Ala
                245                 250                 255

Ser Gln Glu Gly Asp Ala Val Arg Trp Glu Leu Pro Pro Glu Leu Ile
            260                 265                 270

Arg Ala Ala Arg Arg Leu Gly Ala Gly Glu Asn Ala Thr Leu Tyr Met
        275                 280                 285

Thr Leu Leu Ala Ala Phe Gln Leu Val Leu Gly Arg Tyr Val Asp Ser
    290                 295                 300

Asp Asp Ile Thr Val Gly Thr Pro Val Ala Asn Arg Gly Arg Ala Glu
305                 310                 315                 320

Val Glu Gly Leu Ile Gly Phe Phe Val Asn Thr Val Val Leu Arg Thr
                325                 330                 335

Asp Leu Ser Gly Asp Pro Thr Phe Arg Gln Leu Leu Gly Arg Val Arg
            340                 345                 350

Asp Thr Ala Ala Gly Ala Phe Ala His Gly Asp Leu Pro Phe Glu Tyr
        355                 360                 365

Leu Val Glu Gln Val His Pro Glu Arg Asp Leu Ser Arg Asn Pro Leu
    370                 375                 380

Val Gln Val Leu Phe Gln Met Ile Asn Val Pro Ala Glu Arg Leu Glu
385                 390                 395                 400

Leu Pro Gly Ala Arg Thr Glu Pro Tyr Asp His Gly Gly Ile Leu Thr
                405                 410                 415

Arg Met Asp Leu Glu Val His Leu Val Glu Thr Gly Asp Gly Val Leu
            420                 425                 430

Gly His Ile Val Phe Ser Lys Ala Leu Phe Asp Thr Ser Thr Ile Glu
        435                 440                 445

Arg Leu Leu His His Val Thr Val Val Leu Arg Gly Val Leu Ala Glu
    450                 455                 460

Pro Asp Arg Arg Ile Ser Glu Ile Ser Leu Leu Asp Glu Ala Glu Arg
465                 470                 475                 480

Ala Lys Val Leu Glu Lys Phe Asn Thr Thr Thr Gly Pro Val Pro Ala
                485                 490                 495
```

-continued

```
Gly Ser Leu Pro Ala Leu Phe Thr Ala Gln Ala Glu Arg Arg Pro Asp
            500                 505                 510

Ala Val Ala Val Ile Ser Gly Gly Asp Arg Val Thr Tyr Ala Glu Leu
        515                 520                 525

Asp Gln Arg Ala Asn Gln Leu Ala His Leu Leu Glu Gly Arg Gly Val
    530                 535                 540

Gly Pro Glu Thr Leu Val Gly Leu Cys Val Asp Arg Gly Ile Glu Met
545                 550                 555                 560

Ile Val Ala Ile Leu Ala Ile Leu Lys Leu Gly Ala Ala Tyr Val Pro
                565                 570                 575

Ile Asp Pro His His Pro Arg Asp Arg Val Gln Phe Val Leu Ala Asp
            580                 585                 590

Ser Gly Val Thr Val Ala Val Thr Gln Gln Arg Phe Thr Gly Leu Leu
        595                 600                 605

Glu Thr Pro Glu Ala Pro Gly Thr Pro Asp Ala Ser Gly Thr Ser Gly
    610                 615                 620

Ile Arg Leu Ile Leu Leu Asp Ala Glu Arg Glu Pro Leu Ala Gly Gln
625                 630                 635                 640

Pro Arg Thr Pro Pro Thr Ala Arg Pro Ser Ala Gln Asn Leu Ala Tyr
                645                 650                 655

Val Ile Tyr Thr Ser Gly Ser Thr Gly Val Pro Lys Gly Ile Leu Met
            660                 665                 670

Pro Ala Thr Cys Val Leu Asn Leu Val Ala Trp Gln Lys Arg Ala Leu
        675                 680                 685

Pro Ile Gly Pro Asp Ala Lys Thr Ala Gln Phe Ala Thr Leu Thr Phe
    690                 695                 700

Asp Ile Ser Leu Gln Glu Ile Phe Ser Ala Leu Leu Tyr Gly Glu Thr
705                 710                 715                 720

Ile Val Val Pro Gly Glu Glu Leu Arg Met Asp Pro Ala Glu Phe Ala
                725                 730                 735

Thr Trp Val His Ala Asn Glu Ile Asp Gln Leu Phe Val Pro Asn Val
            740                 745                 750

Met Leu Arg Ala Ile Ser Glu Glu Val Asp Pro His Gly Thr Glu Leu
        755                 760                 765

Ala Ala Leu Arg His Leu Ser Gln Ala Gly Glu Pro Leu Ser Leu His
    770                 775                 780

His Asp Leu Arg Glu Leu Cys Ala Arg Arg Pro Glu Leu Arg Leu His
785                 790                 795                 800

Asn His Tyr Gly Pro Ser Glu Ala His Val Val Thr Ser Tyr Ser Leu
                805                 810                 815

Pro Ala Glu Val Ala Glu Trp Pro Leu Thr Ala Pro Ile Gly Arg Pro
            820                 825                 830

Ile Gly Asn Thr Arg Val Tyr Val Val Asp Arg Arg Leu Arg Pro Val
        835                 840                 845

Pro Val Gly Val Pro Gly Glu Leu Cys Val Ala Gly Glu Gly Leu Ala
    850                 855                 860

Arg Gly Tyr Leu Gly Arg Pro Asp Leu Thr Ala Ser Arg Phe Val Ala
865                 870                 875                 880

Asp Pro Phe Arg Gly Asp Gly Ser Arg Met Tyr Arg Ser Gly Asp Leu
                885                 890                 895

Val Arg Trp Leu Pro Asp Gly Asn Leu Glu Phe Leu Gly Arg Ile Asp
            900                 905                 910
```

-continued

```
Asp Gln Val Lys Ile Arg Gly Phe Arg Ile Glu Pro Gly Glu Ile Glu
        915                 920                 925

Ala Ile Leu Ala Arg His Gln Asp Val Leu His Thr Ala Val Met Val
    930                 935                 940

Arg Glu Asp Thr Pro Gly Asp Lys Arg Leu Val Ala Tyr Val Val Ala
945                 950                 955                 960

Asp Ala Thr Ala Ala Asp Arg His Gly Gly Leu Thr Glu Thr Leu Arg
                965                 970                 975

Arg His Val Glu Ser Ala Val Pro Glu Tyr Met Val Pro Ser Ala Phe
            980                 985                 990

Val Leu Leu Asp Thr Met Pro Leu  Thr Ser Gly Gly Lys  Ile Asp Arg
        995                 1000                1005

Lys Ala  Leu Pro Ala Pro Asp  Leu Arg Thr Val Leu  Glu Val Gly
    1010                 1015                 1020

Tyr Val  Ala Pro Arg Thr Pro  Glu Glu Glu Ala Val  Cys Arg Val
    1025                 1030                 1035

Tyr Ala  Asp Leu Leu Gly Ala  Ala Lys Val Gly Ile  Asp Asp Asp
    1040                 1045                 1050

Phe Phe  Ala Leu Gly Gly His  Ser Leu Ile Ala Thr  Arg Val Val
    1055                 1060                 1065

Ala Arg  Leu Arg Ser Ala Leu  Gly Ile Ala Val Pro  Leu Lys Thr
    1070                 1075                 1080

Val Phe  Gln Gln Arg Thr Pro  Arg Glu Leu Ala Ala  Thr Leu Thr
    1085                 1090                 1095

Ala Ala  Ala Arg Ser Gly Pro  Glu Pro Glu Leu Pro  Pro Leu Val
    1100                 1105                 1110

Pro Thr  Arg Arg Asp Gln Pro  Val Pro Leu Thr Phe  Ala Gln Gln
    1115                 1120                 1125

Gln Thr  Asp Leu Phe Phe Asp  Asp Val Leu Asn Ala  Gly His Trp
    1130                 1135                 1140

Asn Ile  Pro Met Ala Val Arg  Val Ser Gly Glu Leu  Asp Leu Asp
    1145                 1150                 1155

Cys Leu  Arg Arg Ala Met Asp  Leu Leu Ile Asp Arg  His Glu Ala
    1160                 1165                 1170

Leu Arg  Thr Thr Phe Val Arg  Glu Ala Asp Gly Tyr  Val Gln Val
    1175                 1180                 1185

Ile Arg  Pro Ser Ala Pro Val  Gln Val Glu Val Ala  Glu Thr His
    1190                 1195                 1200

Asp Glu  Thr Glu Ala Ser Val  Leu Ala Gly Gln Glu  Ala Ala Arg
    1205                 1210                 1215

Pro Phe  Asp Leu Thr Arg Gly  Pro Leu Ala Arg Leu  Arg Val Leu
    1220                 1225                 1230

Arg Leu  Ser Gln Ser Asp His  Val Leu Val Leu Thr  Leu His His
    1235                 1240                 1245

Leu Val  Thr Asp Gly Trp Ser  Gln Gly Val Leu Val  Arg Asp Leu
    1250                 1255                 1260

Ser Ile  Val Tyr Ala Ala Leu  Leu His Gly Thr Glu  Pro Asp Leu
    1265                 1270                 1275

Pro Pro  Ala Pro Val Gln Tyr  Ala Asp Val Ala Ser  Trp Glu Arg
    1280                 1285                 1290

Lys Trp  Leu Arg Gly Pro Leu  Leu Gln Arg Gln Leu  Glu Phe Trp
    1295                 1300                 1305

Lys Arg  His Phe Glu Gly Met  Thr Pro Ala Glu Leu  Pro Thr Asp
```

-continued

```
    1310                1315                1320

Arg Pro  Arg Ala Ala Ser Ala  Arg Tyr Glu Ser Asp  Ile Phe His
    1325                1330                1335

Trp Arg  Leu Pro Thr Asp Ala  Val Glu Thr Ala Arg  Arg Leu Gly
    1340                1345                1350

Glu Ser  Cys Asn Ala Thr Leu  Tyr Met Thr Leu Leu  Thr Ala Leu
    1355                1360                1365

Lys Val  Val Met Ser Ala Arg  Ser Asp Asn Gln Asp  Val Leu Val
    1370                1375                1380

Gly Val  Pro Thr Ala Asn Arg  Gly Arg Asp Glu Leu  Glu Asn Thr
    1385                1390                1395

Val Gly  Leu Val Ser Lys Met  Leu Ala Leu Arg Thr  Glu Val Ser
    1400                1405                1410

Gly Ala  Thr Asp Phe Gly Thr  Leu Leu Ala Thr Val  Arg Asp Ala
    1415                1420                1425

Met Ser  Asp Ala His Thr His  Gln Asp Val Pro Phe  Val Ser Val
    1430                1435                1440

Leu Lys  His Ile Gly Asp His  Thr Ala Gly Pro Ala  Gly Asp Thr
    1445                1450                1455

Ala Gly  Gly Arg Ala Gly Thr  Arg Leu Ser Asp Asp  Pro Pro Val
    1460                1465                1470

Lys Val  Ile Phe Gln Ile Val  Asn Thr Pro Pro Arg  Pro Leu Arg
    1475                1480                1485

Leu Thr  Gly Leu Thr Ala Glu  Pro Phe Pro Met Thr  His Pro Pro
    1490                1495                1500

Val Thr  Val Asn Val Asp Met  Glu Ile Asp Leu Tyr  Glu Ser Ala
    1505                1510                1515

Glu Asp  Gly Gly Leu Ala Gly  Thr Val Leu Phe Ser  Lys Ser Leu
    1520                1525                1530

Phe Asp  Arg Ala Thr Ile Glu  Arg Phe Cys Asp Asp  Val Val Ala
    1535                1540                1545

Val Val  Ser Ala Ala Ala Ala  Asp Pro Gly Arg Pro  Val Ser Gln
    1550                1555                1560

Val Trp  Gln Gly Arg Gly Arg  Asp Gln
    1565                1570


<210> SEQ ID NO 47
<211> LENGTH: 5712
<212> TYPE: PRT
<213> ORGANISM: Streptomyces sp.

<400> SEQUENCE: 47

Val Ala Gly Pro Gly Pro Arg Pro Val Asn Asp Pro Ala Pro Arg Lys
1               5                   10                  15

Arg Met Glu Pro Asp Glu Ala Val Ala Val Val Gly Met Ser Cys Arg
            20                  25                  30

Phe Pro Gln Ala Pro Asp Pro Glu Ala Phe Trp Arg Leu Leu Ser Glu
        35                  40                  45

Gly Ile Ser Ala Ile Gly Glu Val Pro Ala Gly Arg Trp Thr Asp Asp
    50                  55                  60

Gln Pro Thr Pro Ser Gly Thr Asp Glu Arg Ser Thr Pro Pro Ala Ile
65                  70                  75                  80

Arg Arg Gly Gly Phe Ile Asp Asp Val Asp Arg Phe Asp Pro Ala Phe
                85                  90                  95
```

-continued

```
Phe Gly Ile Ser Pro Arg Glu Ala Ala Ala Met Asp Pro Gln Gln Arg
            100                 105                 110

Leu Met Leu Glu Leu Ala Trp Glu Gly Leu Glu Asp Ala Gly Ile Val
        115                 120                 125

Pro Ala Thr Leu Arg Gly Ala Thr Val Gly Ala Phe Ile Gly Ala Gly
    130                 135                 140

Ser Asp Asp Tyr Ala Ser Leu Ile Arg Ala Arg Gly Arg Ser His His
145                 150                 155                 160

Thr Leu Thr Gly Thr Gln Arg Gly Met Ile Ala Asn Arg Leu Ser His
                165                 170                 175

Val Phe Gly Leu Ser Gly Pro Ser Val Thr Val Asp Ala Ala Gln Ala
            180                 185                 190

Ser Ser Leu Val Ala Val His Met Ala Val Glu Ser Val Arg Arg Gly
        195                 200                 205

Glu Ser Arg Leu Ala Leu Ala Gly Gly Val Asn Leu Asn Leu Ser Ala
    210                 215                 220

Glu Thr Ala Ala Asp Ile Ala Ala Phe Gly Ala Leu Ser Pro Asp Gly
225                 230                 235                 240

Arg Cys Phe Thr Phe Asp Ala Arg Ala Asn Gly Tyr Val Arg Gly Glu
                245                 250                 255

Gly Gly Gly Leu Val Val Leu Lys Pro Leu Ser Asp Ala Leu Ala Asp
            260                 265                 270

Gly Asp Thr Val Tyr Cys Val Ile Glu Gly Ser Ala Val Asn Asn Asp
        275                 280                 285

Gly Gly Gly Ala Ser Leu Thr Ala Pro Asp Pro Asp Gly Gln Arg Arg
    290                 295                 300

Val Leu Arg Leu Ala Gln Arg Arg Ala Ala Ile Ser Pro Glu Ala Val
305                 310                 315                 320

Gln Tyr Val Glu Leu His Gly Thr Gly Thr Ala Leu Gly Asp Pro Ala
                325                 330                 335

Glu Ala Ala Ala Leu Gly Ala Val Phe Gly Arg Ser Gly Ala Arg Pro
            340                 345                 350

Val Gln Leu Gly Ser Val Lys Thr Asn Ile Gly His Leu Glu Ala Ala
        355                 360                 365

Ala Gly Ile Ala Gly Leu Leu Lys Thr Ala Leu Ala Ile His His Arg
    370                 375                 380

Gln Leu Pro Ala Gly Leu Asn Tyr Arg Thr Pro Asn Pro Arg Ile Pro
385                 390                 395                 400

Met Gly Glu Leu Asn Leu Glu Met Arg Leu Ala Pro Gly Glu Trp Pro
                405                 410                 415

Lys Pro Asp Asp Arg Leu Val Ala Gly Val Ser Ser Phe Gly Met Gly
            420                 425                 430

Gly Thr Asn Cys His Val Leu Leu Ala Glu Pro Leu Val Gly Val Pro
        435                 440                 445

Ser His Ala Ser Ala His Ala Pro Glu Pro Asp Ser Leu Pro Ser Ser
    450                 455                 460

Ile Pro Ala Pro Val Pro Val Pro Val Pro Val Pro Ala Pro Val Pro
465                 470                 475                 480

Val Pro Ala Pro Ala Pro Ala Pro Ala Pro Val Pro Val Pro Val Pro
                485                 490                 495

Leu Pro Leu Ser Gly Val Ser Ala Ala Ala Leu Arg Gly Gln Ala Met
            500                 505                 510

Arg Leu Arg Pro Tyr Leu Glu Arg Ser Pro Asn Leu Thr Asp Leu Ser
```

-continued

```
        515                 520                 525

Phe Ser Leu Ala Thr Ala Arg Thr Ser Phe Asp His Arg Ala Val Leu
    530                 535                 540

Ile Thr Gly Gln Ala Ala Asp Ala Ala His Gly Leu Asp Ala Leu Val
545                 550                 555                 560

Glu Gly Gly Thr Val Ala Gly Leu Val Thr Gly Thr Ala Arg Ala Ala
                565                 570                 575

Gly Lys Leu Ala Phe Ala Phe Ala Gly Gln Gly Ser Gln Arg Leu Gly
            580                 585                 590

Met Gly Arg Glu Leu Gly Ala Val Phe Pro Val Phe Ala Gln Ala Leu
        595                 600                 605

Asp Glu Val Cys Thr Ala Leu Asp Ala His Leu Asp Arg Pro Leu Arg
    610                 615                 620

Asp Val Ile His Gly Asp Asp Ala Glu Pro Leu Asn Arg Thr Val Tyr
625                 630                 635                 640

Ala Gln Ala Gly Leu Phe Ala Val Glu Val Ala Leu Phe Arg Leu Leu
                645                 650                 655

Glu Asp Phe Gly Leu Val Pro Asp Leu Leu Ile Gly His Ser Leu Gly
            660                 665                 670

Glu Val Ser Ala Ala His Val Ala Gly Val Leu Ser Leu Ala Asp Ala
        675                 680                 685

Ala Thr Phe Val Ala Ala Arg Gly Arg Leu Met Gln Ala Val Thr Glu
    690                 695                 700

Pro Gly Ala Met Val Ser Leu Glu Ala Thr Glu Asp Glu Val Thr Arg
705                 710                 715                 720

Thr Leu Met Ala Gly Gly Ala Ser Asp Asp Gly Ala Arg Val Cys Val
                725                 730                 735

Ala Ala Val Asn Gly Pro Thr Ala Thr Val Ile Ser Gly Asp Glu Arg
            740                 745                 750

Ala Val Leu Asp Leu Ala Val Glu Trp Ala Gly Arg Gly Arg Lys Thr
        755                 760                 765

Lys Arg Leu Arg Thr Ser His Ala Phe His Ser Pro His Leu Asp Pro
    770                 775                 780

Val Leu Asp Glu Leu Arg His Ile Ala Glu Ser Leu Thr Tyr Arg Ala
785                 790                 795                 800

Pro Arg Ile Pro Leu Val Ser Asn Val Thr Gly Arg Arg Ala Thr Ala
                805                 810                 815

Glu Glu Leu Cys Ser Pro Glu Tyr Trp Val Arg His Val Arg Arg Thr
            820                 825                 830

Val Arg Phe Leu Asp Gly Val Arg Cys Leu Glu Asp Glu Gly Val Thr
        835                 840                 845

Thr Ile Leu Glu Leu Gly Pro Asp Lys Ala Leu Thr Thr Leu Ala Arg
    850                 855                 860

Asp Cys Leu Thr Gly Pro Gly Thr Leu Val Gly Thr Leu Arg Arg Asp
865                 870                 875                 880

Arg Pro Glu Pro Gln Ala Leu Val Thr Ala Leu Ala Glu Leu Tyr Val
                885                 890                 895

Ser Gly Val Glu Val Ala Trp Ser Pro Leu Val Ser Gly Gly Arg Arg
            900                 905                 910

Ile Pro Leu Pro Thr Tyr Ala Phe Gln Arg Gln Arg Tyr Trp Phe Ser
        915                 920                 925

Ala Pro Gly Pro Glu Ser Gly Thr Thr Pro Gly His Gly Val Thr Ser
    930                 935                 940
```

-continued

```
Gly Arg Glu Arg Thr Asp Thr Gly Leu Ser Gly Asp Glu Ala Pro Asp
945                 950                 955                 960

Thr Gly Pro Ser Gly Gly Glu Thr Leu Gly Met Val Arg Ala His Ala
                965                 970                 975

Ala Val Val Leu Gly Tyr Ala Ser Ala Thr Ala Ile Gly Ala Glu His
            980                 985                 990

Thr Phe Lys Gln Leu Gly Phe Asp  Ser Ile Thr Ala Val  Glu Leu Cys
        995                 1000                 1005

Glu Arg  Leu Gly Ala Ala Thr  Ala Leu Pro Leu Pro  Gly Thr Leu
    1010                 1015                 1020

Leu Phe  Asp Tyr Pro Thr Pro  Ala Ala Leu Ala Glu  His Leu His
    1025                 1030                 1035

Arg Arg  Leu His Gly Arg Thr  Asp Glu Gln Ala Ala  Pro Ala Thr
    1040                 1045                 1050

Val Pro  Thr Pro Asp Gly Gly  Asp Pro Val Val Ile  Val Gly Met
    1055                 1060                 1065

Gly Cys  Arg Phe Pro Gly Arg  Ala His Ser Pro Glu  Asp Leu Trp
    1070                 1075                 1080

Arg Ile  Val Ala Asp Gly Glu  Asp Ala Ile Ser Gly  Phe Pro Ser
    1085                 1090                 1095

Asp Arg  Gly Trp Asp Leu Ala  Gly Leu Tyr His Pro  Asp Pro Asp
    1100                 1105                 1110

His Pro  Gly Thr Ser Tyr Ala  Arg Asp Gly Gly Phe  Leu Tyr Asp
    1115                 1120                 1125

Ala Ala  Glu Phe Asp Ala Gly  Phe Phe Gly Ile Ser  Pro Arg Glu
    1130                 1135                 1140

Ala Glu  Ala Met Asp Pro Gln  Gln Arg Leu Leu Leu  Glu Thr Ser
    1145                 1150                 1155

Trp Glu  Ala Leu Glu Arg Ala  Gly Ile Pro Ala Glu  His Ile Lys
    1160                 1165                 1170

Gly Ser  Ser Thr Gly Val Phe  Ile Gly Ala Ser Ser  Val Gly Tyr
    1175                 1180                 1185

Ala Ala  Asp Ala Gly Glu Ala  Ala Glu Gly Tyr Gln  Leu Thr Gly
    1190                 1195                 1200

Thr Ala  Ala Ser Val Ala Ser  Gly Arg Val Ser Tyr  Thr Leu Gly
    1205                 1210                 1215

Leu Glu  Gly Pro Ala Val Thr  Val Asp Thr Ala Cys  Ser Ser Ser
    1220                 1225                 1230

Leu Val  Ala Leu His Leu Ala  Val Gln Ser Leu Arg  Ala Gly Glu
    1235                 1240                 1245

Cys Ser  Leu Ala Leu Ala Gly  Gly Val Thr Val Met  Ala Thr Pro
    1250                 1255                 1260

Ala Met  Phe Val Glu Phe Ser  Arg Gln Arg Gly Leu  Ala Met Asp
    1265                 1270                 1275

Gly Arg  Cys Lys Ala Phe Ala  Ala Ala Ala Asp Gly  Thr Gly Trp
    1280                 1285                 1290

Ala Glu  Gly Val Gly Val Leu  Val Val Glu Arg Leu  Ser Asp Ala
    1295                 1300                 1305

Glu Arg  Asn Gly His Arg Val  Leu Ala Val Val Arg  Gly Ser Ala
    1310                 1315                 1320

Val Asn  Gln Asp Gly Ala Ser  Asn Gly Leu Thr Ala  Pro Asn Gly
    1325                 1330                 1335
```

-continued

```
Pro Ser  Gln Gln Arg Val Ile  Arg Gln Ala Leu Ala  Ser Ala Gly
    1340                 1345                 1350

Leu Val  Ala Ser Asp Val Asp  Ala Val Glu Ala His  Gly Thr Gly
    1355                 1360                 1365

Thr Thr  Leu Gly Asp Pro Ile  Glu Ala Gln Ala Leu  Leu Ala Thr
    1370                 1375                 1380

Tyr Gly  Gln Gly Arg Asp Ala  Asp Arg Pro Leu Trp  Leu Gly Ser
    1385                 1390                 1395

Val Lys  Ser Asn Ile Gly His  Thr Gln Ala Ala Ala  Gly Val Ala
    1400                 1405                 1410

Gly Val  Ile Lys Met Val Met  Ala Met Arg His Gly  Val Leu Pro
    1415                 1420                 1425

Arg Thr  Leu His Val Asp Glu  Pro Ser Thr His Val  Asp Trp Ser
    1430                 1435                 1440

Gly Gly  Arg Val Glu Leu Leu  Thr Gly Thr Thr Pro  Trp Pro Thr
    1445                 1450                 1455

Thr Gly  Gly Leu Arg Arg Ala  Gly Val Ser Ser Phe  Gly Val Ser
    1460                 1465                 1470

Gly Thr  Asn Ala His Val Ile  Leu Glu Gln Val Pro  Glu Thr Ala
    1475                 1480                 1485

Arg Pro  Thr Gly Pro Ile Gly  Glu Asp Asp Gly Glu  Ala Ala Pro
    1490                 1495                 1500

Val Ala  Trp Val Leu Ser Gly  Gln Gly Glu Thr Gly  Leu Arg Ala
    1505                 1510                 1515

Gln Ala  Glu Arg Leu Cys Ala  Phe Met Ala Ala Asp  Thr Arg Pro
    1520                 1525                 1530

Thr Pro  Ala Glu Val Gly Trp  Ser Leu Ala Ser Thr  Arg Ala Thr
    1535                 1540                 1545

Leu Ser  His Arg Ala Val Val  Val Gly Ala Gly Arg  Asp Glu Leu
    1550                 1555                 1560

Leu Arg  Gly Val Asn Ala Val  Ala Asn Gly Thr Pro  Val Pro Gly
    1565                 1570                 1575

Val Val  Arg Gly Thr Gly Ala  Ser Gly Asp Val Val  Phe Val Phe
    1580                 1585                 1590

Pro Gly  Gln Gly Ser Gln Trp  Val Gly Met Ala Leu  Glu Leu Val
    1595                 1600                 1605

Glu Ser  Ser Pro Val Phe Ala  Arg Arg Leu Gly Asp  Cys Ala Asp
    1610                 1615                 1620

Ala Leu  Ala Pro Phe Val Glu  Trp Ser Leu Phe Asp  Val Leu Gly
    1625                 1630                 1635

Asp Glu  Val Ala Ile Gly Arg  Val Asp Val Val Gln  Pro Val Leu
    1640                 1645                 1650

Trp Ala  Val Met Val Ser Leu  Ala Glu Leu Trp Arg  Ser Phe Gly
    1655                 1660                 1665

Val Val  Pro Ser Ala Val Val  Gly His Ser Gln Gly  Glu Ile Ala
    1670                 1675                 1680

Ala Ala  Cys Val Ala Gly Ala  Leu Thr Leu Glu Asp  Gly Ala Arg
    1685                 1690                 1695

Val Val  Ala Leu Arg Ser Arg  Ala Leu Leu Ala Leu  Ser Gly Arg
    1700                 1705                 1710

Gly Gly  Met Val Ser Val Pro  Val Ser Ala Asp Arg  Leu Arg Asp
    1715                 1720                 1725

Arg Val  Gly Leu Ser Val Ala  Ala Val Asn Gly Pro  Ala Ser Thr
```

-continued

```
    1730                1735                1740

Val Val  Ser Gly Ala Val Glu  Val Leu Glu Ala Val  Leu Ala Glu
    1745                1750                1755

Phe Pro  Glu Ala Lys Arg Ile  Pro Val Asp Tyr Ala  Ser His Ser
    1760                1765                1770

Val Gln  Val Glu Gly Ile Arg  Glu Gly Leu Ala Glu  Ala Leu Ala
    1775                1780                1785

Pro Val  Arg Pro Arg Thr Gly  Gln Val Pro Phe Tyr  Ser Thr Val
    1790                1795                1800

Thr Gly  Arg Leu Met Asp Thr  Ile Glu Leu Asp Ala  Glu Tyr Trp
    1805                1810                1815

Tyr Arg  Asn Leu Arg Glu Thr  Val Glu Phe Gln Ser  Thr Val Glu
    1820                1825                1830

His Leu  Met Arg Gln Gly His  Thr Val Phe Val Glu  Ala Ser Pro
    1835                1840                1845

His Pro  Val Leu Thr Ile Gly  Val Gln Asp Thr Ala  Asp Thr Thr
    1850                1855                1860

Asp Thr  Asp Ile Val Val Thr  Gly Ser Leu Arg Arg  Asp Asp Gly
    1865                1870                1875

Thr Val  Gln Arg Phe Leu Thr  Ser Leu Ala Glu Leu  His Val Arg
    1880                1885                1890

Gly Val  Arg Ile Asp Trp Gly  Pro Leu Phe Ala Gly  Val Ser Pro
    1895                1900                1905

Val Glu  Leu Pro Thr Tyr Ala  Phe Gln Arg Glu Arg  Phe Trp Leu
    1910                1915                1920

Gly Ala  Asp Ile Ala Glu Ser  Ala Val Asp Thr Trp  Arg Tyr Gln
    1925                1930                1935

Ile Ser  Trp Lys Pro Leu Pro  Asp Met Asp Pro Pro  Ala Leu Ser
    1940                1945                1950

Gly Thr  Trp Leu Ala Val Val  Pro Glu Gly Asp Glu  Trp Ala Met
    1955                1960                1965

Ala Gly  Ala Arg Ala Leu Ile  Glu Ser Gly Thr Ala  Ser Val Arg
    1970                1975                1980

Thr Leu  Gln Val Thr Cys Asp  Ala Asp Arg Arg Thr  Leu Ala Gly
    1985                1990                1995

Pro Leu  Thr Asp Val Ala Gly  Ser Glu Asp Ile Ala  Gly Val Val
    2000                2005                2010

Ser Phe  Leu Ala Ala Asp Glu  Val Pro His Pro Ala  His Pro Ala
    2015                2020                2025

Leu Ser  Arg Gly Met Ala His  Thr Val Glu Leu Leu  Cys Ser Leu
    2030                2035                2040

Thr Thr  Ala Asp Val Glu Ala  Pro Leu Trp Cys Val  Thr Arg Ala
    2045                2050                2055

Ala Val  Thr Ala Leu Pro Ala  Asp Pro Ala Pro Ser  Pro Ala Gln
    2060                2065                2070

Ala Ala  Val Trp Gly Phe Gly  Arg Val Ala Gly Leu  Glu Arg Ser
    2075                2080                2085

Glu Arg  Trp Gly Gly Leu Ile  Asp Leu Pro Val His  Cys Asp Ala
    2090                2095                2100

His Val  Leu Arg Arg Phe Val  Ala Val Leu Ala Gln  Ala Ala Gly
    2105                2110                2115

Glu Asp  Gln Val Ala Val Arg  Pro Ser Ala Ala Leu  Gly Arg Arg
    2120                2125                2130
```

-continued

```
Leu Glu  Pro Ala Pro Arg Thr  Gly Pro Ala Gly Ala  Trp Arg Pro
    2135                 2140                 2145

His Gly  Thr Val Leu Ile Thr  Gly Gly Thr Gly Val  Leu Gly Ala
    2150                 2155                 2160

His Val  Ala Arg Trp Leu Ala  Arg Ser Gly Ala Glu  His Leu Val
    2165                 2170                 2175

Leu Leu  Ser Arg Arg Gly Pro  Gln Ala Pro Gly Ala  Ala Val Leu
    2180                 2185                 2190

Asp Asp  Glu Leu Thr Ala Leu  Gly Val Arg Val Thr  Leu Thr Ala
    2195                 2200                 2205

Cys Asp  Val Thr Asp Arg Ala  Ala Leu Ala Gly Val  Leu Ala Ser
    2210                 2215                 2220

Val Pro  Asp Leu Thr Ala Val  Val His Leu Ala Gly  Thr Val Arg
    2225                 2230                 2235

Phe Gly  Asn Ser Ile Asp Ala  Asp Leu Asp Glu Tyr  Ala Gly Val
    2240                 2245                 2250

Phe Asp  Ala Lys Val Thr Gly  Ala Leu His Leu Asp  Glu Leu Leu
    2255                 2260                 2265

Asp His  Ser Ser Leu Glu Ala  Phe Val Leu Phe Ser  Ser Ala Ala
    2270                 2275                 2280

Ala Val  Trp Gly Gly Val Gly  Gln Ala Gly Tyr Ala  Ala Ala Asn
    2285                 2290                 2295

Ala Leu  Leu Asp Ala Val Ala  Gln Arg Arg Arg Ala  Arg Gly Leu
    2300                 2305                 2310

Pro Ala  Thr Ser Ile Gly Trp  Gly Thr Trp Gly Gly  Ser Leu Ala
    2315                 2320                 2325

Pro Glu  Asp Glu Glu Arg Leu  Ser Arg Ile Gly Leu  Arg Pro Met
    2330                 2335                 2340

Arg Pro  Glu Val Ala Val Thr  Glu Leu Arg His Val  Val Gly Ser
    2345                 2350                 2355

Ala Glu  Pro Cys Pro Ala Ile  Ala Asp Val Asp Trp  Glu Thr Phe
    2360                 2365                 2370

Gly Pro  Ala Phe Thr Ala Gly  Arg Pro Ser Arg Leu  Leu Ser Glu
    2375                 2380                 2385

Leu Pro  Arg Leu Arg Asn Thr  Ser Gly Ala Met Ala  Met Thr Gly
    2390                 2395                 2400

Asp His  Ala Ala Leu Arg Arg  Arg Leu Ala Gly Val  Ser Ala Ala
    2405                 2410                 2415

Asp Gln  Ala Arg Thr Leu Val  Asp Leu Val Arg Glu  His Ala Ala
    2420                 2425                 2430

Glu Leu  Leu Gly His Arg Gly  Pro Ala Ala Ile Asp  Pro Thr Val
    2435                 2440                 2445

Pro Phe  Arg Gln Leu Gly Phe  Asp Ser Leu Thr Ala  Val Glu Leu
    2450                 2455                 2460

Arg Thr  Arg Leu Asn Ala Ala  Thr Gly Leu Arg Leu  Pro Ala Thr
    2465                 2470                 2475

Leu Leu  Phe Asp His Pro Ser  Cys Arg Ala Val Ala  Asp Leu Leu
    2480                 2485                 2490

Arg Ser  Glu Leu Leu Gly Asp  Arg Pro Gly Ser Leu  Ala Ala Ser
    2495                 2500                 2505

Ser Ala  Thr Glu Ala Val Pro  Ala Gly Val Val Ala  Ser Asp Glu
    2510                 2515                 2520
```

-continued

```
Pro Ile Ala Ile Val Ala Met Ser Cys Arg Phe Pro Gly Gly Ile
    2525                2530                2535

Gly Thr Pro Glu Asp Leu Trp Arg Val Val Ser Glu Gly Arg Asp
    2540                2545                2550

Val Leu Ser Asp Phe Pro Asp Asp Arg Gly Trp Asp Val Asp Ala
    2555                2560                2565

Leu Tyr Asp Pro Asp Pro Asp Arg Pro Gly Thr Ser Tyr Val Arg
    2570                2575                2580

Thr Gly Gly Phe Leu His Asp Ala Ala Glu Phe Asp Pro Glu Leu
    2585                2590                2595

Phe Gly Ile Ser Pro Arg Glu Ala Leu Ala Met Asp Pro Gln Gln
    2600                2605                2610

Arg Leu Leu Leu Glu Ser Ala Trp Gln Val Leu Glu Arg Ala Arg
    2615                2620                2625

Met Ala Pro Thr Ser Leu Arg Ser Ser Arg Thr Gly Val Phe Ile
    2630                2635                2640

Gly Gly Trp Gly Gln Gly Tyr Pro Ser Ala Ser Asp Glu Gly Tyr
    2645                2650                2655

Ala Leu Thr Gly Ala Ala Thr Ser Val Met Ser Gly Arg Ile Ala
    2660                2665                2670

Tyr Ala Leu Gly Leu Glu Gly Pro Ala Leu Thr Val Asp Thr Ala
    2675                2680                2685

Cys Ser Ser Ser Leu Val Ala Leu His Leu Ala Ser Glu Ala Leu
    2690                2695                2700

Arg Arg Gly Glu Cys Ser Leu Ala Leu Ala Gly Gly Val Thr Val
    2705                2710                2715

Met Ala Thr Pro Ser Thr Phe Val Glu Phe Ser Arg Gln Arg Gly
    2720                2725                2730

Leu Ala Pro Asp Gly Arg Cys Lys Pro Phe Ala Gly Ala Ala Asp
    2735                2740                2745

Gly Thr Gly Trp Gly Glu Gly Val Gly Met Leu Leu Val Glu Arg
    2750                2755                2760

Leu Ser Asp Ala Glu Arg Leu Gly His Pro Val Leu Ala Val Val
    2765                2770                2775

Ser Gly Ser Ala Val Asn Gln Asp Gly Ala Ser Asn Gly Leu Thr
    2780                2785                2790

Ala Pro Asn Gly Pro Ser Gln Gln Arg Val Ile Arg Gln Ala Leu
    2795                2800                2805

Ala Ser Ala Gly Leu Val Ala Ser Asp Val Asp Ala Val Glu Ala
    2810                2815                2820

His Gly Thr Gly Thr Thr Leu Gly Asp Pro Ile Glu Ala Gln Ala
    2825                2830                2835

Leu Leu Ala Thr Tyr Gly Gln Asp Arg Asp Ala Asp Arg Pro Leu
    2840                2845                2850

Trp Leu Gly Ser Leu Lys Ser Asn Ile Gly His Thr Gln Ala Ala
    2855                2860                2865

Ala Gly Val Ala Gly Val Ile Lys Met Val Met Ala Met Arg His
    2870                2875                2880

Gly Val Leu Pro Arg Thr Leu His Val Asp Glu Pro Thr Pro Lys
    2885                2890                2895

Val Asp Trp Ser Ala Gly Ala Val Gly Leu Leu Thr Glu Ser Ala
    2900                2905                2910

Glu Trp Arg Gln Glu Gly Arg Pro Arg Arg Ala Gly Val Ser Ala
```

-continued 2915 2920 2925

Phe Gly Val Ser Gly Thr Asn Ala His Val Ile Leu Glu Gln Ala
2930 2935 2940

Pro Lys His Ala Pro Gly Val Ala Ala Glu Gly Arg Lys Gly Arg
2945 2950 2955

Gly Glu Pro Pro Thr Val Pro Trp Val Leu Ser Gly Ala Ser Glu
2960 2965 2970

Ala Gly Leu Arg Ala Gln Ile Glu Gly Leu Arg Ala Phe Ala Asp
2975 2980 2985

Asp Asn Pro Thr Leu Asp Pro Ala Asp Val Gly Trp Ser Leu Ala
2990 2995 3000

Ser Thr Arg Ala Leu Leu Pro Tyr Arg Thr Val Val Val Gly Thr
3005 3010 3015

Asp Leu Asp Glu Leu Arg Arg Gly Leu Asp Ala Ala Glu Val Val
3020 3025 3030

Gly Ala Ala Glu Pro Asp Arg Gly Ala Val Leu Val Phe Pro Gly
3035 3040 3045

Gln Gly Ser Gln Trp Val Gly Met Ala Leu Glu Leu Val Glu Ser
3050 3055 3060

Ser Pro Val Phe Ala Gly Arg Met Arg Asp Cys Ala Asp Ala Leu
3065 3070 3075

Ala Pro Phe Ala Glu Trp Ser Leu Phe Gly Val Leu Gly Asp Glu
3080 3085 3090

Val Ala Leu Gly Arg Val Asp Val Val Gln Pro Val Leu Trp Ala
3095 3100 3105

Val Met Val Ser Leu Ala Glu Leu Trp Arg Ser Phe Gly Val Val
3110 3115 3120

Pro Ser Val Val Val Gly His Ser Gln Gly Glu Ile Ala Ala Ala
3125 3130 3135

Cys Val Ala Gly Gly Leu Ser Leu Glu Asp Gly Ala Arg Val Val
3140 3145 3150

Ala Leu Arg Ser Arg Ala Leu Leu Ala Leu Ser Gly Arg Gly Gly
3155 3160 3165

Met Val Ser Val Pro Val Ser Ala Asp Arg Leu Arg Gly Arg Val
3170 3175 3180

Gly Leu Ser Val Ala Ala Val Asn Gly Pro Val Ser Thr Val Val
3185 3190 3195

Ser Gly Ala Val Glu Val Leu Glu Gly Val Leu Ala Glu Phe Pro
3200 3205 3210

Gly Ala Lys Arg Ile Pro Val Asp Tyr Ala Ser His Ser Val Gln
3215 3220 3225

Val Glu Gly Ile Arg Glu Gly Leu Ala Glu Ala Leu Ala Pro Val
3230 3235 3240

Arg Pro Arg Thr Gly Glu Val Pro Phe Tyr Ser Thr Val Thr Gly
3245 3250 3255

Arg Leu Met Asp Thr Val Gly Leu Asp Gly Glu Tyr Trp Tyr Arg
3260 3265 3270

Asn Leu Arg Glu Thr Val Glu Phe Gln Ser Ala Ile Glu Gly Leu
3275 3280 3285

Leu Glu Leu Gly His Thr Val Phe Val Glu Ala Ser Pro His Pro
3290 3295 3300

Val Leu Thr Val Gly Ile Gln Asp Thr Ala Glu Thr Thr Asp Thr
3305 3310 3315

```
Asp Ile Leu Val Thr Gly Ser Leu Arg Arg Asp Gly Gly Gly Leu
    3320                3325                3330

Ala Ser Phe Leu Thr Ala Leu Ala Arg Leu His Val Arg Gly Val
    3335                3340                3345

Ala Val Glu Trp Arg Glu Ala Phe Ala Gly Leu Asp Ala His Ala
    3350                3355                3360

Val Asp Leu Pro Thr Tyr Ala Phe Gln Arg Arg Arg Phe Trp Ala
    3365                3370                3375

Ala Ser Leu Arg Gln Thr Pro Gly Thr Ala Glu Phe Asp His Pro
    3380                3385                3390

Leu Leu Gly Ala Val Leu Pro Leu Pro Asp Ser Gly Gly Gly Leu
    3395                3400                3405

Leu Thr Gly Val Leu Thr Leu Ala Gly Gln Pro Trp Leu Ala Glu
    3410                3415                3420

His Ser Val Ala Gly Val Val Leu Phe Pro Gly Thr Gly Phe Val
    3425                3430                3435

Glu Leu Val Leu Gln Ala Gly Leu Arg Trp Gly Cys Gly Val Val
    3440                3445                3450

Glu Glu Leu Thr Leu Glu Gly Pro Leu Val Leu Pro Glu Arg Gly
    3455                3460                3465

Glu Val Glu Val Gln Val Ser Val Gly Gly Val Asp Gly Ala Gly
    3470                3475                3480

Cys Arg Ser Val Ser Val Phe Ser Cys Arg Gly Gly Glu Trp Val
    3485                3490                3495

Arg His Ala Val Gly Val Leu Gly Val Gly Asp Gly Val Val Pro
    3500                3505                3510

Gly Val Glu Val Trp Pro Pro Val Gly Ala Glu Arg Val Gly Val
    3515                3520                3525

Glu Gly Val Tyr Glu Val Leu Ala Glu Arg Gly Tyr Val Tyr Gly
    3530                3535                3540

Pro Val Phe Gln Gly Leu Arg Asp Ala Trp Arg Arg Gly Asp Glu
    3545                3550                3555

Ile Phe Val Glu Ala Glu Val Pro Ala Glu Ala Arg Gly Asp Ala
    3560                3565                3570

Ala Arg Cys Ala Ile His Pro Ala Leu Leu Asp Ala Gly Leu His
    3575                3580                3585

Gly Val Gly Leu Gly Gly Leu Ile Ser Asp Asp Gly Arg Ala Tyr
    3590                3595                3600

Leu Pro Phe Ser Trp Ser Gly Val Arg Leu His Ala Val Gly Ala
    3605                3610                3615

Ser Ala Val Arg Met Thr Leu Thr Pro Ala Gly Pro Asp Ala Val
    3620                3625                3630

Ser Leu Arg Val Thr Asp Glu Ala Gly Glu Ala Val Leu Thr Ala
    3635                3640                3645

Asp Ser Leu Val Leu Arg Pro Val Thr Glu Gly Gln Leu Ala Glu
    3650                3655                3660

Ala Glu Ile Gly Asn Arg Asp Val Leu His Arg Val Glu Trp Val
    3665                3670                3675

Asp Ala Gly Ala Cys Ser Val Gly Ser Phe Val Glu Trp Gly Glu
    3680                3685                3690

Val Ala Ala Gly Gly Val Val Pro Asp Cys Val Val Leu Ala Gly
    3695                3700                3705
```

-continued

```
Ala Asp  Val Ala Gly Val Leu  Glu Val Leu Arg Thr  Trp Val Val
    3710                 3715                 3720

Glu Glu  Arg Phe Glu Gly Ser  Arg Leu Val Val Val  Thr Arg Gly
    3725                 3730                 3735

Ala Val  Ser Val Gly Gly Glu  Gly Leu Glu Asp Val  Ser Gly Gly
    3740                 3745                 3750

Ala Val  Trp Gly Leu Val Arg  Ser Ala Gln Ser Glu  His Pro Gly
    3755                 3760                 3765

Arg Phe  Val Leu Val Asp Ala  Asp Val Asp Thr Asp  Val Val Pro
    3770                 3775                 3780

Asp Val  Val Gly Leu Gly Glu  Trp Gln Val Ala Val  Arg Ala Gly
    3785                 3790                 3795

Arg Val  Trp Val Pro Arg Leu  Val Asp Val Asp Val  Ser Val Gly
    3800                 3805                 3810

Gly Ala  Val Val Arg Gly Gly  Leu Gly Ser Gly Val  Ala Leu Val
    3815                 3820                 3825

Thr Gly  Gly Thr Gly Leu Leu  Gly Gly Leu Val Ala  Arg His Leu
    3830                 3835                 3840

Val Ser  Ala Tyr Gly Val Gly  Glu Leu Val Leu Val  Ser Arg Arg
    3845                 3850                 3855

Gly Val  Ala Ala Pro Gly Val  Glu Glu Leu Val Gly  Glu Leu Glu
    3860                 3865                 3870

Gly Leu  Gly Ala Arg Val Arg  Val Val Ala Cys Asp  Val Ala Asp
    3875                 3880                 3885

Arg Gly  Ala Val Ala Glu Leu  Val Gly Ser Ile Glu  Gly Leu Arg
    3890                 3895                 3900

Val Val  Val His Ala Ala Gly  Val Val Asp Asp Gly  Val Ile Gly
    3905                 3910                 3915

Ser Leu  Asp Ala Glu Arg Leu  Cys Gly Val Met Gly  Pro Lys Ala
    3920                 3925                 3930

Trp Gly  Ala Trp His Leu His  Glu Leu Thr Arg Gly  Leu Asp Leu
    3935                 3940                 3945

Ser Ala  Phe Val Leu Phe Ser  Ser Ala Ala Gly Val  Leu Gly Asn
    3950                 3955                 3960

Ala Gly  Gln Gly Gly Tyr Ala  Ala Ala Asn Gly Phe  Leu Asp Ala
    3965                 3970                 3975

Leu Ala  Val His Arg Arg Gly  Arg Gly Leu Pro Ala  Val Ser Ile
    3980                 3985                 3990

Ala Trp  Gly Phe Trp Glu Glu  Arg Ser Glu Leu Thr  Ala Asp Leu
    3995                 4000                 4005

Ala Glu  Val Gln Leu Ser Arg  Ile Ser Arg Ser Val  Gly Ala Ser
    4010                 4015                 4020

Ile Ser  Ser Ala Gln Gly Leu  Asp Leu Phe Asp Ala  Ala Leu Ala
    4025                 4030                 4035

Ala Asp  Glu Pro Met Val Leu  Ala Thr Pro Leu Asn  Leu Pro Ala
    4040                 4045                 4050

Leu Arg  Asp Gln Ala Ala Ala  Gly Thr Leu Pro Ser  Ile Leu Ser
    4055                 4060                 4065

Gly Leu  Val Thr Ala Pro Val  Arg Arg Thr Ala Gly  Thr Gly Arg
    4070                 4075                 4080

Thr Pro  Ala Gly Leu Arg His  Gln Leu Ala Gly Val  Thr Glu Ala
    4085                 4090                 4095

Glu Arg  Gln His Gln Ile Met  Arg Leu Val Gln Glu  His Val Ala
```

-continued

```
    4100                4105                4110

Gly Val  Leu Gly His Ala Ser  Ala Glu Leu Val Asp  Ala Ser Arg
    4115                4120                4125

Thr Phe  Gln Glu Ile Gly Phe  Asp Ser Leu Thr Ala  Val Glu Leu
    4130                4135                4140

Arg Asn  Arg Ile Ser Ala Ala  Thr Gly Ile Arg Leu  Pro Ala Thr
    4145                4150                4155

Ala Val  Phe Asp His Pro Thr  Pro Arg Leu Leu Ala  Glu Arg Val
    4160                4165                4170

Leu Ala  Glu Val Gly Gly Ser  Leu Pro Thr Ala Ala  Pro Ile Ala
    4175                4180                4185

Pro Val  Ser Ala Val Asp Asp  Glu Pro Ile Val Ile  Val Gly Met
    4190                4195                4200

Ser Cys  Arg Phe Pro Gly Gly  Val Glu Ser Pro Glu  Asp Leu Trp
    4205                4210                4215

Arg Leu  Val His Ser Ala Thr  Asp Ala Val Ser Ala  Leu Pro Thr
    4220                4225                4230

Asp Arg  Gly Trp Asp Leu Ala  Thr Leu Ser Gly Ala  Lys Gly Gly
    4235                4240                4245

Ala Gly  Ala Ser Tyr Ala Arg  Asp Gly Gly Phe Leu  Tyr Asp Ala
    4250                4255                4260

Ala Glu  Phe Asp Ala Gly Phe  Phe Gly Ile Ser Pro  Arg Glu Ala
    4265                4270                4275

Thr Ala  Met Asp Pro Gln Gln  Arg Leu Leu Leu Glu  Ala Ala Trp
    4280                4285                4290

Glu Val  Phe Glu Arg Ala Gly  Ile Ala Pro Asp Thr  Leu Lys Gly
    4295                4300                4305

Ser Arg  Thr Gly Val Phe Thr  Gly Val Met Tyr His  Asp Tyr Gly
    4310                4315                4320

Ser Trp  Leu Thr Asp Val Pro  Glu Asp Val Glu Gly  Tyr Leu Gly
    4325                4330                4335

Thr Gly  Ile Ala Gly Ser Val  Ala Ser Gly Arg Leu  Ala Tyr Thr
    4340                4345                4350

Phe Gly  Leu Glu Gly Pro Ala  Leu Thr Val Asp Thr  Ala Cys Ser
    4355                4360                4365

Ser Ser  Leu Val Ala Leu His  Leu Ala Ala Glu Ser  Leu Arg Arg
    4370                4375                4380

Gly Glu  Cys Ser Leu Ala Leu  Ala Gly Gly Val Thr  Val Leu Ala
    4385                4390                4395

Thr Pro  Gln Val Phe Val Glu  Phe Thr Arg Gln Gly  Gly Leu Ala
    4400                4405                4410

Pro Asp  Gly Arg Cys Lys Pro  Phe Ala Ala Gly Ala  Asp Gly Thr
    4415                4420                4425

Gly Trp  Ser Glu Gly Val Gly  Leu Leu Leu Val Glu  Arg Leu Ser
    4430                4435                4440

Asp Ala  Glu Arg Asn Gly His  Pro Val Leu Ala Val  Val Ser Gly
    4445                4450                4455

Ser Ala  Val Asn Gln Asp Gly  Ala Ser Asn Gly Leu  Thr Ala Pro
    4460                4465                4470

Asn Gly  Pro Ser Gln Gln Arg  Val Ile Arg Gln Ala  Leu Ala Asn
    4475                4480                4485

Ala Gly  Leu Ala Ala Arg Asp  Val Asp Ala Val Glu  Ala His Gly
    4490                4495                4500
```

-continued

```
Thr Gly  Thr Thr Leu Gly Asp  Pro Ile Glu Ala Gln  Ala Leu Leu
    4505                 4510                 4515

Ala Thr  Tyr Gly Gln Gly Arg  Asp Val Gly Gln Pro  Leu Trp Leu
    4520                 4525                 4530

Gly Ser  Val Lys Ser Asn Ile  Gly His Thr Gln Ala  Ala Ala Gly
    4535                 4540                 4545

Val Ala  Gly Val Ile Lys Met  Val Met Ala Met Arg  His Gly Val
    4550                 4555                 4560

Leu Pro  Arg Thr Leu His Val  Asp Glu Pro Ser Pro  His Val Asp
    4565                 4570                 4575

Trp Ser  Ala Gly Ala Val Glu  Leu Leu Gly Glu His  Met Gly Trp
    4580                 4585                 4590

Pro Glu  Val Gly Arg Pro Arg  Arg Ala Gly Val Ser  Ser Phe Gly
    4595                 4600                 4605

Ala Ser  Gly Thr Asn Ala His  Val Ile Leu Glu Gln  Ala Pro Asp
    4610                 4615                 4620

Met Ala  Gly Glu Pro Glu Gln  Arg Pro Glu Arg Asn  Glu Leu Pro
    4625                 4630                 4635

Ala Ile  Pro Trp Val Phe Ser  Ala Gly Asp Glu Ala  Gly Leu Arg
    4640                 4645                 4650

Ala Gln  Ala Val Arg Leu Arg  Ala Phe Ala Asp Arg  Asn Pro Asp
    4655                 4660                 4665

Leu Asp  Pro Val Asp Val Gly  Trp Ser Leu Ala Thr  Gly Arg Ala
    4670                 4675                 4680

Gly Leu  Ser His Arg Ala Val  Val Val Gly Ala Gly  Arg Gly Glu
    4685                 4690                 4695

Leu Leu  Gly Ala Leu Glu Gly  Val Pro Val Val Gly  Val Pro Val
    4700                 4705                 4710

Val Gly  Gly Leu Gly Val Leu  Phe Ala Gly Gln Gly  Ser Gln Arg
    4715                 4720                 4725

Leu Gly  Met Gly Arg Gly Leu  Tyr Glu Gly Tyr Pro  Val Phe Ala
    4730                 4735                 4740

Ala Val  Trp Asp Glu Val Cys  Ala Gln Leu Asp Gln  His Leu Asp
    4745                 4750                 4755

Arg Pro  Val Gly Glu Val Val  Trp Gly Asp Asp Ala  Gly Leu Val
    4760                 4765                 4770

Gly Glu  Thr Val Tyr Ala Gln  Ala Gly Leu Phe Ala  Leu Glu Val
    4775                 4780                 4785

Ala Leu  Tyr Arg Leu Ile Ala  Ser Trp Gly Val Arg  Gly Asp Tyr
    4790                 4795                 4800

Leu Leu  Gly His Ser Ile Gly  Glu Leu Ala Ala Ala  Tyr Val Ala
    4805                 4810                 4815

Gly Val  Trp Ser Leu Glu Asp  Ala Gly Arg Val Val  Val Ala Arg
    4820                 4825                 4830

Gly Arg  Leu Met Gln Ala Leu  Pro Ser Gly Gly Ala  Met Val Gly
    4835                 4840                 4845

Val Ala  Ala Ser Glu Gly Val  Val Arg Pro Leu Leu  Gly Glu Gly
    4850                 4855                 4860

Val Val  Val Ala Ala Val Asn  Gly Pro Glu Ser Val  Val Leu Ser
    4865                 4870                 4875

Gly Asp  Glu Asp Ala Val Glu  Ala Val Val Asp Val  Leu Ala Gly
    4880                 4885                 4890
```

-continued

```
Arg Gly  Val Arg Thr Arg Arg  Leu Arg Val Ser His  Ala Phe His
    4895                 4900                 4905

Ser Ala  Arg Met Asp Gly Met  Leu Ala Glu Phe Gly  Glu Val Leu
    4910                 4915                 4920

Arg Gly  Val Glu Phe Arg Ala  Pro Ser Val Pro Val  Val Ser Asn
    4925                 4930                 4935

Val Ser  Gly Ala Val Ala Gly  Glu Glu Leu Cys Ser  Pro Glu Tyr
    4940                 4945                 4950

Trp Val  Arg His Val Arg Glu  Thr Val Arg Phe Ala  Asp Gly Leu
    4955                 4960                 4965

Asp Thr  Leu Arg Glu Leu Gly  Val Gly Ser Phe Leu  Glu Leu Gly
    4970                 4975                 4980

Pro Asp  Gly Thr Leu Thr Ala  Leu Ala Asp Gly Asp  Gly Val Pro
    4985                 4990                 4995

Val Leu  Arg Arg Asp Arg Pro  Glu Pro Leu Thr Ala  Met Ala Ala
    5000                 5005                 5010

Leu Gly  Gly Leu Tyr Val Arg  Gly Val Gln Ile Asp  Trp Asp Ala
    5015                 5020                 5025

Val Phe  Pro Gly Ala Arg Arg  Val Asp Leu Pro Thr  Tyr Ala Phe
    5030                 5035                 5040

Gln Arg  Glu Arg Phe Trp Leu  Glu Pro Ser Pro Glu  Arg Pro Thr
    5045                 5050                 5055

Thr Ser  Val Val Asp Ala Ala  Phe Trp Asp Ala Val  Glu Arg Gly
    5060                 5065                 5070

Asp Leu  Gly Ser Phe Gly Ile  Asp Ala Glu Gln Pro  Leu Ser Thr
    5075                 5080                 5085

Ala Leu  Pro Ala Leu Ser Ser  Trp Arg Arg Ala Arg  Gln Glu Gln
    5090                 5095                 5100

Ser Val  Ile Asp Gly Trp Arg  Tyr Arg Leu Gly Trp  Met Pro Ile
    5105                 5110                 5115

Pro Ala  Val Ser Gly Glu Val  Gly Leu Thr Gly Thr  Trp Leu Val
    5120                 5125                 5130

Val Val  Glu Pro Gly Ala Asp  Gly Thr Asp Val Ala  Val Ala Leu
    5135                 5140                 5145

Arg Ser  Ala Gly Ala Gly Val  Glu Val Val Thr Ser  Ala Glu Leu
    5150                 5155                 5160

Ser Ala  Gly Pro Val Ala Gly  Val Val Ser Leu Val  Ser Val Glu
    5165                 5170                 5175

Ala Thr  Val Ser Leu Leu His  Val Leu Val Ala Ala  Gly Val Asp
    5180                 5185                 5190

Ala Pro  Leu Trp Cys Val Thr  Arg Gly Ala Val Ser  Val Val Asp
    5195                 5200                 5205

Gly Asp  Leu Val Asp Pro Gly  Gln Ala Gly Val Trp  Gly Leu Gly
    5210                 5215                 5220

Arg Val  Ile Gly Leu Glu His  Pro Asp Arg Trp Gly  Gly Leu Ile
    5225                 5230                 5235

Asp Leu  Pro Gly Glu Leu Asp  Asp Arg Ala Gly Asn  Ala Leu Val
    5240                 5245                 5250

Gly Ile  Leu Ala Gly Gly Thr  Gly Glu Asp Gln Val  Ala Ile Arg
    5255                 5260                 5265

Val Thr  Gly Ile Trp Gly Ala  Arg Leu Val Arg Ala  Thr Pro Val
    5270                 5275                 5280

Pro Ile  Gly Asp Ala Gly Gly  Glu Ala Ala Ala Ala  Trp Arg Gly
```

-continued

```
        5285                5290                5295

Arg Gly Thr Ala Leu Val Thr Gly Gly Thr Gly Ala Leu Gly Arg
    5300                5305                5310

Gln Val Ala Arg Trp Leu Val Asp Ser Gly Leu Glu Arg Val Val
    5315                5320                5325

Leu Thr Ser Arg Arg Gly Gly Glu Ala Pro Gly Ala Val Glu Leu
    5330                5335                5340

Val Ala Glu Leu Gly Ser Arg Val Arg Val Val Ala Cys Asp Val
    5345                5350                5355

Gly Asp Arg Glu Glu Leu Ala Ala Leu Leu Ala Met Leu Pro Asp
    5360                5365                5370

Val Arg Thr Ile Val His Ala Ala Gly Val Leu Asp Asp Gly Val
    5375                5380                5385

Leu Glu Ser Leu Thr Pro Glu Arg Ile Arg Glu Val Met Arg Ala
    5390                5395                5400

Lys Ala Asp Gly Ala Arg His Leu His Glu Leu Thr Arg Asp Ile
    5405                5410                5415

Asp Leu Asp Ala Phe Val Leu Phe Ser Ser Ala Ala Gly Thr Val
    5420                5425                5430

Gly Asn Ala Gly Gln Gly Ser Tyr Ala Ala Ala Asn Ala Val Leu
    5435                5440                5445

Asp Gly Leu Ala Trp Arg Arg Arg Ala Glu Gly Leu Val Ala Thr
    5450                5455                5460

Ser Val Ala Trp Gly Ala Trp Ala Asp Ser Gly Met Gly Ala Gly
    5465                5470                5475

His Ala Arg Ala Met Ala Pro Arg Leu Ala Leu Ala Ala Leu Gln
    5480                5485                5490

Arg Ala Leu Asp Asp Asp Glu Thr Ala Leu Met Val Ala Asp Val
    5495                5500                5505

Asp Trp Ser Ser Phe Gly Ser Arg Phe Thr Ala Val Arg Pro Ser
    5510                5515                5520

Pro Leu Leu Ser Glu Leu Leu Pro Arg Ser Ser Ala Pro Val Glu
    5525                5530                5535

Pro Val Glu Ala Leu Ala Thr Arg Leu Arg Gly Met Ser Arg Ile
    5540                5545                5550

Glu Arg Asp Arg Ala Val Leu Glu Leu Val Arg Ala Gln Val Ala
    5555                5560                5565

Ala Val Leu Gly His Ala Lys Pro Ala Ser Val Asp Pro Ser Arg
    5570                5575                5580

Thr Phe Gln Glu Val Gly Phe Asp Ser Leu Thr Ala Val Glu Leu
    5585                5590                5595

Arg Asn Arg Leu Ala Thr Ala Thr Gly Val Pro Phe Pro Gly Ser
    5600                5605                5610

Val Ile Phe Asp Tyr Pro Thr Pro Thr Ala Leu Ala Asp His Val
    5615                5620                5625

Arg Ala Arg Phe Val Pro Asp Thr Asp Asn Asp Glu Asp Gly Gly
    5630                5635                5640

Gly Ala Thr Ser Val Leu Asp Glu Leu Thr Arg Leu Glu Ala Val
    5645                5650                5655

Leu Ser Asp Leu Ser Pro Ser Asp Val Ala Gly Ala Glu Val Ala
    5660                5665                5670

Ala Lys Ile Lys Ser Leu Leu Ser His Trp Gly Ala Ala Thr Asn
    5675                5680                5685
```

```
Ser Asp Ile Asp Met Asp Ser Ala Thr Asp Glu Glu Met Phe Asp
    5690                5695                5700

Leu Leu Gly Lys Glu Phe Gly Ile Ser
    5705                5710
```

<210> SEQ ID NO 48
<211> LENGTH: 7102
<212> TYPE: PRT
<213> ORGANISM: Streptomyces sp.

<400> SEQUENCE: 48

```
Val Glu Asn Glu Glu Lys Leu Arg His Tyr Leu Lys Glu Val Thr Lys
1               5                   10                  15

Asp Leu Arg Gln Thr Arg Gln Arg Leu Gln Asp Val Glu Ala Lys Ser
            20                  25                  30

Arg Glu Pro Ile Ala Ile Val Gly Met Ser Cys Arg Phe Pro Gly Gly
        35                  40                  45

Ile Ala Thr Pro Glu Ala Leu Trp Asp Leu Val Arg Glu Gly Gly Asp
    50                  55                  60

Ala Val Ser Glu Phe Pro Ala Asp Arg Gly Trp Asp Thr Glu Gly Leu
65                  70                  75                  80

Tyr Asp Pro Ala Gly Gly Ser Gly Lys Ser Val Thr Arg Tyr Gly Gly
                85                  90                  95

Phe Leu Arg Gly Val Ala Asp Phe Asp Ala Ala Leu Phe Gly Ile Ser
            100                 105                 110

Pro Arg Glu Ala Ile Ala Met Asp Pro Gln Gln Arg Leu Met Leu Glu
        115                 120                 125

Thr Ser Trp Glu Ala Phe Glu Arg Ala Gly Val Asn Arg Asp Ala Val
    130                 135                 140

Arg Gly Ser Arg Thr Gly Val Phe Ile Gly Thr Asn Gly Gln Asp Tyr
145                 150                 155                 160

Ala Thr Leu Leu Ser Ala Ala Arg Asp Asp Val Gln Gly His Leu Gly
                165                 170                 175

Thr Gly Ser Ala Ala Ser Val Leu Ser Gly Arg Val Ala Tyr Thr Phe
            180                 185                 190

Gly Leu Glu Gly Pro Thr Val Thr Val Asp Thr Ala Cys Ser Ser Ser
        195                 200                 205

Leu Ile Ala Leu His Leu Ala Val Gln Ala Leu Arg Asn Gly Glu Cys
    210                 215                 220

Glu Leu Ala Leu Ala Gly Gly Val Thr Val Met Thr Thr Thr Asn Thr
225                 230                 235                 240

Phe Val Glu Leu Ser Lys Gln Gly Gly Leu Ala Pro Asp Gly Arg Ser
                245                 250                 255

Lys Ala Phe Ala Ala Ala Ala Asp Gly Thr Gly Trp Gly Glu Gly Ala
            260                 265                 270

Gly Met Leu Leu Val Glu Arg Leu Ser Asp Ala Glu Arg His Gly His
        275                 280                 285

Pro Val Leu Ala Val Val Arg Gly Thr Ala Ala Asn Gln Asp Gly Ala
    290                 295                 300

Ser Asn Gly Leu Thr Ala Pro Asn Gly Pro Ser Gln Arg Arg Val Ile
305                 310                 315                 320

Arg Ala Ala Leu Ser Asn Ala Gln Leu Ser Thr Gly Asp Val Asp Val
                325                 330                 335

Val Glu Ala His Gly Thr Gly Thr Arg Leu Gly Asp Pro Ile Glu Ala
```

```
            340                 345                 350

Gln Ala Leu Leu Asp Thr Tyr Gly Gln Asp Arg Asp Arg Pro Leu Trp
        355                 360                 365

Leu Gly Ser Val Lys Ser Asn Leu Gly His Thr Gln Ala Ala Ala Gly
    370                 375                 380

Val Ala Gly Val Ile Lys Met Val Leu Ala Met Arg His Gly Val Leu
385                 390                 395                 400

Pro Arg Thr Leu His Val Asp Glu Pro Thr Pro His Val Asp Trp Ser
                405                 410                 415

Ala Gly Ala Val Arg Leu Leu Thr Glu Arg Thr Pro Trp Pro Glu Ala
            420                 425                 430

Asp Arg Pro Arg Arg Ala Gly Val Ser Ala Phe Gly Val Ser Gly Thr
        435                 440                 445

Asn Ala His Val Ile Val Glu Gln Ala Ser Glu Ala Glu Pro Val Glu
    450                 455                 460

Pro Pro Arg Ala Glu Pro Val Thr Val Pro Trp Val Leu Ser Gly Gln
465                 470                 475                 480

Gly Glu Ala Gly Leu Arg Ala Phe Ala Ala Arg Leu Ala Asp Val Ala
                485                 490                 495

Thr Glu Ala His Pro Gly Asp Leu Gly Trp Thr Leu Ala Thr Thr Arg
            500                 505                 510

Ser Ala Leu Pro His Arg Ala Val Val Ile Gly Ser Thr Pro Glu Glu
        515                 520                 525

Leu Arg Ser Gly Leu Ala Ala Val Ala Ala Gly Glu Pro Ala Ser Asn
    530                 535                 540

Val Val Glu Gly Val Ala Gly Ser Asp Thr Gly Val Val Phe Val Phe
545                 550                 555                 560

Pro Gly Gln Gly Ser Gln Trp Ala Gly Met Ala Val Glu Leu Leu Asp
                565                 570                 575

Ser Ser Pro Ala Phe Ala Arg Arg Phe Ala Glu Cys Ala Arg Ala Leu
            580                 585                 590

Glu Thr His Leu Asp Trp Ser Ile Glu Asp Val Val Arg Ser Ala Pro
        595                 600                 605

Gly Ala Pro Ser Leu Asp Leu Ile Glu Val Val Gln Pro Val Leu Phe
    610                 615                 620

Thr Met Met Val Ser Leu Ala Glu Leu Trp Ala Ser Tyr Gly Ile Thr
625                 630                 635                 640

Pro Ser Ala Val Val Gly His Ser Gln Gly Glu Ile Ala Ala Ala Cys
                645                 650                 655

Val Ala Gly Ala Leu Ser Leu Glu Asp Ala Ala Lys Val Val Val Leu
            660                 665                 670

Arg Ser Arg Leu Phe Ala Glu Thr Leu Val Gly Asn Gly Ala Ile Ala
        675                 680                 685

Ser Val Ala Leu Pro Ala Glu Gln Leu Ala Thr Arg Ile Glu Pro Trp
    690                 695                 700

Gly Glu Arg Leu Val Val Ala Gly Val Asn Gly Pro Ala Ala Ala Thr
705                 710                 715                 720

Val Ala Gly Asp Pro Gln Ser Leu Glu Glu Phe Val Ala Ala Cys Ala
                725                 730                 735

Ala Asp Gly Val Arg Ala Arg Val Val Pro Ala Thr Val Ala Ser His
            740                 745                 750

Gly Pro Gln Val Glu Pro Leu Arg Glu Arg Leu Leu Ala Leu Leu Ala
        755                 760                 765
```

-continued

```
Asp Val Ala Pro Arg Gln Ser Thr Val Pro Phe Tyr Ser Thr Val Thr
    770                 775                 780

Gly Gly Leu Leu Asp Thr Thr Glu Leu Asp Ala Asp Tyr Trp Phe Trp
785                 790                 795                 800

Asn Ala Arg Lys Pro Ile Asp Phe Leu Gly Ala Leu Arg Ala Leu Phe
                805                 810                 815

Ala Asp Gly His Arg Val Phe Val Glu Ser Ser Thr His Pro Ala Leu
            820                 825                 830

Thr Met Gly Val Gln Asp Thr Ala Asp Ala Ser Gly Glu Ser Val Glu
        835                 840                 845

Val Thr Gly Ser Leu Arg Arg Gly Glu Gly Gly Leu Asp Gln Phe His
    850                 855                 860

Ser Ala Val Ala Arg Leu His Val His Gly Val Arg Val Asp Trp Ser
865                 870                 875                 880

Ala Ala Phe Gly Ala Ala Arg Arg Val Glu Leu Pro Thr Tyr Pro Phe
                885                 890                 895

Gln Arg Glu Arg Tyr Trp Leu Thr Pro Arg Pro Gly Gln Gly Asp Ala
            900                 905                 910

Ser Ala Leu Gly Leu Gly Ala Leu Asp His Pro Leu Leu Gly Ala Thr
        915                 920                 925

Val Val Leu Pro Glu Ser Gly Gly Cys Leu Leu Thr Gly Arg Leu Ser
    930                 935                 940

Leu Ala Gly Gln Pro Trp Leu Ala Asp His Ala Leu Ser Gly Val Val
945                 950                 955                 960

Leu Leu Pro Gly Thr Gly Phe Val Glu Leu Val Leu Gln Ala Gly Leu
                965                 970                 975

Arg Trp Gly Cys Gly Val Val Glu Glu Leu Thr Leu Glu Gly Pro Leu
            980                 985                 990

Val Leu Pro Glu Arg Gly Glu Val  Glu Val Gln Val Ser  Val Gly Gly
        995                 1000                1005

Val Asp  Gly Ala Gly Cys Arg  Ser Val Ser Val Phe  Ser Cys Arg
    1010                1015                1020

Gly Gly  Glu Trp Val Arg His  Ala Val Gly Val Leu  Gly Val Gly
    1025                1030                1035

Asp Gly  Ala Val Pro Val Ala  Glu Val Trp Pro Pro  Val Gly Ala
    1040                1045                1050

Glu Arg  Val Gly Val Glu Gly  Val Tyr Glu Ala Leu  Ala Glu Arg
    1055                1060                1065

Gly Tyr  Ala Tyr Gly Pro Val  Phe Gln Gly Leu Arg  Asp Ala Trp
    1070                1075                1080

Arg Arg  Gly Asp Glu Ile Phe  Val Glu Val Ala Val  Ala Gln Glu
    1085                1090                1095

Ala Arg  Ala Asp Ala Ala Arg  Cys Ala Ile His Pro  Ala Leu Leu
    1100                1105                1110

Asp Ala  Ala Leu His Gly Val  Arg Phe Gly Asp Phe  Val Ser Asp
    1115                1120                1125

Asp Asp  Gln Ala Tyr Val Pro  Phe Ser Trp Thr Gly  Val Thr Leu
    1130                1135                1140

His Ala  Val Gly Ala Thr Val  Leu Arg Val Thr Leu  Ser Pro Ala
    1145                1150                1155

Gly Arg  Asp Ala Ile Ala Leu  Arg Ala Thr Asp Thr  Thr Gly Ala
    1160                1165                1170
```

-continued

```
Pro Val  Leu Ser Ala Arg Ser  Leu Ala Leu Arg Pro  Val Ser Ala
    1175                 1180                 1185

Gln Gln  Leu Asn Asp Thr Arg  Gly Ser Arg Thr Asp  Ala Leu His
    1190                 1195                 1200

Arg Val  Glu Trp Val Asp Ala  Ser Gly Thr Val Ala  Val Gly Gly
    1205                 1210                 1215

Glu Val  Ala Pro Arg Thr Glu  Val Val Arg Val Val  Ser Glu Gly
    1220                 1225                 1230

Pro Asp  Val Val Gly Glu Ala  Tyr Gly His Val Leu  Glu Val Leu
    1235                 1240                 1245

Glu Arg  Val Gln Ala Trp Val  Ala Asp Glu Asp Leu  Ala Gly Glu
    1250                 1255                 1260

Arg Leu  Val Val Val Thr Arg  Gly Ala Val Asp Thr  Gly Asp Gly
    1265                 1270                 1275

Val Ala  Asp Val Ala Gly Ala  Ala Val Trp Gly Leu  Val Arg Ser
    1280                 1285                 1290

Ala Gln  Ser Glu Asn Pro Gly  Arg Leu Val Leu Val  Asp Thr Asp
    1295                 1300                 1305

Asp Leu  Asp Gly Val Asp Ser  Leu Leu Pro Gly Met  Leu Ala Leu
    1310                 1315                 1320

Asp Glu  Glu Gln Val Leu Val  Arg Ser Gly Ala Val  Arg Val Pro
    1325                 1330                 1335

Arg Leu  Ala Arg Val Pro Ala  Pro Gly Glu Val Ser  Gly Gly Phe
    1340                 1345                 1350

Gly Ser  Gly Ala Val Leu Val  Thr Gly Gly Thr Gly  Val Leu Gly
    1355                 1360                 1365

Gly Leu  Val Ser Arg His Leu  Val Ala Arg His Gly  Val Ser Arg
    1370                 1375                 1380

Leu Val  Leu Leu Ser Arg Arg  Gly Ala Glu Ala Glu  Gly Ala Ala
    1385                 1390                 1395

Glu Leu  Arg Glu Glu Leu Glu  Ala Ala Gly Ala Glu  Val Val Ile
    1400                 1405                 1410

Ala Ala  Cys Asp Ala Ala Asp  Arg Glu Ala Leu Ala  Gly Val Leu
    1415                 1420                 1425

Ser Gly  Leu Ser Ala Asp Phe  Ala Leu Ser Gly Val  Val His Ala
    1430                 1435                 1440

Ala Gly  Val Leu Asp Asp Gly  Leu Leu Thr Ser Leu  Thr Arg Glu
    1445                 1450                 1455

Arg Val  Glu Pro Val Leu Arg  Ala Lys Val Asp Ala  Ala Trp Asn
    1460                 1465                 1470

Leu His  Glu Leu Thr Thr Gly  Met Asp Leu Ser Ala  Phe Val Leu
    1475                 1480                 1485

Phe Ser  Ser Ala Ala Gly Ile  Leu Gly Asn Ala Gly  Gln Gly Ser
    1490                 1495                 1500

Tyr Ala  Ala Ala Asn Gly Phe  Leu Asp Ala Leu Ala  Ala His Arg
    1505                 1510                 1515

Arg Ala  Arg Gly Leu Pro Ala  Val Ser Ile Ala Trp  Gly Phe Trp
    1520                 1525                 1530

Glu Ala  Arg Ser Glu Leu Thr  Gln His Leu Ser Ala  Asp Asp Leu
    1535                 1540                 1545

Ala Arg  Ala His Ala Val Pro  Met Pro Thr Ser Gln  Ala Leu Asp
    1550                 1555                 1560

Leu Phe  Asp Ala Thr Leu Ala  Ala Asp Glu Pro Met  Val Leu Ala
```

-continued

```
    1565                1570                1575

Ala Pro  Leu Asn Pro Gln Ala  Trp Ser Asp Ala Gly  His Leu Pro
    1580                1585                1590

Pro Val  Leu Arg Asp Leu Val  Arg Pro Arg Ile Arg  Arg Ala Ala
    1595                1600                1605

Glu Thr  Thr Gly Ala Pro Glu  Ser Ala Ser Ala Leu  Gly His Arg
    1610                1615                1620

Leu Ala  Ala Val Asp Arg Ser  Glu Trp Asp Gln Val  Val Arg Glu
    1625                1630                1635

Leu Val  Arg Asn His Ile Ala  Ala Val Leu Arg His  Ala Ser Gly
    1640                1645                1650

Glu Ser  Val Asp Thr Ser Arg  Thr Phe Gln Glu Ile  Gly Phe Asp
    1655                1660                1665

Ser Leu  Thr Ala Val Glu Leu  Arg Asn Arg Ile Ser  Ala Ala Thr
    1670                1675                1680

Gly Val  Arg Leu Pro Ala Thr  Ala Val Phe Asp Tyr  Pro Thr Pro
    1685                1690                1695

Gln Ala  Leu Ala Glu Tyr Leu  Leu Ala Glu Val Leu  Gly Lys Asp
    1700                1705                1710

Ser Ala  Ala Ala Ala Thr Pro  Val Gly Thr Ala Leu  Val Ala Asp
    1715                1720                1725

Asp Pro  Ile Val Ile Val Gly  Met Ser Cys Arg Tyr  Pro Gly Gly
    1730                1735                1740

Ile Thr  Ser Pro Glu Ala Leu  Trp Asp Leu Val Arg  Ser Asp Gly
    1745                1750                1755

Asp Ala  Ile Ser Val Leu Pro  Ala Asp Arg Gly Trp  Asp Leu Asp
    1760                1765                1770

Gly Leu  Tyr Asp Pro Asp Pro  Asp Arg Thr Gly Thr  Ser Tyr Ala
    1775                1780                1785

Arg Ser  Gly Gly Phe Val Tyr  Asp Ala Ala Glu Phe  Asp Ala Ala
    1790                1795                1800

Phe Phe  Gly Ile Ser Pro Arg  Glu Ala Ala Ala Met  Asp Pro Gln
    1805                1810                1815

Gln Arg  Leu Leu Leu Glu Thr  Ser Trp Glu Ala Phe  Glu Arg Ala
    1820                1825                1830

Gly Ile  Pro Ala Thr Ser Val  Lys Gly Glu Arg Ile  Gly Val Phe
    1835                1840                1845

Thr Gly  Val Met His His Asp  Tyr Leu Thr Arg Leu  Ser Thr Thr
    1850                1855                1860

Pro Asp  Ala Val Glu Gly Tyr  Leu Gly Thr Gly Ala  Ala Ala Gly
    1865                1870                1875

Val Ala  Ser Gly Arg Val Ala  Tyr Thr Phe Gly Leu  Glu Gly Pro
    1880                1885                1890

Ala Val  Thr Val Asp Thr Ala  Cys Ser Ser Ser Leu  Val Ala Leu
    1895                1900                1905

His Leu  Ala Val Gln Ala Leu  Arg Leu Gly Glu Cys  Ser Leu Ala
    1910                1915                1920

Leu Ala  Gly Gly Val Thr Val  Met Ser Thr Pro Thr  Val Phe Val
    1925                1930                1935

Glu Phe  Ser Arg Gln Arg Gly  Leu Ala Pro Asp Gly  Arg Cys Lys
    1940                1945                1950

Ala Phe  Ala Gly Ala Ala Asp  Gly Thr Gly Phe Ala  Glu Gly Ile
    1955                1960                1965
```

-continued

```
Gly Met  Leu Leu Val Glu Arg  Leu Ser Asp Ala Arg  Arg Asn Gly
    1970                 1975                 1980

His Pro  Val Leu Ala Val Val  Arg Gly Ser Ala Val  Asn Gln Asp
    1985                 1990                 1995

Gly Ala  Ser Asn Gly Leu Thr  Ala Pro Asn Gly Pro  Ser Gln Gln
    2000                 2005                 2010

Arg Val  Ile Arg Gln Ala Leu  Ala Ser Ala Gly Leu  Ser Thr Val
    2015                 2020                 2025

Asp Val  Asp Ala Val Glu Ala  His Gly Thr Gly Thr  Thr Leu Gly
    2030                 2035                 2040

Asp Pro  Ile Glu Ala Gln Ala  Leu Leu Ala Thr Tyr  Gly Gln Gly
    2045                 2050                 2055

Arg Asp  Ser Asp Arg Pro Leu  Leu Leu Gly Ser Ile  Lys Ser Asn
    2060                 2065                 2070

Ile Gly  His Thr Gln Ala Ala  Ala Gly Val Ala Gly  Val Ile Lys
    2075                 2080                 2085

Met Val  Met Ala Met Arg His  Gly Val Leu Pro Gln  Ser Leu His
    2090                 2095                 2100

Ile Asp  Glu Pro Thr Pro His  Val Asp Trp Ser Thr  Gly Ala Val
    2105                 2110                 2115

Glu Leu  Leu Ser Glu Gln Thr  Ala Trp Pro Glu Ala  Gly Arg Pro
    2120                 2125                 2130

Arg Arg  Ala Gly Val Ser Ser  Phe Gly Ile Ser Gly  Thr Asn Ala
    2135                 2140                 2145

His Leu  Ile Leu Glu Gln Ala  Pro Leu Pro Thr Ala  Ala Glu Arg
    2150                 2155                 2160

Pro Gly  Asp Ala Glu Pro Val  Pro Val Glu Pro Ala  Ala Val Val
    2165                 2170                 2175

Pro Trp  Ile Val Ser Gly Arg  Asp Arg His Ala Val  Arg Ala Gln
    2180                 2185                 2190

Ala Glu  Arg Leu Arg Ala His  Val Val Ser His Pro  Asp Arg Arg
    2195                 2200                 2205

Val Ala  Asp Ile Gly Phe Ser  Leu Leu Thr Ser Arg  Ala Val Leu
    2210                 2215                 2220

Glu His  Arg Ala Val Val Leu  Gly Gly Asp His Ala  Glu Leu Leu
    2225                 2230                 2235

Ala Gly  Leu Thr Ala Leu Ala  Arg Asp Glu Pro Ala  Pro Gly Val
    2240                 2245                 2250

Val Glu  Ala Leu Asp Ala Ala  Glu Pro Gly Arg Lys  Val Val Phe
    2255                 2260                 2265

Val Phe  Pro Gly Gln Gly Ser  Gln Trp Ala Gly Met  Ala Leu Glu
    2270                 2275                 2280

Leu Met  Glu Ser Ser Pro Val  Phe Ala Arg Arg Met  Gly Glu Cys
    2285                 2290                 2295

Ala Asp  Ala Leu Ala Pro Leu  Val Glu Trp Ser Leu  Pro Asp Val
    2300                 2305                 2310

Leu Ala  Asp Glu Arg Ala Leu  Ala Arg Val Asp Val  Val Gln Pro
    2315                 2320                 2325

Val Leu  Trp Ala Val Met Val  Ser Leu Ala Glu Leu  Trp Arg Ser
    2330                 2335                 2340

Tyr Gly  Val Val Pro Ser Ala  Val Val Gly His Ser  Gln Gly Glu
    2345                 2350                 2355
```

-continued

```
Ile Ala  Ala Ala Cys Val Ala  Gly Gly Leu Ser Leu  Ala Asp Gly
    2360                 2365                 2370

Ala Arg  Val Val Val Leu Arg  Gly Lys Ala Leu Leu  Ala Leu Ser
    2375                 2380                 2385

Gly Arg  Gly Gly Met Val Ser  Val Pro Val Pro Ala  Asp Arg Leu
    2390                 2395                 2400

Arg Asp  Arg Pro Gly Val Ser  Ile Ala Ala Val Asn  Gly Pro Ser
    2405                 2410                 2415

Ser Thr  Val Val Ser Gly Gly  Asp Glu Val Leu Asp  Ala Val Leu
    2420                 2425                 2430

Ala Glu  Phe Pro Ala Ala Lys  Arg Ile Pro Val Asp  Tyr Ala Ser
    2435                 2440                 2445

His Ser  Pro Gln Ile Asp Asp  Ile Arg Asp Glu Leu  Leu Lys Ala
    2450                 2455                 2460

Leu Ala  Pro Ile Glu Pro Arg  Thr Ala Ala Ile Pro  Phe His Ser
    2465                 2470                 2475

Thr Val  Thr Gly Arg Pro Ile  Asp Thr Ala Asp Leu  Asp Ala Asp
    2480                 2485                 2490

Tyr Trp  Tyr Arg Asn Leu Arg  Glu Thr Val Glu Leu  Glu Arg Val
    2495                 2500                 2505

Ile Arg  Thr Ala Val Glu Asp  Gly His His Thr Phe  Ile Glu Ile
    2510                 2515                 2520

Ser Pro  His Pro Val Leu Thr  Thr Gly Leu Arg Glu  Thr Leu Asp
    2525                 2530                 2535

Asp Ala  Asp Ala His Gly Gly  Leu Val Leu Ala Ser  Leu Arg Arg
    2540                 2545                 2550

Asp Asp  Gly Gly Pro Thr Arg  Phe Leu Thr Ala Leu  Ala Glu Ala
    2555                 2560                 2565

Tyr Ala  His Gly Val Glu Val  Asp Trp Leu Pro Leu  Phe Pro Gly
    2570                 2575                 2580

Ala Arg  Arg Val Asp Leu Pro  Thr Tyr Ala Phe Gln  Arg Glu Arg
    2585                 2590                 2595

Tyr Trp  Leu Asp Ala Pro Thr  Ala Glu Ala Pro Thr  Ser Ala Ile
    2600                 2605                 2610

Asp Ala  Glu Phe Trp Ala Ala  Val Glu Arg Glu Asp  Leu Glu Ser
    2615                 2620                 2625

Leu Ala  Ala Thr Leu Arg Val  Asp Gly Gln Pro Leu  Arg Glu Val
    2630                 2635                 2640

Leu Pro  Ala Leu Ser Gln Trp  Arg Arg Glu Arg Arg  Asp Val Ser
    2645                 2650                 2655

Thr Ile  Asp Ser Trp Arg Tyr  Thr Ile Arg Trp Lys  Pro Leu Thr
    2660                 2665                 2670

Pro Pro  Ala Thr Ser Pro Thr  Gly Thr Trp Leu Val  Val Val Cys
    2675                 2680                 2685

His Ala  Glu Ala Gly His Glu  Trp Val Ala Gly Val  Thr Asp Ala
    2690                 2695                 2700

Leu Thr  Arg His Gly Ala Glu  Pro Leu Val Val Val  Leu Gly Glu
    2705                 2710                 2715

Pro Glu  Leu Asp Arg Ala Ala  Leu Ala Ala Arg Leu  Gly Gly Val
    2720                 2725                 2730

Leu Ala  Asp Thr Pro Arg Ile  Ser Gly Val Val Ser  Leu Thr Ala
    2735                 2740                 2745

Leu Asp  Glu Ser Pro His Pro  Ala Tyr Pro Ser Val  Pro Gln Gly
```

-continued

```
    2750                2755                2760

Tyr Ala  Met Thr Leu Leu Leu  Ser Gln Ala Leu Gly  Asp Ala Arg
    2765                2770                2775

Val Glu  Ala Pro Leu Trp Cys  Leu Thr Gln Arg Gly  Val Ser Leu
    2780                2785                2790

Gly Asp  Ala Gly Gly Ser Gly  Ser Gly Ser Gly Thr  Gly Asp Gly
    2795                2800                2805

Arg Gly  Lys Gly Lys Gly Asp  Val Ala Val Ser Arg  Lys Gln Ala
    2810                2815                2820

Leu Thr  Trp Gly Leu Gly Lys  Val Ile Ala Leu Glu  Gln Pro Leu
    2825                2830                2835

Arg Trp  Gly Gly Leu Ile Asp  Leu Pro Glu Gly Val  Ala Pro His
    2840                2845                2850

Thr Gln  Asp Tyr Leu Ala Gly  Val Leu Ser Gly Thr  Ser Asp Glu
    2855                2860                2865

Asp Gln  Val Ala Ile Arg Pro  Thr Gly Leu Phe Gly  Arg Arg Leu
    2870                2875                2880

Ala His  Ala Pro Ala Arg Glu  Arg Gly Gly Gly Trp  Gln Pro Arg
    2885                2890                2895

Gly Thr  Val Leu Val Thr Gly  Gly Thr Gly Ala Leu  Gly Gly His
    2900                2905                2910

Val Ala  Arg Trp Leu Ala Gly  Gln Gly Ala Glu His  Val Val Leu
    2915                2920                2925

Thr Ser  Arg Arg Gly Met Ala  Ala Pro Gly Ala Glu  Arg Leu Ala
    2930                2935                2940

Gly Glu  Leu Glu Ala Leu Gly  Ala Arg Val Thr Val  Ala Ala Cys
    2945                2950                2955

Asp Val  Gly Asp Arg Asp Ala  Leu Ala Gly Leu Leu  Ala Glu Val
    2960                2965                2970

Gly Pro  Leu Thr Ala Val Val  His Thr Ala Ala Val  Leu Asp Asp
    2975                2980                2985

Gly Thr  Leu Asn Ser Leu Thr  Thr Asp Gln Leu Gln  Arg Val Leu
    2990                2995                3000

Arg Val  Lys Thr Asp Gly Ala  Val His Leu His Glu  Leu Thr Arg
    3005                3010                3015

Asp Met  Glu Leu Ser Ala Phe  Val Leu Phe Ser Ser  Leu Ser Gly
    3020                3025                3030

Thr Leu  Gly Ala Pro Gly Gln  Gly Asn Tyr Ala Pro  Gly His Val
    3035                3040                3045

Phe Val  Asp Thr Leu Ala Glu  Gln Arg Arg Ala Glu  Gly Leu Val
    3050                3055                3060

Ala Thr  Ser Ile Ala Trp Gly  Leu Trp Ala Gly Asp  Gly Met Gly
    3065                3070                3075

Glu Gly  Gly Val Gly Asp Val  Ala Arg Arg His Gly  Val Pro Glu
    3080                3085                3090

Met Ala  Pro Glu Met Ala Val  Ala Ala Met Ala Arg  Ala Val Glu
    3095                3100                3105

Gln Asp  Asp Thr Val Val Thr  Val Ala Glu Ile Asp  Trp Asp Arg
    3110                3115                3120

His Tyr  Val Ala Phe Thr Ala  Thr Arg Pro Ser Pro  Leu Leu Ser
    3125                3130                3135

Asp Leu  Pro Glu Val Arg Ala  Leu Val Asp Ala Gly  Val Gly Gln
    3140                3145                3150
```

-continued

```
Glu Ser Ala Glu Pro Gly His Glu Arg Ser Glu Phe Ala Glu Arg
    3155                3160                3165

Leu Ala Gly Met Ala Glu Thr Asp Arg Asn His Ala Leu Leu Asp
    3170                3175                3180

Leu Val Arg Arg His Val Ala Val Val Leu Gly His Thr Gly Pro
    3185                3190                3195

Asp Ala Ile Asp Pro Gly Arg Ala Phe His Glu Ile Gly Phe Asp
    3200                3205                3210

Ser Val Thr Ala Val Glu Leu Arg Asn Arg Leu Asn Arg Ala Thr
    3215                3220                3225

Gly Leu Arg Leu Pro Ala Thr Val Thr Phe Asp Gln Pro Thr Pro
    3230                3235                3240

Leu Ala Met Ala Gln Tyr Leu Arg Gly Glu Leu Leu His Asp Gly
    3245                3250                3255

Gln Gly Arg Ser Ala Pro Ala Leu Pro Val Arg Ala Thr Gly Ala
    3260                3265                3270

Val Asp Asp Glu Pro Ile Ala Ile Val Gly Met Ser Cys Arg Phe
    3275                3280                3285

Pro Gly Asp Val Ala Ser Pro Glu Asp Leu Trp Arg Leu Leu Ala
    3290                3295                3300

Asp Gly Ser Asp Ala Ile Gly Glu Phe Pro Glu Asn Arg Gly Trp
    3305                3310                3315

Asp Thr Ala His Leu Phe His Pro Asp Pro Asp His Arg Gly Thr
    3320                3325                3330

Ser Ser Thr Arg Ala Ala Ala Phe Val Ser Gly Ala Gly Glu Phe
    3335                3340                3345

Asp Ala Gly Phe Phe Gly Ile Ser Pro Arg Glu Ala Val Ala Met
    3350                3355                3360

Asp Pro Gln Gln Arg Leu Leu Leu Glu Val Ser Trp Glu Ala Leu
    3365                3370                3375

Glu Arg Ala Gly Ile Asp Pro Thr Thr Leu Arg Gly Ser Glu Thr
    3380                3385                3390

Gly Val Phe Thr Gly Thr Asn Gly Gln Asp Tyr Ala Ser Leu Leu
    3395                3400                3405

Lys Ala Asp Glu Thr Gly Asp Phe Glu Gly Arg Val Gly Thr Gly
    3410                3415                3420

Asn Ser Ala Ser Val Met Ser Gly Arg Ile Ser Tyr Val Leu Gly
    3425                3430                3435

Leu Glu Gly Pro Ala Leu Thr Val Asp Thr Ala Cys Ser Ser Ser
    3440                3445                3450

Leu Val Ala Leu His Leu Ala Val Arg Ala Leu Arg Ser Gly Glu
    3455                3460                3465

Cys Ser Leu Ala Leu Ala Gly Gly Ala Ser Val Met Thr Thr Ala
    3470                3475                3480

Gly Ile Phe Val Glu Phe Ser Arg Gln Arg Ala Leu Ala Ala Asp
    3485                3490                3495

Gly Arg Cys Lys Ala Phe Ala Ala Ala Ala Asp Gly Thr Gly Trp
    3500                3505                3510

Gly Glu Gly Ala Gly Met Leu Val Val Glu Arg Leu Ser Asp Ala
    3515                3520                3525

Glu Arg Leu Gly His Arg Val Leu Ala Val Val Arg Gly Ser Ala
    3530                3535                3540
```

-continued

```
Val Asn  Gln Asp Gly Ala Ser  Asn Gly Leu Thr Ala  Pro Asn Gly
    3545                 3550                 3555

Pro Ser  Gln Gln Arg Val Ile  Arg Gln Ala Leu Ala  Ser Ala Gly
    3560                 3565                 3570

Leu Ser  Thr Val Asp Val Asp  Ala Val Glu Ala His  Gly Thr Gly
    3575                 3580                 3585

Thr Thr  Leu Gly Asp Pro Ile  Glu Ala Gln Ala Leu  Leu Ala Thr
    3590                 3595                 3600

Tyr Gly  Gln Gly Arg Asp Ser  Asp Arg Pro Leu Leu  Leu Gly Ser
    3605                 3610                 3615

Ile Lys  Ser Asn Ile Gly His  Thr Gln Ala Ala Ala  Gly Val Ala
    3620                 3625                 3630

Gly Val  Ile Lys Met Val Met  Ala Met Arg His Gly  Val Leu Pro
    3635                 3640                 3645

Gln Ser  Leu His Ile Asp Glu  Pro Thr Pro His Val  Asp Trp Ser
    3650                 3655                 3660

Thr Gly  Ala Val Glu Leu Leu  Ser Glu Gln Thr Ala  Trp Pro Glu
    3665                 3670                 3675

Asn Thr  Arg Pro Arg Arg Ala  Gly Val Ser Ala Phe  Gly Val Ser
    3680                 3685                 3690

Gly Thr  Asn Ala His Val Ile  Leu Glu Gln Ala Pro  Glu Pro Thr
    3695                 3700                 3705

Ala Ala  Gln Pro Glu Leu Ser  Pro Glu Arg Asp Glu  Met Arg Ala
    3710                 3715                 3720

Val Pro  Trp Val Val Thr Gly  Ala Ser Glu Ala Gly  Val Arg Ala
    3725                 3730                 3735

Gln Ala  Ala Arg Leu Met Ala  Phe Val Asp Asp Arg  Pro Glu Leu
    3740                 3745                 3750

Arg Pro  Val Asn Ile Gly Trp  Ser Leu Ala Ser Thr  Arg Ala Ala
    3755                 3760                 3765

Leu Ser  His Arg Ala Val Val  Val Gly Ala Glu Arg  Thr Glu Leu
    3770                 3775                 3780

Leu Arg  Glu Leu Glu Ala Val  Ala Ser Gly Ser Val  Thr Val Gly
    3785                 3790                 3795

Glu Ala  Arg Thr His Ser Gly  Val Val Phe Val Phe  Pro Gly Gln
    3800                 3805                 3810

Gly Ser  Gln Trp Val Gly Met  Ala Leu Glu Leu Val  Glu Ser Ser
    3815                 3820                 3825

Pro Val  Phe Ala Gly Arg Met  Arg Asp Cys Ala Asp  Ala Leu Ala
    3830                 3835                 3840

Pro Phe  Val Glu Trp Ser Leu  Phe Asp Val Leu Gly  Asp Glu Val
    3845                 3850                 3855

Ala Leu  Gly Arg Val Asp Val  Val Gln Pro Val Leu  Trp Ala Val
    3860                 3865                 3870

Met Val  Ser Leu Ala Glu Leu  Trp Arg Ser Phe Gly  Val Val Pro
    3875                 3880                 3885

Ser Val  Val Val Gly His Ser  Gln Gly Glu Ile Ala  Ala Ala Cys
    3890                 3895                 3900

Val Ala  Gly Gly Leu Ser Leu  Glu Asp Gly Ala Arg  Val Val Ala
    3905                 3910                 3915

Leu Arg  Ser Arg Ala Leu Leu  Ala Leu Ser Gly Arg  Gly Gly Met
    3920                 3925                 3930

Val Ser  Val Pro Val Ser Ala  Asp Arg Leu Arg Gly  Arg Val Gly
```

-continued

```
    3935                3940                3945

Leu Ser  Val Ala Ala Val Asn  Gly Pro Val Ser Thr  Val Val Ser
    3950                3955                3960

Gly Ala  Val Glu Val Leu Asp  Gly Val Leu Ala Glu  Phe Pro Glu
    3965                3970                3975

Ala Arg  Arg Ile Pro Val Asp  Tyr Ala Ser His Ser  Val Gln Val
    3980                3985                3990

Glu Gly  Ile Arg Glu Gly Leu  Ala Glu Ala Leu Ala  Pro Val Arg
    3995                4000                4005

Pro Arg  Thr Gly Glu Val Pro  Phe Tyr Ser Thr Val  Thr Gly Arg
    4010                4015                4020

Leu Met  Asp Thr Ile Glu Leu  Asp Ala Glu Tyr Trp  Tyr Arg Asn
    4025                4030                4035

Leu Arg  Glu Thr Val Glu Phe  Gln Ser Ala Ile Glu  Gly Leu Leu
    4040                4045                4050

Glu Leu  Gly His Thr Val Phe  Val Glu Ala Ser Pro  His Pro Val
    4055                4060                4065

Leu Thr  Ile Gly Ile Gln Asp  Thr Ala Asp Thr Thr  Asp Thr Asp
    4070                4075                4080

Ile Val  Val Ser Gly Ser Leu  Arg Arg Asp Asp Gly  Gly Pro Val
    4085                4090                4095

Arg Phe  Leu Ser Thr Val Gly  Arg Leu Phe Thr Glu  Gly Val Pro
    4100                4105                4110

Val Glu  Trp Gln Pro Leu Phe  Ala Ala Ala Gly Ala  Arg Lys Val
    4115                4120                4125

Asp Leu  Pro Thr Tyr Ala Phe  Gln His Glu Trp Phe  Trp Leu Asp
    4130                4135                4140

Pro Val  Arg Gly Ala Ser Asp  Val Gly Gly Ala Gly  Leu Ala Gly
    4145                4150                4155

Leu Ala  His Pro Leu Val Ser  Ala Val Leu Pro Leu  Pro Glu Ser
    4160                4165                4170

Asp Gly  Cys Val Leu Thr Gly  Ser Leu Ser Ser Ala  Thr His Pro
    4175                4180                4185

Trp Leu  Arg Asp His Ala Val  Leu Asp Lys Val Leu  Leu Pro Gly
    4190                4195                4200

Thr Gly  Phe Val Glu Leu Ala  Leu Gln Ala Gly Leu  His Leu Gly
    4205                4210                4215

Cys Arg  Thr Leu Asp Glu Leu  Thr Leu Gln Ala Pro  Leu Met Leu
    4220                4225                4230

Pro Ala  His Gly Asp Val Gln  Ile Gln Val Ala Val  Gly Gly Pro
    4235                4240                4245

Asp Asp  Ser Gly Arg Arg Pro  Val Thr Val Tyr Ser  Arg Pro Gly
    4250                4255                4260

Lys Asp  Arg Thr Trp Met Arg  His Ala Thr Gly Ser  Ile Ser Pro
    4265                4270                4275

Val Gly  Glu Thr Ala Thr Val  Asp Arg Ala Val Trp  Pro Pro Val
    4280                4285                4290

Gly Ala  Thr Pro Val Glu Leu  Thr Asp Val Tyr Ala  Glu Met Ser
    4295                4300                4305

Thr His  Gly Tyr Ala Tyr Gly  Pro Val Phe Gln Gly  Leu Arg Ala
    4310                4315                4320

Ala Trp  Arg Arg Gly Asp Glu  Val Phe Ala Glu Val  Val Leu Pro
    4325                4330                4335
```

```
Glu Thr Ala Glu Ser Asp Ala Gly Arg Cys Ala Ile His Pro Ala
    4340                4345                4350

Leu Leu Asp Ala Ala Leu His Gly Ala Gly Leu Gly Thr Phe Val
    4355                4360                4365

Thr Glu Pro Gly Arg Pro His Leu Pro Phe Thr Trp Thr Gly Val
    4370                4375                4380

Thr Leu His Ala Val Gly Ala Thr Thr Leu Arg Val Val Leu Ser
    4385                4390                4395

Pro Ala Gly Pro Asp Ala Ile Ser Leu Leu Ala Met Asp Gly Thr
    4400                4405                4410

Gly Ala Pro Val Leu Thr Ala Asp Ser Leu Ala Leu Arg Pro Val
    4415                4420                4425

Ser Glu Gly Gly Leu Gly Gly Ser His Asp Asp Ser Leu Phe Arg
    4430                4435                4440

Val Asp Trp Thr Glu Leu Thr Leu Asp Ala Ser Asp Ala Ser Asp
    4445                4450                4455

Ala Pro Glu Val Ser Asp Glu Ala Ala Phe Pro Val Val Glu Ser
    4460                4465                4470

Val Ala Gln Leu Ala Gly Val Ala Ala Ala Arg Ser Gly Arg Gly
    4475                4480                4485

Ala Val Val Phe Arg Leu Ser Thr Thr Glu Thr Thr Gly Gly Ala
    4490                4495                4500

Ala Glu Glu Ser Pro Glu Asp Val Tyr Ala Leu Thr Ser Arg Val
    4505                4510                4515

Leu Lys Val Ala Gln Ala Trp Leu Ala Asp Asp Arg Phe Gly Asp
    4520                4525                4530

Ala Arg Leu Val Val Val Thr Arg Gly Ala Val Ala Thr Thr Pro
    4535                4540                4545

Gly Glu Asn Pro Glu Ser Leu Ala Ala Ala Ala Val Trp Gly Leu
    4550                4555                4560

Ile Arg Thr Ala Gln Thr Glu Asn Pro Gly Arg Phe Val Leu Val
    4565                4570                4575

Asp Thr Val Asp Glu Asp Pro Ser Ala Leu Pro Gly Val Leu Ala
    4580                4585                4590

Thr Asp Glu Pro Gln Val Ala Ile Arg Ala Gly Lys Ala Leu Val
    4595                4600                4605

Pro Arg Leu Val Arg Ala Thr Ser Ser Ala Leu Pro Val Pro Ala
    4610                4615                4620

Glu Thr Asp Thr Trp Arg Leu Glu Thr Asp Gly Gln Gly Thr Leu
    4625                4630                4635

Glu Asn Leu Val Leu Ser Pro Arg Ala Glu Ala Ser Arg Pro Leu
    4640                4645                4650

Ala Ala His Glu Ile Arg Val Ala Val His Ala Ala Gly Val Asn
    4655                4660                4665

Phe Arg Asp Val Leu Leu Ala Leu Gly Met Tyr Pro Asp Lys Ala
    4670                4675                4680

Gly Leu Leu Gly Ser Glu Ala Ala Gly Thr Val Leu Glu Ile Gly
    4685                4690                4695

Ser Gly Val Val Gly Val Ala Pro Gly Asp Arg Val Met Gly Leu
    4700                4705                4710

Phe Ser Gly Ala Phe Ala Pro Val Ala Ile Thr Asp His Arg Leu
    4715                4720                4725
```

-continued

```
Val Ala  Pro Ile Pro Glu Gly  Trp Ser Phe Pro Gln  Ala Ala Ala
    4730                 4735                 4740

Thr Pro  Ile Ala Phe Leu Thr  Ala Met Tyr Ala Leu  Ile Asp Leu
    4745                 4750                 4755

Ala Glu  Val Arg Ser Gly Glu  Ser Val Leu Val His  Ala Ala Ala
    4760                 4765                 4770

Gly Gly  Val Gly Met Ala Ala  Val Gln Val Ala Arg  Trp Leu Gly
    4775                 4780                 4785

Ala Glu  Val Phe Ala Thr Ala  Ser Pro Ala Lys Trp  Asp Ala Val
    4790                 4795                 4800

Arg Ala  Cys Gly Val Ala Pro  Arg Arg Ile Ala Ser  Ser Arg Ser
    4805                 4810                 4815

Pro Glu  Phe Ala Asp Arg Phe  Arg Ser Asp Ala Pro  Asp Gly Val
    4820                 4825                 4830

Asp Val  Val Leu Asn Ser Leu  Thr Gly Glu Leu Leu  Asn Ala Ser
    4835                 4840                 4845

Leu Gly  Leu Leu Arg Pro Gly  Gly Arg Leu Ile Glu  Met Gly Arg
    4850                 4855                 4860

Thr Glu  Leu Arg Asp Ala Gln  Glu Val Met Ala Arg  His Gly Val
    4865                 4870                 4875

Ser Tyr  Arg Ala Phe Glu Leu  Leu Asp Ala Gly Pro  Asp Arg Ile
    4880                 4885                 4890

Gly Arg  Leu Leu Thr Glu Leu  Leu Ala Leu Phe His  Gln Gly Val
    4895                 4900                 4905

Phe Thr  Pro Leu Pro Leu Arg  Val Gln Asp Val Arg  Gln Ala Ser
    4910                 4915                 4920

Asp Ala  Phe Arg His Leu Ser  Gln Ala Arg His Ile  Gly Lys Leu
    4925                 4930                 4935

Ala Leu  Thr Ile Pro Arg Pro  Leu Ser Gly Gly Thr  Ala Leu Ile
    4940                 4945                 4950

Thr Gly  Gly Thr Gly Thr Leu  Gly Gly Leu Val Ala  Arg Gln Leu
    4955                 4960                 4965

Val Arg  Glu His Gly Val Thr  Glu Leu Val Leu Ala  Ser Arg Arg
    4970                 4975                 4980

Gly Asp  Thr Ala Pro Gln Ala  Ala Glu Leu Leu Thr  Glu Leu Glu
    4985                 4990                 4995

Ala Ala  Gly Ala Arg Val Arg  Val Ala Ala Cys Asp  Val Ser Asp
    5000                 5005                 5010

Arg Asp  Ala Ile Ala Ala Leu  Val Ala Ser Leu Pro  Asn Leu Arg
    5015                 5020                 5025

Ser Val  Val His Thr Ala Gly  Val Leu Asp Asp Ala  Val Ile Gly
    5030                 5035                 5040

Ser Leu  Thr Pro Glu Arg Leu  Arg Thr Val Leu Arg  Pro Lys Ala
    5045                 5050                 5055

Asp Ala  Ala Trp His Leu His  Glu Leu Thr Arg Asp  Arg Asp Leu
    5060                 5065                 5070

Ala Glu  Phe Val Leu Phe Ser  Ser Ala Ala Gly Val  Leu Gly Gly
    5075                 5080                 5085

Pro Gly  Gln Gly Asn Tyr Ala  Ala Ala Asn Ala Phe  Leu Asp Ala
    5090                 5095                 5100

Leu Ala  Ala Arg Arg Arg Ala  Gln Gly Leu Pro Ala  Thr Ser Leu
    5105                 5110                 5115

Ala Trp  Gly Phe Trp Glu Gln  Arg Ser Gly Leu Thr  Glu His Leu
```

```
    5120                5125                5130

Thr Thr  Asp Arg Leu Ala Arg  Ala Gly Val Leu Pro  Leu Ser Thr
    5135                5140                5145

Asp Glu  Gly Leu Val Leu Phe  Asp Asp Ala Arg Ala  Thr Gly Asp
    5150                5155                5160

Thr Leu  Leu Val Pro Met Arg  Tyr Glu Pro Ser Ser  Pro Gly Pro
    5165                5170                5175

Glu Pro  Val Pro Ala Leu Leu  Arg Gly Leu Val Arg  Ala Pro Leu
    5180                5185                5190

Ala Arg  Ala Leu Pro Gly Pro  Ala Asp Gly Val Gly  Ser Gly Val
    5195                5200                5205

Ala Glu  Gly Leu Thr Gly Leu  Ala Ala Asp Glu Arg  Leu Gly Ala
    5210                5215                5220

Leu Leu  Asp Leu Val Arg Arg  Glu Ala Ala Ala Val  Leu Gly His
    5225                5230                5235

Gly Gly  Pro Glu Ser Val Thr  Pro Gln Arg Pro Phe  Lys Glu Leu
    5240                5245                5250

Gly Phe  Asp Ser Leu Ser Ala  Val Glu Leu Arg Asn  Arg Leu Arg
    5255                5260                5265

Ala Ala  Thr Gly Arg Arg Leu  Glu Ala Thr Leu Val  Phe Asp His
    5270                5275                5280

Pro Thr  Pro Ala Val Leu Ala  Arg His Leu Asp Ala  Glu Leu Phe
    5285                5290                5295

Gly Ala  Thr Asp Val Ala Ala  Pro Val Pro Ala Pro  Ala Val Ala
    5300                5305                5310

His Pro  Ala Asp Glu Pro Ile  Ala Ile Val Gly Met  Ser Cys Arg
    5315                5320                5325

Leu Pro  Ala Gly Val Asp Ser  Pro Glu Ala Leu Trp  Lys Leu Leu
    5330                5335                5340

Val Ser  Gly Thr Asp Ala Ile  Ser Glu Leu Pro Pro  Asp Arg Gly
    5345                5350                5355

Trp Asp  Leu Asp Arg Leu Tyr  Asp Gln Asp Pro Ser  Arg Pro Gly
    5360                5365                5370

Thr Thr  Tyr Ala Lys Thr Gly  Gly Phe Leu Lys Asn  Ala Ala Asp
    5375                5380                5385

Phe Asp  Ala Gly Phe Phe Thr  Ile Ser Pro Arg Glu  Ala Leu Ala
    5390                5395                5400

Ala Asp  Pro Gln Gln Arg Leu  Trp Leu Glu Ala Cys  Trp Glu Ala
    5405                5410                5415

Phe Glu  Arg Ala Gly Ile Asp  Pro Leu Ala Leu Lys  Gly Thr Arg
    5420                5425                5430

Thr Gly  Val Phe Ala Gly Ala  Val Ser Thr Thr Tyr  Gly Ala Gly
    5435                5440                5445

Gln Ala  Ala Thr Pro Asp Gly  Ser Glu Gly Tyr Leu  Leu Thr Gly
    5450                5455                5460

Asn Ser  Thr Ser Val Ile Ser  Gly Arg Val Ala Tyr  Thr Leu Gly
    5465                5470                5475

Leu Glu  Gly Pro Ala Val Thr  Val Asp Thr Ala Cys  Ser Ser Ser
    5480                5485                5490

Leu Val  Ser Val His Trp Ala  Cys Glu Ser Leu Arg  Arg Gly Glu
    5495                5500                5505

Ser Thr  Leu Ala Leu Ala Gly  Gly Val Ala Val Met  Thr Thr Pro
    5510                5515                5520
```

-continued

```
Asp Leu Leu Val Glu Phe Ser Arg Gln Arg Gly Leu Ala Pro Asp
    5525                5530                5535

Gly Arg Cys Lys Ser Phe Ala Ala Ala Ala Asp Gly Thr Gly Phe
    5540                5545                5550

Ala Glu Gly Val Gly Val Leu Val Leu Glu Arg Leu Ser Asp Ala
    5555                5560                5565

Thr Arg Asn Gly His Gln Val Leu Ala Val Ile Arg Gly Ser Ala
    5570                5575                5580

Val Asn Gln Asp Gly Ala Ser Asn Gly Leu Thr Ala Pro Asn Gly
    5585                5590                5595

Pro Ser Gln Gln Arg Val Ile Arg Gln Ala Leu Val Asn Ala Gly
    5600                5605                5610

Leu Ala Ser Gln Asp Val Asp Val Val Glu Ala His Gly Thr Gly
    5615                5620                5625

Thr Thr Leu Gly Asp Pro Ile Glu Ala Gln Ala Leu Leu Ala Thr
    5630                5635                5640

Tyr Gly Gln Asp Arg Asp Pro Asp Arg Pro Leu Leu Leu Gly Ser
    5645                5650                5655

Val Lys Ser Asn Ile Gly His Thr Gln Ala Ala Ala Gly Ala Ala
    5660                5665                5670

Gly Leu Ile Lys Met Val Leu Ala Leu Arg Asn Gly Val Leu Pro
    5675                5680                5685

Arg Thr Leu His Val Asp Glu Pro Ser Pro His Val Asp Trp Ser
    5690                5695                5700

Ala Gly Ala Met Glu Leu Leu Thr Glu Gln Thr Ala Trp Pro Asp
    5705                5710                5715

Arg Asp His Leu Arg Arg Ala Gly Val Ser Ala Phe Gly Val Ser
    5720                5725                5730

Gly Thr Asn Ala His Val Ile Leu Glu Gln Ala Pro Glu Pro Asp
    5735                5740                5745

Glu Asn Gly Glu Pro Asp Thr Val Arg Ser Trp Leu Pro Ala Val
    5750                5755                5760

Pro Trp Val Leu Ser Gly Ala Gly Ala Ala Gly Leu Arg Ala Gln
    5765                5770                5775

Ala Gln Arg Leu Ala Ser Phe Val Arg Glu Asn Pro Gly Leu Asp
    5780                5785                5790

Pro Val Asp Val Gly Trp Ser Leu Val Ala Thr Arg Ala Ala Leu
    5795                5800                5805

Ser His Arg Ala Val Val Val Gly Ala Asp Arg Thr Glu Leu Leu
    5810                5815                5820

Arg Glu Leu Ala Ala Val Glu Ser Val Gly Ala Ala Glu Ala Glu
    5825                5830                5835

Arg Asp Val Val Phe Val Phe Pro Gly Gln Gly Ser Gln Trp Val
    5840                5845                5850

Gly Met Ala Leu Glu Leu Val Glu Ser Ser Pro Val Phe Ala Gly
    5855                5860                5865

Arg Met Arg Glu Cys Ala Asp Ala Leu Ala Pro Phe Val Glu Trp
    5870                5875                5880

Ser Leu Phe Gly Val Leu Gly Asp Glu Val Ala Leu Gly Arg Val
    5885                5890                5895

Asp Val Val Gln Pro Val Leu Trp Ala Val Met Val Ser Leu Ala
    5900                5905                5910
```

-continued

```
Glu Leu  Trp Arg Ser Phe Gly  Val Val Pro Ser Val  Val Val Gly
    5915                 5920                 5925

His Ser  Gln Gly Glu Ile Ala  Ala Ala Cys Val Ala  Gly Ala Leu
    5930                 5935                 5940

Thr Leu  Glu Asp Gly Ala Arg  Val Val Ala Leu Arg  Ser Arg Ala
    5945                 5950                 5955

Leu Leu  Ala Leu Ser Gly Arg  Gly Gly Met Val Ser  Val Pro Val
    5960                 5965                 5970

Ser Ala  Asp Arg Leu Arg Gly  Arg Val Gly Leu Ser  Val Ala Ala
    5975                 5980                 5985

Val Asn  Gly Pro Val Ser Thr  Val Val Ser Gly Ala  Val Glu Val
    5990                 5995                 6000

Leu Asp  Gly Val Leu Ala Glu  Phe Pro Glu Ala Arg  Arg Ile Pro
    6005                 6010                 6015

Val Asp  Tyr Ala Ser His Ser  Val Gln Val Glu Gly  Ile Arg Glu
    6020                 6025                 6030

Gly Leu  Ala Glu Ala Leu Ala  Pro Val Arg Pro Arg  Thr Gly Glu
    6035                 6040                 6045

Val Pro  Phe Tyr Ser Thr Val  Thr Gly Arg Leu Met  Asp Thr Val
    6050                 6055                 6060

Gly Leu  Asp Gly Glu Tyr Trp  Tyr Arg Asn Leu Arg  Glu Thr Val
    6065                 6070                 6075

Glu Phe  Gln Ser Thr Val Glu  Ala Leu Ile Gly Gln  Gly His Thr
    6080                 6085                 6090

Val Phe  Val Glu Ala Ser Pro  His Pro Val Leu Thr  Val Gly Val
    6095                 6100                 6105

Gln Asp  Thr Ala Asp Ala Met  Glu Thr Pro Ile Val  Ala Thr Gly
    6110                 6115                 6120

Ser Leu  Arg Arg Asp Glu Gly  Gly Val Arg Arg Phe  Leu Thr Ser
    6125                 6130                 6135

Leu Ala  Glu Val Ser Val His  Gly Ile Glu Val Asn  Trp Gln Thr
    6140                 6145                 6150

Val Phe  Asp Gly Thr Gly Ala  Arg Arg Val Asp Leu  Pro Thr Tyr
    6155                 6160                 6165

Ala Phe  Gln Arg Glu Arg Phe  Trp Leu Val Pro Ser  Thr Gly Thr
    6170                 6175                 6180

Gly Asp  Ala Ser Gly Leu Gly  Leu Gly Ala Val Asp  His Pro Leu
    6185                 6190                 6195

Leu Gly  Ala Ala Val Pro Leu  Pro Asp Ala Asp Gly  Cys Val Leu
    6200                 6205                 6210

Thr Gly  Ala Leu Ser Leu Ala  Gly Gln Pro Trp Leu  Ala Asp His
    6215                 6220                 6225

Ser Val  Leu Gly Met Val Leu  Leu Pro Gly Thr Ala  Phe Val Glu
    6230                 6235                 6240

Leu Ala  Leu Gln Ala Gly Ala  Arg Phe Gly Cys Gly  Thr Leu Glu
    6245                 6250                 6255

Glu Leu  Thr Leu His Glu Pro  Leu Val Leu Pro Glu  Arg Glu Thr
    6260                 6265                 6270

Val Gln  Leu Gln Val Ser Val  Gly Gly Ser Asp Asp  Phe Gly Gly
    6275                 6280                 6285

Arg Pro  Phe Thr Val Phe Ser  Arg Cys Glu Gly Glu  Trp Ile Arg
    6290                 6295                 6300

His Ala  Gly Gly Thr Leu Arg  Val Gly Glu Arg Gly  Asp Pro Pro
```

-continued

```
    6305                6310                6315

Ala Asn  Pro Ser Val Trp Pro  Pro Ala Asp Ala Arg  Pro Val Asp
    6320                6325                6330

Val Ala  Glu Leu His Thr Thr  Met Ala Glu Arg Gly  Tyr Gln Tyr
    6335                6340                6345

Gly Pro  Ala Phe Gln Gly Leu  Arg Lys Ala Trp Ile  Arg Asp Ser
    6350                6355                6360

Glu Val  Phe Leu Asp Val Ala  Leu Pro Glu Gln Val  Arg Gly Asp
    6365                6370                6375

Ala Ala  Arg Cys Gly Val His  Pro Ala Leu Leu Asp  Ala Ala Leu
    6380                6385                6390

Gln Gly  Ile Gly Leu Gly Ala  Phe Val Asn Glu Pro  Gly Gln Ala
    6395                6400                6405

His Leu  Pro Phe Ser Trp Ser  Gly Val Thr Leu His  Ala Val Gly
    6410                6415                6420

Ala Thr  Ala Val Arg Val Thr  Leu Ser Pro Ala Gly  Pro Asp Thr
    6425                6430                6435

Val Ala  Ile Arg Met Ala Asp  Thr Ile Gly Ala Pro  Val Leu Ser
    6440                6445                6450

Ile Asp  Ala Leu Ala Met Arg  Pro Leu Ala Glu Gln  Arg Leu Leu
    6455                6460                6465

Glu Ala  Gly Gly Ser Arg Gly  Asp Ala Leu Phe Arg  Leu Glu Trp
    6470                6475                6480

Lys Glu  Leu Pro Val Pro Thr  Gly Ala Thr Gly Pro  Arg Ala Gln
    6485                6490                6495

Ser Trp  Gly Leu Leu Gly Gly  His Asp Glu Pro Arg  Leu Thr Ala
    6500                6505                6510

Ala Leu  Thr Ala Ala Gly Val  Ser Pro Gln Arg His  Arg Asp Leu
    6515                6520                6525

Ala Ser  Ile Asp Gln Val Pro  Asp Val Leu Val Leu  Ser Cys Pro
    6530                6535                6540

Pro Glu  Ala Asp Gly Gly Pro  Ala Pro Glu Ala Thr  Ser Ser Ala
    6545                6550                6555

Leu Arg  Arg Val Leu Glu Val  Val Arg Glu Trp Leu  Gly Asp Ala
    6560                6565                6570

Arg Tyr  Thr Asp Ala Arg Leu  Met Val Leu Thr Arg  Arg Ala Val
    6575                6580                6585

Ala Thr  Ser Thr Gly Asp Asp  Val Glu Asp Leu Ala  Ala Ala Ala
    6590                6595                6600

Val Arg  Gly Leu Leu Arg Thr  Ala Gln Gln Glu Asn  Pro Asp Arg
    6605                6610                6615

Leu Val  Val Ile Asp His Asp  Asp Ser Asp Leu Glu  Val Leu Pro
    6620                6625                6630

Val Val  Leu Gly Thr Gly Glu  Pro Glu Ala Ala Ile  Arg Ala Gly
    6635                6640                6645

Lys Val  Leu Val Pro Arg Leu  Val Lys Ala Ala Val  Ser Glu Gly
    6650                6655                6660

Lys Ala  Pro Ala Trp Asp Ala  Gly Thr Val Leu Ile  Thr Gly Gly
    6665                6670                6675

Thr Gly  Thr Leu Gly Gly Leu  Val Ala Arg His Leu  Val Thr Thr
    6680                6685                6690

His Gly  Ala Arg Asp Leu Val  Leu Ala Ser Arg Gly  Gly Asp Thr
    6695                6700                6705
```

```
Ala Pro  Gly Ala Val Glu Leu  Ala Thr Glu Leu Glu  Ala Leu Gly
    6710                 6715                 6720

Ala Arg  Ile Arg Val Ala Ala  Cys Asp Val Ala Asp  Arg Ala Gln
    6725                 6730                 6735

Leu Thr  Ala Leu Leu Asp Thr  Ile Pro Ala Leu Arg  Ala Val Val
    6740                 6745                 6750

His Thr  Ala Gly Val Val Asp  Asp Gly Val Ile Gly  Ser Met Thr
    6755                 6760                 6765

Ala Glu  Arg Val Glu Thr Val  Leu Arg Pro Lys Ala  Asn Ala Ala
    6770                 6775                 6780

Trp His  Leu His Ala Leu Thr  Arg His Leu Asp Leu  Asp Ala Phe
    6785                 6790                 6795

Val Leu  Phe Ser Ser Ala Thr  Gly Val Leu Gly Ser  Ala Gly Gln
    6800                 6805                 6810

Gly Asn  Tyr Ala Ala Ala Asn  Ala Phe Leu Asp Ala  Leu Ala Val
    6815                 6820                 6825

His Arg  Arg Ala Gln Gly Leu  Pro Ala Val Ser Val  Ala Trp Gly
    6830                 6835                 6840

Leu Trp  Glu Arg Arg Ser Gly  Leu Thr Ala His Leu  Ser Glu Gln
    6845                 6850                 6855

Asp Val  Ala Arg Met Thr Ser  Thr Gly Ala Val Pro  Leu Ser Asp
    6860                 6865                 6870

Glu Arg  Gly Leu Glu Leu Phe  Asp Ala Ala Cys Arg  Ser Gly Glu
    6875                 6880                 6885

Pro Thr  Leu Val Ala Thr Pro  Leu His Leu Arg Ala  Val Ala Ala
    6890                 6895                 6900

Thr Gly  Thr Val Pro His Val  Leu Ser Ala Leu Ala  Pro Thr Pro
    6905                 6910                 6915

Pro Arg  Arg Ala Ala Glu Ala  Gly Asp Gly Gly Val  Ala Leu Arg
    6920                 6925                 6930

Gln Ser  Leu Ala Glu Met Ser  Gly Ala Glu Gln Ser  Gln Thr Val
    6935                 6940                 6945

Leu Gly  Leu Val Arg Gly Gln  Val Ala Ala Val Leu  Arg His Pro
    6950                 6955                 6960

Asp Pro  Ser Ala Ile Asp Thr  Ala Arg Thr Phe Gln  Glu Ile Gly
    6965                 6970                 6975

Phe Asp  Ser Leu Thr Ala Val  Glu Leu Arg Asn Arg  Leu Gly Ala
    6980                 6985                 6990

Thr Thr  Gly Ile Arg Leu Ala  Ala Thr Ala Ile Phe  Asp Tyr Pro
    6995                 7000                 7005

Thr Pro  Ala Thr Leu Ala Gln  His Leu Leu Ala Glu  Ile Val Pro
    7010                 7015                 7020

Glu Thr  Ala Asp Pro Val Ala  Ala Arg Leu Gly Glu  Leu Asp Lys
    7025                 7030                 7035

Val Ala  Ala Met Ile Ser Ala  Met Ala Glu Asp Asp  Thr Leu Arg
    7040                 7045                 7050

Glu Gln  Leu Ser Ser Arg Met  Glu Thr Ile Val Ala  Met Trp Ala
    7055                 7060                 7065

Asp Leu  His Arg Pro Glu Arg  Pro Gly Thr Val Glu  Arg Asp Leu
    7070                 7075                 7080

Glu Ser  Ala Ser Leu Asp Asp  Met Phe Gly Ile Ile  Asp Gln Glu
    7085                 7090                 7095
```

```
Leu Asp  Gly Ser
    7100


<210> SEQ ID NO 49
<211> LENGTH: 7968
<212> TYPE: PRT
<213> ORGANISM: Streptomyces sp.

<400> SEQUENCE: 49

Met Ser Ser Glu Asn Val Arg Pro Glu Ile Glu Gly Thr Gly Thr Arg
1               5                   10                  15

Met Ser Asn Asp Glu Lys Val Leu Glu Tyr Leu Lys Lys Leu Thr Ala
            20                  25                  30

Asp Leu Arg Gln Thr Arg Gln Arg Leu Gln Asp Val Glu Ala Lys Ser
        35                  40                  45

Arg Glu Pro Ile Ala Ile Val Gly Met Ser Cys Arg Phe Pro Gly Gly
    50                  55                  60

Val Ser Ser Pro Glu Asp Leu Trp Arg Leu Thr Glu Ser Ala Val Asp
65                  70                  75                  80

Ala Val Ser Gly Phe Pro Thr Asp Arg Gly Trp Asp Leu Asp Gly Leu
                85                  90                  95

Tyr Asp Pro Asp Pro Asp Arg Ala Gly Arg Ser Tyr Ala Arg Glu Gly
            100                 105                 110

Ala Phe Ile Pro Asp Ala Gly His Phe Asp Pro Gly Leu Phe Gly Ile
        115                 120                 125

Ser Pro Arg Glu Ala Leu Ala Met Asp Pro Gln Gln Arg Leu Leu Leu
    130                 135                 140

Glu Ala Ser Trp Glu Ala Leu Glu Arg Ala Gly Ile Pro Thr Asp Ser
145                 150                 155                 160

Leu Lys Gly Ser Arg Thr Gly Val Phe Ala Gly Leu Met Ser Ser Asp
                165                 170                 175

Tyr Val Ser Arg Leu Ser Ala Val Pro Asp Glu Leu Glu Gly Tyr Val
            180                 185                 190

Gly Ile Gly Ser Ala Ala Ser Val Ala Ser Gly Arg Val Ser Tyr Thr
        195                 200                 205

Leu Gly Leu Glu Gly Pro Ala Val Thr Val Asp Thr Ala Cys Ser Ser
    210                 215                 220

Ser Leu Val Ala Leu His Leu Ala Val Gln Ala Leu Arg Ser Gly Glu
225                 230                 235                 240

Cys Ser Leu Ala Leu Ala Gly Gly Val Thr Val Met Ala Thr Pro Gly
                245                 250                 255

Thr Phe Val Gln Phe Ser Arg Gln Arg Gly Leu Ala Ala Asp Gly Arg
            260                 265                 270

Cys Lys Ala Phe Ala Ala Gly Ala Asp Gly Thr Gly Trp Gly Glu Gly
        275                 280                 285

Val Gly Met Leu Val Val Glu Arg Leu Ser Asp Ala Glu Arg Leu Gly
    290                 295                 300

His Arg Val Leu Ala Val Val Arg Gly Ser Ala Val Asn Gln Asp Gly
305                 310                 315                 320

Ala Ser Asn Gly Leu Thr Ala Pro Asn Gly Pro Ser Gln Gln Arg Val
                325                 330                 335

Ile Arg Gln Ala Leu Ala Asn Ala Arg Leu Ser Ala Val Asp Val Asp
            340                 345                 350

Ala Val Glu Ala His Gly Thr Gly Thr Ala Leu Gly Asp Pro Ile Glu
        355                 360                 365
```

```
Ala Gln Ala Leu Leu Ala Thr Tyr Gly Gln Gly Arg Asp Val Gly Arg
    370                 375                 380

Pro Leu Trp Leu Gly Ser Val Lys Ser Asn Ile Gly His Thr Gln Ala
385                 390                 395                 400

Ala Ala Gly Val Ala Gly Val Ile Lys Met Val Met Ala Met Arg His
                405                 410                 415

Gly Val Leu Pro Arg Thr Leu His Val Asp Glu Pro Ser Pro His Val
            420                 425                 430

Asp Trp Ser Ala Gly Ala Val Glu Leu Leu Thr Gly Gln Val Ala Trp
        435                 440                 445

Pro Glu Val Asp Arg Pro Arg Arg Ala Gly Val Ser Ala Phe Gly Val
    450                 455                 460

Ser Gly Thr Asn Ala His Val Ile Val Glu Gln Ala Pro Glu Val Ala
465                 470                 475                 480

Glu Ser Glu Ala Glu Gly Val Val Leu Pro Ala Val Pro Trp Val Val
                485                 490                 495

Ser Gly Val Gly Glu Val Ala Val Arg Ala Gln Val Glu Arg Leu Arg
            500                 505                 510

Ala Phe Ala Asp Arg Asn Pro Gly Leu Asp Pro Val Asp Val Gly Trp
        515                 520                 525

Ser Leu Ala Thr Gly Arg Ala Gly Leu Ser His Arg Ala Val Val Val
    530                 535                 540

Gly Ala Gly Arg Gly Glu Leu Leu Gly Ala Leu Glu Gly Val Pro Val
545                 550                 555                 560

Val Gly Val Pro Val Val Gly Gly Leu Gly Val Leu Phe Ala Gly Gln
                565                 570                 575

Gly Ser Gln Arg Leu Gly Met Gly Arg Gly Leu Tyr Glu Gly Tyr Pro
            580                 585                 590

Val Phe Ala Ala Val Trp Asp Glu Val Cys Ala Gln Leu Asp Arg Tyr
        595                 600                 605

Leu Asp Arg Pro Val Gly Glu Val Val Trp Gly Asp Asp Ala Gly Leu
    610                 615                 620

Val Gly Glu Thr Val Tyr Ala Gln Ala Gly Leu Phe Ala Leu Glu Val
625                 630                 635                 640

Ala Leu Tyr Arg Leu Ile Ala Ser Trp Gly Val Arg Ala Asp Tyr Leu
                645                 650                 655

Leu Gly His Ser Ile Gly Glu Leu Ala Ala Ala Tyr Val Ala Gly Val
            660                 665                 670

Trp Ser Leu Glu Asp Ala Val Arg Val Val Val Ala Arg Gly Arg Leu
        675                 680                 685

Met Gln Ala Leu Pro Ser Gly Gly Ala Met Val Ala Val Gly Ala Ser
    690                 695                 700

Glu Gly Val Val Arg Pro Leu Leu Gly Glu Gly Val Val Val Ala Ala
705                 710                 715                 720

Val Asn Gly Pro Glu Ser Val Val Leu Ser Gly Asp Glu Asp Ala Val
                725                 730                 735

Gln Val Val Val Asp Val Leu Ala Gly Arg Gly Val Arg Thr Arg Arg
            740                 745                 750

Leu Arg Val Ser His Ala Phe His Ser Ala Arg Met Asp Gly Met Leu
        755                 760                 765

Ala Glu Phe Gly Glu Val Leu Arg Gly Val Glu Phe Arg Ala Pro Ser
    770                 775                 780
```

-continued

```
Val Pro Val Val Ser Asn Val Ser Gly Val Val Ala Gly Glu Glu Leu
785                 790                 795                 800

Cys Ser Pro Glu Tyr Trp Val Arg His Val Arg Glu Thr Val Arg Phe
                805                 810                 815

Ala Asp Gly Leu Glu Thr Leu Arg Glu Leu Gly Val Gly Ser Phe Leu
            820                 825                 830

Glu Leu Gly Pro Asp Gly Thr Leu Thr Ala Leu Ala Asp Gly Asp Gly
        835                 840                 845

Val Ser Ala Leu Arg Arg Asp Arg Pro Glu Pro Thr Ala Val Met Ala
    850                 855                 860

Ala Leu Gly Gly Leu Tyr Val Arg Gly Val Glu Val Asp Trp Asp Ala
865                 870                 875                 880

Val Phe Pro Gly Ala Arg Arg Val Asp Leu Pro Thr Tyr Ala Phe Gln
                885                 890                 895

Arg Glu Arg Phe Trp Leu Glu Pro Ala Ala Glu Gln Pro Ala Thr Ser
            900                 905                 910

Ala Val Asp Ala Ala Phe Trp Asp Ala Val Glu Arg Gly Asp Ala Glu
        915                 920                 925

Ile Leu Gly Val Asp Val Glu Gln Pro Leu Ser Ala Ala Leu Pro Ala
    930                 935                 940

Leu Ala Ser Trp Arg Arg Ala Arg Gln Glu Glu Ser Val Ile Asp Ala
945                 950                 955                 960

Trp Arg Tyr Arg Leu Thr Trp Thr Pro Val Ala Gly Leu Ser Ser Gln
                965                 970                 975

Leu Ser Gly Val Trp Leu Val Val Val Glu Pro Asp Glu Ala Glu Pro
            980                 985                 990

Asp Val Val Ala Ala Leu Arg Gly  Ala Gly Ala Glu Val  Arg Val Val
        995                 1000                1005

Thr Ile  Asp Glu Leu Asp Ala  Gly Pro Val Ala Gly  Val Val Ser
    1010                1015                1020

Leu Leu  Ser Val Glu Thr Thr  Val Ser Leu Leu Gln  Ala Leu Val
    1025                1030                1035

Ala Glu  Gly Gly Asp Ala Pro  Leu Trp Cys Val Thr  Arg Gly Ala
    1040                1045                1050

Val Ser  Val Val Asp Gly Asp  Val Val Asp Pro His  Ala Ser Ala
    1055                1060                1065

Val Trp  Gly Leu Gly Arg Val  Ile Gly Leu Glu His  Pro Asp Arg
    1070                1075                1080

Trp Gly  Gly Leu Ile Asp Leu  Pro Thr Ala Trp Gly  Glu Arg Thr
    1085                1090                1095

Ser Gly  Met Leu Cys Ser Val  Leu Ser Gly Ala Thr  Gly Glu Asp
    1100                1105                1110

His Thr  Ala Ile Arg Gly Asp  Glu Val Leu Gly Cys  Arg Leu Ser
    1115                1120                1125

Arg Ala  Thr Thr Ser Ala Pro  Gly Pro Ser Thr Ala  Trp Glu Ala
    1130                1135                1140

Ser Gly  Thr Ala Leu Ile Thr  Gly Gly Thr Gly Ala  Leu Gly Ser
    1145                1150                1155

His Val  Ala Arg Trp Leu Ala  Asp Thr Gly Val Glu  Glu Ile Val
    1160                1165                1170

Leu Thr  Ser Arg Arg Gly Ala  Asp Ala Pro Gly Ala  Arg Glu Leu
    1175                1180                1185

Val Ala  Glu Leu Ser Ala Met  Gly Val Ser Ala Arg  Val Val Ala
```

-continued

```
    1190                1195                1200

Cys Asp  Val Ala Asp Arg Asp  Ala Val Ala Glu Leu  Ile Glu Thr
    1205                1210                1215

Ile Pro  Asp Leu Arg Val Val  Val His Ala Ala Gly  Val Pro Ser
    1220                1225                1230

Trp Gly  Ala Leu Ser Thr Leu  Thr Ala Gln Gly Leu  Gln Asp Gly
    1235                1240                1245

Met Arg  Ala Lys Val Ala Gly  Ala Ile His Leu Asp  Glu Leu Thr
    1250                1255                1260

Arg Asp  Met Arg Leu Asp Ala  Phe Val Leu Phe Ser  Ser Val Ala
    1265                1270                1275

Gly Val  Trp Gly Ser Gly Ser  Gln Ser Ala Tyr Ala  Ala Ala Asn
    1280                1285                1290

Ala Phe  Leu Asp Gly Leu Ala  Trp Arg Arg Arg Gly  Val Gly Leu
    1295                1300                1305

Val Ala  Thr Ser Val Ala Trp  Gly Met Trp Gly Gly  Gly Gly Met
    1310                1315                1320

Ala Val  Gly Gly Glu Glu Phe  Leu Val Glu Arg Gly  Val Ser Gly
    1325                1330                1335

Met Ala  Pro Gly Ser Ala Val  Ala Ala Leu Arg Arg  Ala Leu Cys
    1340                1345                1350

Asp Gly  Glu Thr Ala Leu Val  Val Ala Asp Val Asp  Trp Glu Arg
    1355                1360                1365

Phe Gly  Pro Arg Phe Thr Ala  Leu Arg Pro Ser Pro  Leu Leu Ser
    1370                1375                1380

Glu Leu  Ile Pro Asp Thr Val  Gly Ser Gly Val Pro  Leu Gly Glu
    1385                1390                1395

Phe Ala  Ala Arg Phe Gln Thr  Met Ser Glu Gly Glu  Arg Met Arg
    1400                1405                1410

Ala Ala  Val Glu Leu Val Arg  Val Ser Ala Ala Ala  Val Leu Gly
    1415                1420                1425

His Gln  Gly Pro Glu Ala Ile  Asp Pro Val Arg Thr  Phe Gln Glu
    1430                1435                1440

Ile Gly  Phe Asp Ser Leu Thr  Ala Val Glu Leu Arg  Asn Arg Ile
    1445                1450                1455

Ala Thr  Ala Thr Gly Ile Arg  Pro Pro Ala Thr Met  Val Phe Asp
    1460                1465                1470

Tyr Pro  Thr Pro Val Ala Leu  Ala Glu Tyr Leu Ser  Val Glu Leu
    1475                1480                1485

Leu Gly  Ser Pro Gln Asp Ser  Val Pro Pro Leu Gln  Val Ala Ala
    1490                1495                1500

Pro Asp  Asp Gly Asp Pro Ile  Val Ile Val Gly Met  Ser Cys Arg
    1505                1510                1515

Phe Pro  Gly Asp Val Glu Ser  Pro Glu Asp Leu Trp  Arg Leu Ile
    1520                1525                1530

Asp Ser  Asp Gly Asp Ala Ile  Thr Ala Phe Pro Thr  Asp Arg Gly
    1535                1540                1545

Trp Asp  Leu Thr Gly Leu Phe  Asp Thr Ala Val Gly  Glu Ser Gly
    1550                1555                1560

Thr Ser  Tyr Ala Arg Val Gly  Gly Phe Val His Asp  Ala Gly Glu
    1565                1570                1575

Phe Asp  Pro Ala Phe Phe Gly  Ile Ser Pro Arg Glu  Ala Thr Ala
    1580                1585                1590
```

-continued

```
Met Asp Pro Gln Gln Arg Leu Leu Leu His Ala Ala Trp Glu Ala
    1595                1600                1605

Phe Glu Arg Ala Gly Ile Pro Ala Ala Ser Val Arg Gly Ser Arg
    1610                1615                1620

Thr Gly Val Phe Val Gly Ala Ser Pro Gln Gly Tyr Gly Ala Ala
    1625                1630                1635

Glu Ala Ser Glu Gly Tyr Phe Leu Thr Gly Ser Ser Gly Ser Val
    1640                1645                1650

Ile Ser Gly Arg Val Ser Tyr Thr Leu Gly Leu Glu Gly Pro Ala
    1655                1660                1665

Val Thr Val Asp Thr Ala Cys Ser Ser Ser Leu Val Ala Leu His
    1670                1675                1680

Leu Ala Val Gln Ala Leu Arg Ser Gly Glu Cys Ser Leu Ala Leu
    1685                1690                1695

Ala Gly Gly Val Thr Val Met Ala Thr Pro Thr Ala Phe Val Glu
    1700                1705                1710

Phe Ser Arg Gln Arg Gly Leu Ala Ala Asp Gly Arg Cys Lys Ser
    1715                1720                1725

Phe Ala Ala Gly Ala Asp Gly Thr Gly Trp Ser Glu Gly Val Gly
    1730                1735                1740

Leu Leu Leu Val Glu Arg Leu Ser Asp Ala Glu Arg Leu Gly His
    1745                1750                1755

Arg Val Leu Ala Val Val Arg Gly Ser Ala Val Asn Gln Asp Gly
    1760                1765                1770

Ala Ser Asn Gly Leu Thr Ala Pro Asn Gly Pro Ser Gln Gln Arg
    1775                1780                1785

Val Ile Arg Gln Ala Leu Ala Asn Ala Arg Leu Ser Ala Val Asp
    1790                1795                1800

Val Asp Ala Val Glu Ala His Gly Thr Gly Thr Ala Leu Gly Asp
    1805                1810                1815

Pro Ile Glu Ala Gln Ala Leu Leu Ala Thr Tyr Gly Gln Gly Arg
    1820                1825                1830

Asp Val Gly Arg Pro Leu Trp Leu Gly Ser Val Lys Ser Asn Ile
    1835                1840                1845

Gly His Thr Gln Ala Ala Ala Gly Val Ala Gly Val Ile Lys Met
    1850                1855                1860

Val Met Ala Leu Arg His Gly Val Leu Pro Arg Thr Leu His Val
    1865                1870                1875

Asp Glu Pro Ser Pro His Val Asp Trp Ser Ser Gly Ala Val Glu
    1880                1885                1890

Leu Leu Ser Glu Arg Ala Ala Trp Pro Glu Met Gly Arg Pro Arg
    1895                1900                1905

Arg Ala Gly Val Ser Ser Phe Gly Val Ser Gly Thr Asn Ala His
    1910                1915                1920

Val Val Leu Glu Gln Ala Pro Gly Ala Val Glu Glu Ser Arg Gly
    1925                1930                1935

Glu Gly Val Ala Leu Pro Ala Val Pro Trp Val Val Ser Gly Ala
    1940                1945                1950

Gly Glu Val Ala Val Arg Ala Gln Val Glu Arg Leu Arg Ala Phe
    1955                1960                1965

Ala Asp Arg Asn Pro Gly Leu Asp Pro Val Asp Val Gly Trp Ser
    1970                1975                1980
```

-continued

```
Leu Val  Ala Thr Arg Ser Gly  Leu Ser His Arg Ala  Val Val Val
    1985                 1990                 1995

Gly Ala  Asp Arg Glu Glu Leu  Leu Gly Gly Leu Gly  Ser Val Val
    2000                 2005                 2010

Val Gly  Val Pro Val Ala Gly  Gly Leu Gly Val Leu  Phe Ala Gly
    2015                 2020                 2025

Gln Gly  Ser Gln Arg Leu Gly  Met Gly Arg Gly Leu  Tyr Glu Gly
    2030                 2035                 2040

Tyr Pro  Val Phe Ala Ala Val  Trp Asp Glu Val Cys  Gly Glu Leu
    2045                 2050                 2055

Asp Arg  Tyr Leu Asp Arg Pro  Val Gly Glu Val Val  Trp Gly Asp
    2060                 2065                 2070

Asp Ala  Gly Leu Val Gly Glu  Thr Val Tyr Ala Gln  Ala Gly Leu
    2075                 2080                 2085

Phe Ala  Leu Glu Val Ser Leu  Tyr Arg Leu Ile Ala  Ser Trp Gly
    2090                 2095                 2100

Val Arg  Gly Asp Tyr Leu Leu  Gly His Ser Ile Gly  Glu Leu Ala
    2105                 2110                 2115

Ala Ala  Tyr Val Ala Gly Val  Trp Ser Leu Glu Asp  Ala Gly Arg
    2120                 2125                 2130

Val Val  Val Ala Arg Gly Arg  Leu Met Gln Ala Leu  Pro Ser Gly
    2135                 2140                 2145

Gly Ala  Met Val Ala Val Ala  Ala Ser Glu Gly Glu  Val Arg Pro
    2150                 2155                 2160

Leu Leu  Gly Glu Gly Val Val  Val Ala Ala Val Asn  Gly Pro Glu
    2165                 2170                 2175

Ser Val  Val Val Ser Gly Asp  Glu Asp Ala Val Glu  Ala Val Val
    2180                 2185                 2190

Asp Val  Leu Ala Gly Arg Gly  Val Arg Thr Arg Arg  Leu Arg Val
    2195                 2200                 2205

Ser His  Ala Phe His Ser Ala  Arg Met Asp Gly Met  Leu Ala Glu
    2210                 2215                 2220

Phe Gly  Glu Val Leu Arg Gly  Val Glu Phe Arg Ala  Pro Ser Val
    2225                 2230                 2235

Pro Val  Val Ser Asn Val Ser  Gly Ala Val Ala Gly  Glu Glu Leu
    2240                 2245                 2250

Cys Ser  Pro Glu Tyr Trp Val  Arg His Val Arg Glu  Thr Val Arg
    2255                 2260                 2265

Phe Ala  Asp Gly Leu Glu Thr  Leu Arg Glu Leu Gly  Val Gly Ser
    2270                 2275                 2280

Phe Leu  Glu Leu Gly Pro Asp  Gly Thr Leu Thr Ala  Leu Ala Asp
    2285                 2290                 2295

Gly Asp  Gly Val Pro Val Leu  Arg Arg Asp Arg Pro  Glu Pro Leu
    2300                 2305                 2310

Thr Val  Met Ala Ala Leu Gly  Gly Leu Tyr Val Arg  Gly Val Gln
    2315                 2320                 2325

Ile Asp  Trp Asp Ala Val Phe  Pro Gly Ala Arg Arg  Val Asp Leu
    2330                 2335                 2340

Pro Thr  Tyr Ala Phe Gln Arg  Glu Arg Phe Trp Leu  Glu Pro Ser
    2345                 2350                 2355

Pro Glu  Gln Pro Thr Thr Ser  Ala Ala Asp Ala Ala  Phe Trp Asp
    2360                 2365                 2370

Ala Val  Glu Arg Gly Asp Leu  Gly Ser Phe Gly Ile  Asp Ala Glu
```

-continued

```
    2375                2380                2385

Gln Pro Leu Ser Ala Ala Leu Pro Ala Leu Ser Ser Trp Arg Arg
    2390                2395                2400

Arg His Gln Glu Arg Ser Leu Val Glu Ser Trp Arg Tyr Arg Leu
    2405                2410                2415

Asp Trp Ser Pro Ile Gly Thr Ala Ser Glu Gln Pro Ser Leu Arg
    2420                2425                2430

Gly Thr Trp Leu Val Val Gly Glu Gly Gly Asp Asp Val Val Ala
    2435                2440                2445

Val Leu Arg Ala Ala Gly Ala Asp Ala Arg Val Val Thr Met Ala
    2450                2455                2460

Glu Leu Gly Glu Val Ala Ala Ala Gly Val Val Ser Leu Leu Pro
    2465                2470                2475

Val Glu Ala Thr Val Ser Leu Val Gln Ala Leu Gly Thr Ala Gly
    2480                2485                2490

Ala Asp Ala Pro Leu Trp Cys Val Thr Arg Gly Ala Val Ser Val
    2495                2500                2505

Val Asp Gly Asp Val Val Asp Pro Gly Gln Ser Gly Val Trp Gly
    2510                2515                2520

Leu Gly Arg Val Ile Arg Leu Glu His Pro Asp Arg Trp Gly Gly
    2525                2530                2535

Leu Ile Asp Val Pro Val Val Val Asp Glu Glu Ala Gly Ala Trp
    2540                2545                2550

Leu Cys Arg Val Leu Gly Gly Gly Thr Gly Glu Asp Gln Val Ala
    2555                2560                2565

Val Arg Gly Gly Gly Ala Trp Gly Ala Arg Leu Val Arg Val Ser
    2570                2575                2580

Gly Ser Gly Ser Gly Ser Gly Gly Ala Val Val Trp Arg Gly Arg
    2585                2590                2595

Gly Ala Ala Leu Val Thr Gly Gly Thr Gly Ala Leu Gly Gly His
    2600                2605                2610

Val Ala Arg Trp Leu Ala Gly Ala Gly Val Glu Thr Val Val Leu
    2615                2620                2625

Ala Ser Arg Arg Gly Met Ala Ala Pro Asp Ala Glu Gln Leu Val
    2630                2635                2640

Ala Glu Leu Glu Gly Leu Gly Val Ala Val Arg Val Val Ala Cys
    2645                2650                2655

Asp Val Ala Asp Arg Gly Ala Val Ala Glu Leu Leu Glu Gly Ile
    2660                2665                2670

Gly Asp Leu Arg Val Val Val His Ala Ala Gly Val Leu Asp Asp
    2675                2680                2685

Gly Val Leu Glu Ser Leu Thr Ser Glu Arg Val Arg Glu Val Met
    2690                2695                2700

Arg Val Lys Ala Glu Gly Ala Arg Tyr Leu Asp Glu Leu Thr Arg
    2705                2710                2715

Gly Trp Asp Leu Asp Ala Phe Val Leu Phe Ser Ser Ala Ala Gly
    2720                2725                2730

Thr Val Gly Asn Ala Gly Gln Gly Ser Tyr Ala Ala Ala Asn Ala
    2735                2740                2745

Val Leu Asp Gly Leu Ala Trp Arg Arg Arg Ala Glu Gly Leu Val
    2750                2755                2760

Ala Thr Ser Val Ala Trp Gly Ala Trp Ala Asp Ser Gly Met Gly
    2765                2770                2775
```

-continued

```
Ala Gly His Ala Arg Ala Met Ala Pro Arg Leu Ala Leu Ala Ala
    2780                2785                2790

Leu Gln Arg Ala Leu Asp Asp Asp Glu Thr Ala Leu Met Ile Ala
    2795                2800                2805

Asp Val Asp Trp Ser Ser Phe Gly Ser Arg Phe Thr Ala Val Arg
    2810                2815                2820

Pro Ser Pro Leu Leu Gly Glu Leu Leu Gly Gly Ala Ala His Pro
    2825                2830                2835

Ala Pro Ala Val Gly Gly Phe Val Asp Arg Leu Arg Asp Leu Pro
    2840                2845                2850

Pro Ala Glu Arg Glu Arg Thr Val Leu Glu Leu Val Arg Gly Gln
    2855                2860                2865

Val Ala Val Val Leu Gly His Ala Thr Pro Gly Ala Ile Asp Thr
    2870                2875                2880

Ala Ala Thr Phe Gln Ser Ala Gly Phe Asp Ser Leu Thr Ala Ile
    2885                2890                2895

Glu Leu Arg Asn Arg Leu Met Ala Ala Thr Gly Val Gln Thr Pro
    2900                2905                2910

Ala Ser Val Val Phe Asp Tyr Pro Thr Pro Glu Leu Leu Ala Gly
    2915                2920                2925

His Leu Arg Glu Gln Leu Leu Gly Ala Gly Ser Ala Ala Leu Ser
    2930                2935                2940

Thr Thr Val Ala Thr Ala Pro Val Asp Asp Asp Pro Ile Ala Ile
    2945                2950                2955

Ile Gly Met Ser Cys Arg Phe Pro Gly Gly Val Asp Ser Pro Glu
    2960                2965                2970

Glu Leu Trp Arg Leu Leu Glu Ser Gly Thr Asp Ala Ile Ser Ala
    2975                2980                2985

Phe Pro Gln Asp Arg Gly Trp Asp Leu Val Gly Gly Val Asp Gly
    2990                2995                3000

Ala Ser Val Arg Ala Gly Gly Phe Leu Tyr Thr Ala Ala Glu Phe
    3005                3010                3015

Asp Pro Ala Phe Phe Gly Ile Ser Pro Arg Glu Ala Ile Ala Met
    3020                3025                3030

Asp Pro Gln Gln Arg Leu Leu Leu Glu Ala Ser Trp Glu Val Phe
    3035                3040                3045

Glu Arg Ala Gly Ile Ala Ala Asp Ala Leu Arg Asp Ser Pro Thr
    3050                3055                3060

Gly Val Phe Val Gly Thr Asn Gly Gln Asp Tyr Ala Ala Leu Val
    3065                3070                3075

Gly Asn Ala Pro Gln Arg Ala Asp Gly His Leu Ala Thr Gly Ser
    3080                3085                3090

Ala Ala Ser Val Ala Ser Gly Arg Leu Ser Tyr Thr Phe Gly Leu
    3095                3100                3105

Glu Gly Pro Ala Ile Thr Val Asp Thr Ala Cys Ser Ser Ser Leu
    3110                3115                3120

Val Ala Met His Leu Ala Ala Gln Ala Leu Arg Ser Gly Glu Cys
    3125                3130                3135

Arg Met Ala Leu Ala Gly Gly Ala Thr Val Met Ala Thr Pro Thr
    3140                3145                3150

Ala Phe Ala Glu Phe Ser Arg Gln Gly Ala Leu Ala Ala Asp Gly
    3155                3160                3165
```

-continued

```
Arg Cys  Lys Ala Phe Ala Ala  Gly Ala Asp Gly Thr  Gly Trp Gly
    3170                 3175                 3180

Glu Gly  Val Gly Ile Leu Leu  Leu Glu Arg Leu Ser  Asp Ala Glu
    3185                 3190                 3195

Arg Asn  Gly His Arg Val Leu  Ala Val Met Arg Gly  Ser Ala Val
    3200                 3205                 3210

Asn Gln  Asp Gly Ala Ser Asn  Gly Leu Thr Ala Pro  Asn Gly Pro
    3215                 3220                 3225

Ser Gln  Gln Arg Val Ile Arg  Gln Ala Leu Ala Asn  Ala Arg Leu
    3230                 3235                 3240

Ser Thr  Val Asp Val Asp Ala  Val Glu Ala His Gly  Thr Gly Thr
    3245                 3250                 3255

Thr Leu  Gly Asp Pro Ile Glu  Ala Gln Ala Leu Leu  Ala Thr Tyr
    3260                 3265                 3270

Gly Gln  Asp Arg Asp Pro Asp  Arg Pro Leu Leu Leu  Gly Ser Val
    3275                 3280                 3285

Lys Ser  Asn Ile Gly His Thr  Gln Ala Ala Ala Gly  Val Ala Gly
    3290                 3295                 3300

Val Ile  Lys Met Val Met Ala  Met Arg His Gly Val  Leu Pro Arg
    3305                 3310                 3315

Ser Leu  His Ile Asp Glu Pro  Thr Pro His Val Asp  Trp Thr Ala
    3320                 3325                 3330

Gly Arg  Ile Ala Leu Leu Thr  Glu Pro Ser Pro Trp  Pro Leu Thr
    3335                 3340                 3345

Gly Ala  Pro Arg Arg Ala Ala  Val Ser Ser Phe Gly  Val Ser Gly
    3350                 3355                 3360

Thr Asn  Ala His Val Ile Leu  Glu Gln Ala Ser Ala  Val Ala Glu
    3365                 3370                 3375

Pro Glu  Glu Thr Asp Thr Ala  Arg Thr Pro Glu Pro  Pro Ala Val
    3380                 3385                 3390

Pro Trp  Val Leu Ser Ala Arg  Ser Glu Ala Gly Leu  Arg Ala His
    3395                 3400                 3405

Ala Leu  Arg Leu Arg Ser Phe  Val Asn Ala Asp Ala  Asp Leu Arg
    3410                 3415                 3420

Pro Val  Asp Val Gly Trp Ser  Leu Ala Ser Ala Arg  Ser Val Leu
    3425                 3430                 3435

Ser His  Arg Ala Val Val Val  Gly Ala Asp Arg Asp  Glu Leu Leu
    3440                 3445                 3450

Arg Glu  Leu Glu Ala Val Ala  Ser Gly Ser Val Thr  Val Gly Glu
    3455                 3460                 3465

Ala Arg  Thr His Ser Gly Val  Val Phe Val Phe Pro  Gly Gln Gly
    3470                 3475                 3480

Ser Gln  Trp Val Gly Met Ala  Leu Glu Leu Leu Glu  His Ser Pro
    3485                 3490                 3495

Val Phe  Ala Gly Arg Met Arg  Asp Cys Ala Asp Ala  Leu Ala Pro
    3500                 3505                 3510

Phe Val  Glu Trp Ser Leu Phe  Asp Val Leu Gly Asp  Glu Val Ala
    3515                 3520                 3525

Leu Gly  Arg Val Asp Val Val  Gln Pro Val Leu Trp  Ala Val Met
    3530                 3535                 3540

Val Ser  Leu Ala Glu Leu Trp  Arg Ser Phe Gly Val  Val Pro Ser
    3545                 3550                 3555

Ala Val  Val Gly His Ser Gln  Gly Glu Ile Ala Ala  Ala Cys Val
```

-continued

```
    3560                3565                3570

Ala Gly  Gly Leu Ser Leu Glu  Asp Gly Ala Arg Val  Val Ala Leu
    3575                3580                3585

Arg Ser  Arg Ala Leu Leu Ala  Leu Ser Gly Arg Gly  Gly Met Val
    3590                3595                3600

Ser Val  Pro Val Ser Ala Asp  Arg Leu Arg Gly Arg  Val Gly Leu
    3605                3610                3615

Ser Val  Ala Ala Val Asn Gly  Pro Val Ser Thr Val  Val Ser Gly
    3620                3625                3630

Ala Val  Glu Val Leu Glu Gly  Val Leu Ala Glu Phe  Pro Glu Ala
    3635                3640                3645

Lys Arg  Ile Pro Val Asp Tyr  Ala Ser His Ser Val  Gln Val Glu
    3650                3655                3660

Gly Ile  Arg Glu Gly Leu Ala  Glu Ala Leu Ala Pro  Val Arg Pro
    3665                3670                3675

Arg Thr  Gly Glu Val Pro Phe  Tyr Ser Thr Val Thr  Gly Arg Leu
    3680                3685                3690

Met Asp  Thr Ile Glu Leu Asp  Gly Glu Tyr Trp Tyr  Arg Asn Leu
    3695                3700                3705

Arg Glu  Thr Val Glu Phe Gln  Ser Thr Val Glu Ala  Leu Ile Gly
    3710                3715                3720

Gln Gly  His Thr Val Phe Val  Glu Ala Ser Pro His  Pro Val Leu
    3725                3730                3735

Thr Val  Gly Val Gln Asp Thr  Ala Asp Thr Thr Asp  Thr Ala Thr
    3740                3745                3750

Asp Ile  Val Val Thr Gly Ser  Leu Arg Arg Asp Asp  Gly Gly Pro
    3755                3760                3765

Ala Arg  Phe Leu Thr Ala Leu  Ala Glu Leu Ser Val  Arg Gly Val
    3770                3775                3780

Ala Thr  Asp Trp Arg Gln Ala  Phe Glu Gly Thr Gly  Ala Arg His
    3785                3790                3795

Val Asp  Leu Pro Thr Tyr Pro  Phe Gln Arg Gln Arg  Phe Trp Ile
    3800                3805                3810

Glu Pro  Thr Ala Pro Asp Val  Ala Arg Glu Asp Ala  Arg Val Thr
    3815                3820                3825

Thr Ala  Asp Gly Glu Phe Trp  Ala Ala Val Glu Arg  Glu Asp Ala
    3830                3835                3840

Ala Ser  Leu Ala Thr Ala Leu  Glu Val Asp Asp Ala  Ser Leu Gly
    3845                3850                3855

Asn Leu  Leu Pro Ala Leu Ser  Ala Trp Arg Arg Arg  Arg His Glu
    3860                3865                3870

Trp Ser  Ala Leu Glu Ala Val  Arg Tyr Gln Val Asn  Trp Lys Arg
    3875                3880                3885

Leu Val  Asp Asp Arg Pro Ala  Met Leu Ser Gly Ala  Trp Leu Val
    3890                3895                3900

Val Val  Ser Gln Ala Asp Ala  Asp His Glu Trp Val  Ser Gly Val
    3905                3910                3915

Ser Glu  Thr Leu Ala Glu Tyr  Gly Ala Glu Pro Val  Val Cys Pro
    3920                3925                3930

Val Asp  Glu Arg His Leu Asp  Arg Ala Val Leu Ala  Asp Arg Leu
    3935                3940                3945

Ala Ser  Met Thr Gly Thr Ser  Ser Thr Thr Ser Thr  Ala Ser Ile
    3950                3955                3960
```

-continued

```
Ser Gly Val Val Ser Leu Val Ala Leu Asp Gln Arg Pro His Pro
    3965                3970                3975

Asp Phe Ala Ser Val Pro Ile Gly Phe Ala Met Thr Val Leu Leu
    3980                3985                3990

Thr Gln Ala Leu Gly Asp Thr Gly Val Glu Ala Pro Leu Trp Ser
    3995                4000                4005

Leu Thr Gln His Ala Val Ser Thr Gly Pro Ala Asp Thr Leu Leu
    4010                4015                4020

Ala Ser Ala Ser Ala Gln Ala Leu Val Trp Gly Val Gly Arg Val
    4025                4030                4035

Ile Ala Leu Glu Gln Pro Leu Arg Trp Gly Gly Leu Ile Asp Leu
    4040                4045                4050

Pro Thr Glu Val Asn Ala Arg Ala Arg Glu Arg Leu Ala Arg Val
    4055                4060                4065

Leu Ser Gly Val Ser Gly Glu Asp Gln Val Ala Ile Arg Thr Val
    4070                4075                4080

Gly Ala Phe Gly Arg Arg Leu Val His Ala Pro Ala Leu Arg Thr
    4085                4090                4095

Asp Leu Pro Ser Trp Gln Pro Ser Gly Thr Val Leu Val Thr Gly
    4100                4105                4110

Gly Thr Gly Ala Leu Gly Gly His Ile Ala Arg Trp Leu Ala His
    4115                4120                4125

Gln Gly Ala Glu His Leu Val Leu Thr Ser Arg Arg Gly Met Ala
    4130                4135                4140

Ala Pro Gly Ala Ser Ala Leu Val Ala Asp Leu Glu Ala Ala Gly
    4145                4150                4155

Ala Ala Val Thr Val Ala Val Cys Asp Val Ala Glu Arg Ala Gln
    4160                4165                4170

Leu Ala Asp Leu Val Ala Asp Val Gly Pro Leu Thr Ala Val Val
    4175                4180                4185

His Thr Ala Ala Leu Leu Asp Asp Ala Thr Val Glu Ser Leu Thr
    4190                4195                4200

Thr Glu Gln Leu His Arg Val Leu Arg Val Lys Val Asp Gly Ala
    4205                4210                4215

Thr His Leu His Glu Leu Thr Arg Asp Met Glu Leu Ser Ala Phe
    4220                4225                4230

Val Leu Phe Ser Ser Leu Ser Gly Thr Val Gly Thr Pro Gly Gln
    4235                4240                4245

Gly Asn Tyr Ala Pro Gly Asn Ala Phe Leu Asp Ala Leu Ala Glu
    4250                4255                4260

Tyr Arg Arg Thr Gln Gly Leu Val Ala Thr Ser Val Ala Trp Gly
    4265                4270                4275

Leu Trp Ala Gly Asp Gly Met Gly Glu Gly Glu Ala Gly Glu Val
    4280                4285                4290

Ala Arg Arg His Gly Val Pro Ala Leu Ser Pro Glu Leu Ala Val
    4295                4300                4305

Ala Ala Leu Arg Ala Ala Val Glu Gln Gly Asp Ala Val Val Thr
    4310                4315                4320

Val Ala Asp Ile Glu Trp Glu Arg His Tyr Ala Ala Phe Thr Ala
    4325                4330                4335

Thr Arg Pro Ser Pro Leu Leu Ala Asp Leu Pro Glu Val Arg Arg
    4340                4345                4350
```

-continued

```
Leu Ile Asp Ala Gly Ala Ala Ser Ala Val Glu Glu Thr Asp Arg
    4355                4360                4365

Asp Arg Ser Gly Leu Ser Gly Arg Leu Ala Gly Leu Asp Gly Ala
    4370                4375                4380

Glu Gln Arg Arg Leu Leu Leu Asp Leu Val Arg Arg Asn Val Ala
    4385                4390                4395

Val Val Leu Gly His Thr Asp Pro Glu Ala Val Ser Ser His Arg
    4400                4405                4410

Ala Phe Gln Glu Leu Gly Phe Asp Ser Val Thr Ala Val Glu Phe
    4415                4420                4425

Arg Asn Arg Leu Gly Ala Ala Thr Gly Leu Arg Leu Pro Ala Thr
    4430                4435                4440

Ala Val Phe Asp Tyr Pro Thr Pro Leu Ala Leu Ala Glu Tyr Ala
    4445                4450                4455

Leu Ser Glu Leu Leu Gly Thr Val Gly Glu Pro Leu Arg Val Glu
    4460                4465                4470

Ser Ser Gly Ser Pro Val Asp Asp Asp Pro Ile Val Ile Val Gly
    4475                4480                4485

Met Ser Cys Arg Phe Pro Gly Gly Val Ser Ser Pro Glu Asp Leu
    4490                4495                4500

Trp Asp Leu Leu Thr Glu Gly Gly Asp Ala Met Ser Ala Phe Pro
    4505                4510                4515

Gly Asp Arg Gly Trp Asp Leu Ala Gly Leu Phe His Ser Asp Pro
    4520                4525                4530

Gly His Pro Gly Thr Ser Tyr Thr Arg Thr Gly Gly Phe Leu His
    4535                4540                4545

Asp Ala Thr Ala Phe Asp Ala Asp Phe Phe Gly Ile Ser Pro Arg
    4550                4555                4560

Glu Ala Leu Ala Met Asp Pro Gln Gln Arg Leu Leu Leu Glu Ala
    4565                4570                4575

Ser Trp Glu Ala Phe Glu Arg Ala Gly Ile Asp Pro Arg Ser Leu
    4580                4585                4590

Arg Gly Ser Glu Thr Gly Val Phe Ala Gly Thr Asn Gly Gln Asp
    4595                4600                4605

Tyr Val Ser Leu Leu Gly Gly Asp Gln Pro Gln Glu Phe Glu Gly
    4610                4615                4620

Tyr Val Gly Thr Gly Asn Ser Ala Ser Val Met Ser Gly Arg Ile
    4625                4630                4635

Ala Tyr Val Leu Gly Leu Glu Gly Pro Ala Leu Thr Val Asp Thr
    4640                4645                4650

Ala Cys Ser Ser Ser Leu Val Ala Leu His Leu Ala Val Gln Ala
    4655                4660                4665

Leu Arg Ser Gly Glu Cys Ser Leu Ala Leu Ala Gly Gly Val Thr
    4670                4675                4680

Val Met Ala Thr Pro Gly Leu Phe Val Glu Phe Ser Arg Gln Arg
    4685                4690                4695

Gly Leu Ala Ala Asp Gly Arg Cys Lys Ala Phe Ala Gly Ala Ala
    4700                4705                4710

Asp Gly Thr Gly Phe Ser Glu Gly Val Gly Met Leu Val Val Glu
    4715                4720                4725

Arg Leu Ser Asp Ala Glu Arg Leu Gly His Arg Val Leu Ala Val
    4730                4735                4740

Val Arg Gly Ser Ala Val Asn Gln Asp Gly Ala Ser Asn Gly Leu
```

```
    4745                4750                4755

Thr Ala  Pro Asn Gly Pro Ser  Gln Gln Arg Val Ile  Arg Gln Ala
    4760                4765                4770

Leu Ala  Ser Ala Gly Leu Val  Ala Val Asp Val Asp  Ala Val Glu
    4775                4780                4785

Ala His  Gly Thr Gly Thr Ala  Leu Gly Asp Pro Ile  Glu Ala Gln
    4790                4795                4800

Ala Leu  Leu Ala Thr Tyr Gly  Gln Gly Arg Asp Val  Gly Arg Pro
    4805                4810                4815

Leu Trp  Leu Gly Ser Val Lys  Ser Asn Ile Gly His  Thr Gln Ala
    4820                4825                4830

Ala Ala  Gly Val Ala Gly Val  Ile Lys Met Val Met  Ala Leu Arg
    4835                4840                4845

His Gly  Val Leu Pro Gln Ser  Leu His Ile Asp Glu  Pro Thr Pro
    4850                4855                4860

His Val  Asp Trp Ser Thr Gly  Ala Val Glu Leu Leu  Gly Glu His
    4865                4870                4875

Thr Gly  Trp Pro Glu Val Asp  Arg Pro Arg Arg Ala  Gly Val Ser
    4880                4885                4890

Ala Phe  Gly Val Ser Gly Thr  Asn Ala His Val Ile  Val Glu Gln
    4895                4900                4905

Ala Pro  Glu Val Val Glu Pro  Glu Ala Glu Gly Val  Val Leu Pro
    4910                4915                4920

Ala Val  Pro Trp Val Val Ser  Gly Val Gly Glu Val  Ala Val Arg
    4925                4930                4935

Ala Gln  Val Glu Arg Leu Arg  Ala Phe Ala Asp Arg  Asn Pro Gly
    4940                4945                4950

Leu Asp  Pro Val Asp Val Gly  Trp Ser Leu Ala Thr  Gly Arg Ala
    4955                4960                4965

Gly Leu  Ser His Arg Ala Val  Val Val Gly Ala Asp  Arg Gly Glu
    4970                4975                4980

Leu Leu  Gly Ala Leu Glu Gly  Val Pro Val Val Gly  Val Pro Val
    4985                4990                4995

Val Gly  Gly Leu Gly Val Leu  Phe Ala Gly Gln Gly  Ser Gln Arg
    5000                5005                5010

Leu Gly  Met Gly Arg Gly Leu  Tyr Glu Gly Tyr Pro  Val Phe Ala
    5015                5020                5025

Ala Val  Trp Asp Glu Val Cys  Ala Gln Leu Asp Gln  His Leu Asp
    5030                5035                5040

Arg Pro  Val Gly Glu Val Val  Trp Gly Asp Asp Ala  Glu Leu Ile
    5045                5050                5055

Gly Glu  Thr Val Tyr Ala Gln  Ala Gly Leu Phe Ala  Leu Glu Val
    5060                5065                5070

Ala Leu  Tyr Arg Leu Ile Ala  Ser Trp Gly Val Arg  Gly Asp Tyr
    5075                5080                5085

Leu Leu  Gly His Ser Ile Gly  Glu Leu Ala Ala Ala  Tyr Val Ala
    5090                5095                5100

Gly Val  Trp Ser Leu Glu Asp  Ala Ala Arg Val Val  Val Ala Arg
    5105                5110                5115

Gly Arg  Leu Met Gln Ala Leu  Pro Ser Gly Gly Ala  Met Val Ala
    5120                5125                5130

Val Ala  Val Ser Glu Gly Val  Val Arg Pro Leu Leu  Gly Glu Gly
    5135                5140                5145
```

```
Val Val  Val Ala Ala Val Asn  Gly Pro Glu Ser Val  Val Leu Ser
    5150                 5155                 5160

Gly Asp  Glu Asp Ala Val Gln  Val Val Val Asp Val  Leu Ala Gly
    5165                 5170                 5175

Arg Gly  Val Arg Thr Arg Arg  Leu Arg Val Ser His  Ala Phe His
    5180                 5185                 5190

Ser Ala  Arg Met Asp Gly Met  Leu Ala Glu Phe Gly  Glu Val Leu
    5195                 5200                 5205

Gly Gly  Val Glu Phe Arg Ala  Pro Ser Val Pro Val  Val Ser Asn
    5210                 5215                 5220

Val Ser  Gly Ala Val Ala Gly  Glu Glu Leu Cys Ser  Pro Glu Tyr
    5225                 5230                 5235

Trp Val  Arg His Val Arg Glu  Thr Val Arg Phe Ala  Asp Gly Leu
    5240                 5245                 5250

Glu Thr  Leu Arg Glu Leu Gly  Val Gly Ser Phe Leu  Glu Leu Gly
    5255                 5260                 5265

Pro Asp  Gly Thr Leu Thr Ala  Leu Ala Asp Gly Asp  Gly Val Pro
    5270                 5275                 5280

Val Leu  Arg Arg Asp Arg Pro  Glu Pro Leu Thr Ala  Met Ala Ala
    5285                 5290                 5295

Leu Gly  Gly Leu Tyr Val Arg  Gly Val Gln Ile Asp  Trp Gly Ala
    5300                 5305                 5310

Val Phe  Pro Gly Ala Arg Arg  Val Asp Leu Pro Thr  Tyr Ala Phe
    5315                 5320                 5325

Gln Arg  Glu Arg Phe Trp Leu  Glu Pro Ser Ala Glu  Gln Pro Ala
    5330                 5335                 5340

Thr Ser  Val Val Asp Ala Ala  Phe Trp Asp Ala Val  Glu Arg Gly
    5345                 5350                 5355

Asp Ala  Glu Ala Leu Gly Gly  Asp Ala Glu Gln Ser  Leu Ser Ala
    5360                 5365                 5370

Ala Leu  Pro Ala Leu Ala Ser  Trp Arg Arg Ala Gln  Gln Glu Glu
    5375                 5380                 5385

Ser Val  Ile Asp Gly Trp Arg  Tyr Arg Leu Gly Trp  Thr Pro Ile
    5390                 5395                 5400

Pro Val  Val Leu Gly Glu Pro  Cys Leu Thr Gly Thr  Trp Arg Val
    5405                 5410                 5415

Val Val  Glu Pro Gly Ala Asp  Gly Thr Asp Val Ala  Ala Ala Leu
    5420                 5425                 5430

Arg Ser  Ala Gly Ala Asp Ala  Glu Val Val Thr Ser  Ala Glu Leu
    5435                 5440                 5445

Ser Ala  Gly Pro Val Ala Gly  Val Val Ser Leu Leu  Ser Val Glu
    5450                 5455                 5460

Ala Thr  Val Ala Leu Val Gln  Ala Leu Gly Thr Val  Gly Ile Asp
    5465                 5470                 5475

Ala Pro  Leu Trp Cys Val Thr  Arg Gly Ala Val Ser  Val Val Asp
    5480                 5485                 5490

Gly Asp  Val Val Glu Pro Tyr  Ala Ser Ala Val Trp  Gly Leu Gly
    5495                 5500                 5505

Arg Val  Ile Gly Leu Glu His  Pro Asp Arg Trp Gly  Gly Leu Ile
    5510                 5515                 5520

Asp Leu  Pro Thr Glu Ala Asp  Ala Arg Val Gly Ala  Leu Leu Ala
    5525                 5530                 5535
```

-continued

```
Gly Val  Leu Ala Gly Arg Thr  Gly Glu Asp Gln Val  Ala Ile Arg
    5540                 5545                 5550

Ala Ala  Gly Ala Trp Gly Ala  Arg Leu Ser Arg Ala  Thr Pro Ile
    5555                 5560                 5565

Ala Asp  Thr Ser Gly Gly Trp  Arg Gly Arg Gly Ala  Ala Leu Ile
    5570                 5575                 5580

Thr Gly  Gly Thr Gly Ala Leu  Gly Gly His Val Ala  Arg Trp Leu
    5585                 5590                 5595

Ala Gly  Thr Gly Val Glu Arg  Ile Val Leu Thr Ser  Arg Arg Gly
    5600                 5605                 5610

Ile Glu  Thr Pro Gly Ala Ala  Glu Leu Val Thr Glu  Leu Glu Glu
    5615                 5620                 5625

Phe Gly  Val Gln Val Thr Val  Val Ala Cys Asp Val  Ala Asp Arg
    5630                 5635                 5640

Glu Ala  Val Ala Thr Leu Leu  Val Thr Ile Pro Asp  Leu Arg Val
    5645                 5650                 5655

Val Val  His Ala Ala Gly Val  Pro Ser Trp Ser Ala  Val Asp Ser
    5660                 5665                 5670

Leu Thr  Pro Glu Glu Phe Glu  Glu Ser Ala Arg Ser  Lys Val Ala
    5675                 5680                 5685

Gly Ala  Ala Asn Leu Asp Ala  Leu Leu Ala Asp Ala  Glu Leu Asp
    5690                 5695                 5700

Ala Phe  Val Leu Phe Ser Ser  Val Ala Gly Val Trp  Gly Ser Gly
    5705                 5710                 5715

Ser Gln  Ser Ala Tyr Ala Ala  Ala Asn Ala Phe Leu  Asp Gly Leu
    5720                 5725                 5730

Ala Trp  Arg Arg Arg Gly Val  Gly Leu Val Ala Thr  Ser Val Ala
    5735                 5740                 5745

Trp Gly  Met Trp Gly Gly Gly  Gly Met Ala Val Gly  Gly Glu Glu
    5750                 5755                 5760

Phe Leu  Val Glu Arg Gly Val  Ser Gly Met Ala Pro  Gly Leu Ala
    5765                 5770                 5775

Val Ala  Ala Leu Arg Arg Ala  Leu Cys Asp Gly Glu  Thr Ala Leu
    5780                 5785                 5790

Val Val  Ala Asp Val Asp Trp  Glu Arg Phe Gly Pro  Arg Phe Thr
    5795                 5800                 5805

Ala Leu  Arg Pro Ser Pro Leu  Leu Ser Glu Leu Ile  Pro Asp Thr
    5810                 5815                 5820

Ser Glu  Pro Leu Ala Ser Thr  Val Gly Glu Phe Ala  Val Glu Leu
    5825                 5830                 5835

Arg Gly  Leu Ser Arg Glu Asp  Arg Asp Arg Ala Val  Val Glu Leu
    5840                 5845                 5850

Val Arg  Thr His Ala Ala Glu  Val Leu Gly His Gln  Asn Pro Ser
    5855                 5860                 5865

Ala Ile  Asp Leu Asp Arg Thr  Phe Gln Glu Leu Gly  Phe Asp Ser
    5870                 5875                 5880

Leu Thr  Ala Val Glu Leu Arg  Asp Arg Leu Gly Thr  Ala Thr Gln
    5885                 5890                 5895

Leu Arg  Phe Pro Ala Ser Val  Ile Phe Asp Tyr Pro  Thr Pro Ala
    5900                 5905                 5910

Ala Leu  Ala Glu His Val Cys  Gly Ala Ala Leu Gly  Leu Ala Glu
    5915                 5920                 5925

Glu Ile  Gln Val Ala His Thr  Pro Ser Ala Val Ala  Asp Asp Pro
```

```
    5930                5935                5940

Ile Val  Ile Ile Gly Met Ser  Cys Arg Phe Pro Gly  Gly Val Asp
    5945                5950                5955

Ser Pro  Glu Ala Leu Trp Arg  Leu Val Ser Ala Gly  Gly Asp Ala
    5960                5965                5970

Val Ser  Ser Phe Pro Ser Asp  Arg Gly Trp Asp Leu  Ala Gly Val
    5975                5980                5985

Tyr Asp  Ala Asp Ala Thr Arg  Ser Gly Arg Ser Tyr  Val Arg Thr
    5990                5995                6000

Gly Gly  Phe Leu His Asp Ala  Ala Glu Phe Asp Ala  Gly Phe Phe
    6005                6010                6015

Gly Ile  Ser Pro Arg Glu Ala  Thr Ala Met Asp Pro  Gln Gln Arg
    6020                6025                6030

Leu Leu  Leu Glu Ala Ser Trp  Glu Ala Phe Glu Arg  Ala Gly Ile
    6035                6040                6045

Pro Ala  Ser Thr Leu Lys Gly  Ser Gln Thr Gly Val  Phe Val Gly
    6050                6055                6060

Ala Ser  Ala Gln Gly Tyr Gly  Gly Gly Asp Gly Gln  Ala Pro Glu
    6065                6070                6075

Gly Ser  Glu Gly Tyr Leu Leu  Thr Gly Asn Ala Gly  Ser Val Val
    6080                6085                6090

Ser Gly  Arg Val Ala Tyr Thr  Phe Gly Leu Glu Gly  Pro Ala Val
    6095                6100                6105

Thr Val  Asp Thr Ala Cys Ser  Ser Ser Leu Val Ala  Leu His Trp
    6110                6115                6120

Ala Val  Arg Ala Leu Arg Ser  Gly Glu Cys Ser Leu  Ala Leu Ala
    6125                6130                6135

Gly Gly  Val Thr Val Met Ala  Thr Pro Ala Thr Phe  Val Glu Phe
    6140                6145                6150

Ser Arg  Gln Arg Gly Leu Ala  Ala Asp Gly Arg Cys  Lys Ser Phe
    6155                6160                6165

Ala Ala  Gly Ala Asp Gly Thr  Gly Trp Ser Glu Gly  Val Gly Leu
    6170                6175                6180

Leu Leu  Val Glu Arg Leu Ser  Asp Ala Glu Arg Asn  Gly His Pro
    6185                6190                6195

Val Leu  Ala Val Val Ser Gly  Ser Ala Val Asn Gln  Asp Gly Ala
    6200                6205                6210

Ser Asn  Gly Leu Thr Ala Pro  Asn Gly Pro Ser Gln  Gln Arg Val
    6215                6220                6225

Ile Arg  Gln Ala Leu Ala Asn  Ala Gly Leu Val Ala  Ser Asp Val
    6230                6235                6240

Asp Ala  Val Glu Ala His Gly  Thr Gly Thr Thr Leu  Gly Asp Pro
    6245                6250                6255

Ile Glu  Ala Gln Ala Leu Leu  Ala Thr Tyr Gly Gln  Gly Arg Asp
    6260                6265                6270

Ala Gly  Arg Pro Leu Trp Leu  Gly Ser Val Lys Ser  Asn Ile Gly
    6275                6280                6285

His Thr  Gln Ala Ala Ala Gly  Val Ala Gly Val Ile  Lys Met Val
    6290                6295                6300

Met Ala  Met Arg His Gly Val  Leu Pro Arg Thr Leu  His Val Asp
    6305                6310                6315

Glu Pro  Ser Pro His Val Asp  Trp Ser Ala Gly Ala  Val Glu Leu
    6320                6325                6330
```

Leu Thr Gly Gln Val Ala Trp Pro Glu Val Asp Arg Pro Arg Arg
6335 6340 6345

Ala Gly Val Ser Ala Phe Gly Val Ser Gly Thr Asn Ala His Val
6350 6355 6360

Ile Val Glu Gln Ala Pro Glu Val Val Glu Pro Glu Ala Glu Gly
6365 6370 6375

Val Val Leu Pro Ala Val Pro Trp Val Val Ser Gly Val Gly Glu
6380 6385 6390

Val Ala Val Arg Ala Gln Val Glu Arg Leu Arg Ala Phe Ala Asp
6395 6400 6405

Arg Asn Pro Gly Leu Asp Pro Val Asp Val Gly Trp Ser Leu Val
6410 6415 6420

Ala Thr Arg Ser Gly Leu Ser His Arg Ala Val Val Val Val Ala
6425 6430 6435

Asp Gly Glu Glu Leu Leu Gly Ala Leu Glu Gly Val Pro Val Val
6440 6445 6450

Gly Gly Leu Gly Val Leu Phe Ala Gly Gln Gly Ser Gln Arg Leu
6455 6460 6465

Gly Met Gly Arg Gly Leu Tyr Glu Gly Tyr Pro Val Phe Ala Ala
6470 6475 6480

Ala Trp Asp Glu Val Cys Ala Gln Leu Asp Gln His Leu Asp Arg
6485 6490 6495

Pro Val Gly Glu Val Val Trp Gly Asp Asp Ala Glu Leu Ile Gly
6500 6505 6510

Glu Thr Val Tyr Ala Gln Ala Gly Leu Phe Ala Leu Glu Val Ala
6515 6520 6525

Leu Tyr Arg Leu Val Ala Ser Trp Gly Val Arg Ala Asp Tyr Leu
6530 6535 6540

Leu Gly His Ser Ile Gly Glu Leu Ala Ala Ala Tyr Val Ala Gly
6545 6550 6555

Val Trp Ser Leu Glu Asp Ala Ala Arg Val Val Ala Ala Arg Gly
6560 6565 6570

Arg Leu Met Gln Ala Leu Pro Ser Gly Gly Ala Met Val Ala Val
6575 6580 6585

Ala Ala Ser Glu Gly Glu Val Arg Pro Leu Leu Gly Glu Gly Val
6590 6595 6600

Val Val Ala Ala Val Asn Gly Pro Glu Ser Val Val Val Ser Gly
6605 6610 6615

Asp Glu Asp Ala Val His Ala Ile Glu Glu Thr Phe Ala Met Gly
6620 6625 6630

Gly Val Arg Thr Arg Arg Leu Arg Val Ser His Ala Phe His Ser
6635 6640 6645

Ala Arg Met Asp Gly Met Leu Ala Glu Phe Gly Glu Val Leu Arg
6650 6655 6660

Gly Val Glu Phe Arg Ala Pro Ser Val Pro Val Val Ser Asn Val
6665 6670 6675

Ser Gly Ala Val Ala Gly Glu Glu Leu Cys Ser Pro Glu Tyr Trp
6680 6685 6690

Val Arg His Val Arg Glu Thr Val Arg Phe Ala Asp Gly Leu Asp
6695 6700 6705

Thr Leu Arg Glu Leu Gly Val Gly Ser Phe Leu Glu Leu Gly Pro
6710 6715 6720

-continued

```
Asp Gly  Thr Leu Thr Ala Leu  Ala Asp Gly Asp Gly  Val Pro Val
    6725                 6730                 6735

Leu Arg  Arg Asp Arg Pro Glu  Pro Leu Thr Ala Met  Ala Ala Leu
    6740                 6745                 6750

Gly Gly  Leu Tyr Val Arg Gly  Val Glu Val Asp Trp  Asp Ala Val
    6755                 6760                 6765

Phe Pro  Gly Gly Arg Arg Val  Asp Leu Pro Thr Tyr  Ala Phe Gln
    6770                 6775                 6780

Arg Gln  Arg Phe Trp Leu Glu  Ser Ala Ser Asp Gln  Pro Ala Thr
    6785                 6790                 6795

Ser Ala  Val Asp Ala Ala Phe  Trp Asp Ala Val Glu  Arg Gly Asp
    6800                 6805                 6810

Ala Arg  Ala Leu Gly Ile Asp  Glu Glu Gln Pro Leu  Ser Ala Val
    6815                 6820                 6825

Leu Pro  Ala Leu Ser Ser Trp  Arg Arg Ala Arg Gln  Glu Gln Ser
    6830                 6835                 6840

Val Ile  Asp Gly Trp Arg Tyr  Arg Leu Gly Trp Met  Pro Ile Pro
    6845                 6850                 6855

Ala Val  Leu Gly Glu Val Gly  Leu Ile Gly Thr Trp  Leu Val Val
    6860                 6865                 6870

Val Glu  Pro Gly Val Asp Gly  Thr Asp Val Ala Ala  Val Leu Arg
    6875                 6880                 6885

Ser Ala  Gly Ala Gly Val Glu  Val Val Thr Ser Ala  Glu Leu Ser
    6890                 6895                 6900

Ala Gly  Pro Val Ala Gly Val  Val Ser Leu Val Ser  Val Glu Ala
    6905                 6910                 6915

Thr Val  Ser Leu Leu Gln Val  Leu Val Ala Ala Gly  Val Asp Ala
    6920                 6925                 6930

Pro Leu  Trp Cys Val Thr Arg  Gly Ala Val Ser Val  Val Asp Gly
    6935                 6940                 6945

Asp Leu  Val Asp Pro Gly Gln  Ala Gly Ile Trp Gly  Leu Gly Arg
    6950                 6955                 6960

Val Ile  Gly Leu Glu Cys Pro  Asp Arg Trp Gly Gly  Leu Ile Asp
    6965                 6970                 6975

Leu Pro  Gly Glu Leu Asp Asp  Arg Ala Gly Asn Ala  Leu Val Gly
    6980                 6985                 6990

Ile Leu  Ala Gly Gly Thr Gly  Glu Asp Gln Val Ala  Ile Arg Val
    6995                 7000                 7005

Thr Gly  Ile Trp Gly Ala Arg  Leu Val Arg Ala Thr  Pro Val Pro
    7010                 7015                 7020

Ile Gly  Asp Ala Gly Gly Glu  Ala Ala Ala Ala Trp  Arg Gly Arg
    7025                 7030                 7035

Gly Thr  Ala Leu Val Thr Gly  Gly Thr Gly Ala Leu  Gly Arg Gln
    7040                 7045                 7050

Val Ala  Arg Trp Leu Val Gly  Ser Gly Leu Glu Arg  Val Val Leu
    7055                 7060                 7065

Thr Ser  Arg Arg Gly Val Glu  Ala Pro Gly Ala Val  Glu Leu Val
    7070                 7075                 7080

Ala Glu  Leu Gly Ser Arg Val  Arg Val Val Ala Cys  Asp Val Gly
    7085                 7090                 7095

Asp Arg  Glu Glu Leu Ala Ala  Leu Leu Val Thr Leu  Pro Asp Val
    7100                 7105                 7110

Arg Thr  Ile Val His Ala Ala  Gly Val Leu Asp Asp  Gly Val Leu
```

-continued

```
    7115                7120                7125

Glu Ser  Leu Thr Pro Glu Arg  Ile Arg Glu Val Met  Arg Ala Lys
    7130                7135                7140

Ala Asp  Gly Ala Arg His Leu  His Glu Leu Thr Arg  Asp Ile Asp
    7145                7150                7155

Leu Asp  Ala Phe Val Leu Phe  Ser Ser Ala Ala Gly  Thr Val Gly
    7160                7165                7170

Asn Ala  Gly Gln Gly Ser Tyr  Ala Ala Ala Asn Ala  Val Leu Asp
    7175                7180                7185

Gly Leu  Ala Trp Arg Arg Arg  Ala Glu Gly Leu Val  Ala Thr Ser
    7190                7195                7200

Val Ala  Trp Gly Ala Trp Ala  Glu Ser Gly Met Ala  Ala Glu Met
    7205                7210                7215

Ala Arg  Ser Gln Gly Met Asp  Pro Arg Ser Ala Leu  Ala Ala Leu
    7220                7225                7230

Gly Leu  Val Leu Ala Ala Asp  Glu Thr Thr Val Met  Val Ala Asp
    7235                7240                7245

Ile Asp  Trp Ala Thr Phe Gly  Ala Arg Phe Thr Ala  Ser Arg Pro
    7250                7255                7260

Ser Pro  Leu Leu Ser Glu Leu  Leu Gly Asp Gly Ser  Val Ser Thr
    7265                7270                7275

Glu Ala  Ala Asp Gly Glu Pro  Ala Asp Ala Phe Ala  Thr Arg Leu
    7280                7285                7290

Glu Ala  Met Ala Glu Arg Glu  Arg Ala Ala Thr Val  Leu Asp Leu
    7295                7300                7305

Val Arg  Thr His Val Ala Ala  Val Leu Gly His Thr  Ala Ser Glu
    7310                7315                7320

Ala Ile  Asp Pro Ala Arg Pro  Phe Gln Glu Ile Gly  Phe Asp Ser
    7325                7330                7335

Leu Thr  Ala Val Glu Leu Arg  Asn Arg Leu Thr Ala  Ala Thr Gly
    7340                7345                7350

Val Arg  Phe Pro Ala Ser Val  Ile Tyr Asp Tyr Pro  Thr Pro Ala
    7355                7360                7365

Ala Leu  Ala Glu His Val Cys  Arg Glu Ala Leu Gly  Pro Gly Gly
    7370                7375                7380

Arg Thr  Pro Ala Pro Val Val  Pro Arg Pro Val Asp  Asp Glu Pro
    7385                7390                7395

Ile Ala  Ile Ile Gly Met Ser  Cys Arg Phe Pro Gly  Gly Val Ser
    7400                7405                7410

Ser Pro  Glu Asp Leu Trp Gly  Leu Leu Ala Glu Gly  Arg Asp Ala
    7415                7420                7425

Val Ser  Asp Phe Pro Ala Asp  Arg Gly Trp Asn Leu  Ala Glu Leu
    7430                7435                7440

Tyr Asp  Pro Asp Pro Asp His  Pro Gly Ser Ser Tyr  Val Arg Ala
    7445                7450                7455

Gly Gly  Phe Leu Asp Asp Ala  Ala Ala Phe Asp Pro  Gly Phe Phe
    7460                7465                7470

Gly Ile  Ser Pro Arg Glu Ala  Leu Ala Met Asp Pro  Gln Gln Arg
    7475                7480                7485

Leu Leu  Leu Glu Val Ala Trp  Glu Ala Phe Glu Arg  Ala His Met
    7490                7495                7500

Ser Pro  Ala Thr Leu Lys Gly  Ser Arg Thr Gly Val  Phe Val Gly
    7505                7510                7515
```

-continued

```
Thr Asn Gly Gln Asp Tyr Ala Ala Leu Ala Ser Gly Ala Pro Arg
    7520                7525                7530

Ser Ala Glu Gly Tyr Leu Gly Thr Gly Ser Ala Ala Ser Val Ala
    7535                7540                7545

Ser Gly Arg Leu Ala Tyr Thr Phe Gly Leu Glu Gly Pro Ala Val
    7550                7555                7560

Thr Val Asp Thr Ala Cys Ser Ser Ser Leu Val Ala Leu His Leu
    7565                7570                7575

Ala Ala Gln Ala Leu Arg Ser Gly Glu Cys Ser Leu Ala Leu Ala
    7580                7585                7590

Gly Gly Ala Thr Val Met Ala Thr Pro Ala Ala Phe Leu Glu Phe
    7595                7600                7605

Ser Arg Gln Arg Ala Leu Ala Ala Asp Gly Arg Cys Lys Ala Phe
    7610                7615                7620

Ala Ala Ala Ala Asp Gly Thr Gly Trp Gly Glu Gly Val Gly Met
    7625                7630                7635

Leu Leu Val Glu Arg Leu Ser Asp Ala Glu Arg Asn Gly His Arg
    7640                7645                7650

Val Leu Ala Val Met Arg Gly Ser Ala Val Asn Gln Asp Gly Ala
    7655                7660                7665

Ser Asn Gly Leu Thr Ala Pro Asn Gly Pro Ser Gln Gln Arg Val
    7670                7675                7680

Ile Arg Gln Ala Leu Ala Asn Ala Arg Leu Ser Ala Thr Asp Ile
    7685                7690                7695

Asp Val Val Glu Ala His Gly Thr Gly Thr Ser Leu Gly Asp Pro
    7700                7705                7710

Ile Glu Ala Gln Ala Leu Leu Ala Thr Tyr Gly Gln Gly Arg Ser
    7715                7720                7725

Gln Asn Lys Pro Leu Trp Leu Gly Ser Val Lys Ser Asn Ile Gly
    7730                7735                7740

His Thr Gln Ala Ala Ala Gly Val Ala Gly Val Ile Lys Met Val
    7745                7750                7755

Met Ala Met Arg His Gly Val Leu Pro Arg Thr Leu His Val Asp
    7760                7765                7770

Ser Pro Ser Pro His Val Asp Trp Ala Ala Ala Arg Val Glu Leu
    7775                7780                7785

Leu Val Glu Ala Arg Glu Trp Pro Arg Thr Gly Ala Pro Arg Arg
    7790                7795                7800

Ala Gly Val Ser Ser Phe Gly Val Ser Gly Thr Asn Ala His Val
    7805                7810                7815

Ile Val Glu Gln Gly Pro Val Val Ala Arg Pro Asp Arg Glu Ser
    7820                7825                7830

Ala Arg Glu Pro Ser Pro Ser Val Pro Trp Val Leu Ser Gly Ala
    7835                7840                7845

Gly Gly Gly Arg Ala Glu Gly Pro Gly Arg Ala Pro Gly Val Leu
    7850                7855                7860

His Arg Arg Pro Ser Gly Pro Gly Ser Arg Arg Cys Arg Val Asp
    7865                7870                7875

Ala Gly Gly Arg Pro Phe Val Ser Val Ala Pro Arg Arg Ser Gly
    7880                7885                7890

Gly Cys Arg Pro Arg Gly Ala Ser Thr Trp Thr Gly Arg Ser Leu
    7895                7900                7905
```

-continued

```
Asp Arg  Trp Arg Arg Pro Val  Arg Pro Gln Gly Gly  Val Arg Leu
    7910                 7915                 7920

Pro Arg  Pro Gly Val Ala Val  Gly Arg Asn Gly Val  Gly Thr Val
    7925                 7930                 7935

Gly Ala  Phe Ala Gly Val Arg  Gly Ala Asp Ala Cys  Met Arg Arg
    7940                 7945                 7950

Cys Ala  His Pro Val Arg Arg  Val Val Ala Val Arg  Cys Ala Gly
    7955                 7960                 7965


<210> SEQ ID NO 50
<211> LENGTH: 3073
<212> TYPE: PRT
<213> ORGANISM: Streptomyces sp.

<400> SEQUENCE: 50

Val Leu Ala Pro Val Arg Pro Arg Gly Gly Gln Ile Ala Phe His Ser
1               5                   10                  15

Thr Val Thr Gly Arg Leu Thr Asp Thr Ser Glu Leu Asp Ala Asp Tyr
            20                  25                  30

Trp Tyr Arg Asn Leu Arg His Thr Val Glu Phe Gln Ser Thr Val Glu
        35                  40                  45

Ala Leu Met Asn Gln Gly His Thr Val Phe Val Glu Val Ser Pro His
    50                  55                  60

Pro Val Leu Thr Ile Gly Ile Gln Asp Thr Ala Glu Thr Pro Gly Thr
65                  70                  75                  80

Pro Asp Thr Pro Gly Thr Pro Asp Thr Ala Asp Ala Thr Asp Ala His
                85                  90                  95

Glu Ala Thr Gly Ala Pro Asp Val Ala Asn Thr Ala Asp Val Thr Gly
            100                 105                 110

Ala Pro Asp Val Thr Gly Ala Asp Ile Val Ile Thr Gly Ser Leu Arg
        115                 120                 125

Arg Asp Asp Gly Gly Pro Ala Arg Phe Leu Thr Ala Leu Gly Asp Leu
    130                 135                 140

His Thr Arg Gly Val Asp Val Asp Trp Ser Pro Val Phe Thr Gly Ala
145                 150                 155                 160

Arg Thr Val Asp Leu Pro Thr Tyr Ala Phe Gln Arg Glu Arg Phe Trp
                165                 170                 175

Leu Lys Pro Ala Arg Ala Val Thr Gln Ala Ser Gly Leu Gly Leu Gly
            180                 185                 190

Asp Ile Glu His Pro Leu Leu Gly Ala Val Leu Pro Leu Pro Gly Asp
        195                 200                 205

Glu Gly Gly Val Leu Thr Gly Leu Leu Ser Leu Asp Gly Gln Pro Trp
    210                 215                 220

Leu Ala His His Met Val Arg Asp Thr Val Val Phe Pro Gly Thr Gly
225                 230                 235                 240

Phe Val Glu Leu Ala Leu Gln Ala Gly Gln His Phe Gly His Ser Val
                245                 250                 255

Ile Glu Glu Leu Thr Leu His Ala Pro Leu Val Val Pro Asp Gln Gly
            260                 265                 270

Gly Val Gln Val Gln Val Ala Val Ser Ala Ala Asp Glu Arg Gly Arg
        275                 280                 285

Arg Pro Val Thr Val His Ser Cys Arg Ala Gly Glu Trp Leu Leu His
    290                 295                 300

Ala Ser Gly Thr Leu Gly Ala Thr Gly Gly Leu Asp Val Thr Glu Pro
305                 310                 315                 320
```

```
Arg Pro Ala Asp Val Ala Arg Pro Leu Glu Val Trp Pro Pro Glu Gly
                325                 330                 335

Ala Arg Ser Leu Asp Val Ser Gly Met Tyr Glu Ala Met Ala Glu Arg
            340                 345                 350

Gly Tyr Gly Tyr Gly Pro Ala Phe Gln Gly Leu Arg Ala Ala Trp Thr
        355                 360                 365

Arg Asp Asp Glu Ile Tyr Ala Glu Val Ala Leu Glu Pro Glu Ala Gln
    370                 375                 380

Asp Val Ala Ala Arg Cys Gly Ala His Pro Ala Leu Leu Asp Ala Ala
385                 390                 395                 400

Leu His Gly Val Gly Leu Gly Arg Phe Leu Thr Asp Pro Gly Gln Ala
                405                 410                 415

Tyr Leu Pro Phe Ser Trp Ser Gly Val Ala Leu His Ala Val Gly Ala
            420                 425                 430

Ser Ala Ile Arg Val Val Leu Ser Pro Ala Gly Thr Asp Ala Val Ser
        435                 440                 445

Leu Glu Val Thr Asp Pro Thr Gly Ala Pro Val Leu Ser Val Ala Ser
    450                 455                 460

Leu Ser Leu Arg Pro Leu Ser Ser Gly Arg Ile Ala Asp Thr Arg Gly
465                 470                 475                 480

Val Asp Gln Asp Ser Leu Tyr Arg Val Asp Trp Val Glu Met Pro Leu
                485                 490                 495

Pro Thr Ala Pro Ala Gly Ser Ala Pro Ala Glu Tyr Asp Ala Pro Ala
            500                 505                 510

Met Phe Asp Ala Leu Val Phe Asp Ala Pro Val Glu Tyr Asp Val Leu
        515                 520                 525

Ala Ser Asp Ala Ser Asp Ala Ser Asp Ala Ser Asp Ala Pro Gly Thr
    530                 535                 540

Pro Asp Ala Ser Ser Ala Pro Val Pro Asp Met Pro Asp Met Val Val
545                 550                 555                 560

Leu Pro Cys Glu Ser Ala Gly Asp Ala Val Ser Thr Val Val Cys Arg
                565                 570                 575

Ala Leu Ala Ala Val Arg Arg Trp Leu Ala Asp Glu Arg Cys Ala Arg
            580                 585                 590

Ser Arg Leu Ala Val Leu Thr Arg Gly Ala Met Ala Thr Ala Pro Gly
        595                 600                 605

Glu Ser Val Glu Asp Leu Gly Ala Ala Ala Val Trp Gly Leu Leu Arg
    610                 615                 620

Ser Ala Gln Ala Glu His Pro Asp Arg Phe Val Leu Val Asp His Asp
625                 630                 635                 640

Gly His Gln Asp Ser Arg Ala Val Leu Ala Ala Ala Leu Ala Ala Ala
                645                 650                 655

Val Asp Gly Gly His Ala His Leu Ala Leu Arg Arg Gly Arg Val Leu
            660                 665                 670

Thr Pro Gln Leu Ala Pro Leu Thr Pro Ser Ala Thr Ala Leu Ser Thr
        675                 680                 685

Thr Ala Pro Pro Ala Ala Thr Pro Thr Pro Glu Ala Gly Ala Pro Trp
    690                 695                 700

Arg Met Asp Val Thr Ser Gln Gly Thr Leu Glu Asn Leu Ala Ala Val
705                 710                 715                 720

Pro Cys Pro Glu Ala Ala Gly Val Leu Gly Ala Gly Gln Val Arg Val
                725                 730                 735
```

-continued

```
Ala Met His Ala Ala Gly Val Asn Phe Arg Asp Val Val Val Ala Leu
            740                 745                 750

Gly Met Ile Pro Gly Gln Asp Val Ile Gly Ser Glu Gly Ala Gly Val
        755                 760                 765

Val Leu Asp Ile Gly Pro Gly Val Ser Gly Leu Ala Pro Gly Asp Arg
    770                 775                 780

Val Met Gly Leu Phe Ser Gly Ala Phe Gly Pro Val Ala Val Thr Asp
785                 790                 795                 800

His Arg Leu Leu Ala Arg Leu Pro Glu Gly Trp Ser Phe Ala Asp Ala
                805                 810                 815

Ala Ala Thr Pro Val Val Phe Leu Thr Ala Met Tyr Gly Leu Met Asp
            820                 825                 830

Leu Ala Gly Leu Arg Pro Gly Glu Ser Val Leu Leu His Ser Ala Ala
        835                 840                 845

Gly Gly Val Gly Met Ala Ala Thr Gln Val Ala Arg Trp Leu Gly Ala
    850                 855                 860

Glu Val Tyr Ala Thr Ala Ser Pro Gly Lys Trp Asp Ala Leu Arg Ala
865                 870                 875                 880

Gly Gly Val Ala Asp Asp Arg Ile Ala Ser Ser Arg Ser Leu Glu Phe
                885                 890                 895

Ala Asp Arg Phe Gly Arg Val Asp Val Val Leu Asn Ser Leu Ala Gly
            900                 905                 910

Glu Tyr Val Asp Ala Ser Leu Gly Leu Leu Ala Asp Gly Gly Arg Phe
        915                 920                 925

Leu Glu Met Gly Lys Thr Asp Ile Arg Asp Gly Glu Arg Val Ala Ala
    930                 935                 940

Glu His Gly Val Arg Tyr Gln Ala Phe Asp Leu Met Asp Ala Gly Pro
945                 950                 955                 960

Asp Arg Val Gly Glu Leu Leu Arg Leu Leu Val Ser Leu Phe Glu Arg
                965                 970                 975

Gly Ile Phe Thr Ala Leu Pro Thr Arg Val Trp Asp Val Arg Gln Ala
            980                 985                 990

Gly Asp Ala Leu Arg Phe Leu Ser  Gln Ala Arg His Ile  Gly Lys Leu
        995                 1000                1005

Val Leu  Ser Ile Pro Gln Pro  Leu Arg Glu Gly Asp  Thr Val Leu
    1010                1015                1020

Ile Thr  Gly Gly Thr Gly Thr  Leu Gly Gly Leu Val  Ala Arg His
    1025                1030                1035

Leu Val  Glu Arg His Gly Val  Arg Asp Val Val Leu  Ala Gly Arg
    1040                1045                1050

Arg Gly  Pro Asp Ala Pro Asp  Ala Ala Glu Leu Ala  Ala Ala Leu
    1055                1060                1065

Arg Glu  Tyr Gly Ala Arg Val  Arg Val Val Ala Cys  Asp Val Ala
    1070                1075                1080

Asp Arg  Asp Gln Leu Ala Arg  Leu Leu Asp Thr Val  Ser Gly Leu
    1085                1090                1095

Arg Met  Val Val His Thr Ala  Gly Val Leu Asp Asp  Gly Val Ile
    1100                1105                1110

Glu Ser  Leu Thr Pro Glu Arg  Val Arg Glu Val Leu  Arg Pro Lys
    1115                1120                1125

Val Asp  Ala Ala Trp Tyr Leu  His Glu Leu Thr Ala  Gly Arg Glu
    1130                1135                1140

Leu Ala  Glu Phe Val Val Phe  Ser Ser Ala Ala Gly  Val Leu Gly
```

-continued

```
    1145                1150                1155

Ser Pro  Gly Gln Gly Ala Tyr  Ala Ala Ala Asn Ala  Trp Leu Asp
    1160                1165                1170

Ala Leu  Met Ala His Arg Arg  Ala Ala Gly Leu Pro  Gly Leu Ser
    1175                1180                1185

Val Ala  Trp Gly Leu Trp Ala  Glu Arg Ser Gly Met  Thr Gly His
    1190                1195                1200

Leu Ser  Asp Arg Asp Leu Ala  Arg Met Ala Arg Ala  Gly Ala Thr
    1205                1210                1215

Pro Leu  Ala Thr Asp Gln Gly  Leu Arg Leu Leu Asp  Ser Ala Arg
    1220                1225                1230

Ala Ala  Thr Glu Ala Leu Val  Leu Ala Thr Pro Leu  Asp Ala Ala
    1235                1240                1245

Ala Leu  Arg Ala Gln Ala Asp  Ala Gly Ala Leu Pro  Ala Leu Phe
    1250                1255                1260

Arg Gly  Leu Val Arg Ala Pro  Ile Arg Arg Ala Thr  Gly Ala Gly
    1265                1270                1275

Pro Val  Glu Asp Glu Ser Ser  Leu Arg Gly Arg Met  Ala Ala Met
    1280                1285                1290

Pro Val  Ala Glu Arg Glu Gln  Leu Val Leu Asp Leu  Val Arg Thr
    1295                1300                1305

Gln Val  Ala Thr Val Leu Gly  His Gly Thr Ala Thr  Ala Val Asp
    1310                1315                1320

Pro Ala  Arg Thr Phe Ala Glu  Thr Gly Phe Asp Ser  Leu Thr Ala
    1325                1330                1335

Val Glu  Leu Arg Asn Arg Leu  Arg Thr Ala Thr Gly  Val Arg Leu
    1340                1345                1350

Ser Ala  Thr Ala Ile Phe Asp  Tyr Pro Thr Pro Ala  Val Leu Ala
    1355                1360                1365

Gly His  Leu Leu Arg Glu Leu  Asp Gly Thr Val Gly  Glu Ala Val
    1370                1375                1380

Thr Arg  Pro Ala Ala Pro Ala  Ala Ala Thr Asp Arg  Asp Pro Ile
    1385                1390                1395

Val Ile  Val Gly Met Ala Cys  Arg Tyr Pro Gly Gly  Val Ala Ser
    1400                1405                1410

Pro Glu  Glu Leu Trp Glu Leu  Leu Ala Thr Gly Arg  Asp Ala Val
    1415                1420                1425

Ala Asp  Leu Pro Asp Asp Arg  Gly Trp Asp Leu Asp  Gly Leu Tyr
    1430                1435                1440

Ser Ala  Asp Pro Asp Ser Ser  Gly Thr Ser Tyr Val  Arg Ser Gly
    1445                1450                1455

Gly Phe  Val Tyr Asp Ala Gly  Glu Phe Asp Ala Asp  Phe Phe Gly
    1460                1465                1470

Ile Ser  Pro Arg Glu Ala Leu  Ala Met Asp Pro Gln  Gln Arg Leu
    1475                1480                1485

Leu Leu  Glu Val Ala Trp Glu  Thr Val Glu Arg Ala  Gly Val Pro
    1490                1495                1500

Ala Ala  Ser Leu Lys Gly Ser  Gln Thr Gly Val Phe  Val Gly Ala
    1505                1510                1515

Ala Ala  Gln Gly Tyr Gly Thr  Gly Ala Gly Gln Ala  Ala Glu Gly
    1520                1525                1530

Ser Glu  Gly Tyr Phe Leu Thr  Gly Gly Ala Gly Ser  Val Val Ser
    1535                1540                1545
```

```
Gly Arg  Leu Ser Tyr Thr Phe  Gly Leu Glu Gly Pro  Ala Val Thr
    1550                 1555                 1560

Val Asp  Thr Ala Cys Ser Ser  Ser Leu Val Ala Leu  His Leu Ala
    1565                 1570                 1575

Ala Gln  Ala Leu Arg Ser Gly  Glu Cys Ser Leu Ala  Leu Ala Gly
    1580                 1585                 1590

Gly Val  Thr Val Met Ala Thr  Pro Gly Ile Phe Val  Glu Phe Ser
    1595                 1600                 1605

Arg Gln  Arg Gly Leu Ala Ala  Asp Gly Arg Cys Lys  Ala Phe Ala
    1610                 1615                 1620

Asp Ala  Ala Asp Gly Thr Gly  Trp Gly Glu Gly Val  Gly Met Leu
    1625                 1630                 1635

Leu Leu  Glu Arg Leu Ser Asp  Ala Arg Arg Asn Gly  His Arg Val
    1640                 1645                 1650

Leu Ala  Val Val Arg Gly Ser  Ala Val Asn Gln Asp  Gly Ala Ser
    1655                 1660                 1665

Asn Gly  Leu Thr Ala Pro Asn  Gly Pro Ser Gln Gln  Arg Val Ile
    1670                 1675                 1680

Arg Ala  Ala Leu Ala Asn Ala  Gly Leu Ala Ala Ser  Asp Val Asp
    1685                 1690                 1695

Ala Val  Glu Ala His Gly Thr  Gly Thr Ser Leu Gly  Asp Pro Ile
    1700                 1705                 1710

Glu Ala  Gln Ala Leu Leu Ala  Thr Tyr Gly Gln Gln  Arg Glu Arg
    1715                 1720                 1725

Pro Leu  Leu Leu Gly Ser Ile  Lys Ser Asn Ile Gly  His Thr Gln
    1730                 1735                 1740

Ser Ala  Ala Gly Val Ala Gly  Val Ile Lys Met Val  Leu Ala Met
    1745                 1750                 1755

Arg His  Gly Ala Leu Pro Arg  Thr Leu His Val Asp  Gln Pro Ser
    1760                 1765                 1770

Thr His  Val Asp Trp Ser Ala  Gly Ala Val Glu Leu  Leu Thr Glu
    1775                 1780                 1785

Pro Ala  Glu Trp Pro Gly Thr  Ser Arg Pro Arg Arg  Ala Gly Val
    1790                 1795                 1800

Ser Ser  Phe Gly Val Ser Gly  Thr Asn Ala His Val  Ile Leu Glu
    1805                 1810                 1815

Gln Pro  Pro Ala Glu Ala Glu  Ser Gly Pro Ala Pro  Glu Ser Ala
    1820                 1825                 1830

Pro Gly  Pro Val Pro Ala Val  Val Pro Gly Pro Val  Pro Ala Val
    1835                 1840                 1845

Val Pro  Trp Val Leu Ser Gly  Gln Gly Glu Arg Gly  Leu Arg Ala
    1850                 1855                 1860

Gln Ala  Ala Arg Leu Arg Ser  Phe Leu Ala Ala Arg  Pro Glu Ser
    1865                 1870                 1875

Gly Pro  Ala Asp Val Gly Trp  Ser Leu Ala Ala Thr  Arg Ser Ala
    1880                 1885                 1890

Leu Ser  His Arg Ala Ala Val  Val Gly Ala Asp Arg  Ala Glu Leu
    1895                 1900                 1905

Leu Asp  Gly Leu Ala Ala Leu  Ala Ala Gly Glu Pro  Ala Pro Gly
    1910                 1915                 1920

Val Val  Leu Gly Thr Ala Asp  Pro Gly Arg Val Gly  Val Leu Phe
    1925                 1930                 1935
```

-continued

```
Ala Gly  Gln Gly Thr Gln Arg  Pro Gly Met Gly Arg  Glu Leu Tyr
    1940                 1945                 1950

Gln Ser  Phe Pro Val Phe Ala  Ala Ala Trp Asp Glu  Val Cys Ala
    1955                 1960                 1965

Ala Leu  Asp Pro His Leu Asp  Arg Pro Leu Gly Glu  Val Val Thr
    1970                 1975                 1980

Asp Ala  Thr Gly Ala Leu Asp  Ala Thr Thr Tyr Thr  Gln Ala Gly
    1985                 1990                 1995

Leu Phe  Ala Leu Glu Val Ser  Leu Phe Arg Leu Val  Ser Ser Trp
    2000                 2005                 2010

Gly Val  Arg Pro Asp Tyr Leu  Leu Gly His Ser Ile  Gly Glu Leu
    2015                 2020                 2025

Ala Ala  Ala Gln Val Ala Gly  Leu Trp Ser Leu Glu  Asp Ala Ala
    2030                 2035                 2040

Lys Val  Val Ala Ala Arg Gly  Arg Leu Met Gly Ala  Leu Pro Pro
    2045                 2050                 2055

Gly Gly  Ala Met Val Ala Leu  Ala Ala Pro Glu Asp  Gln Val Arg
    2060                 2065                 2070

Pro Phe  Leu Thr Asp Arg Val  Ala Leu Ala Ala Val  Asn Gly Pro
    2075                 2080                 2085

Ser Ser  Val Val Val Ser Gly  Asp Glu Asp Ala Val  Cys Gly Val
    2090                 2095                 2100

Ala Glu  Ala Phe Ala Ala Arg  Gly Val Lys Thr Arg  Arg Leu Arg
    2105                 2110                 2115

Val Gly  His Ala Phe His Ser  Pro Leu Met Asp Glu  Met Leu Ile
    2120                 2125                 2130

Ala Phe  Ala Glu Val Leu Asp  Thr Val Asp Phe Arg  Thr Pro Arg
    2135                 2140                 2145

Ile Pro  Val Val Ser Asn Leu  Ser Gly Ala Val Ala  Gly Glu Glu
    2150                 2155                 2160

Leu Cys  Ser Pro Ala Tyr Trp  Val Arg Gln Val Arg  Glu Thr Val
    2165                 2170                 2175

Arg Phe  Ala Ala Gly Leu Glu  Arg Leu Arg Glu Leu  Gly Thr Gly
    2180                 2185                 2190

Thr Phe  Leu Glu Leu Gly Pro  Asp Gly Thr Leu Thr  Ala Leu Ala
    2195                 2200                 2205

Gln Ala  Gln Ile Thr Gly Ala  Asp Ala Glu Phe Ile  Pro Thr Leu
    2210                 2215                 2220

Arg Ala  Asp Arg Pro Glu Pro  Val Thr Val Thr Thr  Ala Leu Ala
    2225                 2230                 2235

Gln Leu  His Thr His Gly Val  Glu Pro Asp Trp Ser  Ala Val Phe
    2240                 2245                 2250

Pro Gly  Ala His Arg Ala Glu  Leu Pro Thr Tyr Ala  Phe Gln Arg
    2255                 2260                 2265

Ser Arg  Phe Trp Leu Glu Pro  Ser Arg Thr Pro Gly  Asp Ala Gly
    2270                 2275                 2280

Asp Phe  Gly Leu Gly Ala Leu  Asp His Pro Leu Val  Gly Ala Arg
    2285                 2290                 2295

Val Pro  Leu Pro Asp Ala Asp  Gly Val Leu Leu Thr  Gly Arg Ile
    2300                 2305                 2310

Ser Ala  Glu Ala His Ser Trp  Leu Ile Gly Gln Arg  Ala Leu Gly
    2315                 2320                 2325

Val Pro  Leu Phe Pro Ala Thr  Gly Phe Leu Glu Leu  Val Leu Gln
```

```
    2330                2335                2340

Ala Gly  Leu Gln Cys Asp Ser  Arg Thr Val Asp Glu  Leu Thr Ile
    2345                2350                2355

His Glu  Pro Leu Val Leu Pro  Glu Arg Gly Gly Val  Glu Val Gln
    2360                2365                2370

Val Ser  Val Arg Gly Ala Asp  Glu Ser Gly Arg Arg  Pro Ala Thr
    2375                2380                2385

Val Tyr  Cys Arg Arg Asp Gln  Arg Trp Val Arg His  Ala Thr Ala
    2390                2395                2400

Val Leu  Gly Ala Asp Arg Pro  Pro Ala Pro Glu Pro  Arg Pro Glu
    2405                2410                2415

Pro Trp  Pro Pro Thr Gly Ala  Arg Pro Leu Glu Ser  Gly Gly Thr
    2420                2425                2430

Pro Ala  Trp Arg Arg Asp Asp  Glu Val Phe Leu Asp  Ile Glu Leu
    2435                2440                2445

Pro Glu  Val Ala Gly Ala Glu  Ala Glu Arg Trp Thr  Leu His Pro
    2450                2455                2460

Ala Leu  Leu Glu Gln Ala Leu  Arg Gly Glu Ala Leu  Ala Gly Leu
    2465                2470                2475

Val Thr  Ala Ala Glu Gly Thr  His Leu Pro Phe Ser  Trp Thr Gly
    2480                2485                2490

Ile Thr  Leu His Thr Thr Gly  Ala Thr Arg Leu Arg  Ala Thr Leu
    2495                2500                2505

Ala Pro  Val Gly Pro Asp Thr  Val Ser Leu His Val  Ala Asp Ala
    2510                2515                2520

Ala Gly  Thr Pro Val Leu Ser  Val Asp Ser Leu Ala  Leu Arg Pro
    2525                2530                2535

Val Ser  Gly Gln Arg Leu Arg  Gln Ala Asn Ala Ala  Leu Phe Arg
    2540                2545                2550

Pro Val  Trp Ala Ala Cys Arg  Thr Arg Ala Glu Pro  Asp Thr Gly
    2555                2560                2565

Ser Val  Arg Trp Gly Leu Val  Gly Asp Pro Asp Ala  Trp Lys Pro
    2570                2575                2580

Asp Thr  Leu Gly Ala Pro Val  Ala Leu Tyr Pro Asp  Leu Ser Ala
    2585                2590                2595

Ile Glu  Asp Val Pro Asp Val  Ile Leu Leu Pro Cys  Val Ser Glu
    2600                2605                2610

Gly Gly  Thr Ala Ser Glu Val  Ala Val Arg Val Ser  Glu Thr Val
    2615                2620                2625

Arg Thr  Trp Leu Ala Gly Glu  Arg Phe Ala Ala Ser  Arg Leu Val
    2630                2635                2640

Leu Val  Thr Arg Gly Ala Leu  Ala Thr Ala Ala Gly  Glu Glu Leu
    2645                2650                2655

Glu Asp  Leu Ala Ala Ala Ala  Val Trp Ser Leu Val  Glu Pro Leu
    2660                2665                2670

Gln Ala  Ala Val Ala Gly Arg  Leu Thr Leu Val Asp  Thr Asp Thr
    2675                2680                2685

Ser Asp  Leu Arg Met Leu Pro  Ala Ala Val Ala Val  Gly Glu Asp
    2690                2695                2700

Arg Val  Ala Val Arg Ala Gly  Ala Val Leu Val Pro  Asp Leu Val
    2705                2710                2715

Thr Pro  Pro Ala Thr Glu Gln  Asp Pro Pro Ala Trp  Gly Pro Gly
    2720                2725                2730
```

```
Thr Val Leu Val Thr Gly Gly Ser Ala Met Ala Val Ser Arg His
    2735                2740                2745

Leu Val Ala Glu Arg Gly Val Arg Asp Leu Val Leu Ala Gly Asp
    2750                2755                2760

Gly Asp Met Ala Glu Leu Ala Ala Leu Gly Ala Thr Val Arg Leu
    2765                2770                2775

Ala Pro Cys Asp Pro Ala Asp Gly Gln Ala Leu Ala Ala Leu Val
    2780                2785                2790

Ala Glu Ile Pro Gly Leu Arg Ser Val Val His Thr Ala Ala Asp
    2795                2800                2805

Ala Pro Glu Arg Thr Arg Ser Leu Leu Pro Glu Ser Leu Arg Pro
    2810                2815                2820

Gln Leu Arg Ser Gly Val Ala Ala Ala Trp Asn Leu His Leu Ala
    2825                2830                2835

Thr Arg Gly Leu Glu Leu Asp Arg Phe Val Leu Phe Thr Ser Ala
    2840                2845                2850

Asp Gly Thr Leu Gly Pro Ala Tyr Ala Asp Ala Leu Ala Ala His
    2855                2860                2865

Arg Arg Ala Arg Gly Leu Pro Ala Val Ser Val Ser Thr Asp Leu
    2870                2875                2880

Gly Leu Ala Leu Phe Asp Glu Ala Cys Ala Gly Pro Gly Glu Ala
    2885                2890                2895

Ile Arg Val Thr Thr Ala Thr Pro Ala Pro Ala Pro Thr Glu Ala
    2900                2905                2910

Asp Arg Gln Pro Val Glu Gln Pro Pro Ala Ala Glu Ala Ser Ala
    2915                2920                2925

Thr Thr Leu Leu Glu Arg Leu Ala Gly Arg Thr Glu Asp Glu Gln
    2930                2935                2940

Asp Glu Ile Leu Leu Glu Leu Val Arg Gly Gln Val Ala Met Val
    2945                2950                2955

Leu Gly His Pro Asp Ala Thr Met Val Asp Pro Asp Arg Gly Phe
    2960                2965                2970

Val Glu Leu Gly Phe Asp Ser Val Ala Ala Val Lys Leu Arg Asn
    2975                2980                2985

Gln Leu Ala Gly Ala Thr Arg Leu Asp Leu Pro Ala Ser Leu Thr
    2990                2995                3000

Phe Asp His Pro Thr Ala Val Asp Leu Ala Arg His Leu Arg Ala
    3005                3010                3015

Glu Met Leu Pro Asp Asp Ala Ala Ala Ala Ile Leu Val Leu Glu
    3020                3025                3030

Glu Leu Asn Lys Leu Asp Asp Ser Ile Leu Val Leu Asp Pro Ala
    3035                3040                3045

Ser Ala Ala Arg Val Arg Ile Ser Thr Leu Leu Gln Asp Leu Ala
    3050                3055                3060

Ala Lys Trp Val Glu Arg Thr Asp Arg Pro
    3065                3070
```

<210> SEQ ID NO 51
<211> LENGTH: 397
<212> TYPE: PRT
<213> ORGANISM: Streptomyces sp.

<400> SEQUENCE: 51

```
Val Ser Glu Thr Leu Ser Leu Pro Gly Thr Val Lys Ala Glu Arg Arg
```

-continued

```
1               5                   10                  15

Cys Pro Tyr Asp Pro Pro Glu Ala His Arg Arg Leu Arg Asp Lys Gly
            20                  25                  30

Glu Leu Gly Lys Leu Glu Leu Pro Gly Gly Leu Val Met Trp Phe Leu
        35                  40                  45

Thr Lys His Asp Asp Ile Arg Ala Met Leu Ala Asp Ser Arg Phe Ser
    50                  55                  60

Gly Ala Arg Val Pro Phe Pro Ala Met Asn Pro Glu Ile Pro Ala Gly
65                  70                  75                  80

Phe Phe Phe Ser Met Asp Pro Pro Asp His Thr Arg Tyr Arg Arg Thr
                85                  90                  95

Leu Thr Ala Glu Phe Ser Val Arg Gly Ala Arg Glu Leu Thr Gly Arg
            100                 105                 110

Ile Glu Arg Leu Ala Asp Arg His Leu Asp Ala Met Glu Ala Ala Gly
        115                 120                 125

Thr Ser Ala Asp Leu Val Ala Ala Tyr Ala Ser Pro Val Pro Ala Met
    130                 135                 140

Val Ile Ser Glu Ile Leu Gly Val Pro Tyr Thr Tyr His Gln Lys Phe
145                 150                 155                 160

Asp His Glu Val Arg Thr Leu Arg Glu Thr Gly Gly Asp Asp Gln Ala
                165                 170                 175

Val Gly Ala Met Ala Thr Ala Trp Trp Asp Glu Met Arg Gly Phe Val
            180                 185                 190

Arg Ala Lys Arg Ala Glu Pro Gly Asp Asp Met Ile Ser Arg Leu Leu
        195                 200                 205

His Asp Glu Val Glu Gly Gly Ala Leu Thr Asp Glu Glu Val Val Gly
    210                 215                 220

Ile Ala Met Thr Ile Ile Phe Ala Gly His Glu Pro Val Glu Asn Leu
225                 230                 235                 240

Ile Gly Leu Gly Met Leu Ala Leu Phe Gln Asp Gly Glu Gln Leu Thr
                245                 250                 255

Arg Leu Arg Glu Asn Pro Asp Leu Ile Asp Ser Ala Val Glu Glu Phe
            260                 265                 270

Leu Arg Tyr Phe Pro Val Asn Asn Phe Gly Thr Val Arg Thr Ala Thr
        275                 280                 285

Glu Asp Ala Val Ile Asn Gly His Pro Ile Ala Lys Gly Glu Ile Val
    290                 295                 300

Ala Gly Leu Val Ser Thr Ala Asn Arg Asp Pro Glu Arg Phe Ala Asp
305                 310                 315                 320

Pro Asp Arg Leu Val Leu Asp Arg Ser His Thr Ser His Leu Ala Phe
                325                 330                 335

Gly His Gly Val His Gln Cys Leu Gly Gln Gln Leu Ala Arg Val Glu
            340                 345                 350

Leu Lys Val Leu Leu Gln Arg Leu Leu Val Arg Phe Pro Ala Leu Arg
        355                 360                 365

Leu Ala Val Ala Pro Glu Glu Ile Arg Tyr Arg Glu Asn Thr Ser Phe
    370                 375                 380

Tyr Gly Val His Glu Leu Pro Val Thr Trp Ala Ala Glu
385                 390                 395
```

<210> SEQ ID NO 52
<211> LENGTH: 172
<212> TYPE: PRT
<213> ORGANISM: Streptomyces sp.

<400> SEQUENCE: 52

```
Val Cys Arg Pro Leu Gly Ser Ser Arg Arg Gly Gly Arg Pro Arg Gly
1               5                   10                  15

Arg Gly Phe Val Val Gly Ser Ser Gly Asn Ala Val Asn Met Thr Glu
            20                  25                  30

Lys Lys Asn Ala His Thr Thr Arg Ser Thr Asn Val Asn Ala Lys Ala
        35                  40                  45

Thr Ala Thr Lys Ala Lys Glu Thr Ala Glu Arg Ala Lys Asp Thr Ala
    50                  55                  60

Gly Lys Ala Glu Thr Thr Ala Lys Thr Ala Ala Ala Gly Ala Ala Thr
65                  70                  75                  80

Thr Ala Ala His Thr Ala His Val Ala Ala Asp Lys Ala Gln Val Ala
                85                  90                  95

Ala Gly Lys Ala Val Thr Thr Gly Arg Thr Val Ala Ala Glu Ala Pro
            100                 105                 110

Lys Lys Ala Ala Ala Ala Ala Gly Ser Ala Trp Met Met Ile Lys Ala
        115                 120                 125

Arg Lys Val Leu Ala Ala Val Ala Gly Ala Gly Ala Ala Ala Ala Gly
    130                 135                 140

Ala Thr Ala Ala Val Val Leu Arg Arg Arg Ala Ala Arg Arg Arg Arg
145                 150                 155                 160

Pro Leu Ala Arg Leu Thr Gly Gly Arg Leu Gly Ser
                165                 170
```

<210> SEQ ID NO 53
<211> LENGTH: 169
<212> TYPE: PRT
<213> ORGANISM: Streptomyces sp.

<400> SEQUENCE: 53

```
Val Gly Phe Ser Phe Gln Pro Phe Gly Ala Cys Phe Ser Leu Thr Ser
1               5                   10                  15

Pro Gly Ser Met Pro Val Gly Asn Thr Val Arg Ile Ser Val Lys Pro
            20                  25                  30

Ala Leu Pro Ser Ser Ala Ser Asp Ser Asn Val Ser Val Thr Ser Phe
        35                  40                  45

Ala Arg Ala Arg Glu Ser Glu Ala Leu Thr Ser Val Trp Ala Arg Ala
    50                  55                  60

Gly Val Ala Val Ala Arg Thr Ser Ala Glu Val Ala Thr Ala Arg Ala
65                  70                  75                  80

Pro Ile Arg Arg Gly Arg Gly Trp Asp Gly Gly Arg Cys Ala Phe Thr
                85                  90                  95

Val Ser Leu Leu Val His Gly Val Val Thr Arg Ala Leu Leu Thr Gly
            100                 105                 110

His Pro Ala Arg Ser Pro Gly Ala Phe Thr Phe Pro Gly Thr Tyr Gly
        115                 120                 125

Pro Gly Ala Met Phe Ile Leu Ala Gln Thr Gly Ser Pro Leu Ala Thr
    130                 135                 140

Arg Gly Ser Lys Glu Phe Arg Arg Leu Arg Gly Pro Arg Lys Ala Asp
145                 150                 155                 160

Arg Gly Gly Arg Arg Val Pro Val Arg
                165
```

<210> SEQ ID NO 54

<211> LENGTH: 494
<212> TYPE: PRT
<213> ORGANISM: Streptomyces sp.

<400> SEQUENCE: 54

```
Met Ser Ala Ala Ser Ser Asp Pro Thr Ser Pro Arg Val Pro Pro Thr
1               5                   10                  15

Arg Arg Leu Ala Leu Gly Val Ile Ala Thr Gly Met Leu Met Val Ile
            20                  25                  30

Leu Asp Gly Ser Ile Val Thr Val Ala Met Pro Ala Ile Gln Ser Asp
        35                  40                  45

Leu Arg Phe Ser Pro Ala Gly Leu Ser Trp Val Val Asn Ala Tyr Leu
    50                  55                  60

Ile Ala Phe Gly Gly Leu Leu Leu Leu Gly Gly Arg Ile Gly Asp Leu
65                  70                  75                  80

Ile Gly Arg Lys Arg Val Phe Leu Thr Gly Thr Ala Val Phe Thr Ala
                85                  90                  95

Ala Ser Leu Leu Ala Ala Val Ala Thr Ser Pro Ala Val Leu Ile Ala
            100                 105                 110

Ala Arg Phe Leu Gln Gly Val Gly Ser Ala Met Ala Ser Ala Val Ser
        115                 120                 125

Leu Gly Ile Leu Val Thr Leu Phe Thr Glu Arg Ala Glu Arg Ser Lys
    130                 135                 140

Ala Ile Ala Val Phe Ser Phe Thr Gly Ala Ala Gly Ala Ser Ile Gly
145                 150                 155                 160

Gln Val Leu Gly Gly Leu Leu Thr Asp Ala Leu Ser Trp His Trp Ile
                165                 170                 175

Phe Leu Ile Asn Leu Pro Ile Gly Leu Leu Thr Leu Ala Val Ala Ile
            180                 185                 190

Pro Val Leu Pro Ala Asp Arg Gly Pro Gly Leu Ala Ala Gly Ala Asp
        195                 200                 205

Val Leu Gly Ala Leu Leu Val Thr Thr Gly Leu Met Leu Gly Ile Tyr
    210                 215                 220

Thr Val Val Lys Val Ala Asp Tyr Gly Trp Thr Ala Ala Arg Thr Leu
225                 230                 235                 240

Gly Leu Gly Ala Val Ser Ile Leu Leu Ile Ala Leu Phe Leu Val Arg
                245                 250                 255

Gln Thr Thr Ala Arg Thr Pro Leu Met Pro Leu Arg Ile Leu Arg Ser
            260                 265                 270

Arg Gly Val Ala Gly Ala Asn Leu Val Gln Leu Leu Met Val Ala Ala
        275                 280                 285

Leu Phe Ser Phe Gln Ile Leu Val Ala Leu Tyr Leu Arg Asn Val Leu
    290                 295                 300

Gly Tyr Asp Ala Thr Gly Thr Gly Leu Ala Met Leu Pro Ala Ala Ile
305                 310                 315                 320

Ala Ile Gly Ala Val Ser Leu Gly Val Ser Ala Arg Leu Ser Ala Arg
                325                 330                 335

Phe Gly Asp Arg Ala Val Leu Leu Thr Gly Leu Ala Leu Leu Thr Gly
            340                 345                 350

Val Leu Gly Leu Leu Val Arg Val Pro Val His Ala Arg Tyr Leu Pro
        355                 360                 365

Asp Leu Leu Pro Val Met Leu Leu Ala Ala Gly Phe Gly Leu Ala Leu
    370                 375                 380

Pro Ala Leu Thr Ser Leu Gly Met Ser Gly Ala Lys Glu Asp Glu Ala
```

-continued

```
385                 390                 395                 400

Gly Leu Val Ser Gly Leu Phe Asn Thr Thr Gln Gln Ile Gly Met Ala
                405                 410                 415

Leu Gly Val Ala Val Leu Ser Thr Leu Ala Ala Ser Arg Thr Asp Ala
            420                 425                 430

Leu Leu Ser Arg Gly Lys Gly Arg Ala Glu Ala Leu Thr Gly Gly Tyr
        435                 440                 445

His Leu Ala Phe Ala Val Gly Thr Gly Leu Ile Val Ala Ala Phe Ala
    450                 455                 460

Val Ala Phe Thr Val Leu Arg Gly Pro Ala Arg Lys Pro Pro Ala Val
465                 470                 475                 480

Pro Arg Asn Ala Asn Pro Pro Ala Thr Pro Val Ala Thr Ala
                485                 490


<210> SEQ ID NO 55
<211> LENGTH: 159
<212> TYPE: PRT
<213> ORGANISM: Streptomyces sp.

<400> SEQUENCE: 55

Met Ala Pro Thr Lys Thr Glu Pro Asp Leu Ser Phe Leu Leu Asp His
1               5                   10                  15

Thr Ser His Val Leu Arg Thr Gln Met Ser Ala Ala Leu Ala Glu Ile
            20                  25                  30

Gly Leu Thr Ala Arg Met His Cys Val Leu Val His Ala Leu Glu Glu
        35                  40                  45

Glu Arg Thr Gln Ala Gln Leu Ala Glu Ile Gly Asp Met Asp Lys Thr
    50                  55                  60

Thr Met Val Val Thr Val Asp Ala Leu Glu Lys Ala Gly Leu Ala Glu
65                  70                  75                  80

Arg Arg Ala Ser Thr His Asp Arg Arg Ala Arg Ile Ile Ala Val Thr
                85                  90                  95

Glu Glu Gly Ala Arg Ile Ala Glu Arg Ser Gln Glu Ile Val Asp Arg
            100                 105                 110

Val His Arg Glu Ala Leu Ala Thr Leu Pro Glu Thr Gln Arg Ala Ala
        115                 120                 125

Leu Leu Lys Ala Leu Thr Arg Leu Ser Glu Gly His Leu Ala Thr Pro
    130                 135                 140

Ala Glu Ser Pro Arg Pro Ala Arg Arg Ala Arg Gln Arg Glu Lys
145                 150                 155


<210> SEQ ID NO 56
<211> LENGTH: 314
<212> TYPE: PRT
<213> ORGANISM: Streptomyces sp.

<400> SEQUENCE: 56

Val Thr Arg Gly Arg Val Ala Cys Val Asp Arg Ala Pro Gly Ser Cys
1               5                   10                  15

Met Arg Lys Met Arg Ser Gly Phe Tyr Leu Tyr Ala Gly Arg Met Asp
            20                  25                  30

Val Glu Leu Arg Gln Leu Arg Cys Leu Val Ala Ile Val Asp Glu Gly
        35                  40                  45

Thr Phe Thr Asp Ala Ala Ile Ala Leu Gly Val Ser Gln Ala Ala Val
    50                  55                  60

Ser Arg Thr Leu Ala Ala Leu Glu Arg Ala Leu Gly Thr Arg Leu Leu
```

-continued

```
65                  70                  75                  80

Arg Arg Thr Ser Arg Glu Val Thr Pro Thr Gly Thr Gly Leu Arg Val
                85                  90                  95

Val Ala His Ala Arg Arg Val Leu Ala Glu Val Asp Gly Leu Ile Arg
            100                 105                 110

Glu Ala Val Ser Gly His Ala His Leu Arg Ile Gly Tyr Ala Trp Ser
        115                 120                 125

Ala Leu Gly Arg His Thr Pro Ala Phe Gln Arg Arg Trp Ala Gln Ala
    130                 135                 140

Tyr Pro Glu Thr Glu Leu His Leu Val Arg Val Asn Ser Ala Thr Ala
145                 150                 155                 160

Gly Leu Thr Glu Gly Ala Cys Asp Leu Ala Val Val Arg Arg Pro Leu
                165                 170                 175

Asp Glu Arg Arg Phe Asp Ser Ala Ile Val Gly Leu Glu Arg Arg Leu
            180                 185                 190

Cys Ala Val Ala Ala Asp Asp Pro Leu Ala Arg Arg Arg Ser Val Arg
        195                 200                 205

Leu Ala Asp Leu Ser Gly Arg Thr Leu Leu Val Asp Arg Arg Thr Gly
    210                 215                 220

Thr Thr Thr Thr Glu Leu Trp Pro Pro Asp Ser Arg Pro Ala Thr Glu
225                 230                 235                 240

Glu Thr His Asp Val Glu Asp Trp Leu Thr Val Ile Ser Ala Gly Arg
                245                 250                 255

Cys Val Gly Met Thr Ala Glu Ser Thr Ala Asn Gln Tyr Pro Arg Pro
            260                 265                 270

Gly Ile Ala Tyr Arg Pro Val Arg Asp Ala Glu Pro Ile Ala Val Arg
        275                 280                 285

Leu Ala Trp Trp Arg Asp Asp Pro His Pro Ala Thr Gln Thr Ala Val
    290                 295                 300

Glu Leu Leu Thr Ala Leu Tyr Arg Asn Gly
305                 310


<210> SEQ ID NO 57
<211> LENGTH: 331
<212> TYPE: PRT
<213> ORGANISM: Streptomyces sp.

<400> SEQUENCE: 57

Met Ser Arg Ala His Asp Arg Arg Met Arg Leu Ala Pro Ala Ser Arg
1               5                   10                  15

Thr Pro Ser Pro Arg Ala Met Asp Thr Ala His Arg Thr Ala Pro Thr
            20                  25                  30

Pro Ala Asp Tyr Asp Leu Gly Gln Gly Leu Glu Arg Gly Leu Ala Pro
        35                  40                  45

Asp Pro Asp Gln Arg Pro Thr Gly Arg Arg Phe Ala Gly Val Ala Thr
    50                  55                  60

Met Ile Gly Ser Gly Leu Ser Asn Gln Thr Gly Ala Ala Ile Gly Ser
65                  70                  75                  80

Gln Ala Phe Pro Val Ile Gly Pro Val Gly Val Val Ala Val Arg Gln
                85                  90                  95

Tyr Val Ala Ala Ile Val Leu Leu Ala Val Gly Arg Pro Arg Leu Arg
            100                 105                 110

Ser Phe Thr Trp Trp Gln Trp Arg Pro Val Val Gly Leu Ala Val Val
        115                 120                 125
```

```
Phe Gly Thr Met Asn Leu Ser Leu Tyr Ser Ala Ile Asp Arg Ile Gly
    130                 135                 140

Leu Gly Leu Ala Val Thr Leu Glu Phe Leu Gly Pro Leu Cys Ile Ala
145                 150                 155                 160

Leu Ala Gly Ser Arg Arg Arg Val Asp Ala Cys Cys Ala Leu Val Ala
                165                 170                 175

Ala Ala Ala Val Val Thr Leu Met Arg Pro Arg Pro Ser Ala Asp Tyr
            180                 185                 190

Leu Gly Met Gly Leu Gly Leu Leu Ala Ala Val Cys Trp Ala Ser Tyr
        195                 200                 205

Ile Leu Leu Asn Arg Thr Val Gly Arg Arg Val Pro Gly Ala Gln Gly
    210                 215                 220

Ser Ala Ala Ala Ala Gly Ile Ser Ala Leu Met Phe Leu Pro Val Gly
225                 230                 235                 240

Ile Ala Val Ala Val His Gln Pro Pro Thr Val Ser Ala Ala Ala Tyr
                245                 250                 255

Ala Ile Ile Ala Gly Val Leu Ser Ser Ala Val Pro Tyr Leu Ala Asp
            260                 265                 270

Leu Phe Thr Leu Arg Arg Val Pro Ala Gln Ala Phe Gly Leu Phe Met
        275                 280                 285

Ser Val Asn Pro Val Leu Ala Ala Leu Val Gly Trp Val Gly Leu Gly
    290                 295                 300

Gln Ser Leu Gly Trp Thr Glu Trp Ile Ser Val Gly Ala Ile Val Ala
305                 310                 315                 320

Ala Asn Ala Leu Ser Ile Leu Thr Arg Arg Gly
                325                 330


<210> SEQ ID NO 58
<211> LENGTH: 274
<212> TYPE: PRT
<213> ORGANISM: Streptomyces sp.

<400> SEQUENCE: 58

Val Arg Ser Val Cys Pro Arg His Pro Ser Ser Thr Ser His Asp Arg
1               5                   10                  15

Ile Arg Met Thr Asp Asp Met Phe Leu Met Thr Asp Asp Thr Phe Leu
            20                  25                  30

Asp Asp Val Ala Glu Arg Leu Ala Ala Leu Pro Ala Val His Ala Val
        35                  40                  45

Ala Leu Gly Gly Ser Arg Ala Gln Gly Thr His Thr Pro Glu Ser Asp
    50                  55                  60

Trp Asp Leu Ala Leu Tyr Tyr Arg Gly Gly Phe Asp Pro Ala Ala Leu
65                  70                  75                  80

Arg Ala Val Gly Trp Glu Gly Glu Val Ser Glu Leu Gly Glu Trp Gly
                85                  90                  95

Gly Gly Val Phe Asn Gly Gly Ala Trp Leu Thr Ile Asp Gly Arg Arg
            100                 105                 110

Val Asp Val His Tyr Arg Asp Leu Glu Val Val Glu His Glu Leu Ala
        115                 120                 125

Glu Ser Arg Arg Gly Arg Phe His Trp Glu Pro Leu Met Phe His Leu
    130                 135                 140

Ala Gly Ile Pro Ser Tyr Leu Val Val Ala Glu Leu Ala Leu Asn Gln
145                 150                 155                 160

Val Leu Arg Gly Thr Leu Pro Arg Pro Glu Tyr Pro Ala Ala Leu Arg
                165                 170                 175
```

```
Glu Ala Ala Pro Pro Ala Trp Arg Gly Arg Ala Ala Leu Thr Leu Arg
            180                 185                 190

Tyr Ala Ser Ala Ala Tyr Val Gly Arg Gly Gln Ala Thr Glu Val Ala
        195                 200                 205

Gly Ala Val Ala Thr Ala Ala Leu Gln Thr Ala His Ala Val Leu Ala
    210                 215                 220

Ala Arg Gly Glu Trp Val Thr Asn Glu Lys Arg Leu Leu Gln Arg Ala
225                 230                 235                 240

Asp Leu Arg Ala Ile Asp Thr Ile Val Ala Gly Leu Arg Pro Glu Pro
                245                 250                 255

Thr Ala Leu Ala Glu Ala Ile Ala Ala Ala Glu Ala Leu Phe Glu Ala
            260                 265                 270

Ala Gly


<210> SEQ ID NO 59
<211> LENGTH: 349
<212> TYPE: PRT
<213> ORGANISM: Streptomyces sp.

<400> SEQUENCE: 59

Val Ser Ala Asp Ala Gly Ala Asp Ala Arg Gly Asp Thr Val Ser Gly
1               5                   10                  15

Glu Leu Val Leu Val Thr Gly Gly Ser Gly Tyr Leu Gly Thr His Val
            20                  25                  30

Ile Ser Gly Leu Leu Arg Ser Gly His Arg Val Arg Thr Thr Val Arg
        35                  40                  45

Ser His Gly Pro Ala Thr Gly Ala Ala Ala Ser Val Arg Ser Ala Ile
    50                  55                  60

Ala Ala Ser Gly Val Asp Pro Gly Gly Arg Leu Asp Ile Val Ser Ala
65                  70                  75                  80

Asp Leu Thr Thr Asp Asp Gly Trp Asp Asp Ala Met Ala Gly Cys Thr
                85                  90                  95

Arg Val His His Val Ala Ser Pro Phe Pro Ala Val Gln Pro Asp Asn
            100                 105                 110

Ala Asp Glu Leu Ile Val Pro Ala Arg Asp Gly Thr Leu Arg Val Leu
        115                 120                 125

Arg Ala Ala Arg Asp Gln Gly Val Lys Arg Val Val Met Thr Ser Ser
    130                 135                 140

Phe Ala Ala Val Gly Tyr Ser His Lys Asp Gly Asp Glu Tyr Asp Glu
145                 150                 155                 160

Ser Asp Trp Thr Asp Pro Glu Asp Asp Asn Pro Pro Tyr Ile Arg Ser
                165                 170                 175

Lys Thr Ile Ala Glu Leu Ala Ala Trp Asp Phe Val Ala Lys Glu Gly
            180                 185                 190

Asp Gly Leu Glu Leu Thr Val Ile Asn Pro Thr Gly Ile Phe Gly Pro
        195                 200                 205

Ala Leu Gly Pro Arg Leu Ser Ala Ser Thr Glu His Val Arg Ala Met
    210                 215                 220

Leu Glu Gly Ala Met Ser Ala Val Pro Arg Ala His Phe Gly Met Val
225                 230                 235                 240

Asp Val Arg Asp Val Ala Glu Leu His Leu Arg Ala Met Ala His Pro
                245                 250                 255

Ala Ala Ala Gly Glu Arg Phe Leu Ala Ser Gly Asp Arg Thr Val Ser
            260                 265                 270
```

```
Phe Leu Trp Ile Ala Gln Val Leu Ala Glu His Leu Gly Glu Arg Ala
        275                 280                 285

Ala Arg Val Pro Thr Arg Glu Phe Asp Asp Glu Arg Ala Arg Glu Ala
    290                 295                 300

Val Gly Val Thr Glu Arg Val Pro Ile Leu Arg Thr Glu Lys Ala Arg
305                 310                 315                 320

Ser Val Phe Gly Trp Thr Pro Arg Asp Pro Val Thr Thr Ile Leu Asp
                325                 330                 335

Thr Ala Glu Ser Leu Phe Arg Leu Gly Leu Val Lys Asp
            340                 345


<210> SEQ ID NO 60
<211> LENGTH: 135
<212> TYPE: PRT
<213> ORGANISM: Streptomyces sp.

<400> SEQUENCE: 60

Val Ser Arg Leu Ser Gly Leu Ser Glu Pro Thr Leu Arg Tyr Tyr Glu
1               5                   10                  15

Lys Ile Gly Leu Ile Pro Ala Val Asp Arg Asp Arg Asp Ser Gly His
            20                  25                  30

Arg Arg Tyr Pro Pro Ser Val Val Glu Thr Ile Arg Ser Leu Gly Cys
        35                  40                  45

Leu Arg Ser Thr Gly Met Ser Met Gln Asp Met Arg Ala Tyr Leu Gly
    50                  55                  60

His Leu Asp Glu Gly Asp Gln Gly Ala Ala Pro Leu Arg Asp Leu Phe
65                  70                  75                  80

Gln Arg Asn Ala Asp Arg Leu Glu Arg Glu Ile Ala Leu Met Glu Val
                85                  90                  95

Arg Leu Arg Tyr Leu Arg Leu Lys Ala Asp Met Trp Asp Ala Arg Glu
            100                 105                 110

Arg Ala Asp Ala Asp Ala Glu Arg Arg Ala Ile Asp Glu Leu Thr Asp
        115                 120                 125

Val Ile Asp Ala Leu Arg Pro
    130                 135


<210> SEQ ID NO 61
<211> LENGTH: 497
<212> TYPE: PRT
<213> ORGANISM: Streptomyces sp.

<400> SEQUENCE: 61

Val Thr Gly Pro Asp Gly Tyr Glu Ala Leu Pro His Arg Arg Arg Ala
1               5                   10                  15

Leu Val Thr Ile Ala Leu Leu Gly Cys Ala Phe Leu Ala Met Leu Asp
            20                  25                  30

Gly Thr Val Val Gly Thr Ala Leu Pro Arg Ile Val Glu Gln Ile Gly
        35                  40                  45

Gly Gly Asp Ser Trp Tyr Val Trp Leu Val Thr Ala Tyr Leu Leu Thr
    50                  55                  60

Ser Ser Val Ser Val Pro Val Tyr Gly Arg Phe Ser Asp Leu His Gly
65                  70                  75                  80

Arg Arg Arg Leu Leu Ile Gly Gly Leu Gly Val Phe Leu Ile Gly Ser
                85                  90                  95

Ile Ala Cys Gly Leu Ser Ala Ser Met Pro Ala Leu Ile Leu Ser Arg
            100                 105                 110
```

```
Ala Leu Gln Gly Leu Gly Ala Gly Ser Leu Leu Thr Leu Gly Met Ala
        115                 120                 125

Leu Val Arg Asp Leu His Pro Pro Ser Arg Pro Gln Gly Leu Ile Arg
    130                 135                 140

Met Gln Thr Ala Met Ala Ala Met Met Ile Leu Gly Met Val Gly Gly
145                 150                 155                 160

Pro Leu Leu Gly Gly Leu Leu Ala Asp His Ile Gly Trp Arg Trp Ala
                165                 170                 175

Phe Trp Leu Asn Leu Pro Leu Gly Leu Ala Ala Gly Ala Val Ile Val
            180                 185                 190

Leu Ala Leu Pro Asp Arg Arg Pro Ala Thr Pro Pro Ser Gly Arg Leu
        195                 200                 205

Asp Val Ala Gly Ile Leu Leu Leu Ala Ala Gly Leu Ala Leu Ala Leu
    210                 215                 220

Thr Gly Leu Ser Leu Lys Gly Asn Ala Thr Ala Gly His Ala Pro Ser
225                 230                 235                 240

Trp Thr Asp Pro Ala Val Leu Gly Cys Leu Leu Gly Gly Leu Ala Leu
                245                 250                 255

Leu Thr Thr Leu Ile Pro Val Glu Arg Arg Ala Ala Val Pro Val Leu
            260                 265                 270

Pro Leu Arg Leu Phe Arg His Arg Thr Tyr Thr Ala Leu Leu Thr Ala
        275                 280                 285

Gly Phe Phe Phe Gln Val Ala Ala Ala Pro Val Gly Ile Phe Leu Pro
    290                 295                 300

Leu Tyr Phe Gln His Ile Arg Gly His Ser Ala Thr Ala Ser Gly Leu
305                 310                 315                 320

Leu Leu Leu Pro Leu Leu Ile Gly Met Thr Leu Gly Asn Arg Leu Thr
                325                 330                 335

Ala Ala Thr Val Leu Arg Ser Gly His Val Lys Pro Val Leu Leu Ile
            340                 345                 350

Gly Ala Gly Leu Leu Thr Ala Gly Thr Ala Ala Phe Val Ala Leu Arg
        355                 360                 365

Ala Thr Thr Pro Leu Ala Leu Thr Ser Val Leu Leu Leu Leu Val Gly
    370                 375                 380

Leu Gly Ala Gly Pro Ala Met Gly Gly Leu Thr Ile Ala Thr Gln Ser
385                 390                 395                 400

Ala Val Pro Arg Ala Asp Met Gly Thr Ala Thr Ala Gly Ser Ala Leu
                405                 410                 415

Thr Lys Gln Leu Gly Gly Ala Val Gly Leu Ala Ser Ala Gln Ser Leu
            420                 425                 430

Ile Gly His Ser Gly Ala Ala Ala Pro Thr Ala Thr Ala Ile Gly Ser
        435                 440                 445

Thr Val Ser Trp Ser Gly Gly Ala Ala Gly Leu Leu Ala Leu Gly Ala
    450                 455                 460

Leu Leu Leu Met Arg Asp Ile Ser Ile Ala Thr Ala Gly Lys Arg Pro
465                 470                 475                 480

Gly Ala Pro Thr Ser Gly Thr Ala Val Pro Ala Lys Ala Asp Arg Leu
                485                 490                 495

Ala
```

<210> SEQ ID NO 62
<211> LENGTH: 213
<212> TYPE: PRT

<213> ORGANISM: Streptomyces sp.

<400> SEQUENCE: 62

Met Thr Glu Lys Ala Glu Asn Pro Ser Thr Pro Thr Arg Arg Arg Ala
1 5 10 15

Pro Ala Met Asp Pro Asp Gln Arg Arg Ala Met Ile Val Ala Ala Ala
20 25 30

Leu Pro Leu Val Val Glu Tyr Gly Ala Thr Val Thr Thr Ala Lys Ile
35 40 45

Ala Arg Ala Ala Gly Ile Gly Glu Gly Thr Ile Phe Arg Val Phe Glu
50 55 60

Asp Lys Asp Ala Leu Leu Ala Ala Cys Met Ala Glu Ala Val Arg Pro
65 70 75 80

Asp Asp Thr Val Ala His Leu Glu Ser Ile Ala Leu Asp Gln Pro Leu
85 90 95

Ala Asp Arg Leu Ala Glu Ala Ala Asp Val Val Arg Gly His Met Ala
100 105 110

Arg Ile Gly Ala Val Ala Gly Ala Leu Ala Ala Ala Gly Arg Leu Glu
115 120 125

Arg Met Ala Pro Lys Pro Gly Lys Asp Gly Arg Leu Pro Asp Arg Glu
130 135 140

Ala Ser Leu Val Arg Pro Arg Ala Ala Leu Ala Ala Leu Phe Glu Pro
145 150 155 160

Asp Arg Asp Arg Leu Arg Leu Ala Pro Glu Arg Leu Ala Asp Ala Phe
165 170 175

Gln Leu Thr Leu Met Ser Ala Gly Arg Leu Gly Ala Pro Glu Pro Leu
180 185 190

Thr Thr Glu Glu Val Val Asp Leu Phe Leu His Gly Ala Leu Val Ala
195 200 205

Pro Gly Glu Ala Arg
210

<210> SEQ ID NO 63
<211> LENGTH: 348
<212> TYPE: PRT
<213> ORGANISM: Streptomyces sp.

<400> SEQUENCE: 63

Val Lys Cys Ala Gly Thr Arg Gly Ser Trp Gly Ala Trp Arg Arg Thr
1 5 10 15

Gly Pro Ser Gly Arg Gly Val Pro Leu Pro Leu His Gly Gly Gly Pro
20 25 30

Ile Gly Ile Val Ser Asn Asp Asp Val Cys Cys Val Ala Ser Arg Met
35 40 45

Glu Met Met Val Glu Leu Arg Gln Leu Ala Tyr Phe Val Ala Val Ala
50 55 60

Glu Glu Arg Ser Phe Thr Arg Gly Ala Gln Arg Glu His Val Val Gln
65 70 75 80

Ser Ala Ala Ser Ala Ala Val Ala Arg Leu Glu Gln Glu Phe Gln Thr
85 90 95

Ala Leu Phe Asp Arg Ser His Arg Thr Leu Glu Leu Thr Thr Ala Gly
100 105 110

Arg Thr Leu Leu Ala Arg Ala Arg Ile Leu Leu Ala Glu Ala Gln Arg
115 120 125

Ala Arg Asp Asp Met Gly Arg Leu Thr Gly Gly Leu Ser Gly Thr Val

```
    130                 135                 140

Thr Leu Gly Thr Val Leu Ser Thr Gly Ser Phe Asp Leu Ile Gly Ala
145                 150                 155                 160

Leu Ser Thr Phe Gln Ala Glu His Pro Asp Val Val Val Arg Leu Arg
                165                 170                 175

His Ser Thr Gly Pro Leu Ala Gly His Ala Thr Ala Leu Arg Glu Gly
            180                 185                 190

Arg Phe Asp Leu Met Leu Leu Pro Val Pro Pro His Gly Pro Ala Val
        195                 200                 205

Leu Gly Pro Asp Leu Ile Ile Asp Asp Val Ser Arg Ile Arg Leu Gly
    210                 215                 220

Leu Ala Cys Arg Thr Asp Asp Pro Leu Ala Glu Ala His Gly Val Thr
225                 230                 235                 240

Tyr Ala Asp Leu Ala Asp Arg Arg Phe Ile Asp Phe Pro Thr Gly Trp
                245                 250                 255

Gly Asp Arg Thr Ile Val Asp Ser Leu Phe Gly Thr Ala Gly Val Gln
            260                 265                 270

Arg Thr Val Ala Leu Glu Val Val Asp Thr Thr Thr Ala Leu Thr Met
        275                 280                 285

Val Arg Arg Arg Leu Gly Leu Ala Phe Val Ala Glu Glu Thr Ile Ala
    290                 295                 300

Ser Arg Pro Gly Leu Thr Gln Val Asp Leu Ala Asp Pro Pro Pro Leu
305                 310                 315                 320

His Gly Leu Gly Leu Ala Ala Ser Arg Asn His Pro Pro Ser Glu Ala
                325                 330                 335

Gly Arg Ala Leu Arg Arg Ala Leu Leu Ala Ala Arg
            340                 345


<210> SEQ ID NO 64
<211> LENGTH: 218
<212> TYPE: PRT
<213> ORGANISM: Streptomyces sp.

<400> SEQUENCE: 64

Met Pro His Ser Thr His His Arg Trp Thr Arg Tyr Leu Trp Asp Arg
1               5                   10                  15

His Arg Gly Gly Glu Ala Glu Arg Pro Gly Arg Thr Ala Arg Phe Gly
            20                  25                  30

Ala Thr Pro Pro Asn Phe Pro Val Cys Gln His Thr Ser Pro Arg Lys
        35                  40                  45

Ala Ser Ile Val Met Ser Val Ser Ala Ile Gln Ile Gly Leu His Pro
    50                  55                  60

Asp Ala Ile Asp Tyr Glu Ala Pro Glu Phe Ala Ala Phe Ala Gly Leu
65                  70                  75                  80

Ser Arg Glu Thr Leu Arg Ala Ala Asn Asp Asp Asn Leu Ala Leu Leu
                85                  90                  95

Leu Asp Ala Gly Tyr Glu Ala Asp Gly Cys Gln Ile Asp Phe Gly Glu
            100                 105                 110

Thr Ala Leu Asp Thr Ile Arg Ala Met Leu Gly Arg Lys Arg Tyr Asp
        115                 120                 125

Ala Val Leu Ile Gly Ala Gly Val Arg Leu Thr Ala Gly Asn Thr Leu
    130                 135                 140

Leu Phe Glu Ser Ile Val Asn Leu Val His Thr Ala Leu Pro His Ala
145                 150                 155                 160
```

```
Arg Phe Ile Phe Asn His Ser Ala Ala Ala Thr Pro Asp Asp Ile Arg
                165                 170                 175

Arg His Tyr Pro Asp Pro Ala Ser Thr Val Pro Leu Asp Val Pro Arg
            180                 185                 190

Asp Leu Glu Glu Ala Ala Leu Lys Asn Pro Gly Asn Ala Ala Arg Pro
        195                 200                 205

Glu Ala Ala His Gly Pro Arg Glu Thr Arg
    210                 215


<210> SEQ ID NO 65
<211> LENGTH: 459
<212> TYPE: PRT
<213> ORGANISM: Streptomyces sp.

<400> SEQUENCE: 65

Val Leu Glu Arg Arg Pro Ala Ile His Pro Ser Ser Arg Ala Phe Val
1               5                   10                  15

Thr Met Pro Arg Thr Leu Glu Val Leu Asp Ser Arg Gly Leu Ala Asp
            20                  25                  30

Asp Leu Leu Ala Gly Ala Asn Thr Thr Glu Ala Val His Leu Phe Ala
        35                  40                  45

Gly Ala Thr Leu Asp Leu Thr His Leu Pro Ser Arg His Arg Tyr Gly
    50                  55                  60

Met Ile Thr Pro Gln Thr Asn Val Asp Gln Ala Leu Glu Arg Tyr Ala
65                  70                  75                  80

Arg Asp Gln Gly Ala Arg Val Leu Arg Gly Thr Glu Val Thr Gly Leu
                85                  90                  95

Ala Gln Asp Ala Asp Ala Val Thr Val Thr Ala Arg Ala Asp Gly Gly
            100                 105                 110

Gly Pro Ala Ser Thr Trp Arg Ala Arg Tyr Val Val Gly Ala Asp Gly
        115                 120                 125

Ala His Ser Thr Val Arg Gly Leu Leu Gly Ala Asp Phe Pro Gly Arg
    130                 135                 140

Thr Val Leu Thr Ser Val Val Leu Ala Asp Val Arg Leu Ala Asp Gly
145                 150                 155                 160

Pro Thr Gly Asn Gly Leu Thr Leu Gly Asn Thr Pro Glu Val Phe Gly
                165                 170                 175

Phe Leu Val Pro Tyr Gly Lys Ala Arg Pro Gly Trp Tyr Arg Ser Met
            180                 185                 190

Thr Trp Asp Arg Arg His Gln Leu Pro Asp Lys Ala Ala Val Glu Glu
        195                 200                 205

Ala Glu Val Thr Arg Val Leu Ala Glu Ala Met Gly Arg Asp Val Gly
    210                 215                 220

Val Arg Glu Ile Gly Trp His Ser Arg Phe His Cys Asp Glu Arg Gln
225                 230                 235                 240

Val Arg Ser Tyr Arg His Gly Arg Val Phe Leu Ala Gly Asp Ala Ala
                245                 250                 255

His Val His Ser Pro Met Gly Gly Gln Gly Met Asn Thr Gly Val Gln
            260                 265                 270

Asp Ala Ala Asn Leu Ala Trp Lys Leu Asp Leu Ala Leu Gly Gly Ala
        275                 280                 285

Asp Pro Ala Ile Leu Asp Thr Tyr His Arg Glu Arg His Pro Val Gly
    290                 295                 300

Arg Arg Val Leu Leu Gln Ser Gly Ala Met Met Arg Ala Val Thr Leu
305                 310                 315                 320
```

Gly Pro Arg Pro Ala Arg Trp Leu Arg Asp His Leu Ala Pro Ala Leu
325 330 335

Leu Gly Val Gly Arg Val Arg Asp Thr Ile Ala Gly Ser Phe Thr Gly
340 345 350

Val Thr Pro Arg Tyr Pro Arg Gly Arg Arg Gln His Ala Leu Val Gly
355 360 365

Thr Arg Ala Thr Glu Val Pro Leu Ala Glu Gly Arg Leu Thr Glu Leu
370 375 380

Gln Arg Ala Gly Gly Phe Leu Leu Ile Arg Glu Arg Gly Ala Ala Arg
385 390 395 400

Val Asp Thr Thr Val Ala Gln Ala Glu Arg Thr Asp Ser Gly Pro Ala
405 410 415

Leu Leu Val Arg Pro Asp Gly Tyr Ile Ala Trp Ala Gly Pro Gly Val
420 425 430

Arg Thr Asp Gly Pro Asp Gly Trp His Thr Thr Trp Arg Ala Trp Thr
435 440 445

Gly Pro Ala Thr Asp Ala Val Arg Ala Gly Arg
450 455

<210> SEQ ID NO 66
<211> LENGTH: 135
<212> TYPE: PRT
<213> ORGANISM: Streptomyces sp.

<400> SEQUENCE: 66

Met Ser Leu Ile Arg Glu Pro His Arg Arg Arg Phe Asn Ala Ile Met
1 5 10 15

Val Gly Gly Ala Gly Ala Ala Tyr Leu Ser Gly Gly Gly Leu Asp Gly
20 25 30

Trp Glu Phe Ala Phe Thr Val Val Ala Thr Tyr Val Ala Tyr Arg Gly
35 40 45

Leu Glu Ser Trp Thr Phe Ile Gly Ile Gly Trp Leu Leu His Thr Ala
50 55 60

Trp Asp Ile Val His His Ile Lys Gly Asn Pro Ile Val Pro Phe Ala
65 70 75 80

His Gly Ser Ser Leu Gly Cys Ala Ile Cys Asp Pro Val Ile Ala Leu
85 90 95

Trp Cys Phe Arg Gly Gly Pro Ser Leu Leu Arg Phe Phe Arg Lys Gly
100 105 110

Arg Pro Glu Glu Pro Ala Ala Ala Ala Leu Pro Asp Ser Leu Ser Ala
115 120 125

Gly Gln Ala Thr Gly Asn Gly
130 135

<210> SEQ ID NO 67
<211> LENGTH: 816
<212> TYPE: PRT
<213> ORGANISM: Streptomyces sp.

<400> SEQUENCE: 67

Met Ser Gly Ala Thr Arg Leu Pro Arg His Pro Thr Asp Arg Ser Arg
1 5 10 15

Thr Met Pro Leu Asp Arg Arg Arg Phe Leu Arg Thr Ser Ala Leu Thr
20 25 30

Leu Gly Ala Pro Ala Leu Ala Gly His Leu Ala Thr Asp Ala Val Ala
35 40 45

```
Ser Pro Ala Arg Arg Pro Arg Ala Pro Leu Ser Asp Ala Phe Asp Arg
    50                  55                  60

Leu Pro Ser Gly Ser Ile Thr Pro Arg Gly Trp Leu Ala Glu Gln Leu
65                  70                  75                  80

Arg Leu Gln Leu His Gly Leu Cys Gly Arg Tyr Gln Glu Arg Ser His
                85                  90                  95

Phe Leu Asp Ile Asn Ala Thr Gly Trp Thr His Pro Asp Arg Asp Gly
            100                 105                 110

Trp Glu Glu Val Pro Tyr Trp Leu Arg Gly Tyr Val Pro Leu Ala Val
        115                 120                 125

Ala Thr Arg Asp Gln Ala Ala Leu Ala Asn Ala Arg Gly Trp Ile Asp
    130                 135                 140

Ala Ile Leu Ala Thr Gln Gln Ser Asp Gly Phe Phe Gly Pro Arg Ser
145                 150                 155                 160

Leu Arg Thr Lys Leu Asn Gly Gly Pro Asp Phe Trp Pro Phe Leu Pro
                165                 170                 175

Leu Leu Met Ala Leu Arg Thr His Glu Glu Phe Thr Gly Asp Gln Arg
            180                 185                 190

Ile Val Pro Phe Leu Thr Arg Phe Leu Arg Phe Met Asn Ala Gln Gly
        195                 200                 205

Pro Gly Ala Phe Asp Ser Ser Trp Val Ser Tyr Arg Trp Gly Asp Gly
    210                 215                 220

Ile Asp Thr Ala Met Trp Leu His Arg Arg Thr Gly Glu Ala Phe Leu
225                 230                 235                 240

Leu Asp Leu Val Gln Lys Met His Thr Tyr Gly Ala Asn Trp Val Asp
                245                 250                 255

Asn Ile Pro Thr Pro His Asn Val Asn Ile Ala Gln Gly Phe Arg Glu
            260                 265                 270

Pro Ala Gln Tyr Ala Gln Leu Thr Gly Ser Ala Glu Leu Arg Gln Ala
        275                 280                 285

Thr Tyr Arg Gly Tyr Thr Ser Val Leu Gly Ala Tyr Gly Gln Phe Pro
    290                 295                 300

Gly Gly Gly Phe Ala Gly Asp Glu Asn Tyr Arg Pro Gly Phe Gly Asp
305                 310                 315                 320

Pro Arg Gln Gly Phe Glu Thr Cys Gly Ile Val Glu Phe Met Ala Ser
                325                 330                 335

His Glu Leu Leu Thr Arg Ile Thr Gly Asp Pro Val Trp Ala Asp Arg
            340                 345                 350

Cys Glu Asp Leu Ala Phe Asn Met Leu Pro Ala Ala Leu Asp Pro Gln
        355                 360                 365

Gly Thr Gly Thr His Tyr Ile Thr Ser Ala Asn Ser Ile Asp Leu Asn
    370                 375                 380

Asn Ala Val Lys Ser Gln Gly Gln Phe Gln Asn Gly Phe Ala Met Gln
385                 390                 395                 400

Ser Tyr Gln Pro Gly Val Asp Gln Tyr Arg Cys Cys Pro His Asn Tyr
                405                 410                 415

Gly Met Gly Trp Pro Tyr Phe Ser Glu Glu Leu Trp Leu Ala Thr Pro
            420                 425                 430

Asp Lys Gly Leu Ala Ala Ser Leu Tyr Ala Ala Ser Gln Val Ser Ala
        435                 440                 445

Lys Val Ala Gly Gly Thr Thr Val Thr Val Thr Glu Asp Thr Asp Tyr
    450                 455                 460
```

```
Pro Phe Asp Glu Thr Ile Thr Leu Thr Leu Ser Thr Pro Glu Lys Val
465                 470                 475                 480

Ala Phe Pro Leu His Leu Arg Val Pro Gly Trp Cys Lys Asn Pro Arg
                485                 490                 495

Ile Glu Val Asn Gly Arg Ala Val Ala Thr Arg Gly Gly Pro Ala Phe
            500                 505                 510

Val Lys Val Asp Arg Ser Trp Thr Asp Gly Asp Val Val Thr Ile Arg
        515                 520                 525

Leu Pro Gln Arg Thr Ala Leu Arg Thr Trp Ser Ala Gln His Gly Ala
    530                 535                 540

Val Ser Val Asp His Gly Pro Leu Thr Tyr Ser Leu Arg Ile Gly Glu
545                 550                 555                 560

Asp Phe Val Arg Tyr Ala Gly Thr Asp Thr Phe Pro Glu Tyr Glu Val
                565                 570                 575

His Ala Thr Thr Pro Trp Asn Tyr Gly Leu Ala Pro Gly Ala Leu Pro
            580                 585                 590

Val Leu Thr Arg Asp Asp Gly Pro Leu Ala Ala Asn Pro Phe Thr His
        595                 600                 605

Glu Thr Thr Pro Val Arg Met Thr Ala Gln Ala Arg Arg Ile Ala Glu
    610                 615                 620

Trp Val Ser Asp Asp Glu His Val Val Thr Pro Leu Gln Gln Ser Pro
625                 630                 635                 640

Ala Arg Ala Asp Ala Pro Ala Glu Thr Val Thr Leu Ile Pro Met Gly
                645                 650                 655

Ala Ala Arg Leu Arg Ile Thr Cys Phe Pro Thr Ala Ala Pro Asp Gly
            660                 665                 670

Arg Ala Trp Thr Pro Glu Pro Pro Phe Arg Arg Leu Leu Asn Lys His
        675                 680                 685

Ser Gly Lys Val Leu Ala Val Asp Glu Met Ser Thr Ala Asn Ser Ala
    690                 695                 700

Arg Val Val Gln Tyr Asp Asn Thr Pro Thr Gly Asp His Ala Trp Gln
705                 710                 715                 720

Trp Ile Asp Arg Gly Asp Gly Trp Phe Leu Ile Arg Asn Gly His Ser
                725                 730                 735

Gly Lys Val Leu Gly Val Asp Arg Met Ser Thr Ala Asn Ser Ala Ile
            740                 745                 750

Val Val Gln Tyr Glu Asp Asn Gly Thr Ala Asp His Leu Trp Arg Lys
        755                 760                 765

Val Asp Asn Gly Asp Gly Trp Phe Arg Val Leu Asn Lys Asn Ser Gln
    770                 775                 780

Lys Val Leu Gly Val Asp Gly Met Ser Thr Ala Asn Ser Ala Gln Val
785                 790                 795                 800

Val Gln Tyr Asp Asp Asn Gly Thr Asp Asp His Leu Trp Arg Leu Leu
                805                 810                 815
```

<210> SEQ ID NO 68
<211> LENGTH: 134
<212> TYPE: PRT
<213> ORGANISM: Streptomyces sp.

<400> SEQUENCE: 68

```
Met Ser Ala Pro Gln Gly Gln Gly Pro Thr Phe Arg Glu Leu Val Val
1               5                   10                  15

Gln Ala Leu Ser Ser Val Glu Arg Gly Tyr Asp Leu Leu Ala Pro Lys
            20                  25                  30

Phe Asp His Thr Gly Tyr Arg Thr Ser Ala Ser Val Leu Asp Ser Val
        35                  40                  45

Thr Gly Ala Leu Arg Pro Leu Gly Pro Phe Asp Ser Gly Leu Asp Val
    50                  55                  60

Cys Cys Gly Thr Gly Ala Gly Met Gly Val Leu Arg Gln Val Cys Arg
65                  70                  75                  80

Glu Arg Ile Thr Gly Val Asp Phe Ser Ala Gly Met Leu Ala Val Gly
                85                  90                  95

Arg Glu Arg Thr Arg Thr Val Pro Asp Ala Pro Arg Thr Asp Trp Val
            100                 105                 110

Arg Ala Asp Ala Arg Ala Leu Pro Phe Glu Pro Val Phe Asp Leu Ala
        115                 120                 125

Val Ser Phe Gly Ala Phe
    130
```

<210> SEQ ID NO 69
<211> LENGTH: 28
<212> TYPE: DNA
<213> ORGANISM: Streptomyces sp.

<400> SEQUENCE: 69
tgcaagcttc tcgcgtctgg tgctggtg 28

<210> SEQ ID NO 70
<211> LENGTH: 23
<212> TYPE: DNA
<213> ORGANISM: Streptomyces sp.

<400> SEQUENCE: 70
atcttcgccc ttgtcccgca gtc 23

<210> SEQ ID NO 71
<211> LENGTH: 21
<212> TYPE: DNA
<213> ORGANISM: Streptomyces sp.

<400> SEQUENCE: 71
atcgctctgc ggctggcggt g 21

<210> SEQ ID NO 72
<211> LENGTH: 28
<212> TYPE: DNA
<213> ORGANISM: Streptomyces sp.

<400> SEQUENCE: 72
tgctctagag ccacgaagac gccggaac 28